US011937499B2

(12) United States Patent
Zhao et al.

(10) Patent No.: US 11,937,499 B2
(45) Date of Patent: Mar. 19, 2024

(54) AROMATIC AMINE DERIVATIVE AND ORGANIC ELECTROLUMINESCENT DEVICES CONTAINING THE SAME

(71) Applicant: BEIJING SUMMER SPROUT TECHNOLOGY CO., LTD., Beijing (CN)

(72) Inventors: Chunliang Zhao, Beijing (CN); Zheng Wang, Beijing (CN); Dan Ye, Beijing (CN); Shaobo Zhang, Beijing (CN); Hongbo Li, Beijing (CN); Xin Bi, Beijing (CN); Xuechao Tian, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 374 days.

(21) Appl. No.: 17/000,576

(22) Filed: Aug. 24, 2020

(65) Prior Publication Data

US 2021/0066595 A1 Mar. 4, 2021

(30) Foreign Application Priority Data

Aug. 26, 2019 (CN) ......................... 201910788747.0

(51) Int. Cl.

| | |
|---|---|
| ***C07C 211/61*** | (2006.01) |
| ***C07C 255/58*** | (2006.01) |
| ***C09K 11/06*** | (2006.01) |
| ***H10K 85/60*** | (2023.01) |
| *H10K 50/11* | (2023.01) |
| *H10K 101/10* | (2023.01) |

(52) U.S. Cl.

CPC .......... *H10K 85/633* (2023.02); *C07C 211/61* (2013.01); *C07C 255/58* (2013.01); *C09K 11/06* (2013.01); *C09K 2211/1007* (2013.01); *C09K 2211/1011* (2013.01); *H10K 50/11* (2023.02); *H10K 85/622* (2023.02); *H10K 85/626* (2023.02); *H10K 2101/10* (2023.02)

(58) Field of Classification Search

None

See application file for complete search history.

(56) References Cited

U.S. PATENT DOCUMENTS

| | | | | |
|---|---|---|---|---|
| 5,703,436 A | 12/1997 | Forrest et al. | | |
| 5,707,745 A | 1/1998 | Forrest et al. | | |
| 5,844,363 A | 12/1998 | Gu et al. | | |
| 6,097,147 A | 8/2000 | Baldo et al. | | |
| 6,303,238 B1 | 10/2001 | Thompson et al. | | |
| 7,279,704 B2 | 10/2007 | Walters et al. | | |
| 7,968,146 B2 | 6/2011 | Wagner et al. | | |
| 11,639,339 B2 * | 5/2023 | Koenen | C07D 493/04 | 257/40 |
| 2003/0230980 A1 | 12/2003 | Forrest et al. | | |
| 2004/0174116 A1 | 9/2004 | Lu et al. | | |
| 2010/0052526 A1 * | 3/2010 | Je | C07D 213/74 | 548/440 |
| 2012/0181520 A1 | 7/2012 | Kim et al. | | |
| 2013/0234118 A1 * | 9/2013 | Kwon | C07D 307/91 | 558/418 |
| 2014/0361266 A1 | 12/2014 | Jung et al. | | |
| 2015/0048323 A1 | 2/2015 | Kim et al. | | |
| 2015/0102290 A1 | 4/2015 | Kwong et al. | | |
| 2015/0243892 A1 * | 8/2015 | Ogita | H10K 85/6574 | 257/40 |
| 2015/0255736 A1 | 9/2015 | Kim et al. | | |
| 2015/0349273 A1 | 12/2015 | Hung et al. | | |
| 2016/0099423 A1 | 4/2016 | Kim et al. | | |
| 2016/0104847 A1 | 4/2016 | Xia et al. | | |
| 2016/0149139 A1 | 5/2016 | Xia et al. | | |
| 2016/0218294 A1 | 7/2016 | Xia et al. | | |
| 2016/0322569 A1 | 11/2016 | Yen | | |
| 2016/0359122 A1 | 12/2016 | Boudreault et al. | | |
| 2017/0155048 A1 | 6/2017 | Kim et al. | | |
| 2019/0006592 A1 * | 1/2019 | Jeong | H10K 99/00 | |
| 2019/0081253 A1 | 3/2019 | Xia | | |
| 2020/0028084 A1 * | 1/2020 | Song | C07C 211/61 | |
| 2021/0024481 A1 * | 1/2021 | Koenen | H10K 85/626 | |

FOREIGN PATENT DOCUMENTS

| | | | |
|---|---|---|---|
| CN | 105503622 A | 4/2016 | |
| CN | 107778213 A | 3/2018 | |
| CN | 108129332 A * | 6/2018 | C07C 211/57 |
| CN | 108129332 A | 6/2018 | |

(Continued)

OTHER PUBLICATIONS

Dabestani et al. Photochemistry and Photobiology 1999 70(1), 10-34.*

T.A. Baillie, Pharmacological Reviews, 33(2), 81-132 (1981) (Year: 1981).*

Notice of Reason for Refusal, and its english translation, issued in Japanese Application No. 2020-142806, dated Aug. 17, 2021, 8 pages.

Tang, 1987, Organic electroluminescent diodes, Applied Physics Letters, 51(12):913-915.

Uoyama, 2012, Highly efficient organic light-emitting diodes from delayed fluorescence, Nature, 492(7428):234-238.

(Continued)

*Primary Examiner* — Alexander R Pagano

(74) *Attorney, Agent, or Firm* — Brown Rudnick LLP; Matthew P. York

(57) ABSTRACT

Disclosed are an aromatic amine derivative and an organic electroluminescent device including the same. A fluorenyl/silafluorenyl group having an ortho-substituted group is introduced into the structure of the aromatic amine derivative. The aromatic amine derivative may be used as a light-emitting material in a light-emitting layer of an organic electroluminescent device. These novel compounds can provide better device performance.

17 Claims, 1 Drawing Sheet

(56) References Cited

FOREIGN PATENT DOCUMENTS

| | | | | | |
|---|---|---|---|---|---|
| CN | 108129431 A | | 6/2018 | | |
| CN | 108558678 A | * | 9/2018 | ........... | C07C 211/61 |
| CN | 108558678 A | | 9/2018 | | |
| CN | 109776335 A | | 5/2019 | | |
| CN | 109928887 A | | 6/2019 | | |
| CN | 111039800 | * | 4/2020 | ........... | C07C 211/61 |
| EP | 1437395 A2 | | 7/2004 | | |
| IN | 109651174 A | | 4/2019 | | |
| JP | H1135532 A | | 2/1999 | | |
| JP | 2009185024 A | | 8/2009 | | |
| JP | WO-2018151077 | * | 8/2018 | ........... | C07D 307/91 |
| KR | 20130101830 A | | 9/2013 | | |
| KR | 101740858 B1 | | 5/2017 | | |
| KR | 1020190085997 | * | 7/2019 | | |
| TW | 201925161 A | | 7/2019 | | |
| WO | 2018095382 A1 | | 5/2018 | | |
| WO | 2018151077 A1 | | 8/2018 | | |
| WO | 2018160003 A1 | | 9/2018 | | |

OTHER PUBLICATIONS

First Office Action for Chinese Patent Application No. 201910788747.0 dated Jun. 6, 2022 (5 pages).

English translation of First Office Action issued for Chinese Patent Application No. 201910788747.0 dated Jun. 6, 2022 (5 pages).

Search Report issued for Chinese Patent Application No. 201910788747.0 dated May 30, 2022 (2 pages).

English translation of Search Report issued for Chinese Patent Application No. 201910788747.0 dated May 30, 2022 (2 pages).

First Office Action issued for German Patent Application No. 10 2020 210 743.2 dated Nov. 2, 2022 (6 pages).

English translation of First Office Action issued for German Patent Application No. 10 2020 210 743.2 dated Nov. 2, 2022 (3 pages).

Second Office Action issued for Japanese Patent Application No. 2020-142806 dated Apr. 5, 2022 (2 pages).

English translation of Second Office Action issued for Japanese Patent Application No. 2020-142806 dated Apr. 5, 2022 (2 pages).

Korean Office Action and the english translation, issued in Korean Application No. 10-2020-0107818, dated Jun. 2, 2023, 13 pages.

* cited by examiner

AROMATIC AMINE DERIVATIVE AND ORGANIC ELECTROLUMINESCENT DEVICES CONTAINING THE SAME

CROSS-REFERENCE TO RELATED APPLICATION(S)

The present disclosure claims priority to a Chinese patent application No. CN 201910788747.0 filed on Aug. 26, 2019, disclosure of which is incorporated herein by reference in its entirety.

TECHNICAL FIELD

The present disclosure relates to aromatic amine derivative compounds for organic electronic devices, for example, organic light-emitting devices. More particularly, the present disclosure relates to an aromatic amine derivative compound, and an organic electroluminescent device and a compound formulation including the compound.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green.

Although fluorescent blue OLEDs have longer lifetimes than phosphorescent blue OLEDs, the lifetime and the efficiency of fluorescent blue OLEDs need to be further improved to meet the increasing requirements in the display field. Therefore, it is a very important project to improve the lifetime and the efficiency of fluorescent blue devices.

CN108558678A disclosed a compound having a structure represented by the following general formula:

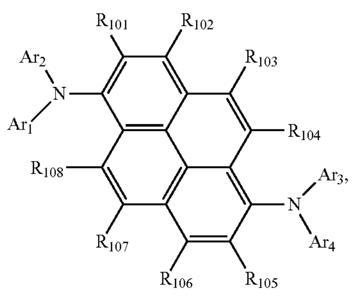

wherein at least one of $Ar_1$ to $Ar_4$ is selected from a naphthyl substituent having the following structures:

(I-a)

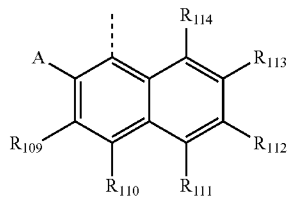

(I-b)

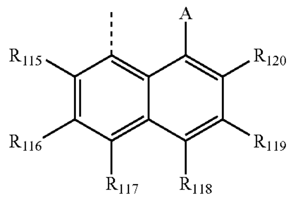

(I-c)

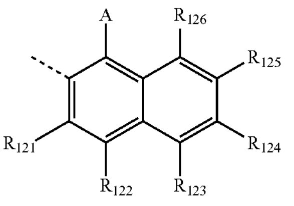

-continued (I-d)

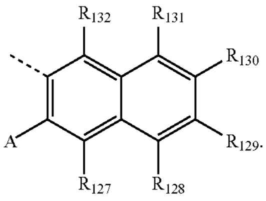

Specific examples include

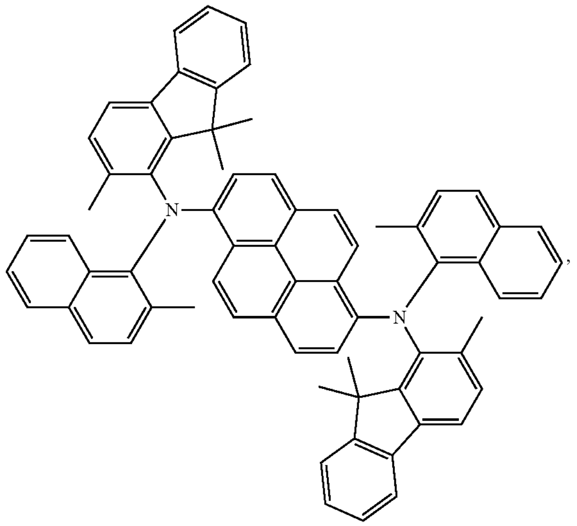

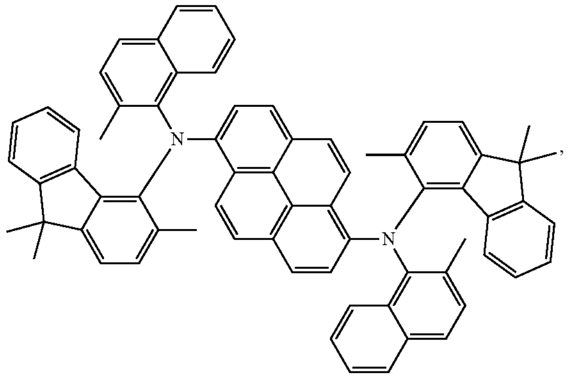

-continued

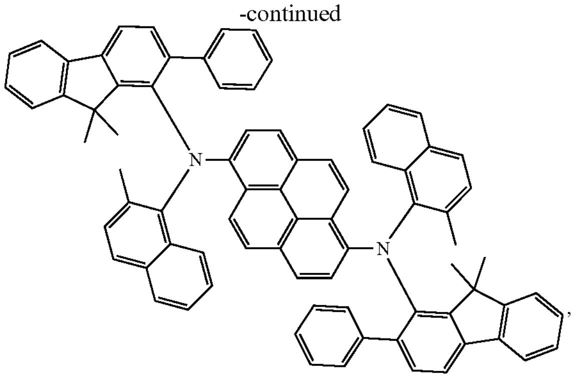

etc. Compounds disclosed in this application have to include a naphthalene ring structure, and the inventors focus on the use of 1-naphthalene and 2-naphthalene substituents in pyrene-based triarylamine compounds rather than the use of fluorene/silafluorene structures with ortho-substituents. This application has neither disclosed or instructed the use of aryl/heteroaryl groups other than naphthalene in triarylamine compounds based on pyrene or other aryl/heteroaryl groups, nor noticed the special advantages of fluorene/silafluorene structures with ortho-substituents.

US20150255736A disclosed a pyrene-based triarylamine compound substituted with silafluorene:

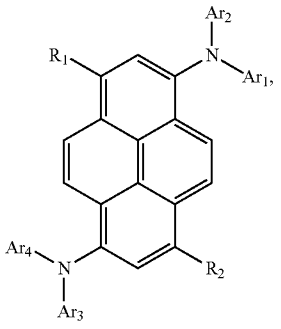

wherein at least one of $Ar_1$ to $Ar_4$ has a structure represented by the following general formula:

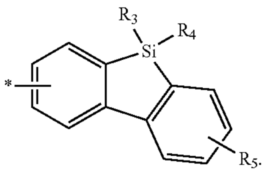

Specific examples include

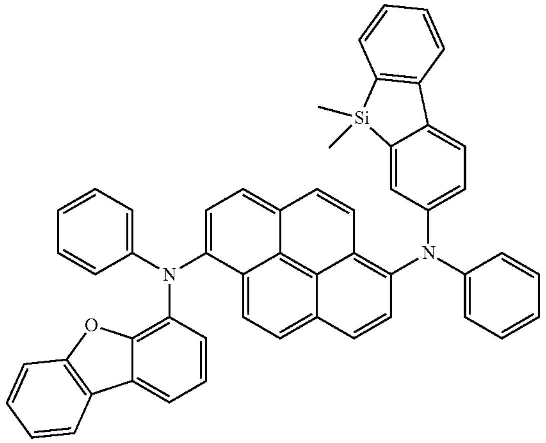

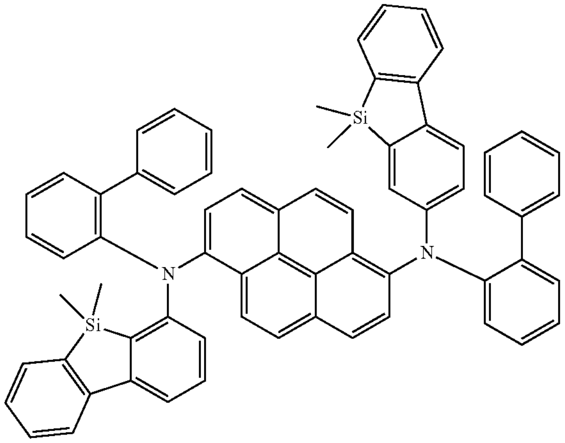

-continued

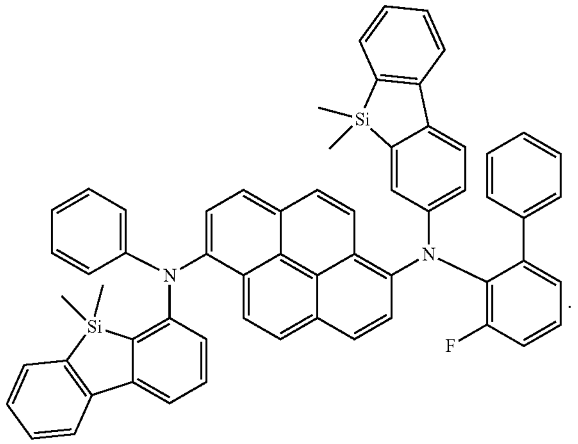

This application has disclosed the introduction of a silafluorene structure into pyrene-based triarylamine compounds, but not noticed the special advantages of fluorene/silafluorene structures with ortho-substituents.

TW201925161A disclosed a compound represented by the following general formula:

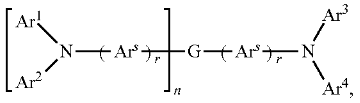

wherein $Ar^4$ has a structure represented by the general formula:

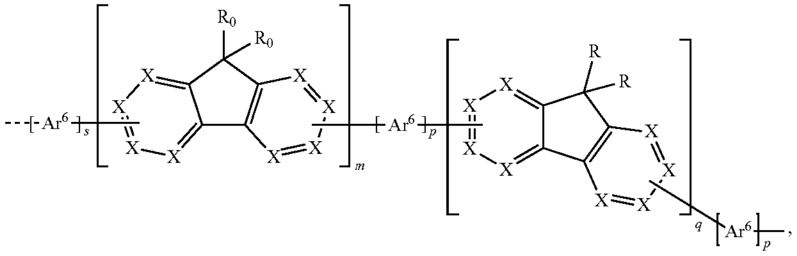

wherein G is a central segment of a fluorescent material such as pyrene, chrysene, and anthracene, n is 0 or 1, r is 0 to 2, s and p each have a range from 0 to 10, and m and q each have a range from 1 to 10. Specific examples disclosed include

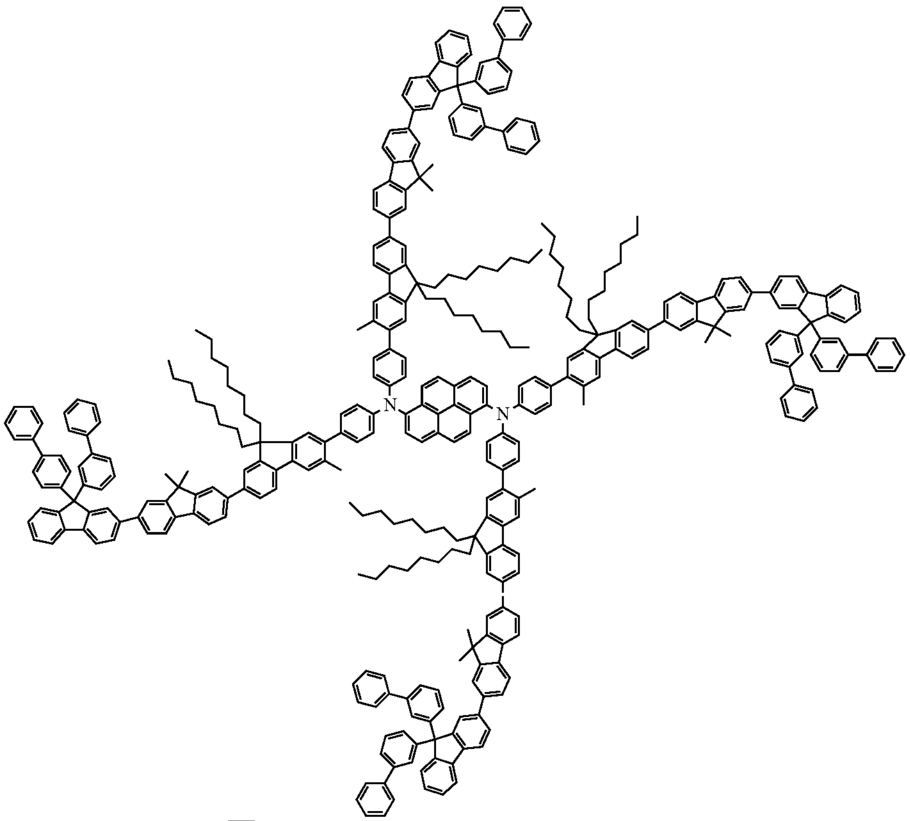

and

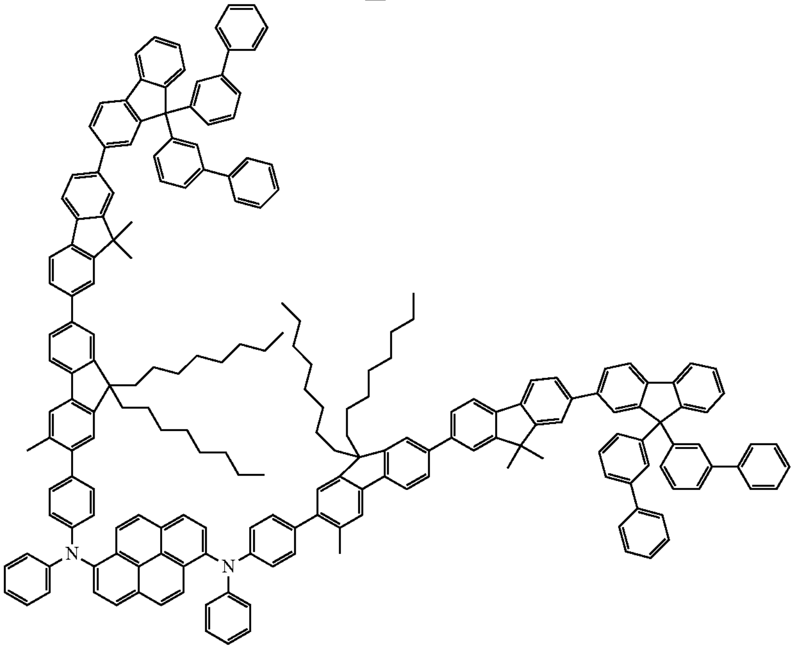

.

This application relates to the study of blue materials having a fluorene ring-based triarylamine structure. However, in structures disclosed in this application, two or more structural units of fluorene rings have to be included in a single Ar group. Moreover, OLED devices are prepared by a solution method in this application, and multiple fluorene ring structures and long alkyl chains in the disclosed compounds are all favorable to the use of the solution method for preparing devices. Meanwhile, due to the introduction of multiple structural units of fluorene rings and the long alkyl chains, the compounds disclosed in this application are not favorable to the use of a vacuum evaporation method for preparing OLED devices. Therefore, this application has neither disclosed or instructed the inclusion of only one structural unit of fluorene ring in a single Ar group nor noticed the special advantages of fluorene/silafluorene structures with ortho-substituents.

These documents have disclosed a large number of fluorescent light-emitting materials with an aromatic amine structure with a pyrene core. However, the fluorescent light-emitting materials still need to be further developed to obtain higher device efficiency, a longer device lifetime, and bluer light emission. After in-depth researches, the inventor has found that novel aromatic amine derivative compounds obtained through the introduction of a fluorenyl/silafluorenyl group with ortho-substituted groups into the aromatic amine structure of this kind of material can provide better device performance when used as light-emitting materials in organic light-emitting devices.

SUMMARY

The present disclosure aims to provide a series of novel compounds having an aromatic amine structure to solve at least part of the above-mentioned problems. These compounds may be used as light-emitting materials in organic electroluminescent devices. These novel compounds can provide better device performance.

According to an embodiment of the present disclosure, disclosed is a compound having a structure of Formula 1:

Formula 1

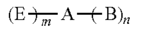

in Formula 1,

A is substituted or unsubstituted aryl having 10 to 60 ring atoms or substituted or unsubstituted heteroaryl having 10 to 60 ring atoms;

n is an integer greater than or equal to 1, m is an integer greater than or equal to 0, and n+m is greater than or equal to 2; when n is greater than or equal to 2, B may be the same or different structures; when m is greater than or equal to 2, E may be the same or different structures;

E has a structure represented by Formula 2:

Formula 2

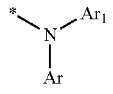

in Formula 2, * represents a position where E is joined to A;

wherein Ar and $Ar_1$ are each independently selected from the group consisting of: substituted or unsubstituted aryl having 6 to 30 ring carbon atoms and substituted or unsubstituted heteroaryl having 3 to 30 ring atoms;

B has a structure represented by Formula 3:

Formula 3

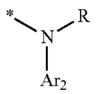

in Formula 3, * represents a position where B is joined to A;

wherein R is selected from the group consisting of: substituted or unsubstituted aryl having 6 to 30 ring carbon atoms and substituted or unsubstituted heteroaryl having 3 to 30 ring atoms; and when R is selected from aryl, R is not substituted or unsubstituted naphthyl;

wherein $Ar_2$ has a structure represented by Formula 4:

Formula 4

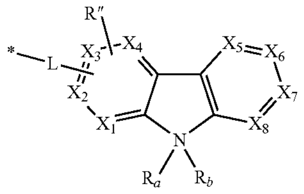

and $Ar_2$ includes only one fluorene ring structure, azafluorene ring structure, spirobifluorene ring structure, or azaspirobifluorene ring structure;

in Formula 4, * represents a position where $Ar_2$ is joined to N shown in Formula 3;

X is C or Si;

L is selected from a single bond, substituted or unsubstituted arylene having 6 to 60 carbon atoms, or substituted or unsubstituted heteroarylene having 3 to 60 carbon atoms;

$X_1$ to $X_8$ are each independently selected from C, CR' or N, and two adjacent C are present in $X_1$ to $X_4$, wherein one of the two adjacent C is joined to L, and the other one of the two adjacent C is joined to R'';

wherein $R_a$, $R_b$, and R' are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof;

wherein R'' is each independently selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof; and wherein in Formula 4, substituents $R_a$ and $R_b$ can be optionally joined to form a ring, and two adjacent substituents R' can be optionally joined to form a ring.

According to another embodiment of the present disclosure, further disclosed is an electroluminescent device, including an anode, a cathode, and an organic layer disposed between the anode and the cathode, wherein the organic layer includes the compound having a structure represented by Formula 1. The specific structure of the compound is shown above.

According to another embodiment of the present disclosure, further disclosed is a compound formulation including the compound having a structure represented by Formula 1. The specific structure of the compound is shown above.

The novel pyrene compounds having an aromatic amine structure disclosed by the present disclosure may be used as light-emitting materials in electroluminescent devices. These novel compounds can provide better device performance, such as higher efficiency, bluer light emission, and a longer lifetime.

DETAILED DESCRIPTION

Figure 1:
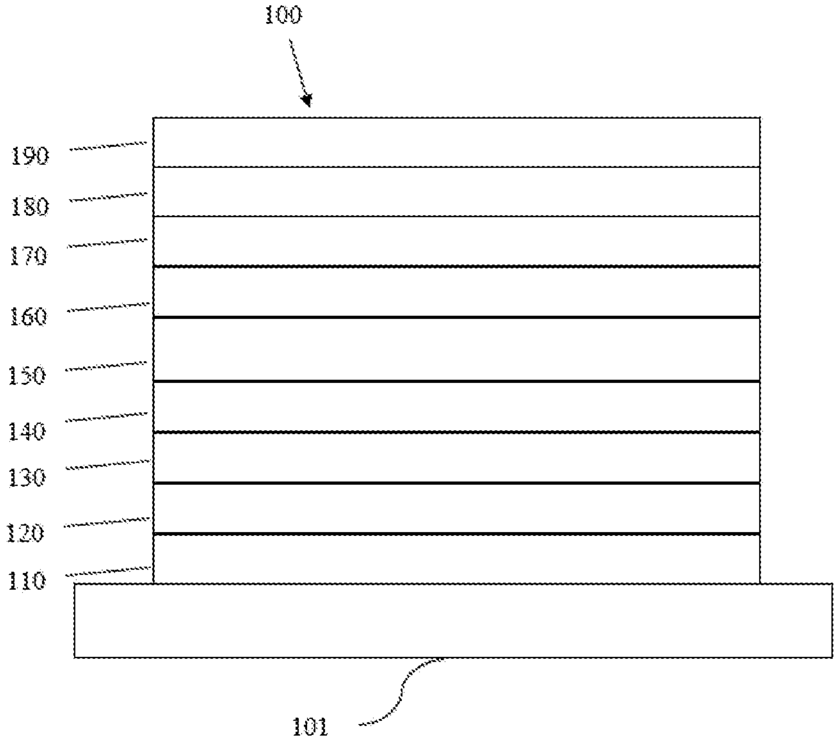
FIG. 1 is a schematic diagram of an organic light-emitting apparatus that may include a compound and a compound formulation disclosed by the present disclosure.

OLEDs can be fabricated on various types of substrates such as glass, plastic, and metal foil. FIG. 1 schematically shows an organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
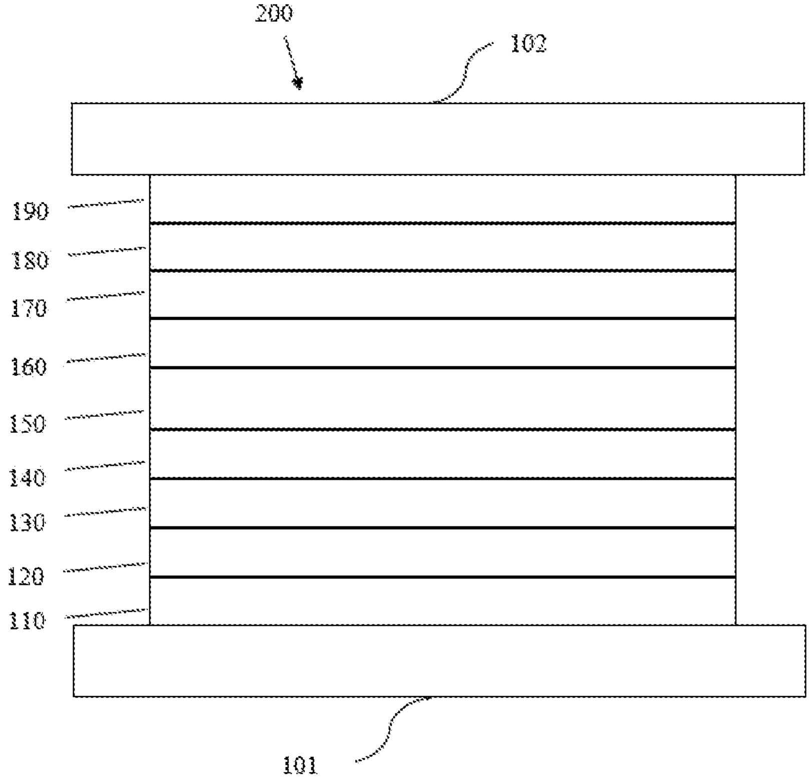
FIG. 2 is a schematic diagram of another organic light-emitting apparatus that may include a compound and a compound formulation disclosed by the present disclosure.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small $\Delta E_{S-T}$. These states may involve CT states. Generally, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, and 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and include cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing 2 to 15 carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing 2 to 15 carbon atoms. Additionally, the alkynyl group may be optionally substituted.

Aryl or aromatic group—as used herein includes noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein includes aromatic and non-aromatic cyclic groups. Heteroaromatic also means heteroaryl. Preferred non-aromatic heterocyclic groups are those containing 3 to 7 ring atoms which include at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein includes noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azafluorene, azaspirobifluorene, azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, substituted arylalkyl, substituted alkoxy, substituted aryloxy, substituted alkenyl, substituted aryl, substituted heteroaryl, substituted alkylsilyl, substituted arylsilyl, substituted amino, substituted acyl, substituted carbonyl, substituted carboxylic acid group, substituted ester group, substituted sulfinyl, substituted sulfonyl and substituted phosphino is used, it means that any group of alkyl, cycloalkyl, heteroalkyl, arylalkyl, alkoxy, aryloxy, alkenyl, aryl, heteroaryl, alkylsilyl, arylsilyl, amino, acyl, carbonyl, carboxylic acid group, ester group, sulfinyl, sulfonyl and phosphino may be substituted with one or more groups selected from the group consisting of deuterium, an unsubstituted alkyl having 1 to 20 carbon atoms, an unsubstituted cycloalkyl having 3 to 20 ring carbon atoms, an unsubstituted heteroalkyl having 1 to 20 carbon atoms, an unsubstituted arylalkyl having 7 to 30 carbon atoms, an unsubstituted alkoxy having 1 to 20 carbon atoms, an unsubstituted aryloxy having 6 to 30 carbon atoms, an unsubstituted alkenyl having 2 to 20 carbon atoms, an unsubstituted aryl having 6 to 30 carbon atoms or preferably, an unsubstituted aryl having 6 to 12 carbon atoms, an unsubstituted heteroaryl having 3 to 30 carbon atoms or preferably, an unsubstituted heteroaryl having 3 to 12 carbon atoms, an unsubstituted alkylsilyl having 3 to 20 carbon atoms, an unsubstituted arylsilyl group having 6 to 20 carbon atoms, an unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or an attached fragment are considered to be equivalent.

In the compounds mentioned in the present disclosure, hydrogen atoms can be partially or fully replaced by deuterium. Other atoms such as carbon and nitrogen can also be replaced by their other stable isotopes. The replacement by other stable isotopes in the compounds may be preferred due to its enhancements of device efficiency and stability. In the compounds mentioned in the present disclosure, a deuterated substituent, such as deuterated methyl, refers to that at least one hydrogen atom in the substituent (methyl) is replaced by deuterium.

In the compounds mentioned in the present disclosure, multi-substitution refers to a range that includes a di-substitution, up to the maximum available substitution. When a substitution in the compounds mentioned in the present disclosure represents multi-substitution (including di-, tri-, and tetra-substitution etc.), that means the substituent may exist at a plurality of available substitution positions on its linking structure, the substituents present at a plurality of available substitution positions may have the same structure or different structures.

In the compounds mentioned in the present disclosure, adjacent substituents in the compounds cannot be joined to form a ring unless otherwise explicitly defined, for example, adjacent substituents can be optionally joined to form a ring. In the compounds mentioned in the present disclosure, that adjacent substituents can be optionally joined to form a ring includes a case where adjacent substituents may be joined to form a ring and a case where adjacent substituents are not joined to form a ring. When adjacent substituents can be optionally joined to form a ring, the ring formed may be monocyclic or polycyclic, as well as alicyclic, heteroalicyclic, aromatic or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that two adjacent substituents can be optionally joined to form a ring is also intended to mean that two substituents bonded to the same carbon atom are joined to each other via a chemical bond to form a ring, which can be exemplified by the following formula:

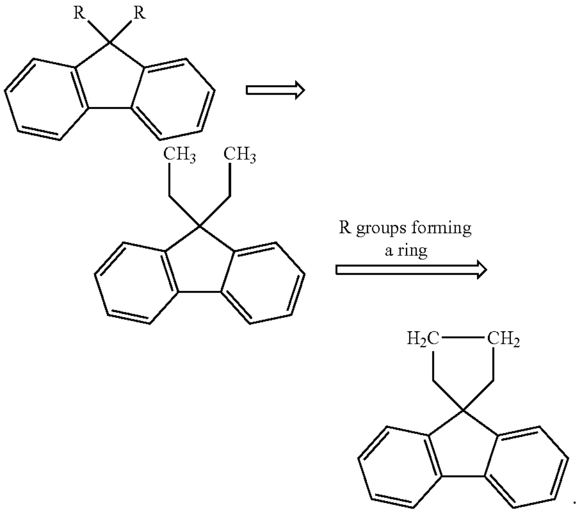

The expression that two adjacent substituents can be optionally joined to form a ring is also intended to mean that two substituents bonded to carbon atoms which are directly bonded to each other are joined to each other via a chemical bond to form a ring, which can be exemplified by the following formula:

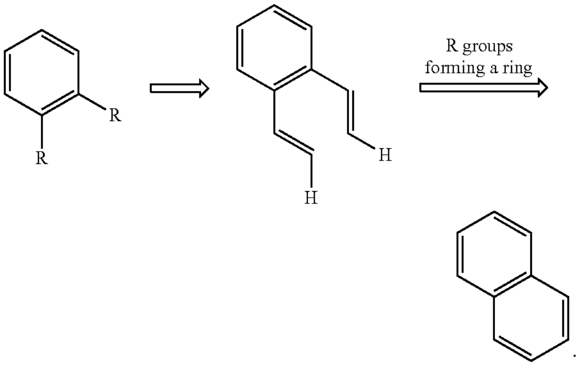

Furthermore, the expression that two adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

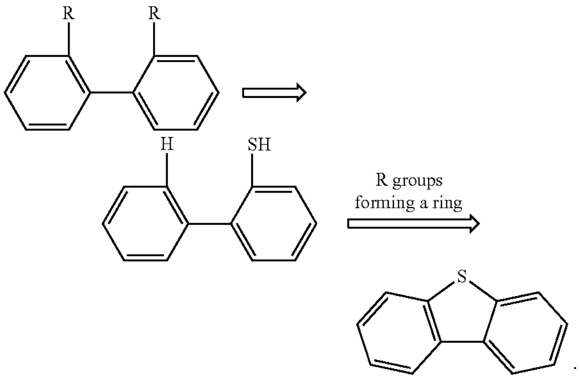

According to an embodiment of the present disclosure, disclosed is a compound having Formula 1:

Formula 1

$(E)_m$—A—$(B)_n$;

in Formula 1,

A is substituted or unsubstituted aryl having 10 to 60 ring carbon atoms or substituted or unsubstituted heteroaryl having 10 to 60 ring atoms;

n is an integer greater than or equal to 1, m is an integer greater than or equal to 0, and n+m is greater than or equal to 2; when n is greater than or equal to 2, B may be the same or different structures; when m is greater than or equal to 2, E may be the same or different structures;

E has a structure represented by Formula 2:

Formula 2

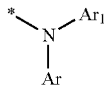

in Formula 2, * represents a position where E is joined to A;

Ar and $Ar_1$ are each independently selected from the group consisting of: substituted or unsubstituted aryl having 6 to 30 ring carbon atoms and substituted or unsubstituted heteroaryl having 3 to 30 ring atoms;

B has a structure represented by Formula 3:

Formula 3

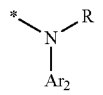

in Formula 3, * represents a position where B is joined to A;

wherein R is selected from the group consisting of: substituted or unsubstituted aryl having 6 to 30 ring carbon atoms and substituted or unsubstituted heteroaryl having 3 to 30 ring atoms; and when R is selected from aryl, R is not substituted or unsubstituted naphthyl;

wherein $Ar_2$ has a structure represented by Formula 4:

Formula 4

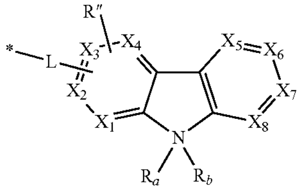

and $Ar_2$ includes only one fluorene ring structure, azafluorene ring structure, spirobifluorene ring structure, or azaspirobifluorene ring structure;

in Formula 4, * represents a position where $Ar_2$ is joined to N shown in Formula 3; X is C or Si;

L is selected from a single bond, substituted or unsubstituted arylene having 6 to 60 carbon atoms, or substituted or unsubstituted heteroarylene having 3 to 60 carbon atoms;

$X_1$ to $X_8$ are each independently selected from C, CR' or N, and two adjacent C (referring to two C directly bonded to each other) are present in $X_1$ to $X_4$ (such as $X_1$ and $X_2$, $X_2$ and $X_3$, or $X_3$ and $X_4$), wherein one of the two adjacent C is joined to L, and the other one of the two adjacent C is joined to R";

wherein $R_a$, $R_b$, and R' are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof;

wherein R" is each independently selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof; and wherein in Formula 4, substituents $R_a$ and $R_b$ can be optionally joined to form a ring, and two adjacent substituents R' can be optionally joined to form a ring.

In this embodiment, in Formula 4, only substituents $R_a$ and $R_b$, and two adjacent substituents R' can be optionally joined to form a ring. Other substituents are not joined to form a ring, for example, adjacent substituents R' and R" are not joined to form a ring. In some cases, only part of two adjacent substituents R may be optionally joined to form a ring. For example, two adjacent R' in only $X_5$ to $X_8$ are optionally joined to form a ring. In another example, two adjacent R' in $X_5$ to $X_4$ are not joined to form a ring. In some cases, none of substituents in Formula 4 may be joined to form a ring.

In this embodiment, when R is selected from the aryl, R is not substituted or unsubstituted naphthyl, which means that the above Formula 3 does not include the following structure:

(a)

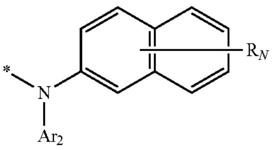

and (b)

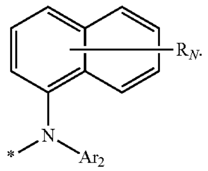

In the structure of a or b, $R_N$ may represent mono-substitution, multi-substitution, or non-substitution. The range of a substituent $R_N$ is not particularly limited. In some cases, the range of $R_N$ may be the same as the range of R defined in this embodiment.

In this embodiment, the expression that $Ar_2$ includes only one fluorene ring structure, azafluorene ring structure, spirobifluorene ring structure, or azaspirobifluorene ring structure refers to that Formula 4 includes only one in terms of the sum of numbers of the four ring structures, i.e., the fluorene ring structure, the azafluorene ring structure, the spirobifluorene ring structure, and the azaspirobifluorene ring structure. The only one structure included is a ring structure containing atoms or groups comprising $X_1$ to $X_8$ and X (X is C). Therefore, it is to be understood that in the above Formula 4, none of L, R' and R" includes a fluorene ring structure, an azafluorene ring structure, a spirobifluorene ring structure, or an azaspirobifluorene ring structure. It is to be noted that even if one or more arbitrary substituents are present in the fluorene ring structure, the azafluorene ring structure, the spirobifluorene ring structure, or the azaspirobifluorene ring structure, such structures will still be counted into the number of the ring structures included in $Ar_2$.

In some embodiments, R in Formula 3 only includes at most one fluorene ring structure, azafluorene ring structure, spirobifluorene ring structure, or azaspirobifluorene ring structure. Even if one or more arbitrary substituents are present in the fluorene ring structure, the azafluorene ring structure, the spirobifluorene ring structure, or the azaspirobifluorene ring structure, such structures will still be counted into the number of the ring structures included in R. In this case, R includes one or less the above ring structure in total.

According to an embodiment of the present disclosure, A in Formula 1 is substituted or unsubstituted aryl having 10 to 40 ring atoms or substituted or unsubstituted heteroaryl having 10 to 40 ring atoms. Further, A in Formula 1 is substituted or unsubstituted aryl having 10 to 30 ring atoms or substituted or unsubstituted heteroaryl having 10 to 30 ring atoms. Further, A in Formula 1 is substituted or unsubstituted aryl having 10 to 20 ring atoms or substituted or unsubstituted heteroaryl having 10 to 20 ring atoms.

According to an embodiment of the present disclosure, in Formula 1, n is 1, and m is 1; or n is greater than or equal to 2, and m is 0.

According to an embodiment of the present disclosure, A in Formula 1 is selected from a structure represented by any one of Formula I to Formula IX:

Formula I

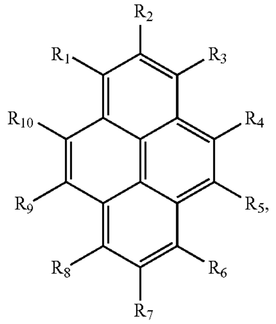

Formula II

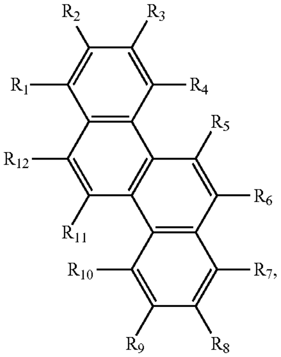

Formula III

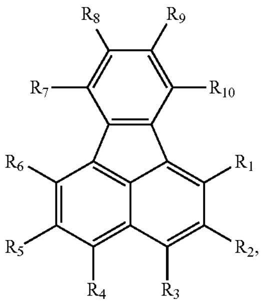

-continued

Formula IV

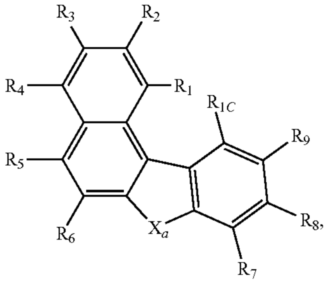

Formula V

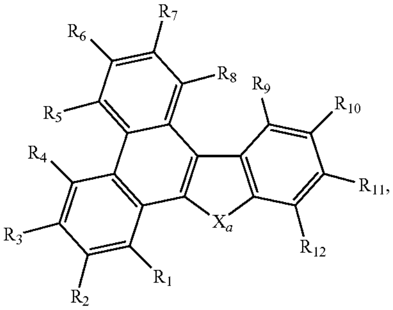

Formula VI

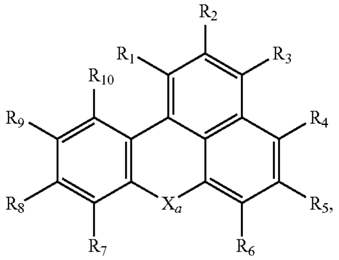

Formula VII

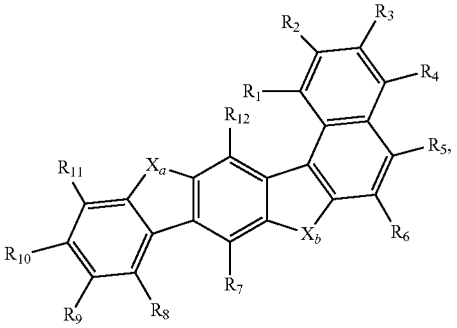

Formula VIII

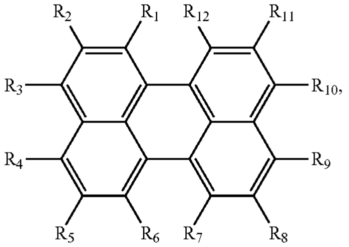

-continued

Formula IX

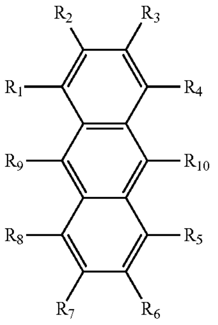

in Formula I to Formula IX, n of $R_1$ to $R_i$ have the structure of B represented by Formula 3, and m of $R_1$ to $R_i$ have the structure of E represented by Formula 2;

n is 1, 2, 3, or 4, m is 0, 1, 2, 3, or 4, and n+m is greater than or equal to 2;

$R_i$ represents the R with the largest number in any one of Formula I to Formula IX;

the rest of $R_1$ to $R_i$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

$X_a$ and $X_b$ are each independently selected from the group consisting of: $CR_xR_y$, $SiR_xR_y$, $NR_x$, O, S, and Se;

$R_x$ and $R_y$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof; and substituents $R_x$ and $R_y$ can be optionally joined to form a ring.

In this embodiment, taking Formula I as an example, $R_i$ represents the R with the largest number in Formula I (i.e., $R_{10}$), n of $R_1$ to $R_{10}$ have the structure of B represented by Formula 3, and m of $R_1$ to $R_{10}$ have the structure of E represented by Formula 2. In another example, in Formula I, $R_1$ has the structure of B represented by Formula 3, $R_6$ has the structure of E represented by Formula 2, the rest of $R_1$ to $R_{10}$ are each independently selected from the group defined above, which means that $R_2$ to $R_5$ and $R_7$ to $R_{10}$ are each independently selected from the group defined above. This is also suitable for Formula II to Formula IX.

According to an embodiment of the present disclosure, for Formula I, $R_2$, $R_4$-$R_5$, $R_7$, and $R_9$-$R_{10}$ are each a hydrogen atom, and substituent $R_3$ and $R_8$ are each independently selected from hydrogen, substituted or unsubstituted alkyl having 1 to 20 carbon atoms, or substituted or unsubstituted cycloalkyl having 3 to 20 ring carbon atoms.

According to an embodiment of the present disclosure, for Formula II, $R_1$-$R_2$, $R_4$-$R_5$, $R_7$-$R_8$, and $R_{10}$-$R_{11}$ are each a hydrogen atom, and substituent $R_3$ and $R_9$ are each independently selected from hydrogen, substituted or unsubstituted alkyl having 1 to 20 carbon atoms, or substituted or unsubstituted cycloalkyl having 3 to 20 ring carbon atoms.

According to an embodiment of the present disclosure, in Formula I to Formula IX, two of $R_1$ to $R_i$ have the structure of B represented by Formula 3, and none of $R_1$ to $R_i$ has the structure of E represented by Formula 2, wherein $R_i$ represents the R with the largest number in any one of Formula I to Formula IX.

According to an embodiment of the present disclosure, the compound has a structure represented by one of Formula 5 to Formula 13:

Formula 5

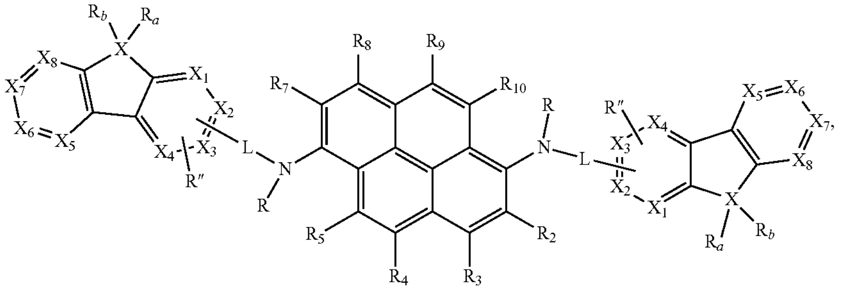

-continued
Formula 6
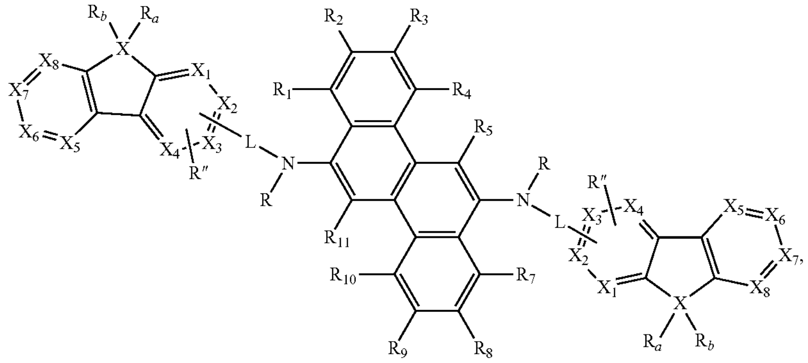
Formula 7
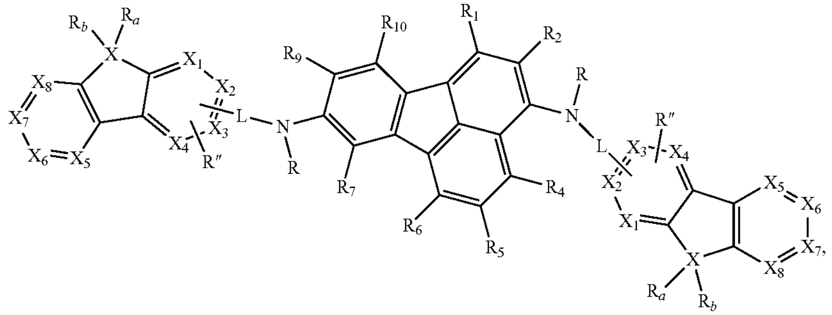
Formula 8
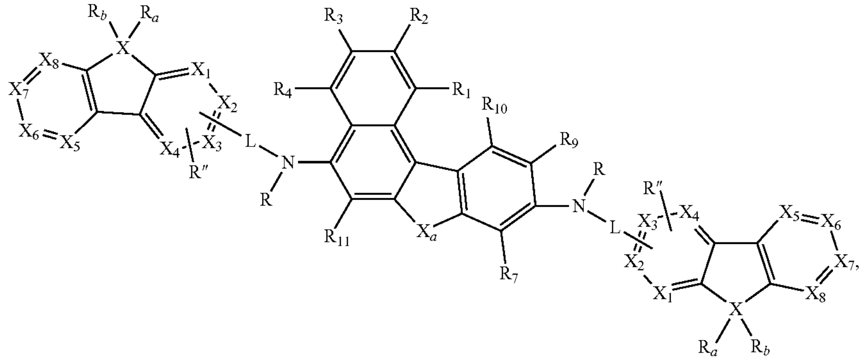
Formula 9
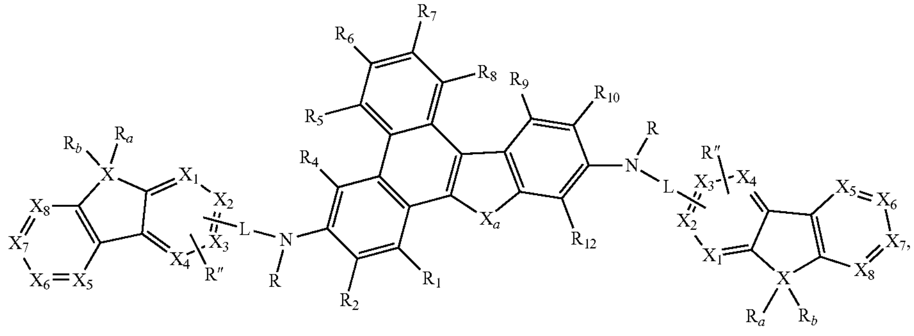

-continued

Formula 10

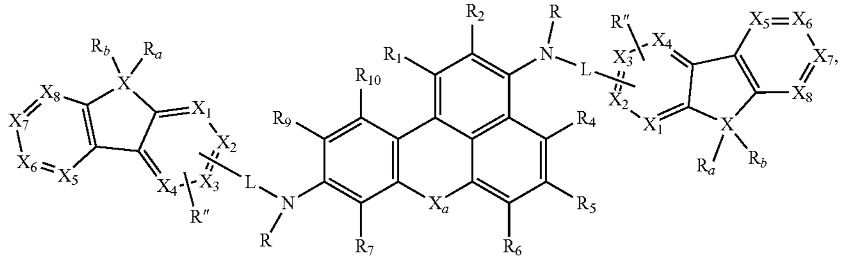

Formula 11

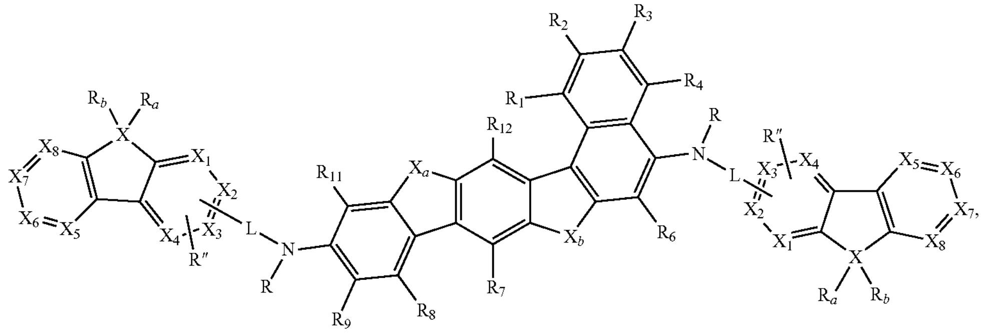

Formula 12

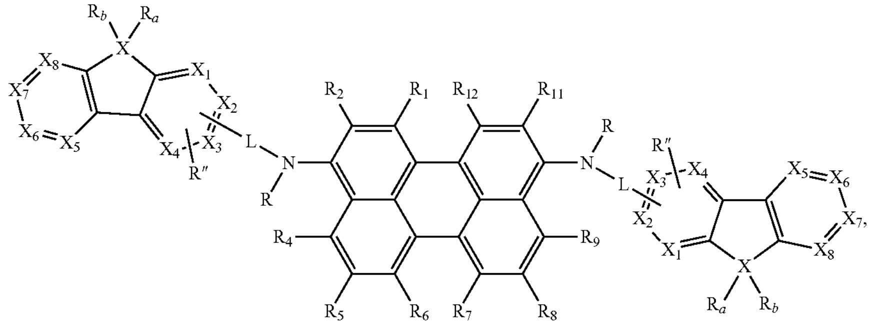

Formula 13

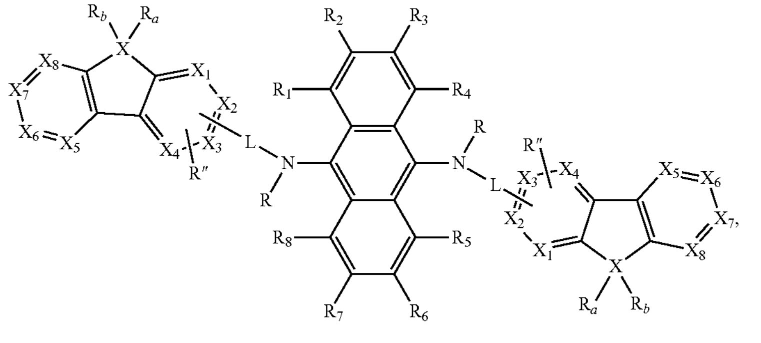

in Formula 5 to Formula 13, $R_1$ to $R_{12}$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

$X_a$ and $X_b$ are each independently selected from the group consisting of: $CR_xR_y$, $SiR_xR_y$, $NR_x$, O, S, and Se;

$R_x$ and $R_y$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof;

substituents $R_x$ and $R_y$ can be optionally joined to form a ring; and

R, $R_a$, $R_b$, R", L, X, and $X_1$ to $X_8$ have same ranges as defined in Formula 3 and Formula 4 in the embodiments described above.

According to an embodiment of the present disclosure, for Formula 5, $R_2$, $R_4$-$R_5$, $R_7$, and $R_9$-$R_{10}$ are each a hydrogen atom, and substituent $R_3$ and $R_8$ are each independently selected from hydrogen, substituted or unsubstituted alkyl having 1 to 20 carbon atoms, or substituted or unsubstituted cycloalkyl having 3 to 20 ring carbon atoms.

According to an embodiment of the present disclosure, in Formula 5 to Formula 13, each L is joined to $X_2$.

According to an embodiment of the present disclosure, in Formula 5 to Formula 13, each L is joined to $X_3$.

According to an embodiment of the present disclosure, L in Formula 4 is selected from a single bond, substituted or unsubstituted arylene having 6 to 30 carbon atoms, or substituted or unsubstituted heteroarylene having 3 to 30 carbon atoms; further, L in Formula 4 is selected from a single bond, substituted or unsubstituted arylene having 6 to 20 carbon atoms, or substituted or unsubstituted heteroarylene having 3 to 20 carbon atoms; further, L in Formula 4 is selected from a single bond, substituted or unsubstituted arylene having 6 to 12 carbon atoms, or substituted or unsubstituted heteroarylene having 3 to 12 carbon atoms; further, L is selected from a single bond, substituted or unsubstituted phenylene, substituted or unsubstituted biphenylene, or substituted or unsubstituted naphthylene.

According to an embodiment of the present disclosure, $X_1$ to $X_8$ are each independently selected from C or CR', wherein R' is each independently selected from the group consisting of: hydrogen, deuterium, halogen, substituted or unsubstituted alkyl having 1 to 6 carbon atoms, substituted or unsubstituted cycloalkyl having 3 to 10 ring carbon atoms, substituted or unsubstituted aryl having 6 to 12 carbon atoms, substituted or unsubstituted heteroaryl having 3 to 12 carbon atoms, a nitrile group, and combinations thereof.

According to an embodiment of the present disclosure, $X_1$ to $X_8$ are each independently selected from C or CR', wherein R' is each independently selected from hydrogen, deuterium, fluorine, methyl, ethyl, n-propyl, isopropyl, n-butyl, isobutyl, t-butyl, cyclohexyl, phenyl, or cyano.

According to an embodiment of the present disclosure, R" is selected from halogen, substituted or unsubstituted alkyl having 1 to 20 carbon atoms, or substituted or unsubstituted cycloalkyl having 3 to 20 ring carbon atoms.

According to an embodiment of the present disclosure, R" is selected from fluorine, methyl, ethyl, n-propyl, isopropyl, cyclopropyl, n-butyl, isobutyl, t-butyl, cyclopentyl, neopentyl, cyclohexyl, 4,4-dimethylcyclohexyl, deuterated methyl, deuterated ethyl, deuterated n-propyl, deuterated isopropyl, deuterated cyclopropyl, deuterated n-butyl, deuterated isobutyl, deuterated t-butyl, deuterated cyclopentyl, deuterated neopentyl, deuterated cyclohexyl, or deuterated 4,4-dimethylcyclohexyl.

According to an embodiment of the present disclosure, $R_a$ and $R_b$ are each independently selected from substituted or unsubstituted alkyl having 1 to 6 carbon atoms or substituted or unsubstituted cycloalkyl having 3 to 10 ring carbon atoms, and $R_a$ and $R_b$ are not joined to form a ring.

According to an embodiment of the present disclosure, $R_a$ and $R_b$ are each methyl, ethyl, n-propyl, isopropyl, n-butyl, isobutyl, or t-butyl, and $R_a$ and $R_b$ are not joined to form a ring.

According to an embodiment of the present disclosure, R in Formula 3 has a structure represented by Formula 17:

Formula 17

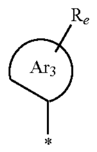

in Formula 17, * represents a position wherein R is joined to N shown in Formula 3;

wherein the ring $Ar_3$ is aryl having 6 to 30 ring carbon atoms or heteroaryl having 3 to 30 ring atoms; and when the ring $Ar_3$ is aryl, the ring $Ar_3$ is not a naphthalene ring;

wherein $R_e$ represents mono-substitution, multi-substitution, or non-substitution; and $R_e$ is selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof.

According to an embodiment of the present disclosure, the substituent $R_e$ in Formula 17 is selected from the group consisting of: halogen, substituted or unsubstituted alkyl having 1 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof.

According to an embodiment of the present disclosure, the substituent $R_e$ in Formula 17 is selected from the group consisting of: fluorine, nitrile, isonitrile, substituted or unsubstituted alkyl having 1 to 6 carbon atoms, and substituted or unsubstituted aryl having 6 to 12 carbon atoms.

According to an embodiment of the present disclosure, R in Formula 3 has a structure represented by Formula 14:

Formula 14

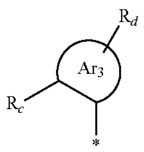

wherein * represents a position wherein R is joined to N in Formula 3;

wherein the ring $Ar_3$ is aryl having 6 to 30 ring carbon atoms or heteroaryl having 3 to 30 ring atoms; and when the ring $Ar_3$ is aryl, the ring $Ar_3$ is not a naphthalene ring structure;

$R_c$ represents ortho-substitution of the position wherein R is joined to N in Formula 3, and $R_d$ represents mono-substitution, multi-substitution, or non-substitution;

wherein $R_c$ is selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof;

wherein $R_d$ is each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof.

In this embodiment, the ring $Ar_3$ in Formula 14 refers to a ring structure composed of only ring atoms (which may be all ring carbon atoms or may also include ring heteroatoms). All substituents that have to be present and might be present on the ring $Ar_3$ are particularly represented by $R_c$ and $R_d$ in Formula 14. When the ring $Ar_3$ is aryl having 6 to 30 ring carbon atoms or heteroaryl having 3 to 30 ring atoms, it means that the ring $Ar_3$ is an aryl ring structure comprising 6 to 30 ring carbon atoms or a heteroaryl ring structure comprising 3 to 30 ring atoms. Therefore, that the ring $Ar_3$ is not a naphthalene ring includes that the ring $Ar_3$ is not an unsubstituted or optionally substituted naphthalene ring structure. Formula 14 does not include the following structures:

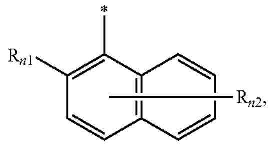

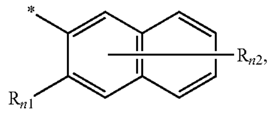

and

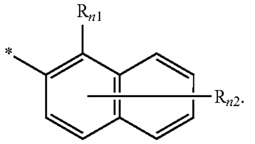

In the three structures, $R_{n2}$ may represent mono-substitution, multi-substitution, or non-substitution. Ranges of substituents $R_{n1}$ and $R_{n2}$ are not particularly limited. For example, a range of $R_{n1}$ may be the same as a range of $R_c$ defined in this embodiment, and a range of $R_{n2}$ may be the same as a range of $R_d$ defined in this embodiment.

According to an embodiment of the present disclosure, the ring $Ar_3$ is selected from any one of the following ring structures: a benzene ring, a triphenylene ring, a tetraphenylene ring, a phenanthrene ring, an anthracene ring, an indene ring, a fluorene ring, a chrysene ring, an indole ring, a carbazole ring, a benzofuran ring, a dibenzofuran ring, a benzosilole ring, a dibenzosilole ring, a benzothiophene ring, a dibenzothiophene ring, a dibenzoselenophene ring, or aza-structures of any one of the above ring structures. In this embodiment, for example, when the ring $Ar_3$ is selected from a benzene ring, the structure of Formula 14 is accordingly

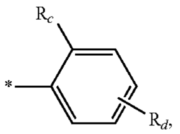

wherein $R_c$ and $R_d$ are defined as in Formula 14. When the ring $Ar_3$ is selected from other ring structures, the cases are similar to the example of the benzene ring. When the ring $Ar_3$ is selected from an azabenzene ring, it refers to that one or more C—H groups in the benzene ring are replaced by a nitrogen atom. Accordingly, the structure of Formula 14 is

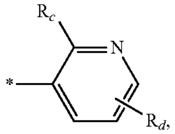

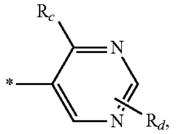

or other structures. When the ring $Ar_3$ is selected from other aza-ring structures, the cases are similar to the example of the benzene ring.

According to an embodiment of the present disclosure, $R_d$ represents non-substitution, or $R_d$ represents mono-substitution and $R_d$ is selected from the group consisting of: substituted or unsubstituted aryl having 6 to 12 carbon atoms and substituted or unsubstituted heteroaryl having 3 to 12 carbon atoms; preferably, $R_d$ is selected from phenyl, biphenyl, or terphenyl.

According to an embodiment of the present disclosure, $R_c$ is selected from methyl, deuterated methyl, ethyl, deuterated ethyl, n-propyl, deuterated n-propyl, isopropyl, deuterated isopropyl, cyclopropyl, deuterated cyclopropyl, n-butyl, deuterated n-butyl, isobutyl, deuterated isobutyl, t-butyl, deuterated t-butyl, cyclopentyl, deuterated cyclopentyl, neopentyl, deuterated neopentyl, cyclohexyl, deuterated cyclohexyl, 4,4-dimethylcyclohexyl, or deuterated 4,4-dimethylcyclohexyl.

According to an embodiment of the present disclosure, B is selected from B-1-1 to B-1-72, B-2-1 to B-2-218, B-3-1 to B-3-235, B-4-1 to B-4-72, B-5-1 to B-5-72, or B-6-1 to B-6-18 whose specific structures are as shown in claim 15.

According to an embodiment of the present disclosure, the compound is selected from $$A(-B)_n$$

compounds 1 to 2398 which have a structure represented by Formula 15: Formula 15, wherein n in the structure represented by Formula 15 equals 2, two B are the same, and A has a structure selected from $A_1$ to $A_{10}$:

$A_1$

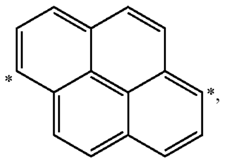

$A_2$

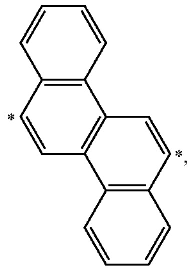

-continued $A_3$

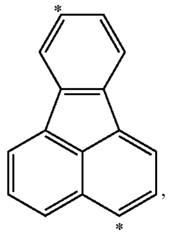

$A_4$

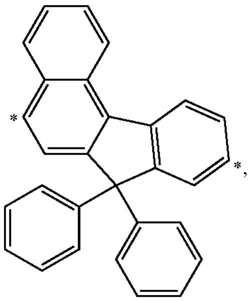

$A_5$

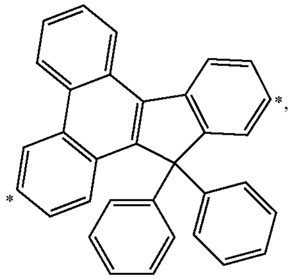

$A_6$

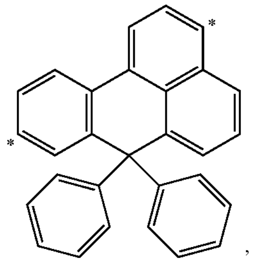

$A_7$

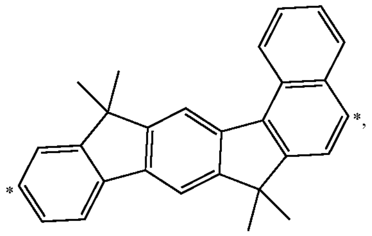

$A_8$

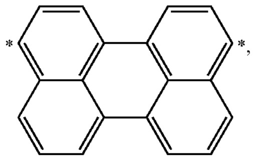

-continued

A9

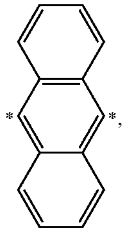

A10

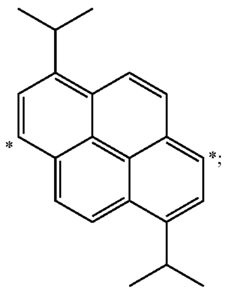

wherein in the structures of $A_1$ to $A_{10}$, * represents a position wherein the group B is joined;

the structure of B is selected from B-1-1 to B-1-72, B-2-1 to B-2-218, B-3-1 to B-3-235, B-4-1 to B-4-72, B-5-1 to B-5-72, or B-6-1 to B-6-18 whose specific structures are as shown in claim 15. The compound is selected from the compounds 1 to 2398 whose specific structures are as shown in claim 16.

According to an embodiment of the present disclosure, hydrogen in the compounds 1 to 2398 may be partially or fully deuterated.

According to an embodiment of the present disclosure, the compound has a molecular weight which is less than 2500, further has a molecular weight which is less than 2000, and more further has a molecular weight which is less than 1500. Such small molecular compounds are more applicable to vacuum evaporation.

According to an embodiment of the present disclosure, further disclosed is an electroluminescent device, including:

an anode, a cathode, and an organic layer disposed between the anode and the cathode, wherein the organic layer includes the compound represented by Formula 1;

wherein the compound represented by Formula 1 has specific structures as shown in any one of the embodiments described above.

According to an embodiment of the present disclosure, the organic layer is a light-emitting layer, and the compound is a light-emitting material.

According to an embodiment of the present disclosure, the light-emitting layer further includes a compound represented by Formula 16:

Formula 16

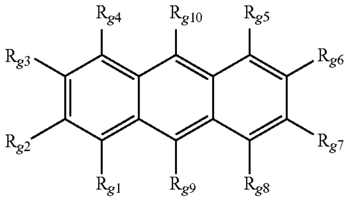

wherein $R_{g1}$ to $R_{g8}$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof; and wherein $R_{g9}$ to $R_{g10}$ are each independently selected from substituted or unsubstituted aryl having 6 to 30 carbon atoms or substituted or unsubstituted heteroaryl having 3 to 30 carbon atoms.

According to another embodiment of the present disclosure, further disclosed is a compound formulation which includes the compound represented by Formula 1. The compound has specific structures as shown in any one of the embodiments described above.

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, dopants disclosed herein may be used in combination with a wide variety of hosts, transport layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

MATERIAL SYNTHESIS EXAMPLE

A method for preparing a compound in the present disclosure is not limited herein. Typically, the following compounds are taken as examples without limitations, and synthesis routes and preparation methods thereof are described below.

Synthesis Example 1: Synthesis of Compound 339

Step 1:

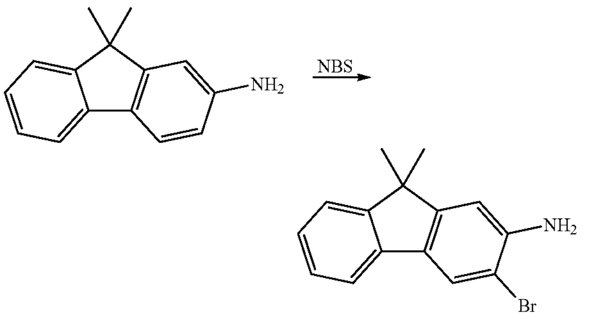

9,9-Dimethyl-9H-fluoren-2-amine (200 g, 0.96 mol) was dissolved in 2 L of dimethyl formamide (DMF) and cooled to 0° C., and then N-bromosuccinimide (190 g, 1.06 mol) was added portion-wise into the reaction solution, slowly warmed to room temperature, and stirred overnight. After the reaction was finished, most of dimethyl formamide was removed through rotary evaporation, and a large amount of water was added. The solution was extracted with dichloromethane (DCM), and then the organic phases were concentrated through rotary evaporation to be nearly saturated. The solution was filtered with silica gel powder and washed with PE, and the filtrate was concentrated through rotary evaporation and crystallized from PE to obtain the product, 3-bromo-9,9-dimethyl-9H-fluoren-2-amine (259 g with a yield of 94%).

Step 2:

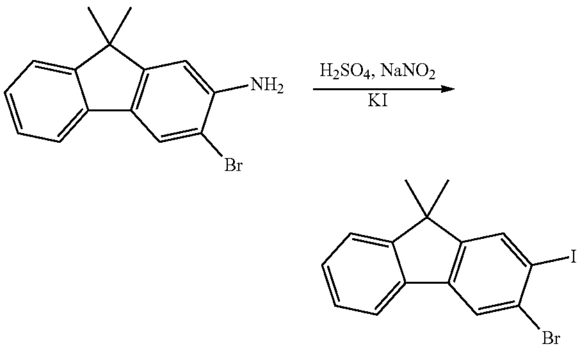

3-Bromo-9,9-dimethyl-9H-fluoren-2-amine (259 g) was dissolved in 1.5 L of 10% concentrated sulfuric acid solution, stirred at room temperature for 1 h, and then cooled to 0° C. $NaNO_2$ (73 g, 1.06 mol) solids were added portion-wise. After the reaction mixture was stirred at low temperature for 1 h, KI (634 g, 3.82 mol) was slowly added portion-wise. After the reaction mixture was stirred overnight at room temperature, a saturated solution of sodium thiosulfate was added and stirred for 10 min. The solution was extracted three times with DCM. Then the organic phases were subjected to rotary evaporation to dryness, and purified through column chromatography (with PE as an eluent) to obtain the product, 3-bromo-2-iodo-9,9-dimethyl-9H-fluorene (240 g with a yield of 67%).

Step 3:

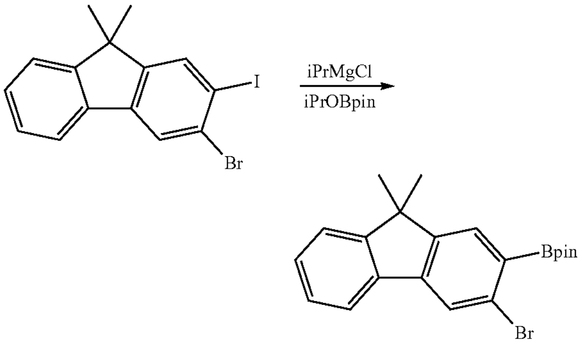

Under nitrogen protection, 3-bromo-2-iodo-9,9-dimethyl-9H-fluorene (240 g, 0.6 mol) was dissolved in 1 L of anhydrous tetrahydrofuran and cooled to −78° C. Isopropylmagnesium chloride (1.3M, 0.66 mol) was slowly added and reacted at low temperature for 1 h. iPrOBpin (148.8 g, 0.8 mol) was added, slowly warmed to room temperature, and reacted overnight. After the reaction was finished, water was added to quench the reaction. The aqueous phase was extracted three times with DCM. The organic phases were combined and filtered through Celite. After silica gel powder was added, samples were dry-mixed and subjected to column chromatography to obtain the product, (3-bromo-9,9-dimethyl-9H-fluoren-2-yl)-4,4,5,5-tetramethyl-1,3,2-dioxaborolane (100 g with a yield of 42%).

Step 4:

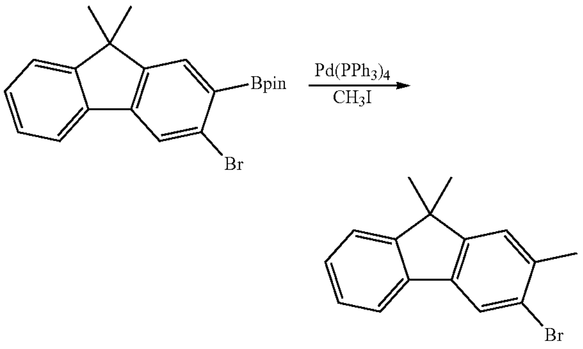

Under nitrogen protection, (3-bromo-9,9-dimethyl-9H-fluoren-2-yl)-4,4,5,5-tetramethyl-1,3,2-dioxaborolane (100 g, 250 mmol) was dissolved in 1 L of toluene/ethanol/water (at a volume ratio of 5:2:2), tetra(triphenylphosphine)palladium (5.5 g, 5 mmol), iodomethane (1.6 g, 750 mmol), and potassium carbonate (69 g, 500 mmol) were added, and the reaction was heated to 100° C. and stirred for 4 h. After the reaction was cooled to room temperature, layers were separated, the aqueous phase was extracted three times with DCM, and the organic phases were combined. After silica gel powder was added, samples were dry-loaded and separated through column chromatography using PE. The obtained crude product was crystallized from PE to finally obtain 3-bromo-2,9,9-trimethyl-9H-fluorene (66.87 g with a yield of 93.2%).

Step 5:

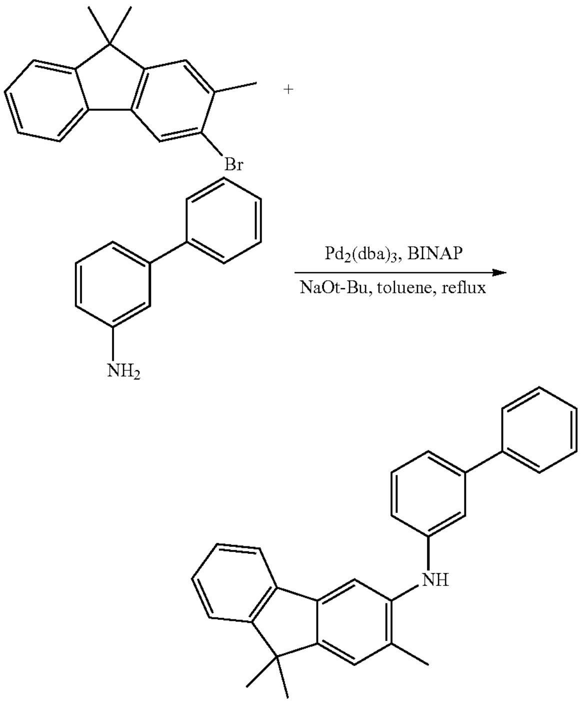

$Pd_2(dba)_3$ (2.05 g, 2.24 mmol) and BINAP (2.98 g, 4.48 mmol) were put into a 500 mL three-neck flask, and toluene (200 mL) was added. The solution was purged with $N_2$ for 20 min until the color no longer changed, and 3-bromo-2,9,9-trimethyl-9H-fluorene (12.6 g, 44 mmol), [1,1'-biphenyl]-3-amine (11.1 g, 66 mmol), and sodium tert-butoxide (12.86 g, 134 mmol) were sequentially added. $N_2$ was continued to be introduced for 10 min and the system was heated to 110° C. until 3-bromo-2,9,9-trimethyl-9H-fluorene was reacted completely. The reaction solution was filtered with basic alumina and $MgSO_4$, washed with toluene, solvents were removed through rotary evaporation and the resultant was subjected to column chromatography (PE: toluene=10:1 to 5:1) to obtain the product N-([1,1'-biphenyl]-3-yl)-2,9,9-trimethyl-9H-fluoren-3-amine (13.1 g with a yield of 79%).

Step 6:

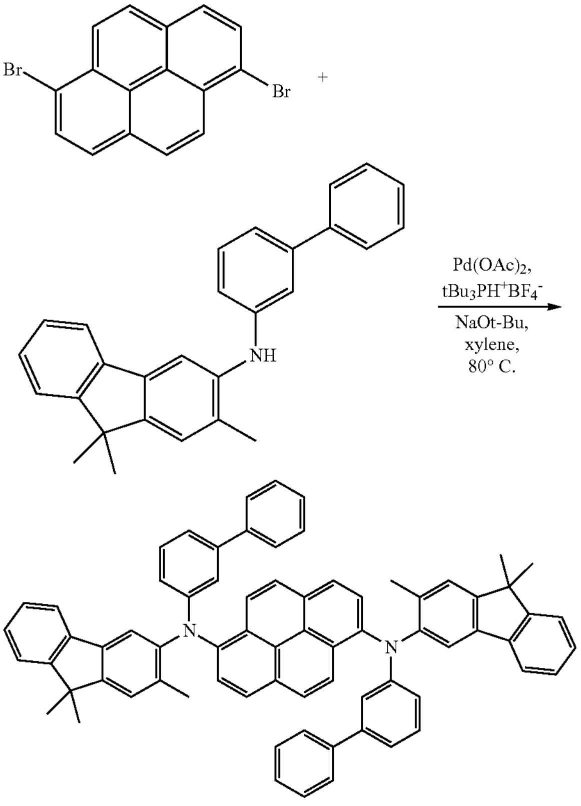

Compound 339

$Pd(OAc)_2$ (60 mg, 0.25 mmol) and $t\text{-}Bu_3PH{\cdot}BF_4$ (145 mg, 0.5 mmol) were put into a 100 mL three-neck flask, and xylene (50 mL) was added. The solution was purged with $N_2$ for 20 min until the color no longer changed, and 1,6-dibromopyrene (1.8 g, 5 mmol), N-([1,1'-biphenyl]-3-yl)-2,9,9-trimethyl-9H-fluoren-3-amine (5.625 g, 15 mmol), and sodium tert-butoxide (2.0 g, 20 mmol) were sequentially added. $N_2$ was continued to be introduced for 10 min and the system was heated to 80° C. until the raw materials were reacted completely.

After the reaction was finished, the reaction solution was purified through column chromatography to obtain the product, compound 339 (1 g with a yield of 21%). The product was confirmed as the target product with a molecular weight of 948.4.

Synthesis Example 2: Synthesis of Compound 347

Step 1:

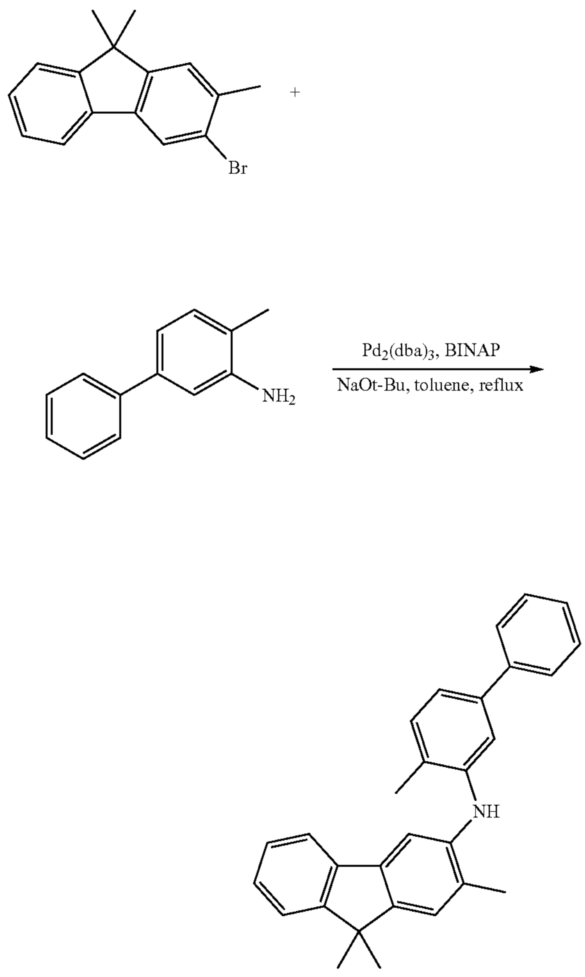

$Pd_2(dba)_3$ (2.05 g, 2.24 mmol) and BINAP (2.98 g, 4.48 mmol) were put into a 500 mL three-neck flask, and toluene (200 mL) was added. The solution was purged with $N_2$ for 20 min until the color no longer changed, and 3-bromo-2, 9,9-trimethyl-9H-fluorene (12.6 g, 44 mmol), 4-methyl-[1, 1'-biphenyl]-3-amine (11.5 g, 66 mmol), and sodium tert-butoxide (12.86 g, 134 mmol) were sequentially added. $N_2$ was continued to be introduced for 10 min and the system was heated to 110° C. until 3-bromo-2,9,9-trimethyl-9H-fluorene was reacted completely. Column chromatography (PE:toluene=10:1 to 5:1) was performed to obtain the product, 2,9,9-trimethyl-N-(4-methyl-[1,1'-biphenyl]-3-yl)-9H-fluoren-3-amine (15 g with a yield of 88%).

Step 2:

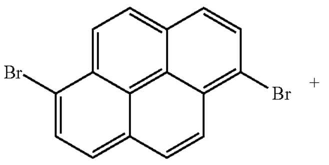

-continued

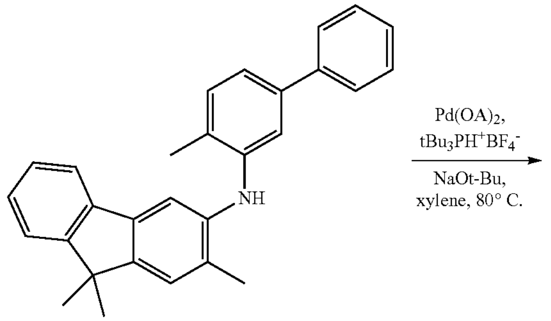

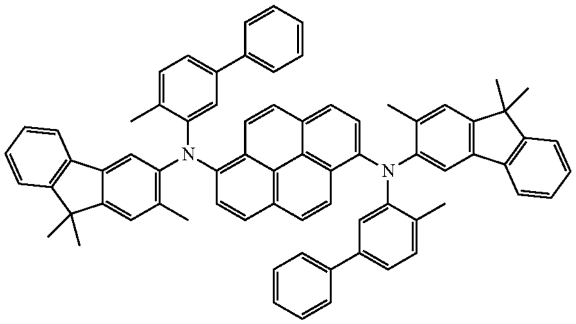

Compound 347

$Pd(OAc)_2$ (60 mg, 0.25 mmol) and t-$Bu_3PH{\cdot}BF_4$ (145 mg, 0.5 mmol) were put into a 100 mL three-neck flask, and xylene (50 mL) was added. The solution was purged with $N_2$ for 20 min until the color no longer changed, and 1,6-dibromopyrene (1.8 g, 5 mmol), 2,9,9-trimethyl-N-(4-methyl-[1,1'-biphenyl]-3-yl)-9H-fluoren-3-amine (5.835 g, 15 mmol), and sodium tert-butoxide (2.0 g, 20 mmol) were sequentially added. $N_2$ was continued to be introduced for 10 min and the system was heated to 80° C. until the raw materials were reacted completely. After the reaction was finished, the reaction solution was separated through column chromatography to obtain the product, compound 347 (1.9 g with a yield of 38.9%). The product was confirmed as the target product with a molecular weight of 976.5.

Synthesis Example 3: Synthesis of Compound 73

Step 1:

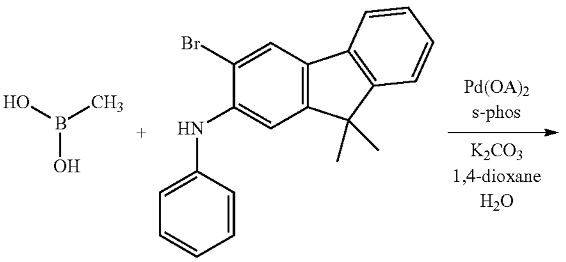

-continued

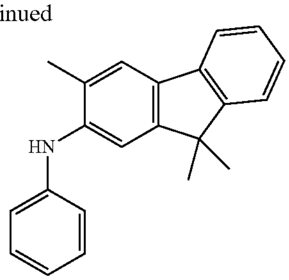

$Pd(OAc)_2$ (462 mg, 2.06 mmol), S-phos (1.69 g, 4.12 mmol), methylboronic acid (4.93 g, 82.34 mmol), 3-bromo-9,9-dimethyl-N-phenyl-9H-fluoren-2-amine (15 g, 41.17 mmol), and potassium carbonate (11.38 g, 82.34 mmol) were put into a 500 mL two-neck flask, and 1,4-dioxane (150 mL) and water (50 mL) were added. The solution was purged with $N_2$ for 10 min, and then under nitrogen protection, the reaction system was heated to 100° C. until the raw materials were reacted completely. After the reaction was finished, the reaction was cooled to room temperature. Most of the solvents were removed through rotary evaporation under reduced pressure, and the resultant was extracted with dichloromethane and washed twice with water. The organic phases were combined, dried with anhydrous sodium sulfate, subjected to column chromatography (toluene:PE=1:10 to 1:5) and recrystallized to obtain a compound 3,9,9-trimethyl-N-phenyl-9H-fluoren-2-amine (8.5 g with a yield of 69%).

Step 2:

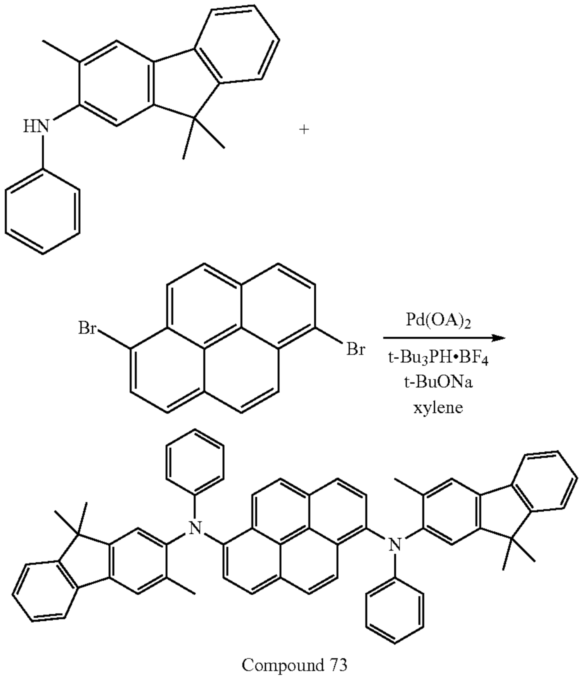

Compound 73

$Pd(OAc)_2$ (37 mg, 0.17 mmol) and $t\text{-}Bu_3PH{\cdot}BF_4$ (97 mg, 0.33 mmol) were put into a 250 mL two-neck flask, and xylene (70 mL) was added. The solution was purged with $N_2$ for 10 min until the color no longer changed, and 1,6-dibromopyrene (2 g, 5.55 mmol), the compound 3,9,9-trimethyl-N-phenyl-9H-fluoren-2-amine (3.66 g, 12.21 mmol), and sodium tert-butoxide (2.67 g, 27.75 mmol) were sequentially added. $N_2$ was continued to be introduced for 10 min and the system was heated to 90° C. until the raw materials were reacted completely. After the reaction was finished, column chromatography was performed to obtain the product, compound 73 (2.7 g with a yield of 61%). The product was confirmed as the target product with a molecular weight of 796.4.

Synthesis Example 4: Synthesis of Compound 743

Step 1:

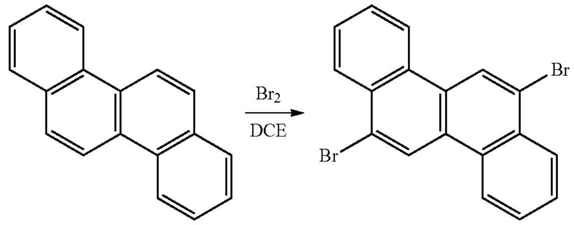

Under nitrogen protection and at room temperature, chrysene (8.2 g, 35.92 mmol) was added into 1,2-dichloroethane (DCE, 400 mL) and stirred for 10 min (not fully dissolved), and then bromine (12.6 g, 79.02 mmol in 50 mL of DCE) was added dropwise. After the dropwise addition, the reaction solution was heated to 85° C. for 16 h. The reaction was monitored by TLC. After the reaction was finished, the reaction solution was concentrated. Methanol was added, and solids were precipitated. The solids were filtered and collected, and recrystallized twice from toluene. The solids were refluxed in THF overnight, filtered, and collected to obtain 6,12-dibromochrysene (7 g, 50%) as a white solid.

Step 2:

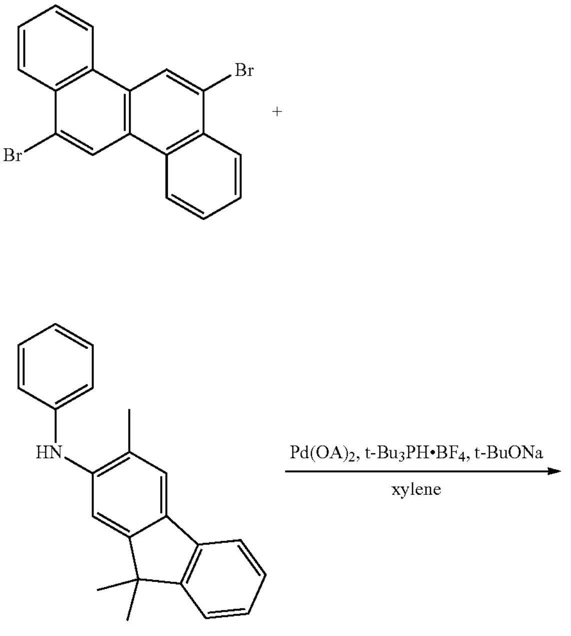

-continued

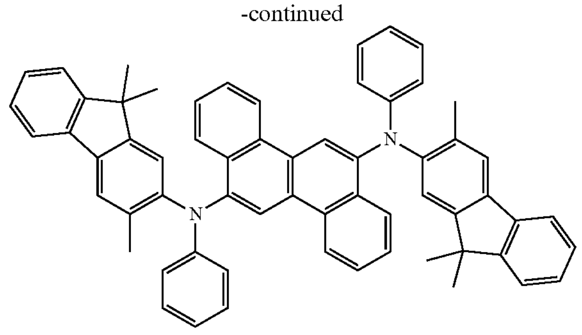

Compound 743

Under nitrogen protection and at room temperature, cyclic $Pd(OAc)_2$ (35.0 mg, 0.16 mmol) was added into xylene (100 mL) and stirred for 10 min, and then t-$Bu_3PH{\cdot}BF_4$ (90.0 mg, 0.31 mmol) was added and stirred for 20 min. 6,12-Dibromochrysene (2.0 g, 5.18 mmol) was added into the reaction system and stirred for 5 min. Then 3,9,9-trimethyl-N-phenyl-9H-fluoren-2-amine (3.9 g, 12.95 mmol) was added into the reaction solution and stirred for 5 min. Then sodium tert-butoxide (2.0 g, 20.72 mmol) was added, and the reaction solution was heated to 95° C. for 3 h. The reaction was monitored by TLC. After the reaction was finished, column chromatography was performed to obtain the product, compound 743 (2.6 g with a yield of 63%). The product was confirmed as the target product with a molecular weight of 822.4.

Synthesis Example 5: Synthesis of Compound 466

Step 1:

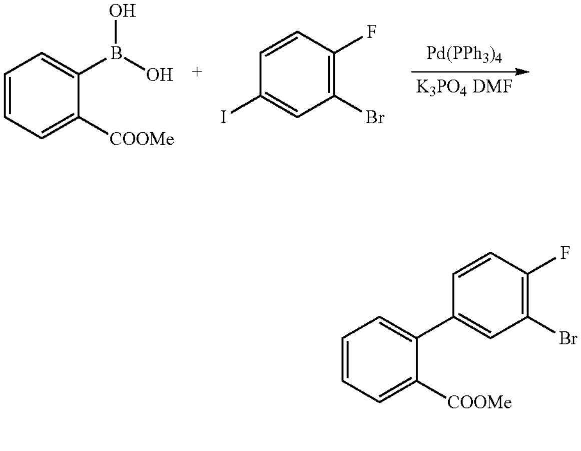

Under nitrogen protection, (2-(methoxycarbonyl)phenyl) boronic acid (59.4 g, 330 mmol), 2-bromo-1-fluoro-4-iodobenzene (90 g, 300 mmol), tetra(triphenylphosphine)palladium (5 g, 4 mmol), potassium phosphate (127 g, 600 mmol), and DMF (1 L) were sequentially added. The reaction was heated to 100° C. and reacted overnight. The organic phases were removed through rotary evaporation, and the crude product was dissolved in DCM and separated through column chromatography to obtain the product, methyl 3'-bromo-4'-fluoro-[1,1'-biphenyl]-2-carboxylate (31 g with a yield of 33.3%).

Step 2:

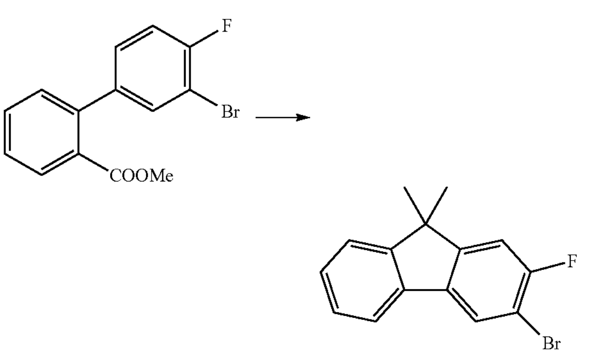

Methyl 3'-bromo-4'-fluoro-[1,1'-biphenyl]-2-carboxylate (31 g, 100 mmol) was dissolved in 500 mL of THF and cooled to 0° C. under nitrogen protection. MeMgBr (250 mL, 250 mmol) was slowly dropwise added. The reaction mixture was slowly heated to 60° C. and refluxed for 3 h. After the reaction was cooled to room temperature, water was added to quench the reaction. The aqueous phase was extracted three times with DCM. The organic phases were combined and subjected to rotary evaporation to dryness. 200 mL of acetic acid and a catalytic amount of sulfuric acid were added, heated to 120° C., and reacted for 3 h. Water was added to quench the reaction, and the reaction solution was extracted with DCM to obtain the crude product and separated through column chromatography to finally obtain the product, 3-bromo-2-fluoro-9,9-dimethyl-9H-fluorene (26.19 g with a yield of 90%).

Step 3:

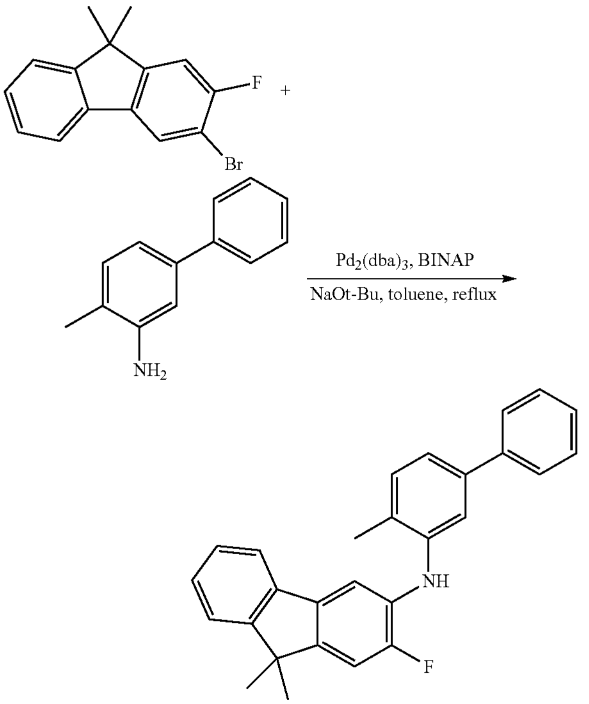

$Pd_2(dba)_3$ (2.05 g, 2.24 mmol) and BINAP (2.98 g, 4.48 mmol) were put into a 500 mL three-neck flask, and toluene (200 mL) was added. The solution was purged with $N_2$ for 20 min until the color no longer changed, and 3-bromo-2-fluoro-9,9-dimethyl-9H-fluorene (12.8 g, 44 mmol), 4-methyl-[1,1'-biphenyl]-3-amine (11.5 g, 66 mmol), and sodium tert-butoxide (12.86 g, 134 mmol) were sequentially added. $N_2$ was continued to be introduced for 10 min and the system was heated to 110° C. until 3-bromo-2-fluoro-9,9-dimethyl-9H-fluorene was reacted completely. The resultant was purified through column chromatography (PE:toluene=10:1 to 5:1) to obtain the product, 2-fluoro-9,9-dimethyl-N-(4-methyl-[1,1'-biphenyl]-3-yl)-9H-fluoren-3-amine (10 g with a yield of 58%).

Step 4:

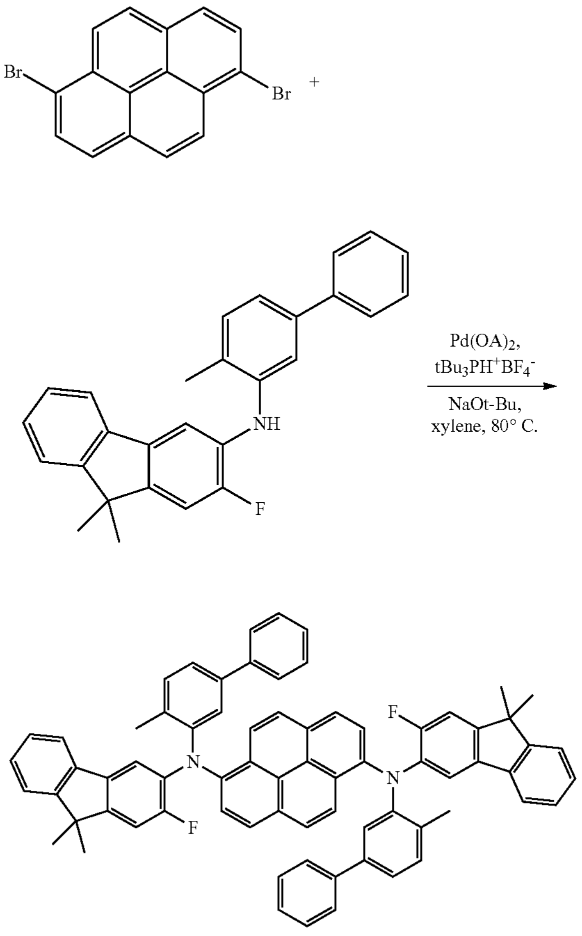

Compound 466

$Pd(OAc)_2$ (60 mg, 0.25 mmol) and t-$Bu_3PH{\cdot}BF_4$ (145 mg, 0.5 mmol) were put into a 100 mL three-neck flask, and xylene (50 mL) was added. The solution was purged with $N_2$ for 20 min until the color no longer changed, and 1,6-dibromopyrene (1.8 g, 5 mmol), 2-fluoro-9,9-dimethyl-N-(4-methyl-[1,1'-biphenyl]-3-yl)-9H-fluoren-3-amine (5.9 g, 15 mmol), and sodium tert-butoxide (2.0 g, 20 mmol) were sequentially added. $N_2$ was continued to be introduced for 10 min and the system was heated to 80° C. until the raw materials were reacted completely. After the reaction was finished, the reaction solution was purified through column chromatography to obtain the product, compound 466 (1 g with a yield of 20%). The product was confirmed as the target product with a molecular weight of 984.4.

Synthesis Example 6: Synthesis of Compound 419

Step 1:

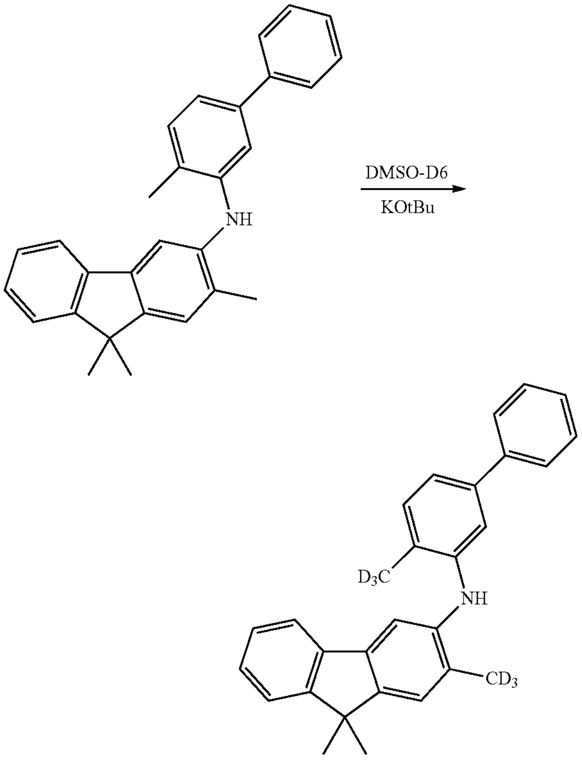

Under nitrogen protection, the compound 2,9,9-trimethyl-N-(4-methyl-[1,1'-biphenyl]-3-yl)-9H-fluoren-3-amine (5.835 g, 15 mmol) was added into a dry 100 mL three-neck flask, and 20 mL of deuterated DMSO and potassium tert-butoxide (2.24 g, 20 mmol) were added, heated to 80° C., and reacted for 4 h. The reaction solution was cooled to room temperature and separated through column chromatography to finally obtain an intermediate, 2,9,9-trimethyl-N-(4-methyl(d3)-[1,1'-biphenyl]-3-yl)-9H-fluoren-3-amine (5.44 g with a yield of 93%).

Step 2:

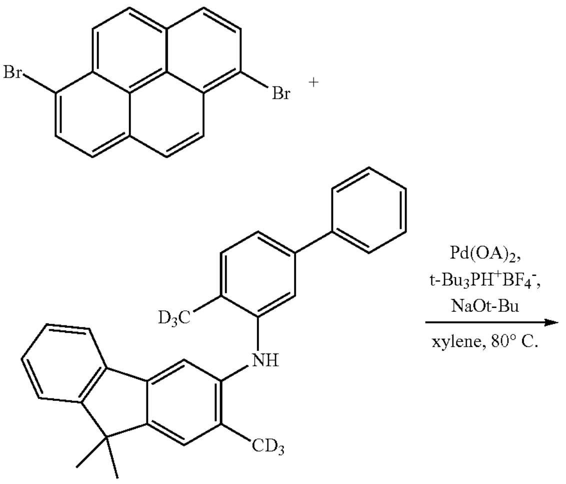

-continued

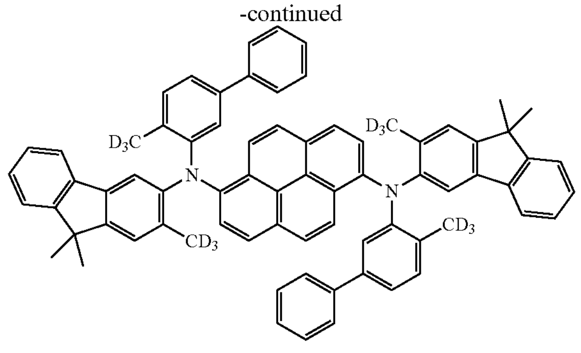

Compound 419

$Pd(OAc)_2$ (60 mg, 0.25 mmol) and $t\text{-}Bu_3PH{\cdot}BF_4$ (145 mg, 0.5 mmol) were put into a 100 mL three-neck flask, and xylene (50 mL) was added. The solution was purged with $N_2$ for 20 min until the color no longer changed, and 1,6-dibromopyrene (1.8 g, 5 mmol), 2,9,9-trimethyl-N-(4-methyl(d3)-[1,1'-biphenyl]-3-yl)-9H-fluoren-3-amine (5.44 g, 14 mmol), and sodium tert-butoxide (2.0 g, 20 mmol) were sequentially added. $N_2$ was continued to be introduced for 10 min and the system was heated to 80° C. until the raw materials were reacted completely. After the reaction was finished, the reaction solution was separated through column chromatography to obtain the product, compound 419 (1.9 g with a yield of 38.9%). The product was confirmed as the target product with a molecular weight of 988.5.

Synthesis Example 7: Synthesis of Compound 422

Step 1:

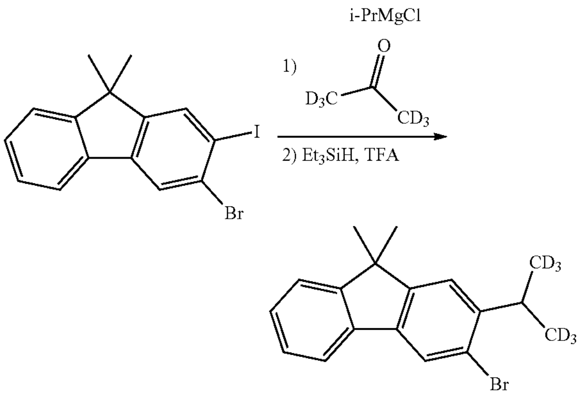

Under nitrogen protection, 3-bromo-2-iodo-9,9-dimethyl-9H-fluorene (24 g, 0.06 mol) was dissolved in 1 L of anhydrous tetrahydrofuran and cooled to −78° C. Isopropylmagnesium chloride (1.3M, 0.066 mol) was slowly added and reacted at low temperature for 1 h. Deuterated propanone (10.44 g, 0.18 mol) was added, slowly warmed to room temperature, and reacted overnight. After the reaction was finished, water was added to quench the reaction. The aqueous phase was extracted three times with DCM. The organic phases were combined, filtered through Celite, and the solvent was removed through rotary evaporation under reduced pressure, and then purified through column chromatography to obtain a tertiary alcohol intermediate. The intermediate was dissolved in 500 mL of dichloromethane. Triethylsilane (17.4 g, 0.15 mmol) was added at room temperature and stirred for half an hour. Trifluoroacetic acid (11.4 g, 0.1 mmol) was slowly dropwise added and stirred overnight at room temperature. Column chromatography was performed to obtain the product, 3-bromo-9,9-dimethyl-2-(propyl-2-yl-1,1,1,3,3,3-d6)-9H-fluorene (15.7 g with a yield of 67%).

Step 2:

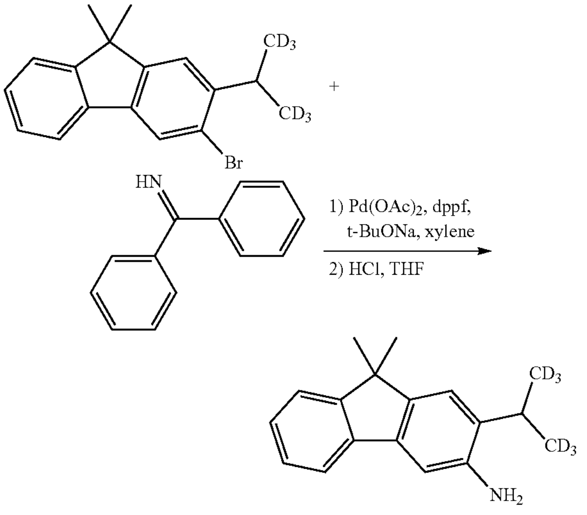

Under nitrogen protection, 3-bromo-9,9-dimethyl-2-(propyl-2-yl-1,1,1,3,3,3-d6)-9H-fluorene (16 g, 50 mmol), benzophenone imine (10 g, 55 mmol), $Pd(OAc)_2$ (567 mg, 2.5 mmol), dppf (2.8 g, 5 mmol), and sodium tert-butoxide (10 g, 101 mmol) were sequentially added into a dry 500 mL three-neck flask, and xylene (125 mL) was added into the reaction flask which was purged with nitrogen for 5 min. The system was heated to 100° C. until the raw materials were reacted completely. The reaction solution was purified through column chromatography to obtain an intermediate. The intermediate was dissolved in 100 mL of THE HCl (30 mL) was added at room temperature and stirred overnight at room temperature, and column chromatography was performed to obtain the product, 9,9-dimethyl-2-(propyl-2-yl-1,1,1,3,3,3-d6)-9H-fluoren-3-amine (10 g with a yield of 77%).

Step 3:

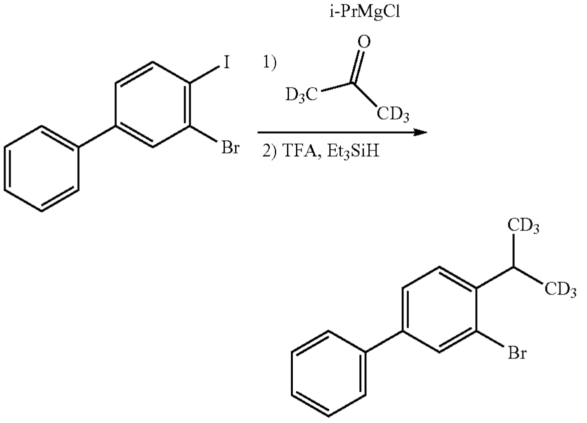

Under nitrogen protection, 3-bromo-4-iodo-1,1'-biphenyl (24 g, 0.06 mol) was dissolved in 1 L of anhydrous tetrahydrofuran and cooled to −78° C. Isopropylmagnesium chloride (1.3M, 0.066 mol) was slowly added and reacted at low temperature for 1 h. Propanone (10.44 g, 0.18 mol) was added, slowly warmed to room temperature, and reacted overnight. After the reaction was finished, water was added to quench the reaction. The aqueous phase was extracted three times with DCM. The organic phases were combined and filtered through Celite. After silica gel powder was added, samples were dry-mixed and subjected to column chromatography to obtain a tertiary alcohol intermediate. The intermediate was dissolved in 500 mL of dichloromethane. Triethylsilane (17.4 g, 0.15 mmol) was added at room temperature and stirred for half an hour. Trifluoroacetic acid (11.4 g, 0.1 mmol) was slowly dropwise added and stirred overnight at room temperature. Column chromatography was performed to obtain the product, 3-bromo-4-(propyl-2-yl-1,1,1,3,3,3-d6)-1,1'-biphenyl (15.7 g with a yield of 67%).

Step 4:

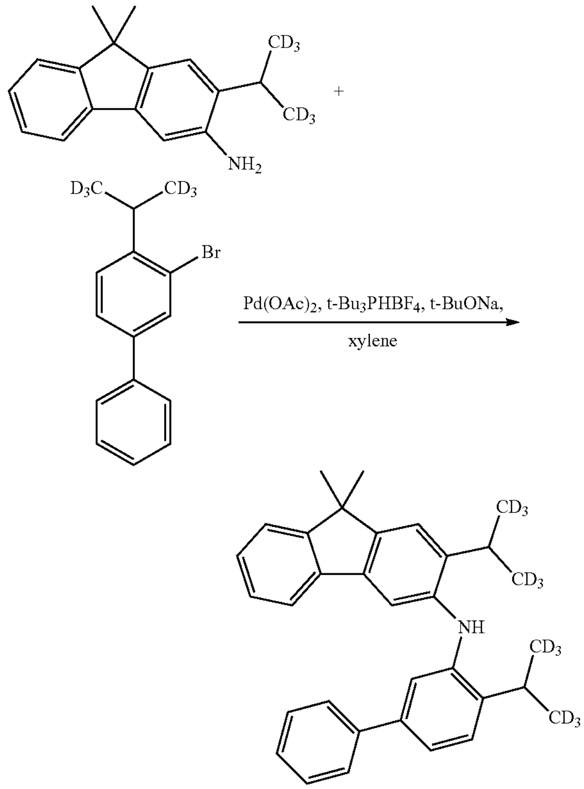

Under nitrogen protection, 3-bromo-9,9-dimethyl-2-(propyl-2-yl-1,1,1,3,3,3-d6)-9H-fluorene (8 g, 31.1 mmol), 3-bromo-4-(propyl-2-yl-1,1,1,3,3,3-d6)-1,1'-biphenyl (6.7 g, 23.8 mmol), $Pd(OAc)_2$ (530 mg, 2.4 mmol), $t\text{-}Bu_3PHBF_4$ (0.96 g, 4.76 mmol), and sodium tert-butoxide (5 g, 52.4 mmol) were sequentially added into a dry 500 mL three-neck flask, and xylene (125 mL) was added into the reaction flask, then the reaction system was purged with nitrogen for 5 min. The system was heated to 100° C. until the raw materials were reacted completely. The reaction solution was diluted with toluene, filtered through Celite, distilled under reduced pressure, and purified through column chromatography to obtain a compound, 9,9-dimethyl-2-(propyl-2-yl-1,1,1,3,3,3-d6)-N-4-(propyl-2-yl-1,1,1,3,3,3-d6)-[1,1'-biphenyl]-3-yl)-9H-fluoren-3-amine (8 g, 17.5 mmol, 74%).

Step 5:

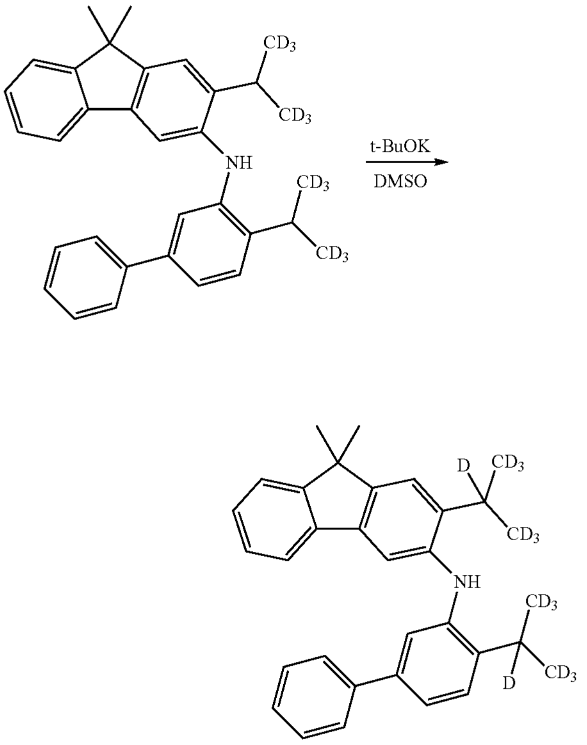

Under nitrogen protection, 9,9-dimethyl-2-(propyl-2-yl-1,1,1,3,3,3-d6)-N-4-[(propyl-2-yl-1,1,1,3,3,3-d6)-1,1'-biphenyl]-3-yl)-9H-fluoren-3-amine (7.5 g, 16.3 mmol) and potassium tert-butoxide (2.8 g, 24.5 mmol) were sequentially added into a dry 100 mL three-neck flask, and DMSO (40 mL) was added into the reaction flask, then the reaction system was purged with nitrogen for 5 min. The system was heated to 140 □ until the raw materials were reacted completely. Water was added to quench the reaction. The aqueous phase was extracted three times with DCM. The organic phases were combined, filtered through Celite, and purified through column chromatography to obtain a compound, 9,9-dimethyl-2-(propyl-2-yl-d7)-N-4-(propyl-2-yl-1,1,3,3,3-d6)-[1,1'-biphenyl]-3-yl)-9H-fluoren-3-amine (4 g with a yield of 54%).

Step 6:

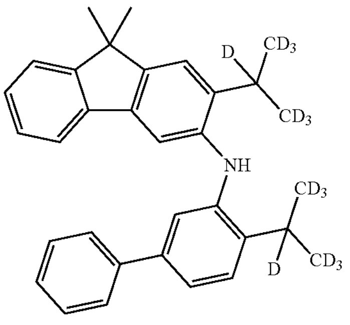
+

-continued

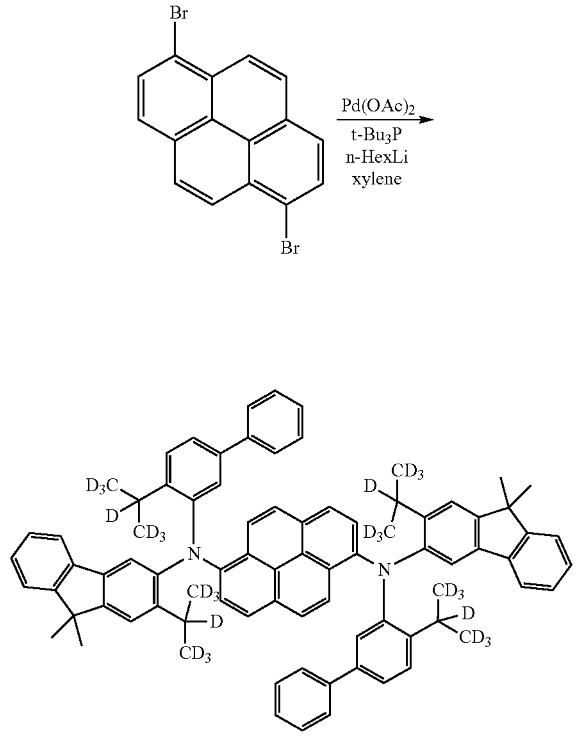

Compound 422

Under nitrogen protection and at room temperature, 9,9-dimethyl-2-(propyl-2-yl-d7)-N-4-(propyl-2-yl-1,1,1,3,3,3-d6)-[1,1'-biphenyl]-3-yl)-9H-fluoren-3-amine (3.6 g, 7.8 mmol) was dissolved in 20 mL of THF and cooled to −78° C., and n-hexyl lithium (7 mmol) was slowly dropwise added. The reaction mixture was warmed to room temperature and stirred for 30 min Additionally, xylene (20 mL), 1,6-dibromopyrene (1.1 g, 3.1 mmol), $Pd(OAc)_2$ (37.0 mg, 0.17 mmol), and $t\text{-}Bu_3P$ (0.33 mmol) were added into another flask under nitrogen protection. The prepared amino-lithium solution was slowly dropwise added into the reaction system under nitrogen protection, warmed to 90° C., and stirred for 3 h. After the reaction was finished, the reaction solution was purified through column chromatography to obtain the product, compound 422 (1.2 g with a yield of 35%). The product was confirmed as the target product with a molecular weight of 1116.8.

Synthesis Example 8: Synthesis of Compound 2333

Step 1:

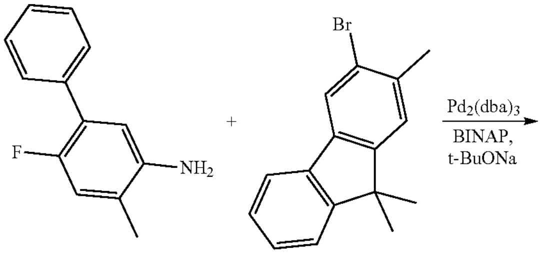

-continued

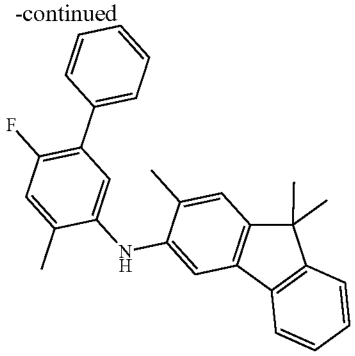

At room temperature and under nitrogen protection, $Pd_2(dba)_3$ (910 mg, 0.99 mmol), BINAP (1.18 g, 1.99 mmol), 6-fluoro-4-methyl-[1,1'-biphenyl]-3-amine (6.03 g, 30 mmol), 3-bromo-2,9,9-trimethyl-9H-fluorene (5.6 g, 20 mmol), and t-BuONa (3.8 g, 39.8 mmol) were added into toluene (200 mL), and the system was heated to 120° C. for 2 h. After the reaction was finished, the reaction solution was purified through column chromatography to obtain a compound 2,9,9-trimethyl-N-(6-fluoro-4-methyl-[1,1'-biphenyl]-3-yl)-9H-fluoren-3-amine (7.8 g with a yield of 95%).

Step 2:

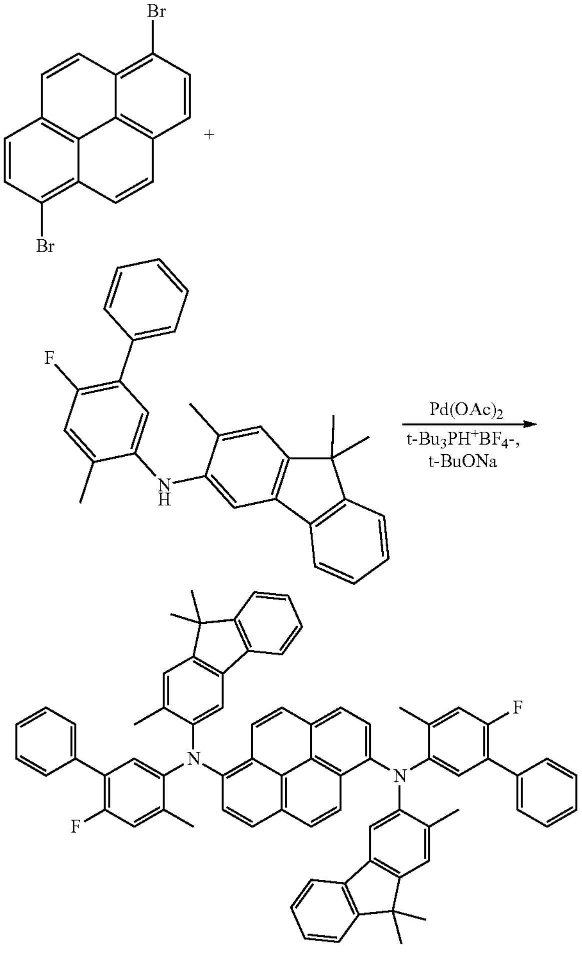

Compound 2333

At room temperature and under nitrogen protection, 1,6-dibromopyrene (2.2 g, 6.1 mmol), 2,9,9-trimethyl-N-(6-fluoro-4-methyl-[1,1'-biphenyl]-3-yl)-9H-fluoren-3-amine (5.52 g, 16 mmol), $Pd(OAc)_2$ (68 mg, 0.3 mmol), $t\text{-}Bu_3PH^+BF_4^-$ (174 mg, 0.6 mmol), and t-BuONa (1.3 g, 14 mmol) were added into xylene (30 mL), and the system was heated to 95 □. After the reaction was finished, the reaction solution was separated through column chromatography to obtain the product, compound 2333 (1.95 g, 1.9 mmol, with a yield of 37%). The product was confirmed as the target product with a molecular weight of 1012.5.

Synthesis Example 9: Synthesis of Compound 2334

Step 1:

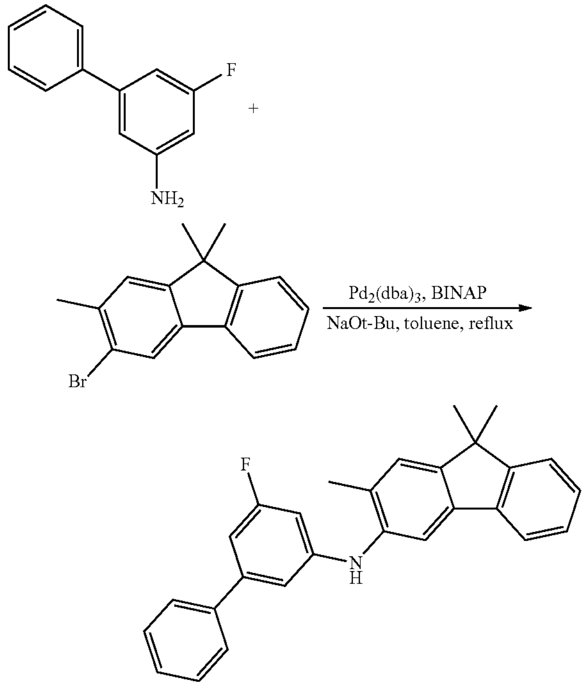

At room temperature and under nitrogen protection, $Pd_2(dba)_3$ (910 mg, 0.99 mmol), BINAP (1.18 g, 1.99 mmol), 3-bromo-2,9,9-trimethyl-9H-fluorene (8.6 g, 30 mmol), 5-fluoro-[1,1'-biphenyl]-3-amine (3.75 g, 19.9 mmol), and t-BuONa (3.8 g, 39.8 mmol) were added into toluene (200 mL), and the system was heated to 120° C. for 2 h. After the reaction was finished, the reaction solution was purified through column chromatography to obtain a compound 2,9,9-trimethyl-N-(3-fluoro-[1,1'-biphenyl]-3-yl)-9H-fluoren-3-amine (6.29 g with a yield of 53%).

Step 2:

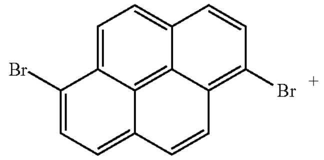

-continued

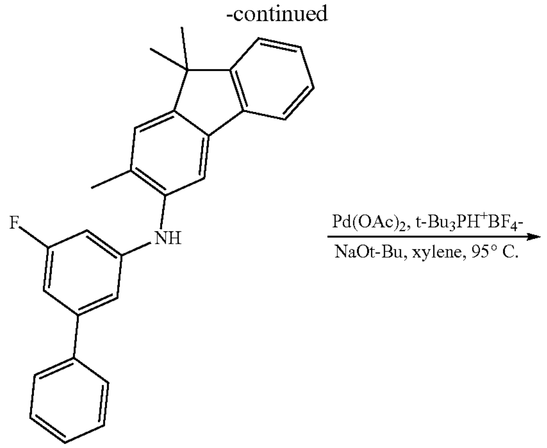

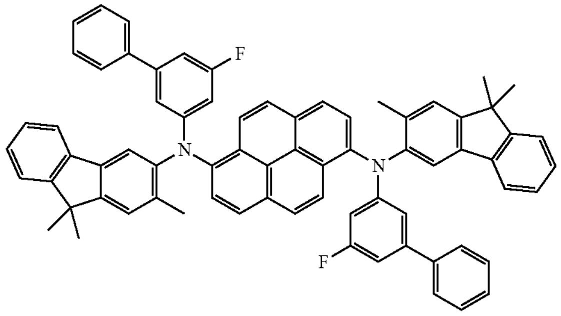

Compound 2334

At room temperature and under nitrogen protection, 1,6-dibromopyrene (2.2 g, 6.1 mmol), 2,9,9-trimethyl-N-(3-fluoro-[1,1'-biphenyl]-3-yl)-9H-fluoren-3-amine (6.29 g, 16 mmol), $Pd(OAc)_2$ (68 mg, 0.3 mmol), $tBu_3PHBF_4$ (174 mg, 0.6 mmol), and t-BuONa (1.3 g, 14 mmol) were added into xylene (30 mL), and the system was heated to 95 □. After the reaction was finished, the reaction solution was separated through column chromatography to obtain the product, compound 2334 (1.8 g, 2 mmol, with a yield of 33%). The product was confirmed as the target product with a molecular weight of 984.4.

Synthesis Example 10: Synthesis of Compound 506

Step 1:

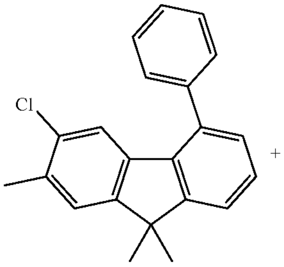

-continued

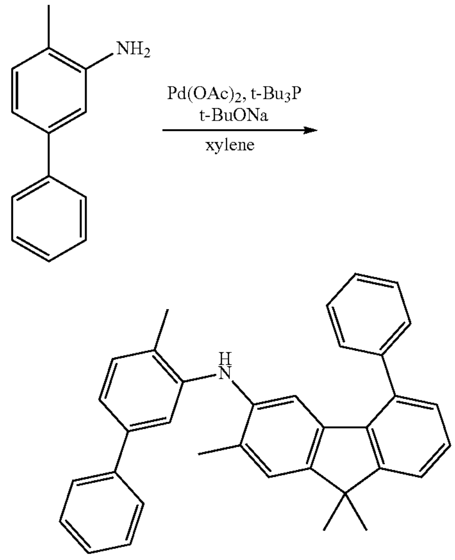

At room temperature and under nitrogen protection, $Pd(OAc)_2$ (0.2 g, 1 mmol), 3-chloro-2,9,9-trimethyl-5-phenyl-9H-fluorene (3.3 g, 10.3 mmol), 4-methyl-[1,1'-biphenyl]-3-amine (3.8 g, 20.7 mmol), $t\text{-}Bu_3P$ (4 mL, 2 mmol), and t-BuONa (3 g, 31 mmol) were added into xylene (40 mL), and the system was heated to 140 □ and reacted overnight. The reaction solution was filtered, washed with toluene, solvents were removed through rotary evaporation and the resultant was subjected to column chromatography (PE/EA=20/1) to obtain a crude product. The crude product was recrystallized to obtain a compound 2,9,9-trimethyl-N-(4-methyl-[1,1'-biphenyl]-3-yl)-5-phenyl-9H-fluoren-3-amine (3.8 g with a yield of 79%).

Step 2:

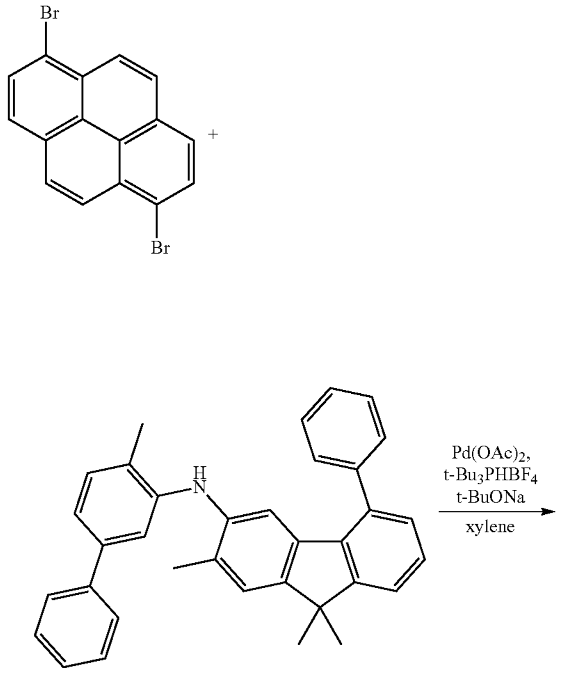

-continued

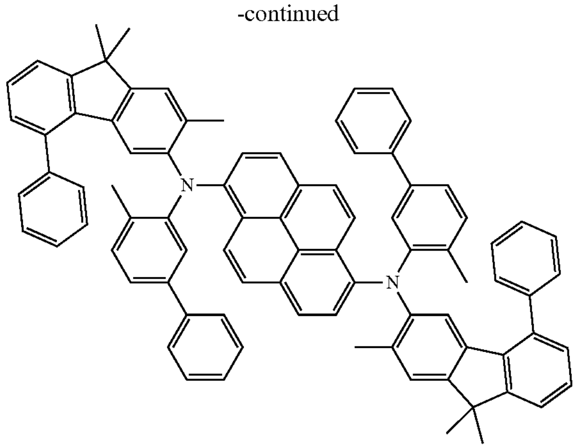

Compound 506

At room temperature and under nitrogen protection, 1,6-dibromopyrene (1 g, 2.89 mmol), 2,9,9-trimethyl-N-(4-methyl-[1,1'-biphenyl]-3-yl)-5-phenyl-9H-fluoren-3-amine (3 g, 6.36 mmol), $Pd(OAc)_2$ (31 mg, 0.14 mmol), $t\text{-}Bu_3PHBF_4$ (81.2 mg, 0.28 mmol), and t-BuONa (1.4 g, 14.5 mmol) were added into xylene (20 mL), and the system was heated to 100 □ until the reaction was finished. After the reaction was finished, the reaction solution was purified through column chromatography to obtain the product, compound 506 (1.2 g with a yield of 36%). The product was confirmed as the target product with a molecular weight of 1128.5.

Synthesis Example 11: Synthesis of Compound 609

Step 1:

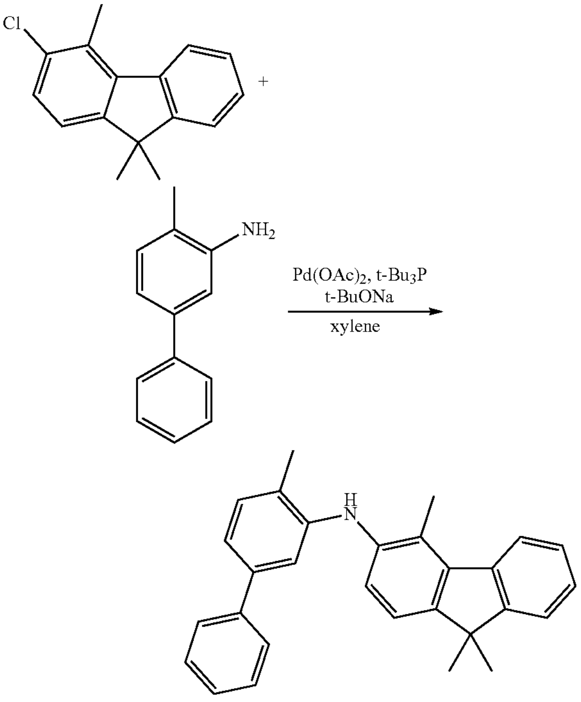

At room temperature and under nitrogen protection, $Pd(OAc)_2$ (0.2 g, 1 mmol), 3-chloro-4,9,9-trimethyl-9H- fluorene (6 g, 24.9 mmol), 4-methyl-[1,1'-biphenyl]-3-amine (9.3 g, 49.8 mmol), t-$Bu_3P$ (4 mL, 2 mmol), and t-BuONa (7.1 g, 74.7 mmol) were added into xylene (40 mL), and the system was heated to 140 □ and reacted overnight. The reaction solution was filtered with basic alumina and $MgSO_4$, washed with toluene, solvents were removed through rotary evaporation and the resultant was subjected to column chromatography (PE/EA=20/1) to obtain a crude product. The crude product was recrystallized from PE to obtain a compound 4,9,9-trimethyl-N-(4-methyl-[1,1'-biphenyl]-3-yl)-9H-fluoren-3-amine (7 g with a yield of 72%).

Step 2:

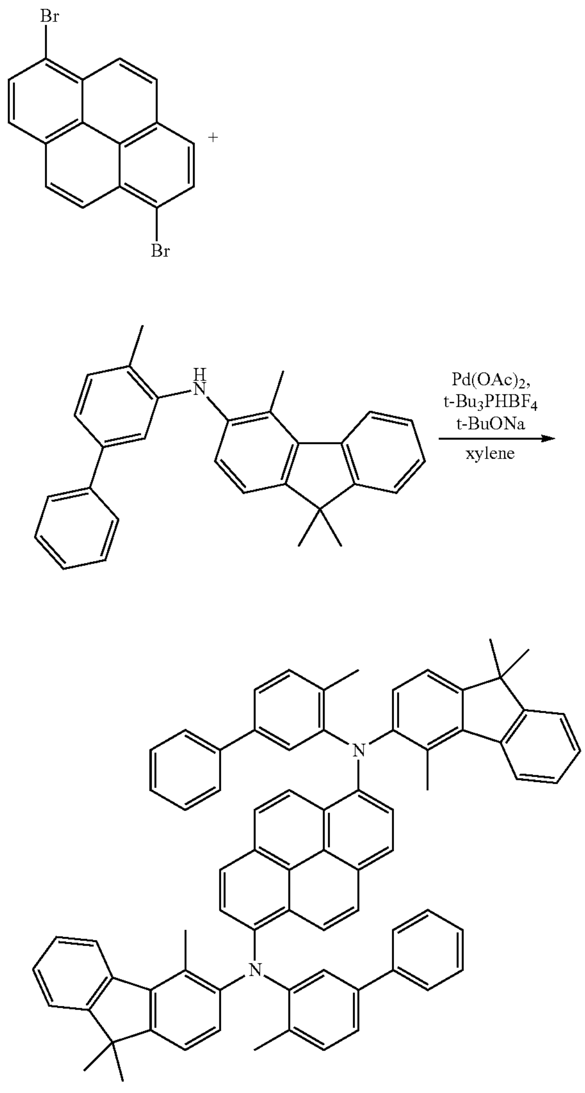

Compound 609

At room temperature and under nitrogen protection, 1,6-dibromopyrene (2 g, 5.56 mmol), 4,9,9-trimethyl-N-(4-methyl-[1,1'-biphenyl]-3-yl)-9H-fluoren-3-amine (4.4 g, 12.2 mmol), $Pd(OAc)_2$ (31 mg, 0.14 mmol), t-$Bu_3PHBF_4$ (81.2 mg, 0.28 mmol), and t-BuONa (2.1 g, 22.2 mmol) were added into xylene (20 mL), and the system was heated to 100 □ until the reaction was finished. After the reaction was finished, the reaction solution was separated through column chromatography to obtain the product, compound 609 (1.3 g with a yield of 24%). The product was confirmed as the target product with a molecular weight of 976.5.

Synthesis Example 12: Synthesis of Compound 2350

Step 1:

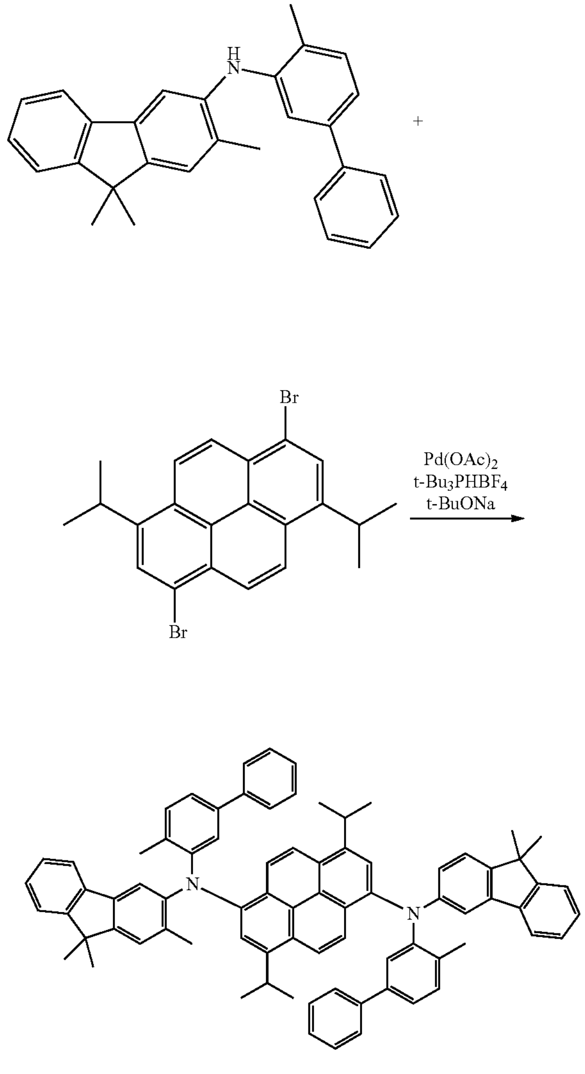

Compound 2350

At room temperature and under nitrogen protection, 1,6-dibromo-3,8-diisopropylpyrene (2 g, 4.5 mmol), 2,9,9-trimethyl-N-(4-methyl-[1,1'-biphenyl]-3-yl)-9H-fluoren-3-amine (4 g, 10.35 mmol), $Pd(OAc)_2$ (50 mg, 0.225 mmol), t-$Bu_3PHBF_4$ (130 mg, 0.45 mmol), and t-BuONa (1 g, 10.23 mmol) were added into xylene (25 mL), and the system was heated to 95 □. The reaction was monitored by TLC until it was finished. After the reaction was finished, the reaction was purified through column chromatography to obtain the product, compound 2350 (2.5 g with a yield of 50%). The product was confirmed as the target product with a molecular weight of 1060.6.

Synthesis Example 13: Synthesis of Compound 505

Step 1:

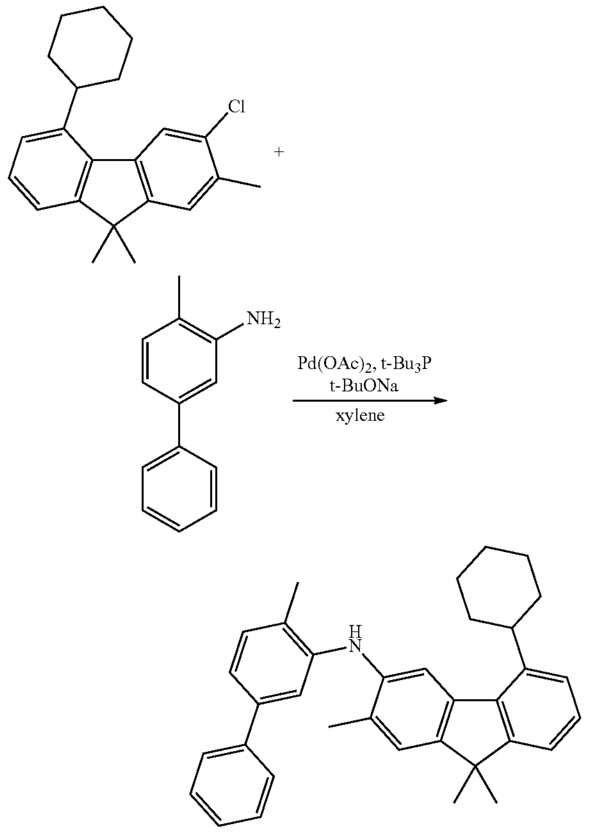

At room temperature and under nitrogen protection, $Pd(OAc)_2$ (0.2 g, 1 mmol), 3-chloro-5-cyclohexyl-2,9,9-trimethyl-9H-fluorene (3 g, 9.2 mmol), 4-methyl-[1,1'-biphenyl]-3-amine (3.3 g, 18.5 mmol), t-$Bu_3P$ (4 mL, 2 mmol), and t-BuONa (2.7 g, 27.7 mmol) were added into xylene (40 mL), and the system was heated to 140 □ and reacted overnight. The reaction solution was filtered with basic alumina and $MgSO_4$, washed with toluene, solvents were removed through rotary evaporation and the resultant was subjected to column chromatography (PE/EA=20/1) to obtain a crude product. The crude product was crystallized from PE to obtain a compound 5-cyclohexyl-2,9,9-trimethyl-N-(4-methyl-[1,1'-biphenyl]-3-yl)-9H-fluoren-3-amine (3.2 g with a yield of 75%).

Step 2:

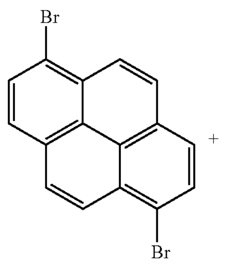

-continued

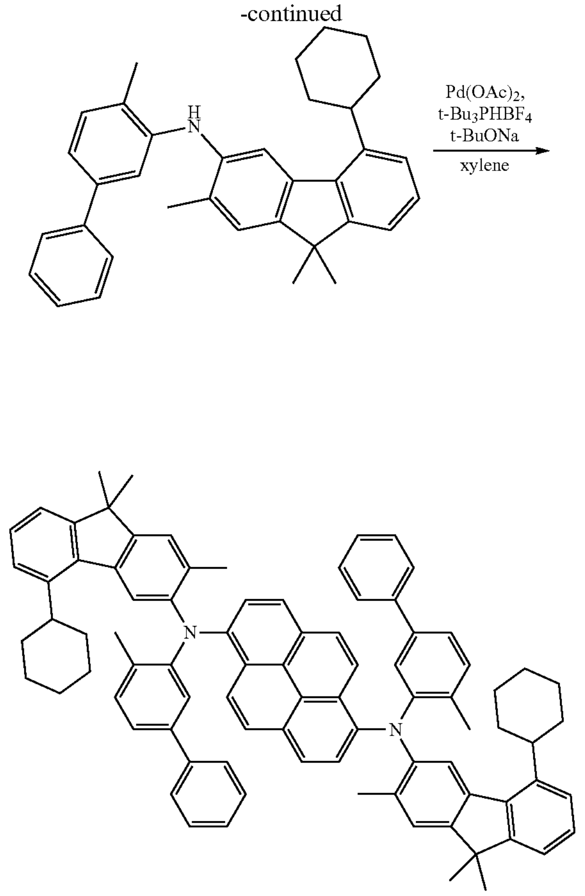

Compound 505

At room temperature and under nitrogen protection, 1,6-dibromopyrene (1 g, 2.89 mmol), 5-cyclohexyl-2,9,9-trimethyl-N-(4-methyl-[1,1'-biphenyl]-3-yl)-9H-fluoren-3-amine (3 g, 6.36 mmol), $Pd(OAc)_2$ (31 mg, 0.14 mmol), t-$Bu_3PHBF_4$ (81.2 mg, 0.28 mmol), and t-BuONa (1.4 g, 14.5 mmol) were added into xylene (20 mL), and the system was heated to 100 □ until the reaction was finished. After the reaction was finished, the reaction solution was separated through column chromatography to obtain the product, compound 505 (1.3 g with a yield of 39%). The product was confirmed as the target product with a molecular weight of 1140.6.

Synthesis Example 14: Synthesis of Compound 508

Step 1:

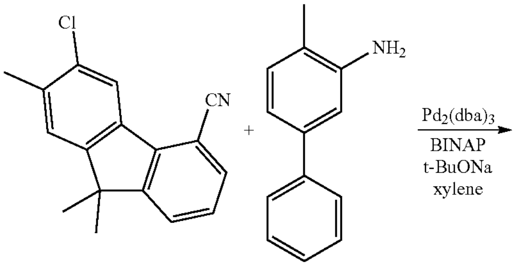

-continued

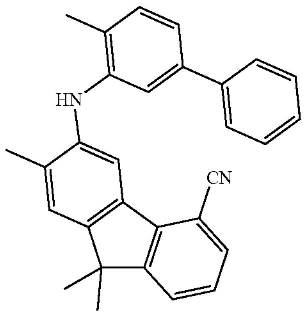

At room temperature and under nitrogen protection, $Pd_2(dba)_3$ (0.4 g, 0.45 mmol) and BINAP (0.56 g, 0.90 mmol) were added into xylene (100 mL). The solution was purged with $N_2$ for 20 min, and 7-chloro-6,9,9-trimethyl-9H-fluoren-4-cyano (4.0 g, 14.98 mmol), 4-methyl-[1,1'-biphenyl]-3-amine (5.0 g, 26.96 mmol), and sodium tert-butoxide (3.6 g, 37.45 mmol) were sequentially added. $N_2$ was continued to be introduced for 10 min and the system was heated to 140 □ for 18 h. The reaction solution was filtered with basic alumina and $MgSO_4$, washed with toluene, solvents were removed through rotary evaporation and the resultant was subjected to column chromatography (PE:EA=20:1) to obtain a crude product. The crude product was crystallized from petroleum ether to obtain 6,9,9-trimethyl-7-((4-methyl-[1,1'-biphenyl]-3-yl)amino)-9H-fluoren-4-cyano (4.0 g with a yield of 64%) as a white solid.

Step 2:

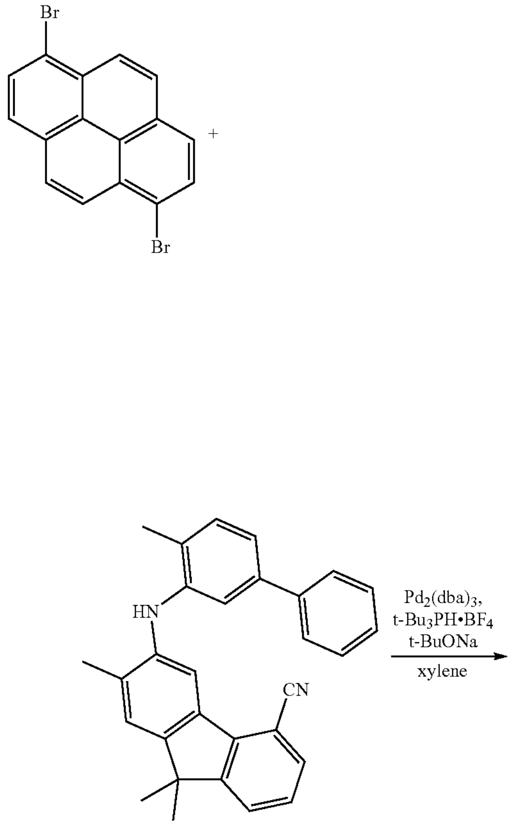

-continued

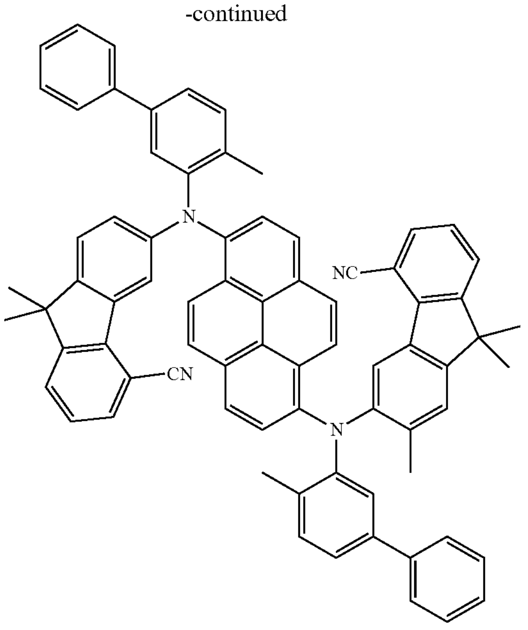

Compound 508

At room temperature and under nitrogen protection, $Pd_2(dba)_3$ (356 mg, 0.39 mmol) and t-$Bu_3PHBF_4$ (225 mg, 0.78 mmol) were added into xylene (20 mL). The solution was purged with $N_2$ for 20 min, and 1,6-dibromopyrene (1.4 g, 3.89 mmol), 6,9,9-trimethyl-7-((4-methyl-[1,1'-biphenyl]-3-yl)amino)-9H-fluoren-4-cyano (3.7 g, 8.94 mmol), and sodium tert-butoxide (0.9 g, 9.72 mmol) were sequentially added. $N_2$ was continued to be introduced for 10 min and the system was heated to 100 □ until the reaction was finished. The reaction solution was filtered with basic alumina and $MgSO_4$, washed with toluene, solvents were removed through rotary evaporation and the resultant was subjected to column chromatography (PE:toluene=10:1 to 1:5) to obtain compound 508 (0.75 g with a yield of 19%) as a yellow-green solid. The product was confirmed as the target product with a molecular weight of 1026.5.

Synthesis Example 15: Synthesis of Compound 349

Step 1:

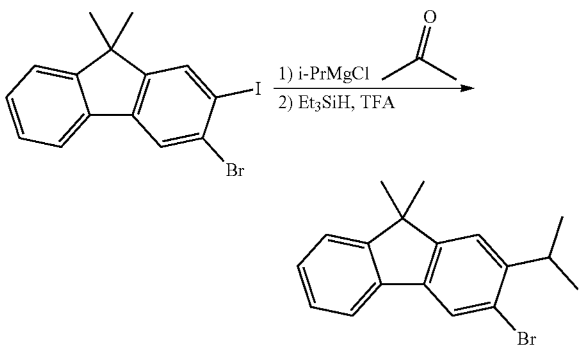

Under nitrogen protection, 3-bromo-2-iodo-9,9-dimethyl-9H-fluorene (24 g, 0.06 mol) was dissolved in 1 L of anhydrous tetrahydrofuran and cooled to −78° C. Isopropylmagnesium chloride (1.3M, 0.066 mol) was slowly added and reacted at low temperature for 1 h. Propanone (10.44 g, 0.18 mol) was added, slowly warmed to room temperature, and reacted overnight. After the reaction was finished, water was added to quench the reaction. The aqueous phase was extracted three times with DCM. The organic phases were combined, filtered through Celite, and subjected to column chromatography to obtain a tertiary alcohol intermediate. The intermediate was dissolved in 500 mL of dichloromethane. Triethylsilane (17.4 g, 0.15 mmol) was added at room temperature and stirred for half an hour. Trifluoroacetic acid (11.4 g, 0.1 mmol) was slowly dropwise added and stirred overnight at room temperature. Column chromatography was performed to obtain the product, 3-bromo-9,9-dimethyl-2-isopropyl-9H-fluorene (15.7 g with a yield of 67%).

Step 2:

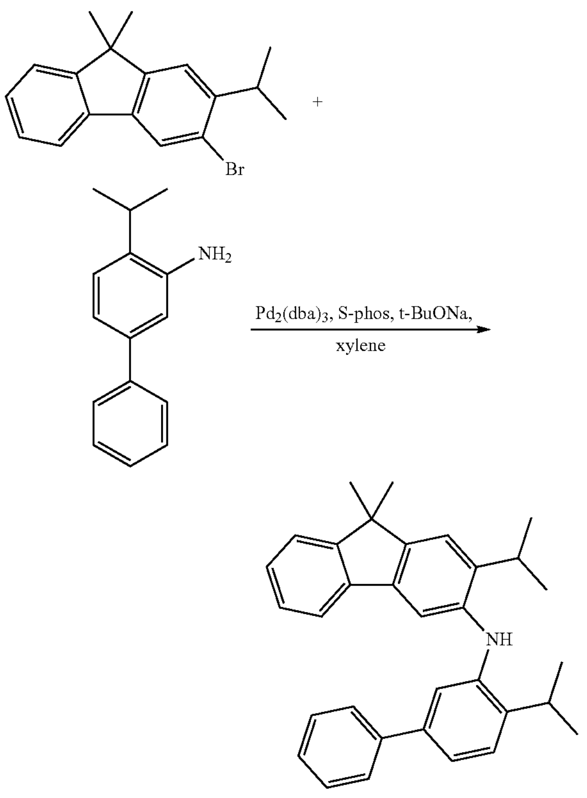

Under nitrogen protection, 3-bromo-9,9-dimethyl-2-isopropyl-9H-fluorene (8 g, 25.6 mmol), 4-isopropyl-[1,1'-biphenyl]-3-amine (3 g, 14.22 mmol), $Pd_2(dba)_3$ (586 mg, 0.64 mmol), S-Phos (1.05 g, 2.56 mmol), and sodium tert-butoxide (3 g, 31.3 mmol) were sequentially added into a dry 500 mL three-neck flask, and xylene (125 mL) was added into the reaction flask which was purged with nitrogen for 5 min. The system was heated to 100° C. until the raw materials were reacted completely. The reaction solution was diluted with toluene and filtered. The filtrate was distilled under reduced pressure and separated through column chromatography to obtain a product 2-isopropyl-N-(4-isopropyl-[1,1'-biphenyl]-3-yl)-9,9-dimethyl-9H-fluoren-3-amine (9.1 g with a yield of 80%) as a light yellow oil.

Step 3:

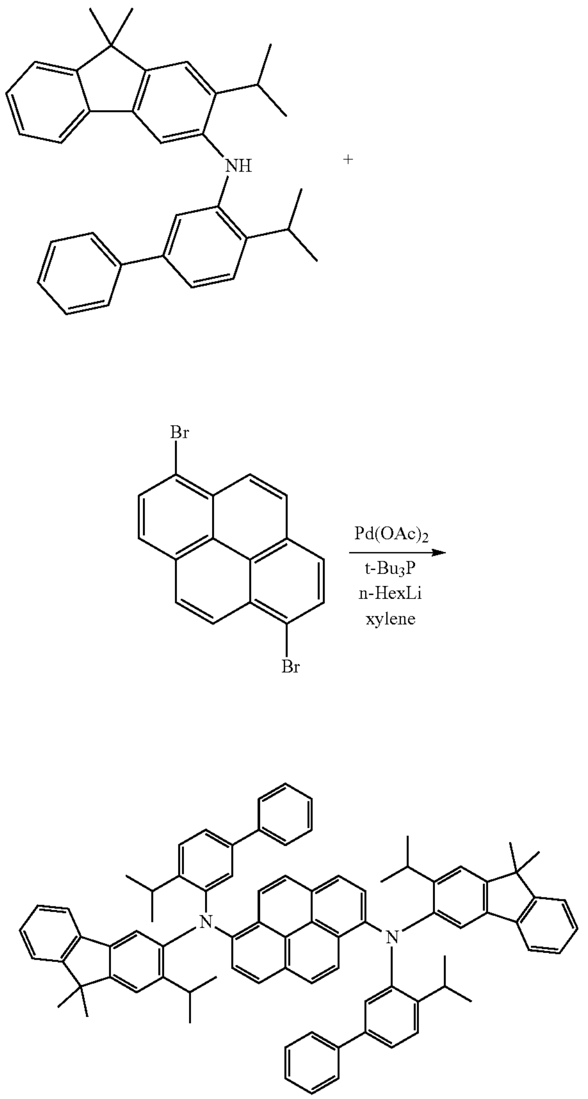

Compound 349

Under nitrogen protection and at room temperature, 2-isopropyl-N-(4-isopropyl-[1,1'-biphenyl]-3-yl)-9,9-dimethyl-9H-fluoren-3-amine (8.9 g, 20 mmol) was dissolved in 40 mL of THF and cooled to −78 □, and n-hexyl lithium (20 mmol) was slowly dropwise added. The reaction mixture was warmed to room temperature and stirred for 30 min. Additionally, xylene (40 mL), 1,6-dibromopyrene (2.88 g, 8 mmol), $Pd(OAc)_2$ (37.0 mg, 0.17 mmol), and t-$Bu_3P$ (0.33 mmol) were added into another flask under nitrogen protection. The prepared amino-lithium solution was slowly dropwise added into the reaction system under nitrogen protection, warmed to 90° C., and stirred for 3 h. After the reaction was finished, the reaction was purified through column chromatography to obtain the product, compound 349 (2.8 g with a yield of 33%). The product was confirmed as the target product with a molecular weight of 1088.6.

Synthesis Example 16: Synthesis of Compound 2335

Step 1:

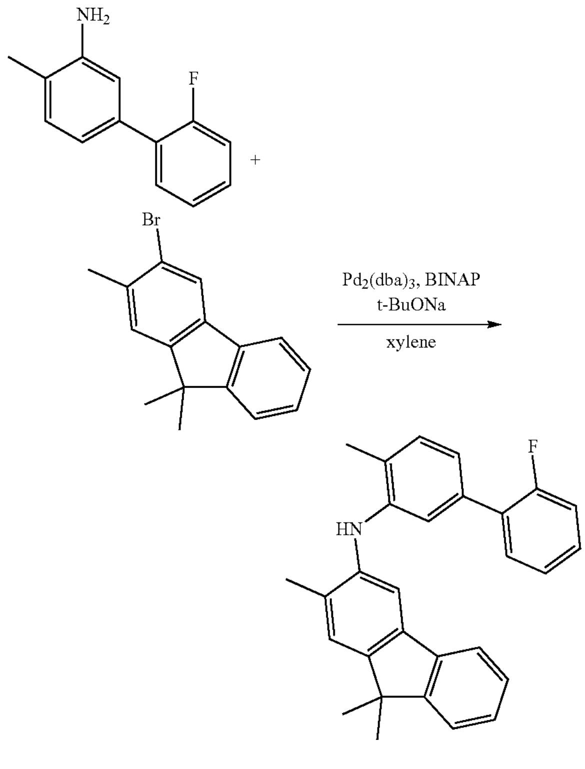

At room temperature and under nitrogen protection, $Pd_2(dba)_3$ (1.7 g, 1.88 mmol) and BINAP (2.3 g, 3.76 mmol) were added into xylene (300 mL). The solution was purged with $N_2$ for 20 min, and 3-bromo-2,9,9-trimethyl-9H-fluorene (18.0 g, 62.67 mmol), 2'-fluoro-4-methyl-[1,1'-biphenyl]-3-amine (13.0 g, 64.6 mmol), and sodium tert-butoxide (15.0 g, 156.8 mmol) were sequentially added. $N_2$ was continued to be introduced for 10 min and the system was heated to 140 □ for 4 h. The reaction solution was filtered with basic alumina and $MgSO_4$, washed with toluene, solvents were removed through rotary evaporation and the resultant was subjected to column chromatography (PE: toluene=50:1) to obtain a compound N-(2'-fluoro-4-methyl-[1,1'-biphenyl]-3-yl)-2,9,9-trimethyl-9H-fluoren-3-amine (6.0 g with a yield of 23%).

Step 2:

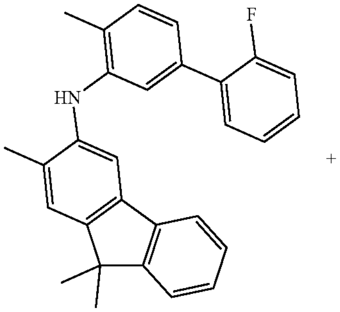

-continued

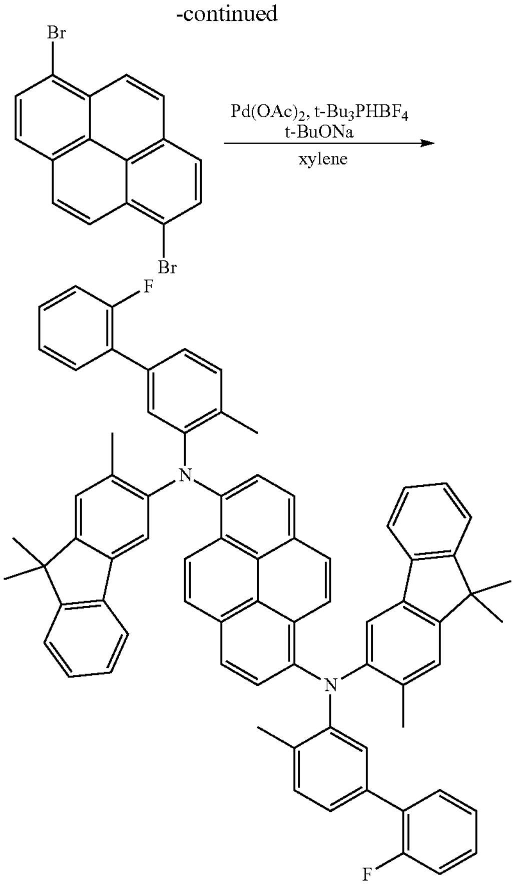

Compound 2335

At room temperature and under nitrogen protection, $Pd(OAc)_2$ (65 mg, 0.29 mmol) and t-$Bu_3PHBF_4$ (169 mg, 0.58 mmol) were added into xylene (30 mL). The solution was purged with $N_2$ for 20 min, and 1,6-dibromopyrene (2.1 g, 5.89 mmol), N-(2'-fluoro-4-methyl-[1,1'-biphenyl]-3-yl)-2,9,9-trimethyl-9H-fluoren-3-amine (6.0 g, 14.72 mmol), and sodium tert-butoxide (1.7 g, 17.5 mmol) were sequentially added. $N_2$ was continued to be introduced for 10 min and the system was heated to 100° C. until the reaction was finished. After the reaction was finished, the reaction solution was purified through column chromatography to obtain the product, compound 2335 (1.0 g, 0.98 mmol, with a yield of 17%). The product was confirmed as the target product with a molecular weight of 1012.5.

Synthesis Example 17: Synthesis of Compound 2336

Step 1:

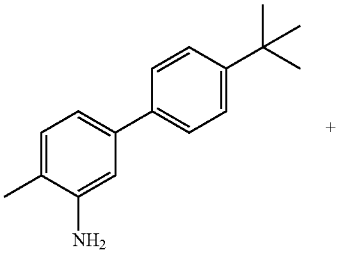

-continued

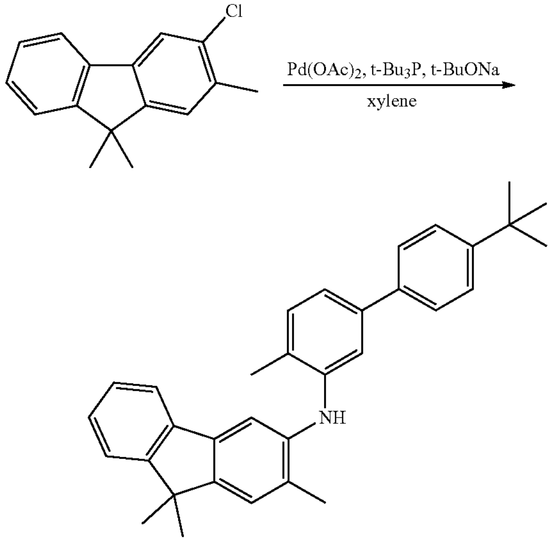

At room temperature and under nitrogen protection, $Pd(OAc)_2$ (0.2 g, 1 mmol), 4'-t-butyl-4-methyl-[1,1'-biphenyl]-3-amine (8 g, 33.5 mmol), 3-chloro-2,9,9-trimethyl-9H-fluorene (6.8 g, 27.9 mmol), $t\text{-}Bu_3P$ (4 mL, 2 mmol), and t-BuONa (8.3 g, 86.9 mmol) were added into xylene (100 mL), and the system was heated to 140 □ and reacted overnight. The reaction solution was filtered with basic alumina and $MgSO_4$, washed with toluene, solvents were removed through rotary evaporation and the resultant was subjected to column chromatography (PE/EA=20/1) to obtain a crude product. The crude product was crystallized from PE to obtain a compound 2,9,9-trimethyl-N-(4'-t-butyl-4-methyl-[1,1'-biphenyl]-3-yl)-9H-fluoren-3-amine (10.7 g with a yield of 86%).

Step 2:

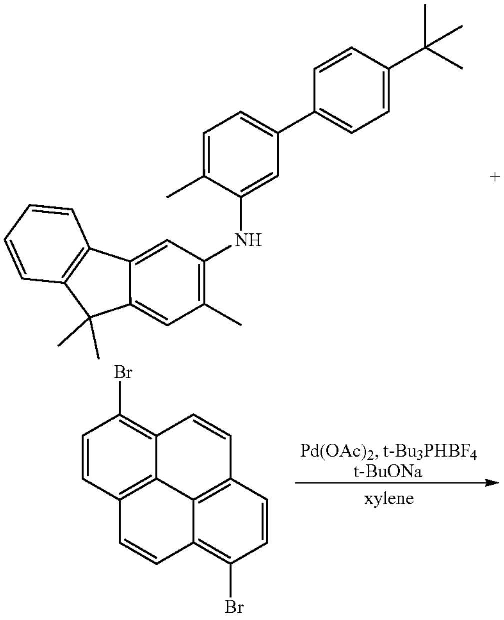

-continued

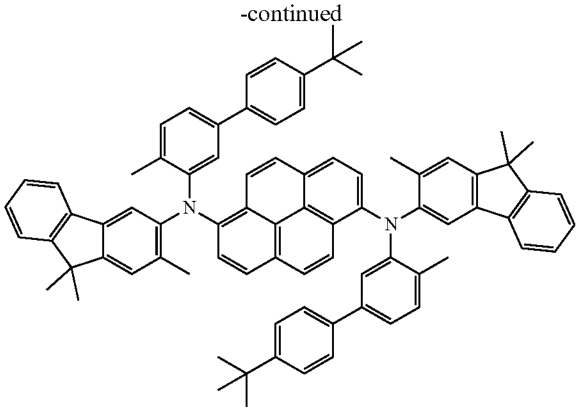

Compound 2336

At room temperature and under nitrogen protection, 2,9,9-trimethyl-N-(4'-t-butyl-4-methyl-[1,1'-biphenyl]-3-yl)-9H-fluoren-3-amine (2.4 g, 5.38 mmol), 1,6-dibromopyrene (0.77 g, 2.15 mmol), $Pd(OAc)_2$ (63 mg, 0.28 mmol), $t\text{-}Bu_3PHBF_4$ (162 mg, 0.56 mmol), and t-BuONa (2.13 g, 22.22 mmol) were added into xylene (20 mL), and the system was heated to 100 □ until the reaction was finished. After the reaction was finished, column chromatography was performed to obtain the product, compound 2336 (0.8 g with a yield of 34%). The product was confirmed as the target product with a molecular weight of 1088.6.

Synthesis Example 18: Synthesis of Compound 2337

Step 1:

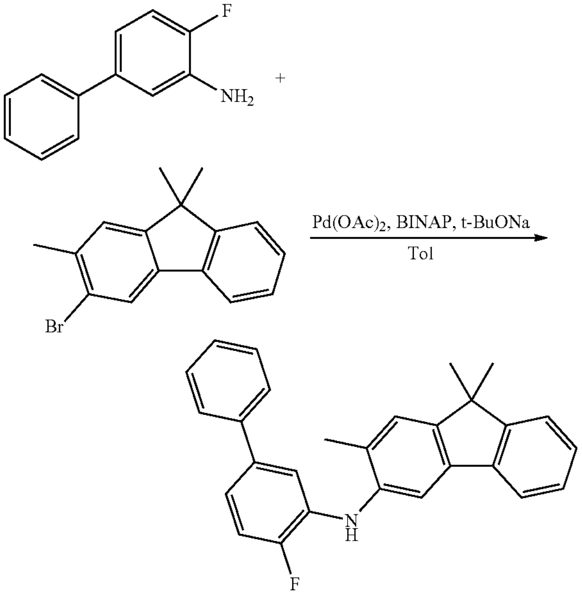

At room temperature and under nitrogen protection, palladium acetate (234.0 mg, 1.1 mmol) and BINAP (1.3 g, 2.1 mmol) were added into toluene (100 mL). The solution was purged with $N_2$ for 20 min, and 3-bromo-2,9,9-trimethyl-9H-fluorene (10.0 g, 34.9 mmol), 4-fluoro-[1,1'-biphenyl]-3-amine (6.7 g, 35.66 mmol), and sodium tert-butoxide (8.4 g, 87.4 mmol) were sequentially added. $N_2$ was continued to be introduced for 10 min and the system was heated to 110 □ for 4 h. After the reaction was finished, the solvent was removed through rotary evaporation under reduced pressure, and the resultant was subjected to column chromatography to obtain a compound N-(4-fluoro-[1,1'-biphenyl]-3-yl)-2,9,9-trimethyl-9H-fluoren-3-amine (9.0 g, 22.9 mmol, with a yield of 66%).

Step 2:

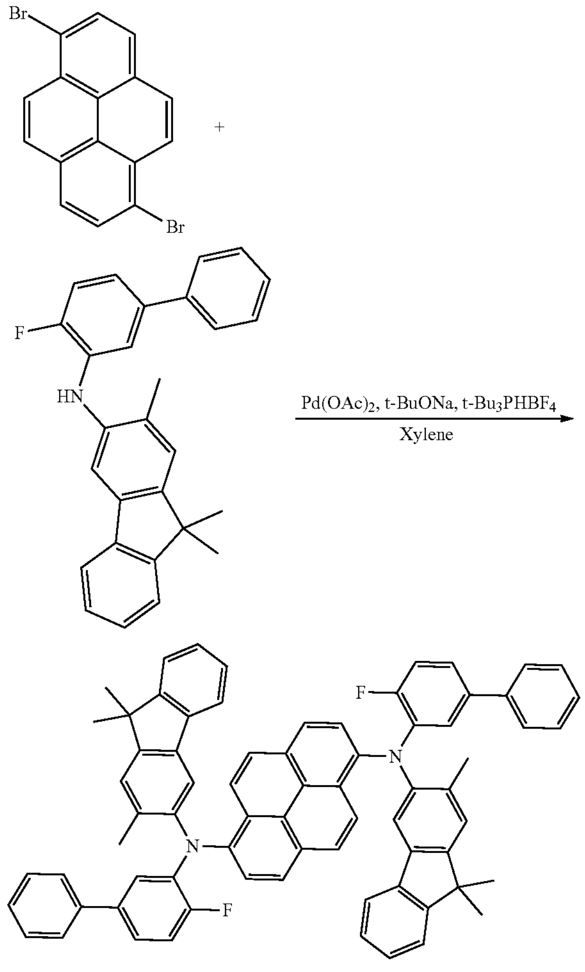

Compound 2337

At room temperature and under nitrogen protection, $Pd(OAc)_2$ (47.0 mg, 0.24 mmol) and t-$Bu_3PHBF_4$ (121.0 mg, 0.42 mmol) were added into xylene (50 mL). The solution was purged with $N_2$ for 20 min, and 1,6-dibromopyrene (2.5 g, 6.94 mmol), N-(4-fluoro-[1,1'-biphenyl]-3-yl)-2,9,9-trimethyl-9H-fluoren-3-amine (6.8 g, 17.36 mmol), and sodium tert-butoxide (1.7 g, 17.36 mmol) were sequentially added. $N_2$ was continued to be introduced for 10 min and the system was heated to 100 □ until the reaction was finished. The solvent was removed through rotary evaporation under reduced pressure, and the resultant was purified through column chromatography to obtain the product, compound 2337 (4.0 g, 4.07 mmol, with a yield of 59%). The product was confirmed as the target product with a molecular weight of 984.4.

Comparative Synthesis Example 1: Synthesis of Comparative Compound A

Step 1:

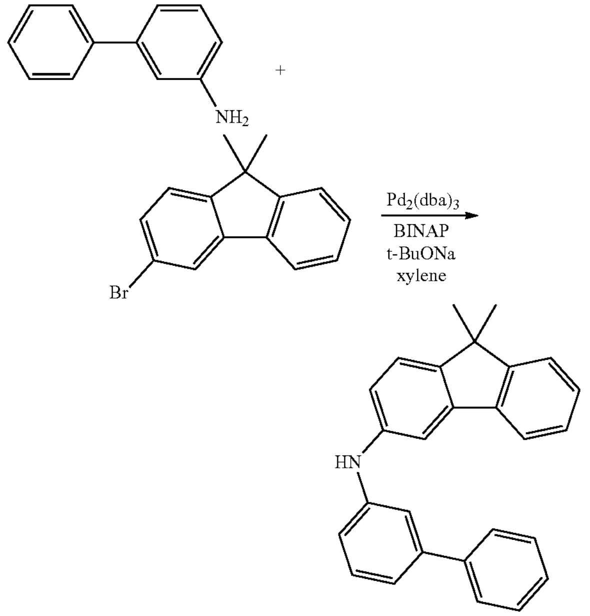

$Pd_2(dba)_3$ (587 mg, 1.28 mmol) and BINAP (1.59 g, 2.56 mmol) were added into a 500 mL three-neck flask, and xylene (130 mL) was added. The solution was purged with $N_2$ for 20 min until the color no longer changed, and [1,1'-biphenyl]-3-amine (5.6 g, 32.9 mmol), 3-bromo-9,9-dimethyl-fluorene (6.0 g, 21.9 mmol), and sodium tert-butoxide (5.3 g, 54.91 mmol) were sequentially added. $N_2$ was continued to be introduced for 10 min and the system was stirred at 110° C. until the raw materials were reacted completely. The solvent was removed through rotary evaporation under reduced pressure, and the resultant was purified through column chromatography to obtain a compound 9,9-dimethyl-N-([1,1'-biphenyl]-3-yl)-9H-fluoren-3-amine (6.5 g with a yield of 82%).

Step 2:

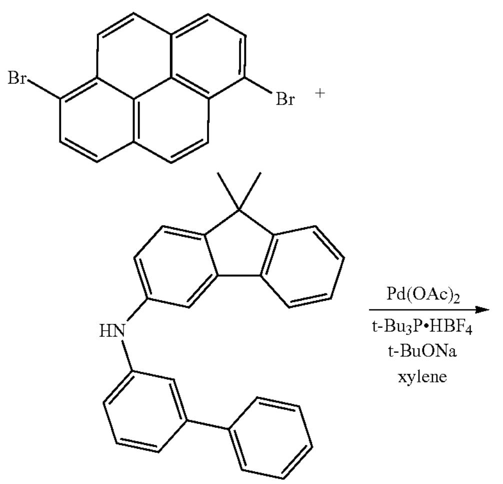

-continued

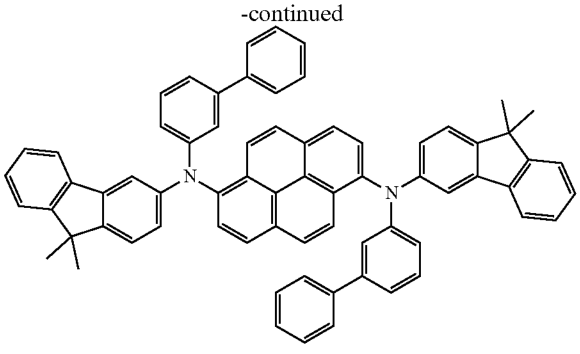

Compound A $Pd(OAc)_2$ (56 mg, 0.25 mmol) and t-$Bu_3PH{\cdot}BF_4$ (145 mg, 0.5 mmol) were added into a 250 mL three-neck flask, and xylene (100 mL) was added. The solution was purged with $N_2$ for 20 min until the color no longer changed, and 1,6-dibromopyrene (2.0 g, 5.5 mmol), the compound 9,9-dimethyl-N-([1,1'-biphenyl]-3-yl)-9H-fluoren-3-amine (6.5 g, 17.9 mmol), and sodium tert-butoxide (1.6 g, 16.6 mmol) were sequentially added. $N_2$ was continued to be introduced for 10 min and the system was stirred at 90° C. until the raw materials were reacted completely. The solvent was removed through rotary evaporation under reduced pressure, and the resultant was purified through column chromatography to obtain the product, compound A (4.0 g with a yield of 78%). The product was confirmed as the target product with a molecular weight of 920.4.

Comparative Synthesis Example 2: Synthesis of Comparative Compound B

Step 1:

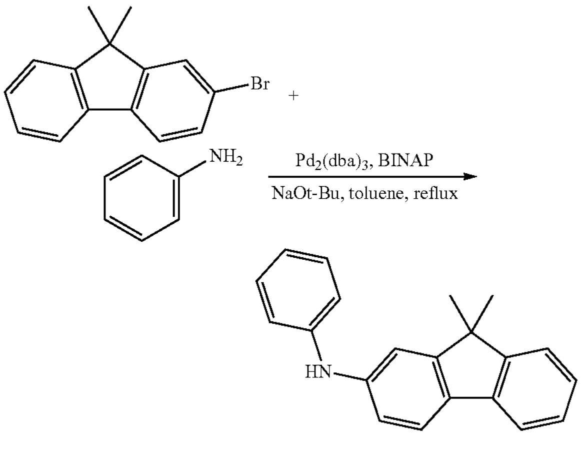

Under nitrogen protection and at room temperature, $Pd_2(dba)_3$ (2.1 g, 2.2 mmol) was added into toluene (200 mL) and stirred for 10 min, and then BINAP (3.0 g, 4.5 mmol) was added and stirred for 20 min. 2-Bromo-9,9-dimethyl-9H-fluorene (11.9 g, 44.1 mmol) was added into the reaction solution and stirred until it was completely dissolved. Phenylamine (6.1 g, 66.0 mmol) was added and stirred for 5 min. Then sodium tert-butoxide (12.9 g, 134.0 mmol) was added, and the reaction solution was warmed to 110° C. for 3 h. After the reaction was finished, the solvent was removed through rotary evaporation under reduced pressure, and the resultant was purified through column chromatography to obtain 9,9-dimethyl-N-phenyl-9H-fluoren-2-amine (11.5 g with a yield of 93%) as a white solid.

Step 2:

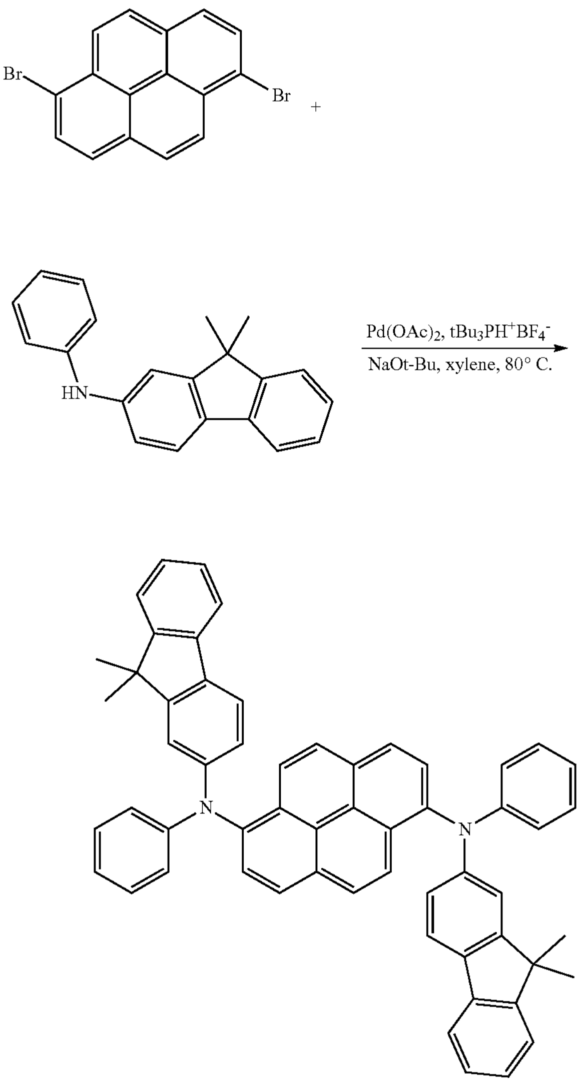

Compound B

Under nitrogen protection and at room temperature, $Pd(OAc)_2$ (60.0 mg, 0.25 mmol) was added into xylene (50 mL) and stirred for 10 min, and then t-$Bu_3PH{\cdot}BF_4$ (145.0 mg, 0.5 mmol) was added and stirred for 20 min 1,6-Dibromopyrene (1.8 g, 5.0 mmol) was added into the reaction system and stirred until it was dissolved completely. Then 9,9-dimethyl-N-phenyl-9H-fluoren-2-amine (4.2 g, 15.0 mmol) was added into the reaction solution and stirred until it was dissolved completely. Then sodium tert-butoxide (2.0 g, 20.0 mmol) was added, and the reaction solution was warmed to 95° C. After the reaction was finished, the solvent was removed through rotary evaporation under reduced pressure, and the resultant was purified through column chromatography to obtain compound B (3.0 g with a yield of 78%). The product was confirmed as the target product with a molecular weight of 768.4.

Comparative Synthesis Example 3: Synthesis of Comparative Compound C

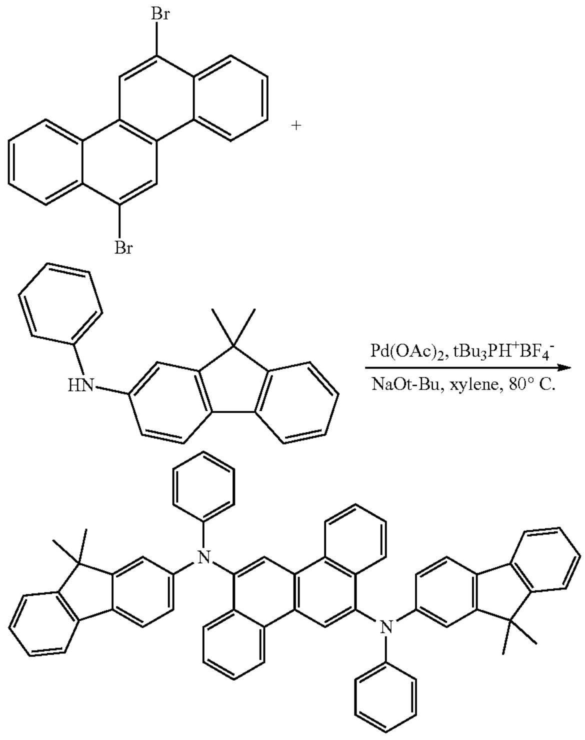

Compound C $Pd(OAc)_2$ (60 mg, 0.25 mmol) and t-$Bu_3PH{\cdot}BF_4$ (145 mg, 0.5 mmol) were put into a 100 mL three-neck flask, and xylene (50 mL) was added. The solution was purged with $N_2$ for 20 min until the color no longer changed, and 6,12-dibromochrysene (1.9 g, 5 mmol), 9,9-dimethyl-N-phenyl-9H-fluoren-2-amine (4.275 g, 15 mmol), and sodium tert-butoxide (2.0 g, 20 mmol) were sequentially added. $N_2$ was continued to be introduced for 10 min and the system was heated to 80° C. until the raw materials were reacted completely. After the reaction was finished, column chromatography was performed to obtain the product, compound C (2.8 g with a yield of 70%). The product was confirmed as the target product with a molecular weight of 794.4.

Those skilled in the art will appreciate that the above preparation methods are merely illustrative. Those skilled in the art can obtain other compound structures of the present disclosure through the improvements of the preparation methods.

Device Example

First, a glass substrate having an Indium Tin Oxide (ITO) anode with a thickness of 80 nm was cleaned and then treated with oxygen plasma and UV ozone. After the treatment, the substrate was dried in a glovebox to remove water. The substrate was mounted on a substrate holder and placed in a vacuum chamber. Organic layers specified below were sequentially deposited through vacuum thermal evaporation on the ITO anode at a rate of 0.2 to 2 Angstroms per second at a vacuum degree of about $10^{-8}$ torr. Compound HI was used as a hole injection layer (HIL). Compound HT was used as a hole transport layer (HTL). Compound EB was used as an electron blocking layer (EBL). Compound BH and the compound of the present disclosure were co-deposited as an emissive layer (EML). Compound HB was used as a hole blocking layer (HBL). On the HBL, Compound ET and 8-hydroxyquinolinolato-lithium (Liq) were co-deposited as an electron transport layer (ETL). Finally, 8-hydroxyquinolinolato-lithium (Liq) with a thickness of 1 nm was deposited as an electron injection layer, and Al with a thickness of 120 nm was deposited as a cathode. The device was transferred back to the glovebox and encapsulated with a glass lid and a moisture getter to complete the device.

Comparative Examples were prepared in the same manner except that the compound of the present disclosure was substituted with comparative compounds.

Detail structures and thicknesses of part of layers of the device are shown in tables 1 to 5. A layer using more than one material was obtained by doping different compounds in their weight proportions as described.

TABLE 1

Part device structures in Device Examples 1, 2, and 5 and Comparative Example 1

| Device ID | HIL | HTL | EBL | EML | HBL | ETL |
|---|---|---|---|---|---|---|
| Example 1 | Compound HI (100 Å) | Compound HT (1200 Å) | Compound EB (50 Å) | Compound BH:compound 339 (98:2) (250 Å) | Compound HB (50 Å) | Compound ET:Liq (40:60) (120 Å) |
| Example 2 | Compound HI (100 Å) | Compound HT (1200 Å) | Compound EB (50 Å) | Compound BH:compound 347 (98:2) (250 Å) | Compound HB (50 Å) | Compound ET:Liq (40:60) (120 Å) |
| Example 5 | Compound HI (100 Å) | Compound HT (1200 Å) | Compound EB (50 Å) | Compound BH:compound 609 (98:2) (250 Å) | Compound HB (50 Å) | Compound ET:Liq (40:60) (120 Å) |
| Comparative Example 1 | Compound HI (100 Å) | Compound HT (1200 Å) | Compound EB (50 Å) | Compound BH:compound A (98:2) (250 Å) | Compound HB (50 Å) | Compound ET:Liq (40:60) (120 Å) |

Structures of the materials used in the devices are shown as follows:
Compound HI
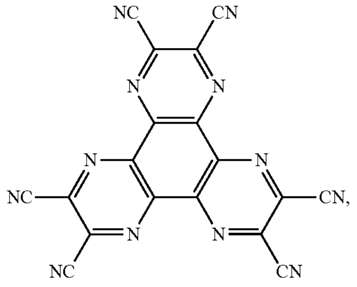
Compound HT
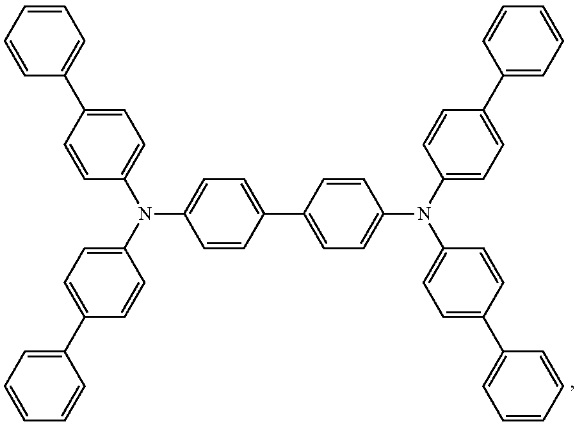
Compound EB
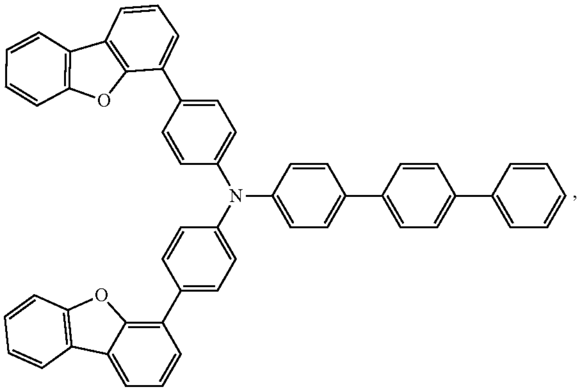
Compound BH
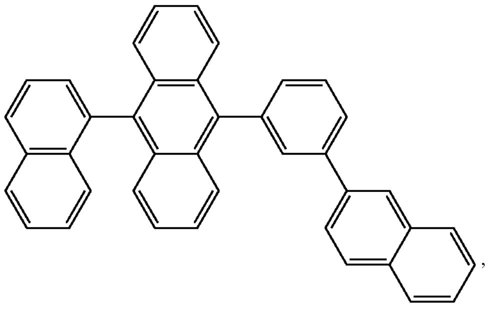
-continued
Compound HB
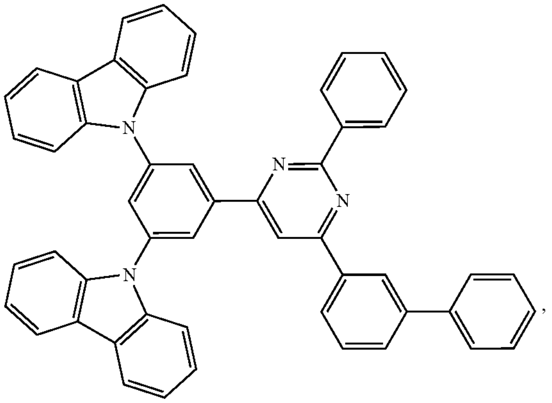
Compound ET
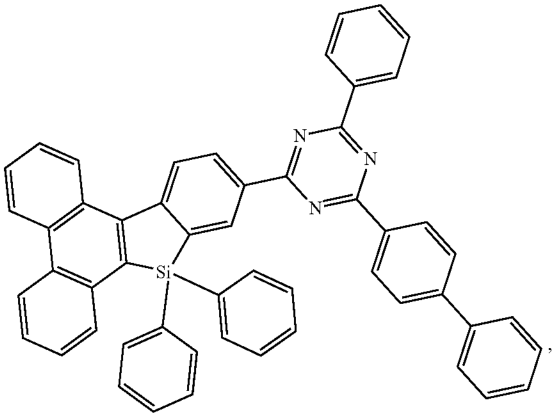
Compound 339
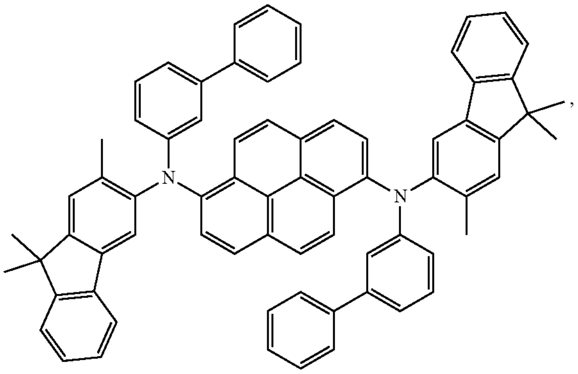
Compound 347
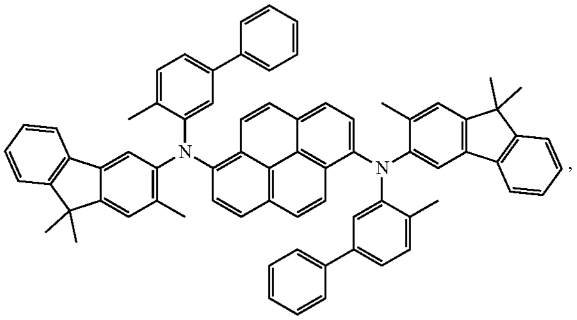

-continued

Compound 609

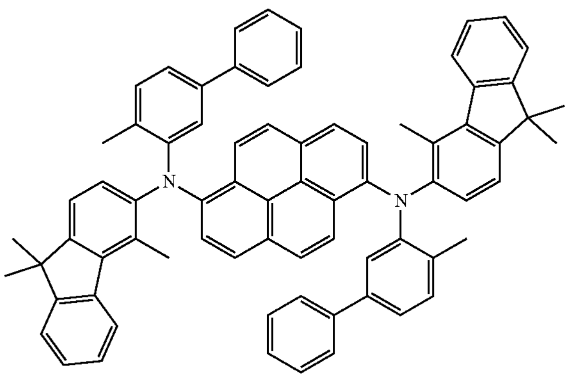

,

Compound A

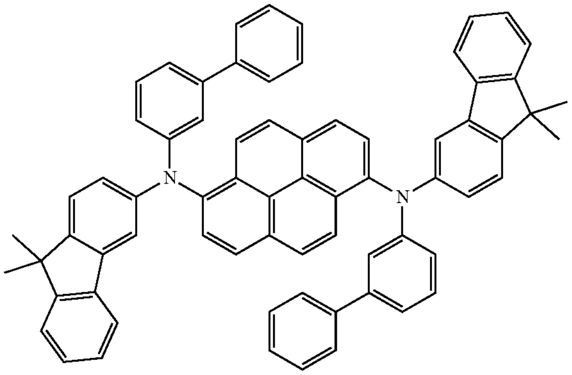

.

IVL of the devices was measured at different current densities and voltages. Device data, including LT97, external quantum efficiency (EQE), maximum emission wavelength ($\lambda_{max}$), full width at half maximum (FWHM), and CIE, were measured at a constant current of 10 mA/cm$^2$ in all Examples and Comparative Examples. LT97 represents the lifetime for a device to decay to 97% of initial brightness.

Discussion:

When the materials of the present disclosure are used as doping materials in the emissive layer, at the constant current of 10 mA/cm$^2$, Example 1 (with a doping proportion of 2%) exhibits EQE of 9.46%, maximum emission wavelength of 464 nm, CIE of (0.131, 0.137), LT97 of 360 h, and a half-peak width of 32.7 nm. Compared with Comparative Example 1 with the same doping proportion of 2% (which exhibits EQE of 8.06%, maximum emission wavelength of 469 nm, CIE of (0.127, 0.181), LT97 of 271 h, and a half-peak width of 37.1 nm), Example 1 has improved the EQE by 17.3% and the lifetime by 32.8%, narrowed the half-peak width by 4.4 nm, and achieved a blue-shift of 5 nm of the maximum emission wavelength. Example 2 (with a doping proportion of 2%) exhibits EQE of 9.56%, maximum emission wavelength of 461 nm, CIE of (0.134, 0.121), LT97 of 553 h, and a half-peak width of 34.3 nm. Compared with Comparative Example 1 (with a doping proportion of 2%), Example 2 has improved the lifetime by 104% and the EQE by 18.6%, narrowed the half-peak width by 2.8 nm, and achieved a blue-shift of 8 nm, thereby effectively improving blue light-emitting performance Example 5 (with a doping proportion of 2%) exhibits EQE of 9.06%, maximum emission wavelength of 460 nm, CIE of (0.136, 0.121), LT97 of 482 h, and a half-peak width of 33.8 nm. Compared with Comparative Example 1 (with a doping proportion of 2%), Example 5 has improved the lifetime by about 77.9% and the EQE by 12.4%, narrowed the half-peak width by 3.3 nm, and achieved a blue-shift of 9 nm.

It can be seen that through the introduction of an ortho-substituent into the fluorene ring, that is, the introduction of R" in Formula 4, the compounds of the present disclosure can significantly improve the EQE and the lifetime of the devices, and decrease the CIE y value to achieve deep-blue emission of less than 0.14, thereby improving device performance significantly.

TABLE 2

Part device structures in Device Examples 3 and 4 and Comparative Examples 2 and 3

| Device ID | HIL | HTL | EBL | EML | HBL | ETL |
|---|---|---|---|---|---|---|
| Example 3 | Compound HI (100 Å) | Compound HT (1200 Å) | Compound EB (50 Å) | Compound BH:compound 73 (96:4) (250 Å) | Compound HB (50 Å) | Compound ET:Liq (40:60) (120 Å) |
| Example 4 | Compound HI (100 Å) | Compound HT (1200 Å) | Compound EB (50 Å) | Compound BH:compound 743 (96:4) (250 Å) | Compound HB (50 Å) | Compound ET:Liq (40:60) (120 Å) |
| Comparative Example 2 | Compound HI (100 Å) | Compound HT (1200 Å) | Compound EB (50 Å) | Compound BH:compound B (96:4) (250 Å) | Compound HB (50 Å) | Compound ET:Liq (40:60) (120 Å) |
| Comparative Example 3 | Compound HI (100 Å) | Compound HT (1200 Å) | Compound EB (50 Å) | Compound BH:compound A (96:4) (250 Å) | Compound HB (50 Å) | Compound ET:Liq (40:60) (120 Å) |

Structures of the new materials used in the devices are shown as follows:

Compound 73

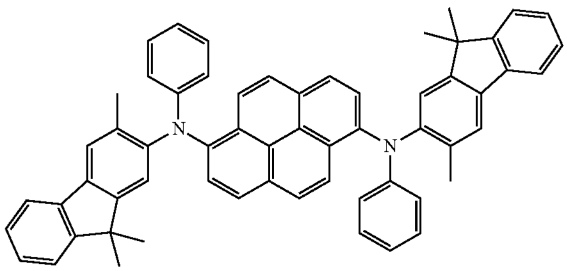

,

-continued

Compound 743

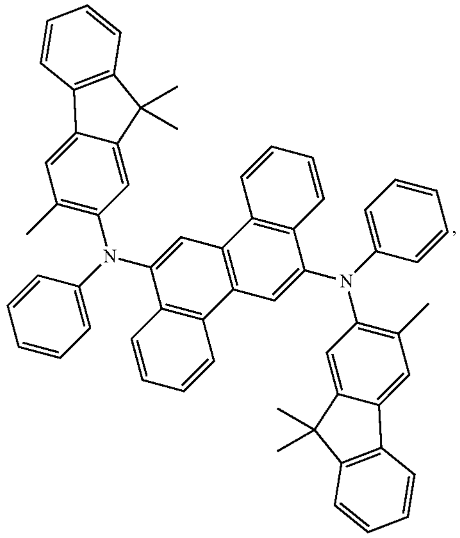

,

Compound B

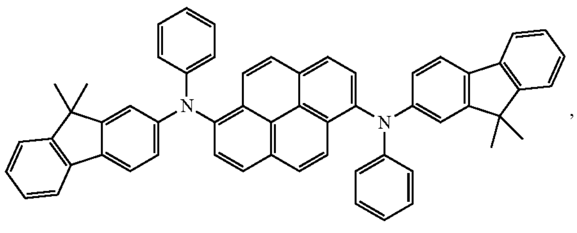

,

-continued

Compound C

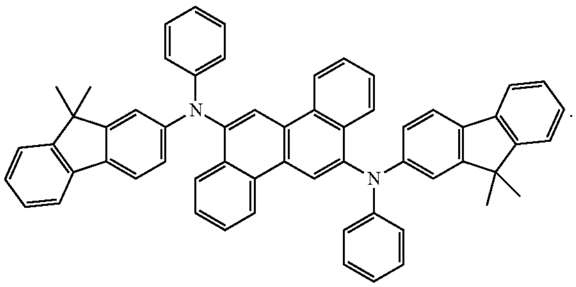

.

Discussion:

Additionally, when the compounds of the present disclosure have a pyrene core, Example 3 (with a doping proportion of 4%) exhibits EQE of 8.38%, maximum emission wavelength of 474 nm, CIE of (0.125, 0.239), and a half-peak width of 34.9 nm. Comparative Example 2 (with a doping proportion of 4%) exhibits EQE of 7.57%, maximum emission wavelength of 481 nm, CIE of (0.132, 0.334), and a half-peak width of 38.3 nm. Compared with Comparative Example 2, Example 3 has improved the EQE by 10.7%, narrowed the half-peak width by 3.4 nm, achieved a blue-shift of 7 nm of the maximum emission wavelength, and significantly decreased the CIE y value at the same doping proportion. When the compounds of the present disclosure have a chrysene core, Example 4 (with a doping proportion of 4%) exhibits EQE of 7.20%, maximum emission wavelength of 461 nm, CIE of (0.137, 0.126), and a half-peak width of 47.4 nm. Comparative Example 3 (with a doping proportion of 4%) exhibits EQE of 6.88%, maximum emission wavelength of 466 nm, CIE of (0.134, 0.165), and a half-peak width of 47.0 nm. Compared with Comparative Example 3, Example 4 has improved the EQE by 4.6%, achieved a blue-shift of 5 nm of the maximum emission wavelength, and significantly decreased the CIE y value at the same doping proportion.

It can be seen that through the introduction of the ortho-substituent into the fluorene ring, that is, the introduction of R" in Formula 4, the compounds of the present disclosure can also significantly improve the device performance when the doping proportion is changed.

TABLE 3

Part device structures in Device Examples 6 and 7

| Device ID | HIL | HTL | EBL | EML | HBL | ETL |
|---|---|---|---|---|---|---|
| Example 6 | Compound HI (100 Å) | Compound HT (1200 Å) | Compound EB (50 Å) | Compound BH:compound 419 (98:2) (250 Å) | Compound HB (50 Å) | Compound ET:Liq (40:60) (120 Å) |
| Example 7 | Compound HI (100 Å) | Compound HT (1200 Å) | Compound EB (50 Å) | Compound BH:compound 422 (98:2) (250 Å) | Compound HB (50 Å) | Compound ET:Liq (40:60) (120 Å) |

Structures of the new materials used in the devices are shown as follows:

Compound 419

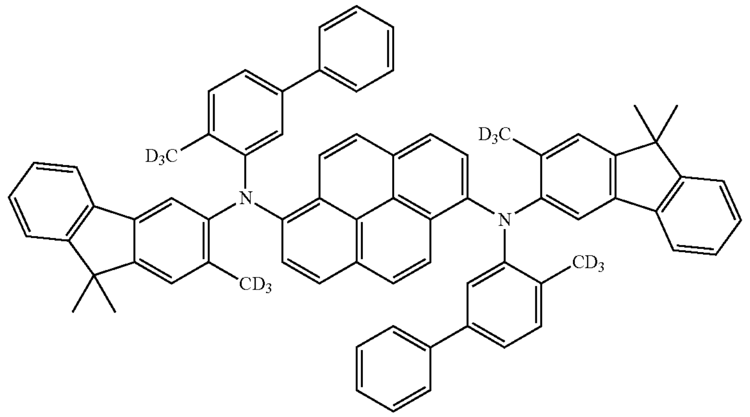

and

Compound 422

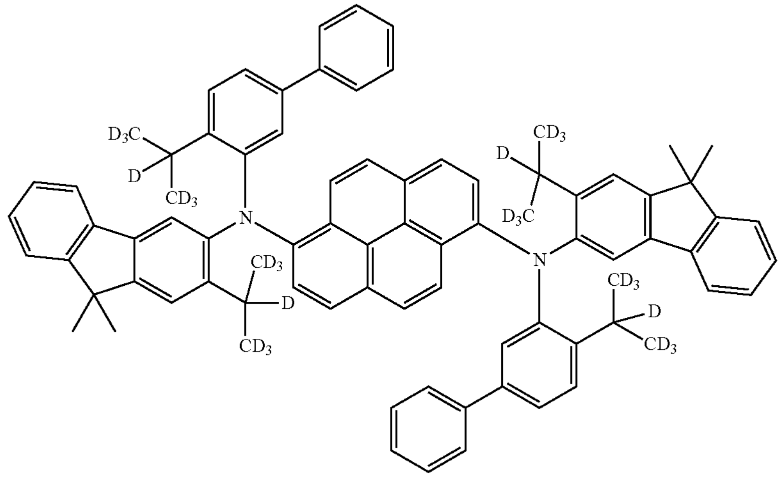

.

Discussion:

Example 6 (with a doping proportion of 2%) exhibits EQE of 9.72%, maximum emission wavelength of 461 nm, CIE of (0.134, 0.123), LT97 of 879 h, and a half-peak width of 33.7 nm. Compared with Comparative Example 1, Example 6 has improved the lifetime by 224% and the EQE by 20.5%, narrowed the half-peak width by 3.4 nm, and achieved a blue-shift of 8 nm at the same doping proportion. Based on the excellent device performance of Example 2, Example 6 has further improved the lifetime by 58.9% and the EQE by 1.6%, and narrowed the half-peak width by 0.6 nm. Example 7 (with a doping proportion of 2%) exhibits EQE of 9.59%, maximum emission wavelength of 460 nm, CIE of (0.134, 0.114), LT97 of 395 h, and a half-peak width of 30.2 nm. Compared with Comparative Example 1, Example 7 has improved the lifetime by 45.7% and the EQE by 18.9%, narrowed the half-peak width by 6.9 nm, and achieved a blue-shift of 9 nm at the same doping proportion. Moreover, based on Example 6, Example 7 has further narrowed the half-peak width by 3.5 nm.

It can be seen that through the introduction of the ortho-substituent into the fluorene ring, that is, the introduction of R" in Formula 4, the compounds of the present disclosure can more significantly improve the EQE and the lifetime of the devices by introducing deuterated alkyl compared with common alkyl. Meanwhile, the half-peak width can be further narrowed.

TABLE 4

Part device structures in Device Examples 8 and 9

| Device ID | HIL | HTL | EBL | EML | HBL | ETL |
|---|---|---|---|---|---|---|
| Example 8 | Compound HI (100 Å) | Compound HT (1200 Å) | Compound EB (50 Å) | Compound BH:compound 2333 (98:2) (250 Å) | Compound HB (50 Å) | Compound ET:Liq (40:60) (120 Å) |
| Example 9 | Compound HI (100 Å) | Compound HT (1200 Å) | Compound EB (50 Å) | Compound BH:compound 2334 (98:2) (250 Å) | Compound HB (50 Å) | Compound ET:Liq (40:60) (120 Å) |

Structures of the new materials used in the devices are shown as follows:

Compound 2333

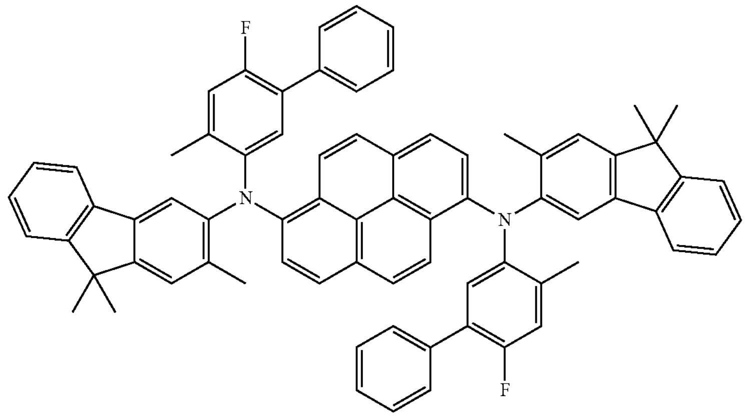

and

Compound 2334

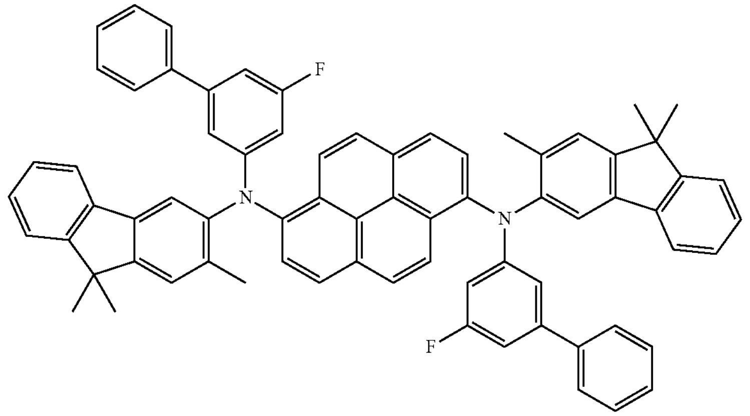

.

Discussion:

Example 8 (with a doping proportion of 2%) exhibits EQE of 9.54%, maximum emission wavelength of 460 nm, CIE of (0.135, 0.114), LT97 of 796 h, and a half-peak width of 33.6 nm. Compared with Comparative Example 1, Example 8 has improved the lifetime by 193% and the EQE by 18.3%, narrowed the half-peak width by 3.5 nm, and achieved a blue-shift of 9 nm at the same doping proportion. Based on the excellent device performance of Example 2, Example 8 has further improved the lifetime by 43.9% and narrowed the half-peak width by 0.7 nm.

Example 9 (with a doping proportion of 2%) exhibits EQE of 9.16%, maximum emission wavelength of 456 nm, CIE of (0.139, 0.090), LT97 of 683 h, and a half-peak width of 32.2 nm. Compared with Comparative Example 1, Example 9 has improved the lifetime by 152% and the EQE by 13.6%, narrowed the half-peak width by 4.9 nm, and achieved a blue-shift of 13 nm at the same doping proportion. Based on the excellent device performance of Example 1, Example 9 has further improved the lifetime by 89.7% and narrowed the half-peak width by 0.5 nm.

It can be seen that through the introduction of an electron-deficient group into the aromatic ring directly connecting to nitrogen, which is in the substituent R of Formula 3, the maximum emission wavelength can be further blue-shifted and the device lifetime can be further improved, while maintaining a longer device lifetime and higher EQE.

TABLE 5

Part device structures in Device Examples 10 and 11

| Device ID | HIL | HTL | EBL | EML | HBL | ETL |
|---|---|---|---|---|---|---|
| Example 10 | Compound HI (100 Å) | Compound HT (1200 Å) | Compound EB (50 Å) | Compound BH:compound 506 (98:2) (250 Å) | Compound HB (50 Å) | Compound ET:Liq (40:60) (120 Å) |
| Example 11 | Compound HI (100 Å) | Compound HT (1200 Å) | Compound EB (50 Å) | Compound BH:compound 2350 (98:2) (250 Å) | Compound HB (50 Å) | Compound ET:Liq (40:60) (120 Å) |

Structures of the new materials used in the devices are shown as follows:

Compound 506

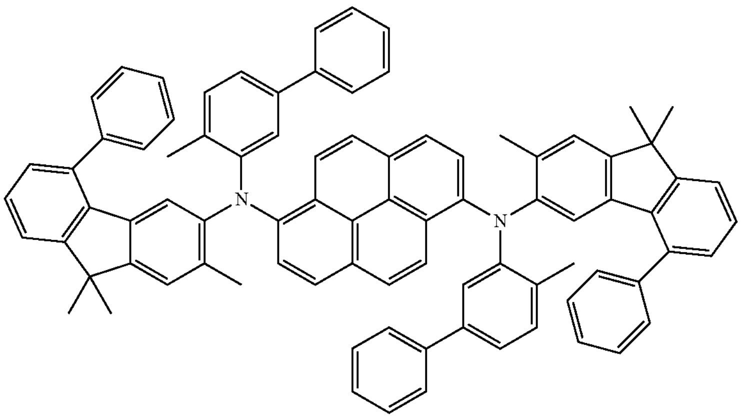

and

Compound 2350

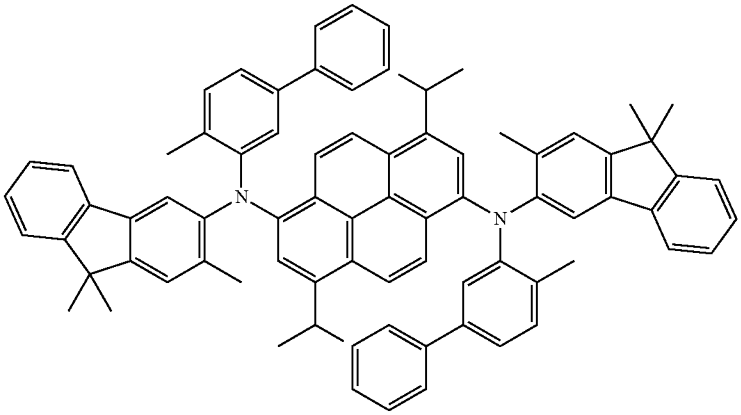

.

Example 10 (with a doping proportion of 2%) exhibits EQE of 9.57%, maximum emission wavelength of 461 nm, CIE of (0.135, 0.117), LT97 of 382 h, and a half-peak width of 33.5 nm. Compared with Comparative Example 1, Example 10 has improved the lifetime by 40.9% and the EQE by 18.7%, narrowed the half-peak width by 3.6 nm, and achieved a blue-shift of 8 nm at the same doping proportion.

It can be seen that through further substitution in the fluorene ring in Formula 4, that is, an aryl substituent further included in R' in Formula 4, the EQE and the lifetime of the device can also be improved, thereby improving the overall performance of the device.

Example 11 (with a doping proportion of 2%) exhibits EQE of 9.35%, maximum emission wavelength of 463 nm, CIE of (0.136, 0.137), LT97 of 459 h, and a half-peak width of 31.5 nm. Compared with Comparative Example 1, Example 11 has improved the lifetime by about 69.4% and the EQE by 16%, narrowed the half-peak width by 5.6 nm, and achieved a blue-shift of 6 nm at the same doping proportion. Moreover, compared with Example 2 in which the half-peak width has been narrowed by 2.8 nm, Example 11 has further narrowed the half-peak width by 2.8 nm.

It is seen from the above comparison that when the substituents of the nitrogen atom, that is, $Ar_2$ and R in Formula 3 remain the same, the introduction of substituents into $R_3$ and $R_8$ in Formula 5 can achieve a narrower half-peak width while maintaining relatively high EQE and lifetime, thereby further improving performance.

In summary, for compounds with different structures of A such as pyrene and chrysene in the present disclosure, the introduction of the ortho-substituent into the fluorene ring, that is, the introduction of R" in Formula 4 exhibits significant improvements in overall blue light-emitting performance. In addition, the further introduction of substituents at different positions, such as the introduction of substituents into $R_3$ and $R_8$ in Formula 5 and the introduction of an electron-deficient group into the aromatic ring joined to the nitrogen atom in Formula 3, can achieve longer device lifetime, higher EQE, narrower half-peak width, and deep-blue emission with CIE y being less than 0.14, thereby achieving a very large improvement in device performance. These compounds are of great help to the commercial use of blue light-emitting materials in OLEDs.

It should be understood that various embodiments described herein are merely examples and not intended to limit the scope of the present disclosure. Therefore, it is apparent to those skilled in the art that the present disclosure as claimed may include variations from specific embodiments and preferred embodiments described herein. Many of materials and structures described herein may be substituted with other materials and structures without departing from the spirit of the present disclosure. It should be understood that various theories as to why the present disclosure works are not intended to be limitative.

What is claimed is:

1. A compound having a structure represented by one of Formula 5 to Formula 6:

Formula 5

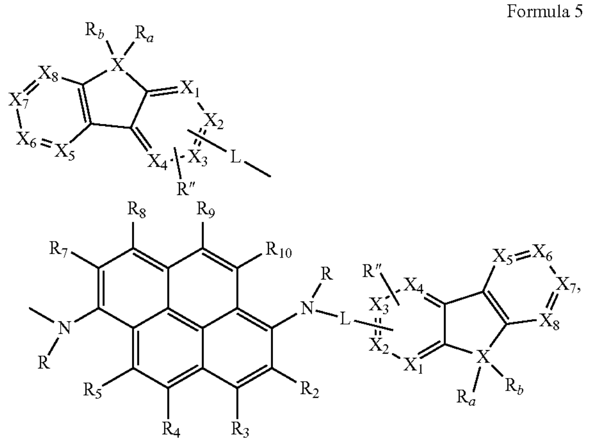

Formula 6

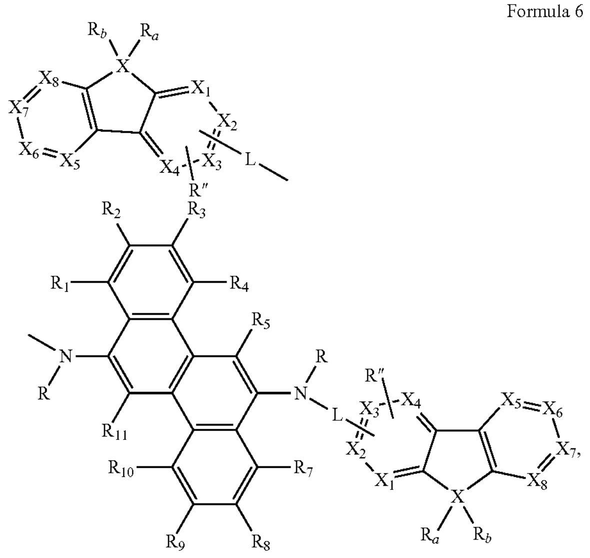

in Formula 5 to Formula 6, $R_1$ to $R_5$ and $R_7$ to $R_{11}$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

R is selected from the group consisting of: substituted or unsubstituted aryl having 6 to 30 ring carbon atoms and substituted or unsubstituted heteroaryl having 3 to 30 ring atoms; and when R is selected from the aryl, R is not substituted or unsubstituted naphthyl;

the moiety

Formula 4

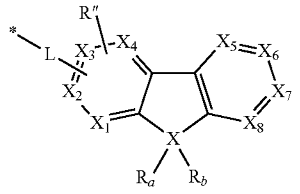

comprises only one fluorene ring structure, azafluorene ring structure, spirobifluorene ring structure, or azaspirobifluorene ring structure;

X is C or Si;

L is selected from a single bond, substituted or unsubstituted arylene having 6 to 60 carbon atoms, or substituted or unsubstituted heteroarylene having 3 to 60 carbon atoms;

$X_5$ to $X_8$ are each independently selected from CR' or N, and two adjacent C are present in $X_1$ to $X_4$, wherein one of the two adjacent C is joined to L, and the other one of the two adjacent C is joined to R"; and the other two of $X_1$ to $X_4$ are each independently selected from CR' or N;

$R_a$, $R_b$, and R' are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof;

substituents $R_a$ and $R_b$ can be optionally joined to form a ring, and two adjacent substituents R' can be optionally joined to form a ring; and R" is selected from halogen, substituted or unsubstituted alkyl having 1 to 20 carbon atoms, or substituted or unsubstituted cycloalkyl having 3 to 20 ring carbon atoms.

2. The compound of claim 1, wherein in Formula 5 to Formula 6, each L is joined to $X_2$, or each L is joined to $X_3$.

3. The compound of claim 1, wherein L is independently selected from a single bond, substituted or unsubstituted arylene having 6 to 12 carbon atoms, or substituted or unsubstituted heteroarylene having 3 to 12 carbon atoms.

4. The compound of claim 1, wherein R' is each independently selected from hydrogen, deuterium, halogen, substituted or unsubstituted alkyl having 1 to 6 carbon atoms, substituted or unsubstituted cycloalkyl having 3 to 10 ring carbon atoms, substituted or unsubstituted aryl having 6 to 12 carbon atoms, substituted or unsubstituted heteroaryl having 3 to 12 carbon atoms, a nitrile group, or combinations thereof.

5. The compound of claim 1, wherein $R_a$ and $R_b$ are each independently selected from substituted or unsubstituted alkyl having 1 to 6 carbon atoms or substituted or unsubstituted cycloalkyl having 3 to 10 ring carbon atoms, and $R_a$ and $R_b$ are not joined to form a ring.

6. The compound of claim 1, wherein R has a structure represented by Formula 17:

Formula 17

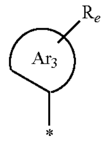

in Formula 17, * represents a position where R is joined to N shown in Formula 5 or 6;

wherein the ring $Ar_3$ is aryl having 6 to 30 ring carbon atoms or heteroaryl having 3 to 30 ring atoms; and when the ring $Ar_3$ is aryl, the ring $Ar_3$ is not a naphthalene ring structure;

wherein $R_e$ represents mono-substitution, multi-substitution, or non-substitution; and $R_e$ is selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof.

7. The compound of claim 1, wherein R has a structure represented by Formula 14:

Formula 14

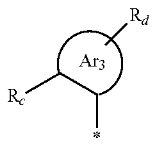

in Formula 14, * represents a position where R is joined to N shown in Formula 5 or 6;

wherein the ring $Ar_3$ is aryl having 6 to 30 ring carbon atoms or heteroaryl having 3 to 30 ring atoms; and when the ring $Ar_3$ is aryl, the ring $Ar_3$ is not a naphthalene ring structure;

$R_c$ represents ortho-substitution of the position where R is joined to N shown in Formula 5 or 6, and $R_d$ represents mono-substitution, multi-substitution, or non-substitution;

wherein $R_d$ is selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof;

wherein $R_c$ is selected from the group consisting of: deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a nitrile group, an isonitrile group, a thiol group, a sulfinyl group, a sulfonyl group, a phosphino group, and combinations thereof.

8. The compound of claim 6, wherein the ring $Ar_3$ is selected from any one of the following ring structures: a benzene ring, a triphenylene ring, a tetraphenylene ring, a phenanthrene ring, an anthracene ring, an indene ring, a fluorene ring, a chrysene ring, an indole ring, a carbazole ring, a benzofuran ring, a dibenzofuran ring, a benzosilole ring, a dibenzosilole ring, a benzothiophene ring, a dibenzothiophene ring, a dibenzoselenophene ring, or aza-structures of any one of the above ring structures.

9. The compound of claim 7, wherein the ring $Ar_3$ is selected from any one of the following ring structures: a benzene ring, a triphenylene ring, a tetraphenylene ring, a phenanthrene ring, an anthracene ring, an indene ring, a fluorene ring, a chrysene ring, an indole ring, a carbazole ring, a benzofuran ring, a dibenzofuran ring, a benzosilole ring, a dibenzosilole ring, a benzothiophene ring, a dibenzothiophene ring, a dibenzoselenophene ring, or aza-structures of any one of the above ring structures.

10. The compound of claim 7, wherein $R_c$ is selected from methyl, deuterated methyl, ethyl, deuterated ethyl, n-propyl, deuterated n-propyl, isopropyl, deuterated isopropyl, cyclopropyl, deuterated cyclopropyl, n-butyl, deuterated n-butyl, isobutyl, deuterated isobutyl, t-butyl, deuterated t-butyl, cyclopentyl, deuterated cyclopentyl, neopentyl, deuterated neopentyl, cyclohexyl, deuterated cyclohexyl, 4,4-dimethylcyclohexyl, or deuterated 4,4-dimethylcyclohexyl, $R_d$ represents non-substitution, or $R_d$ represents mono-substitution and $R_d$ is each independently selected from the group consisting of: substituted or unsubstituted aryl having 6 to 12 carbon atoms or substituted or unsubstituted heteroaryl having 3 to 12 carbon atoms.

11. The compound of claim 1, wherein the moiety

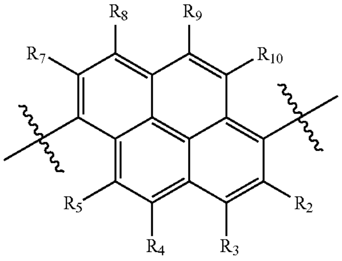

in Formula 5 or the moiety

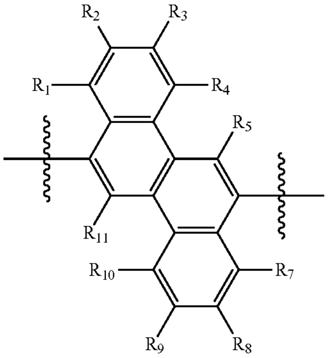

in Formula 6 is referred as A, and the moiety

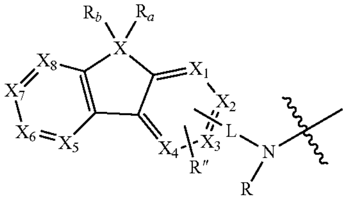

is referred as B, and

B is selected from the group consisting of the following structures:

B-1-1

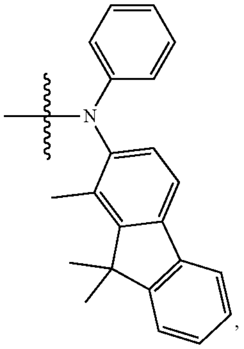

-continued

B-1-2

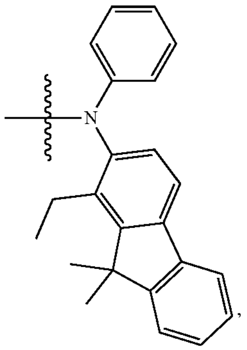

B-1-3

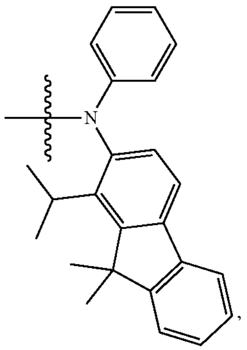

B-1-4

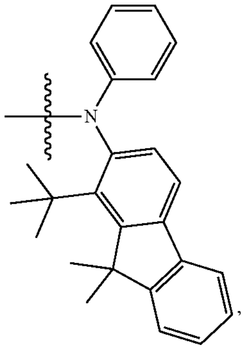

B-1-5

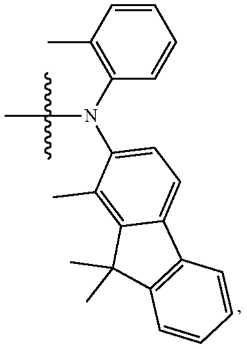

-continued
B-1-6
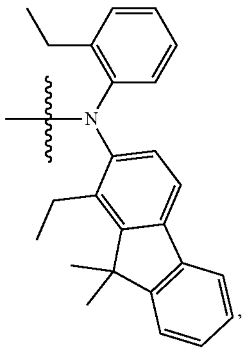
B-1-7
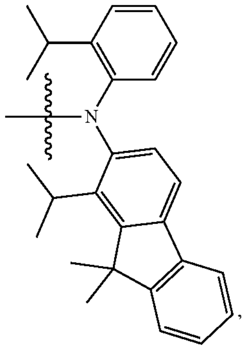
B-1-8
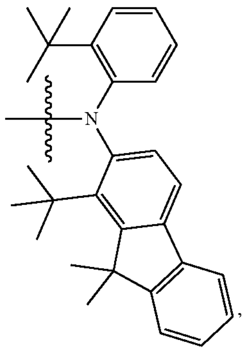
B-1-9
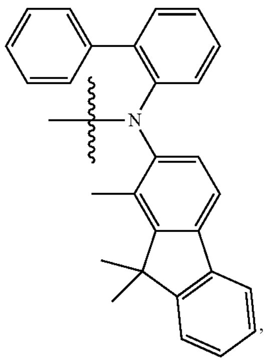
-continued
B-1-10
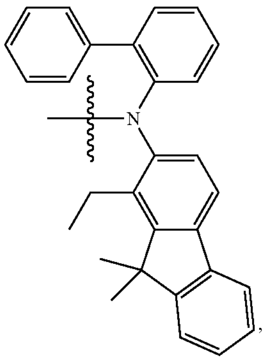
B-1-11
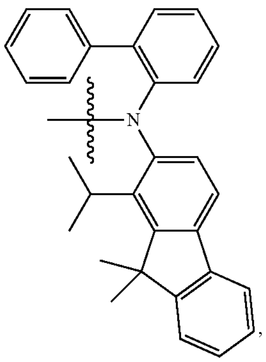
B-1-12
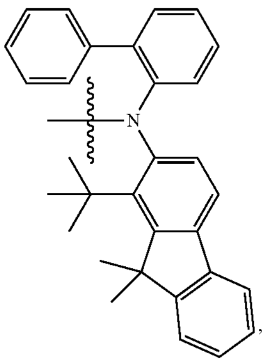
B-1-13
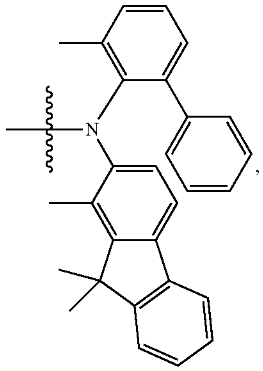

-continued
B-1-14
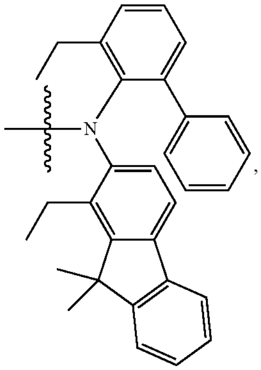
,
B-1-15
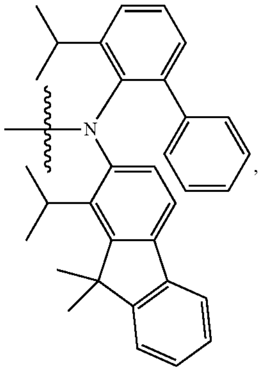
,
B-1-16
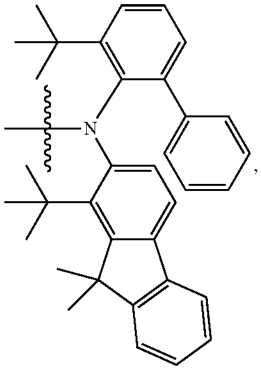
,
B-1-17
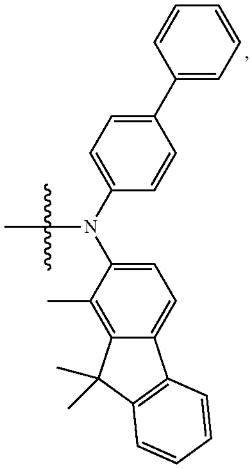
,
-continued
B-1-18
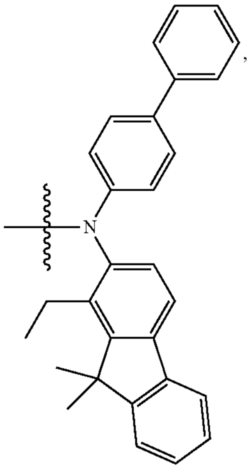
,
B-1-19
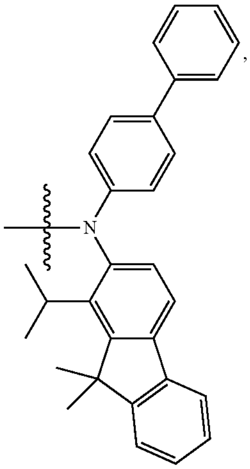
,
B-1-20
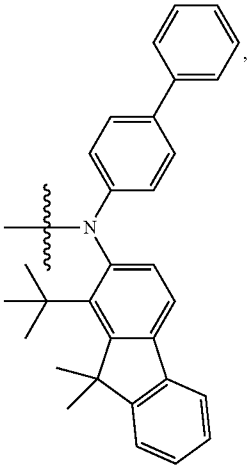
, -continued
B-1-21
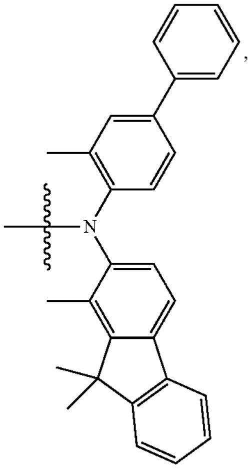
,
B-1-22
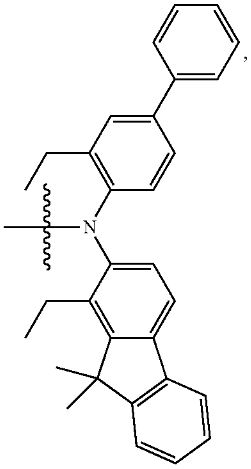
,
B-1-23
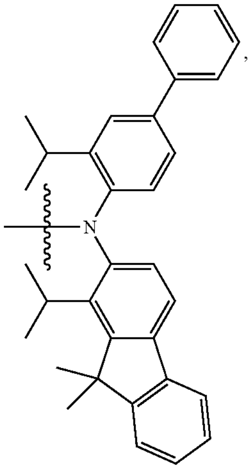
,
-continued
B-1-24
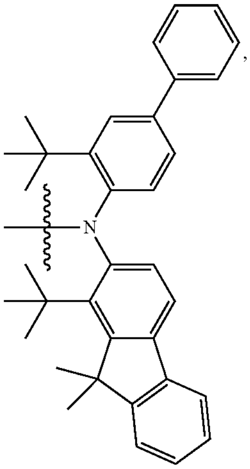
,
B-1-25
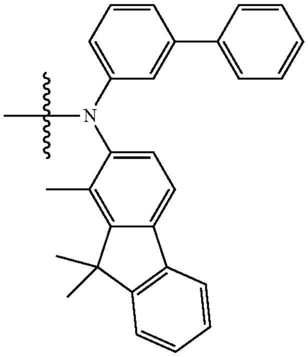
,
B-1-26
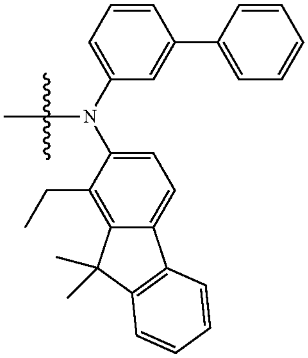
,
B-1-27
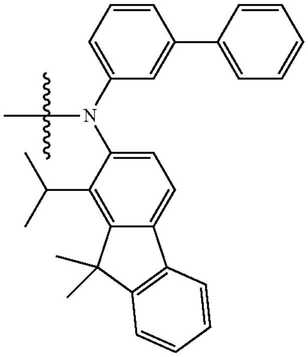
, B-1-28
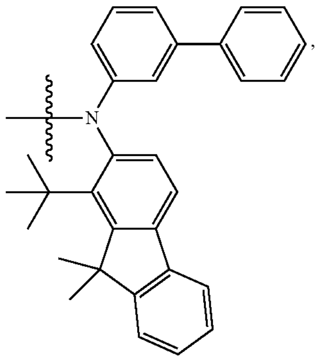
B-1-29
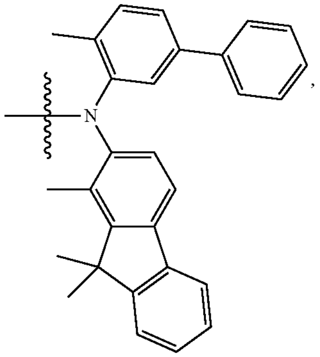
B-1-30
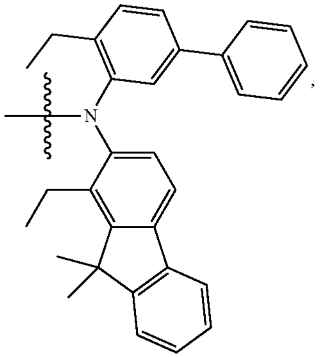
B-1-31
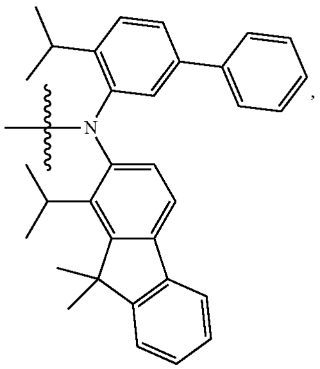
B-1-32
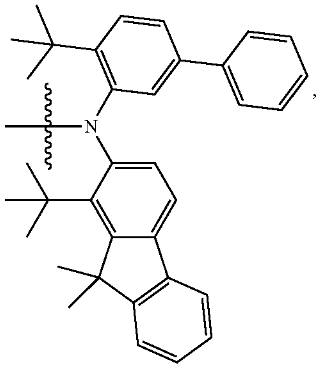
B-1-33
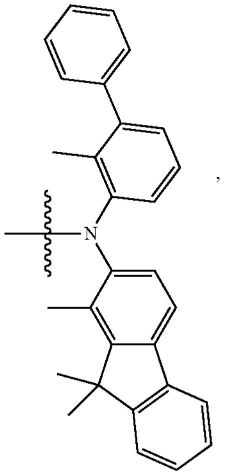
B-1-34
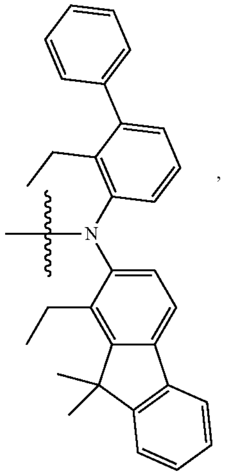

-continued
B-1-35
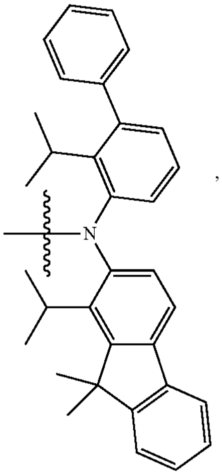
,
B-1-36
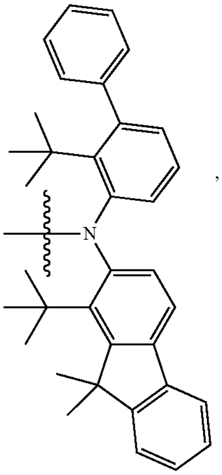
,
B-1-37
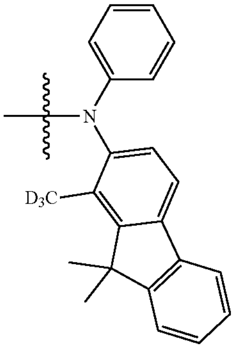
,
B-1-38
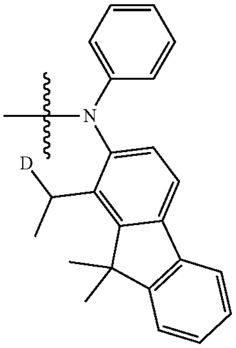
,
-continued
B-1-39
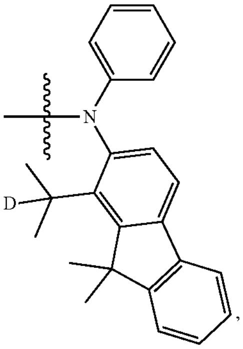
,
B-1-40
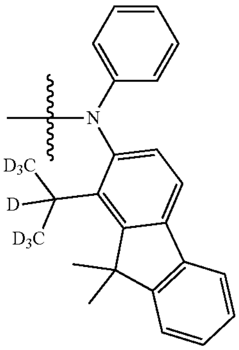
,
B-1-41
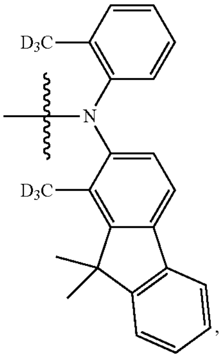
,
B-1-42
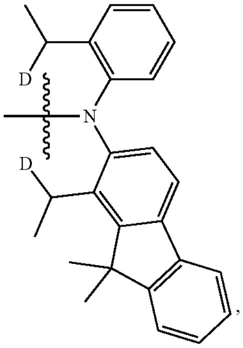
, -continued
B-1-43
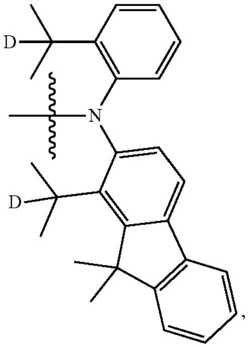
B-1-44
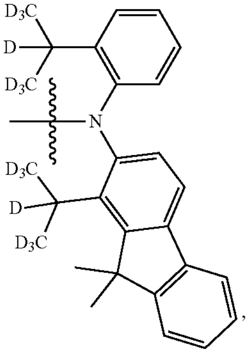
B-1-45
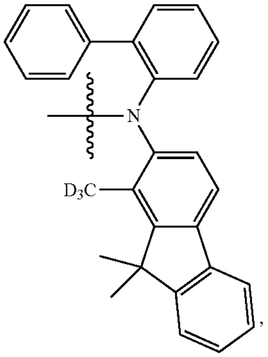
B-1-46
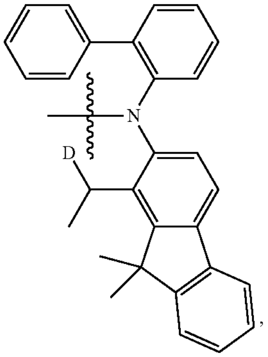
-continued
B-1-47
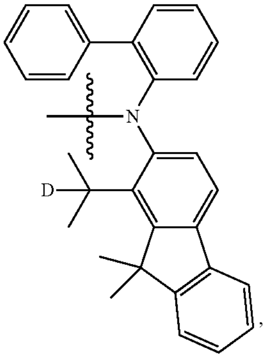
B-1-48
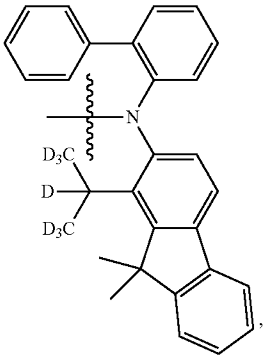
B-1-49
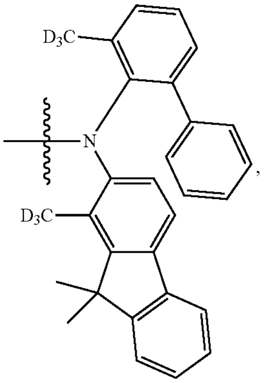
B-1-50
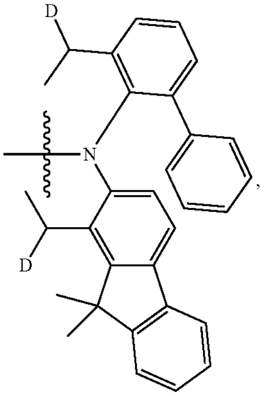

-continued
B-1-51
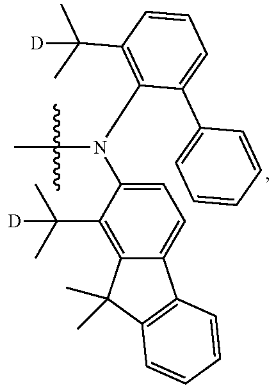
B-1-52
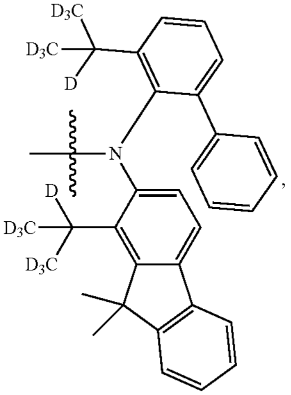
B-1-53
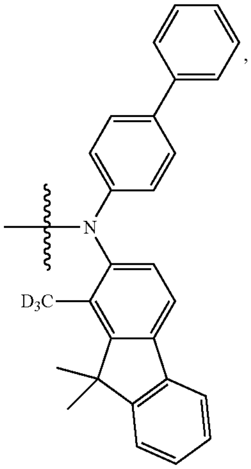
-continued
B-1-54
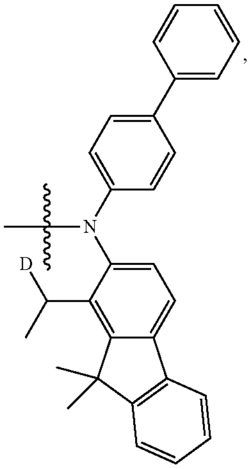
B-1-55
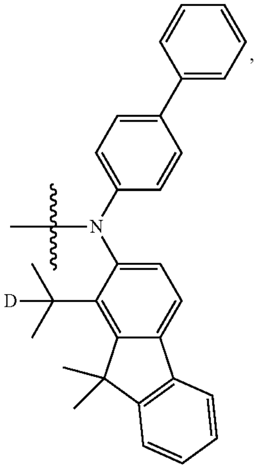
B-1-56
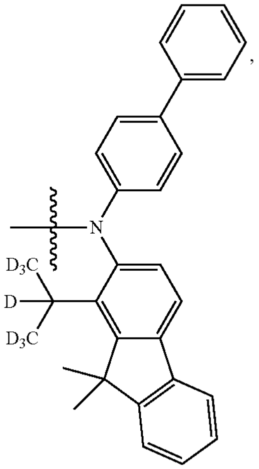

-continued
B-1-57
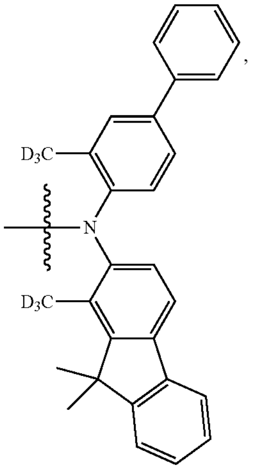
B-1-58
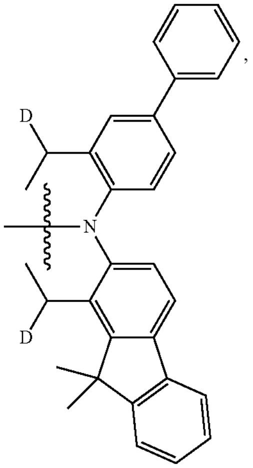
B-1-59
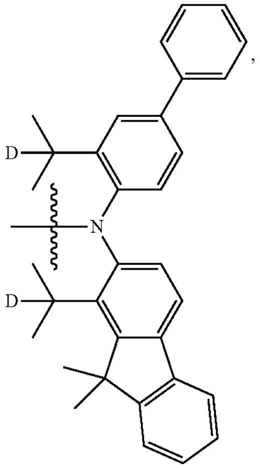
-continued
B-1-60
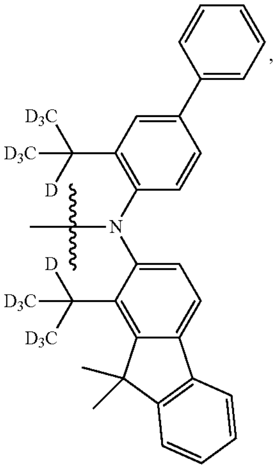
B-1-61
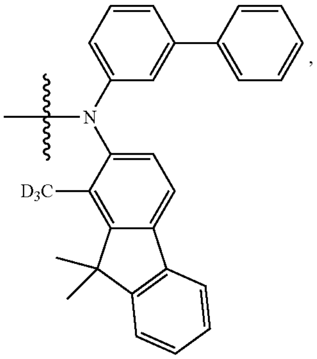
B-1-62
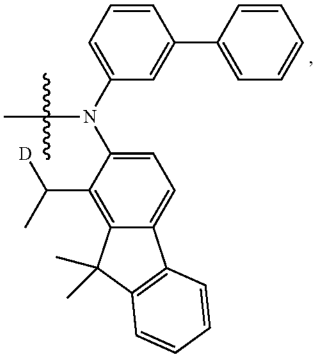
B-1-63
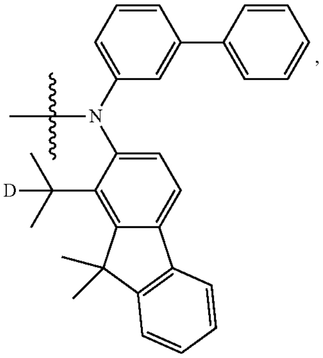

-continued
B-1-64
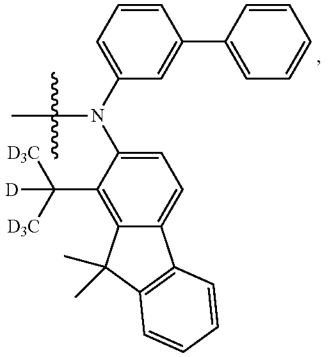
B-1-65
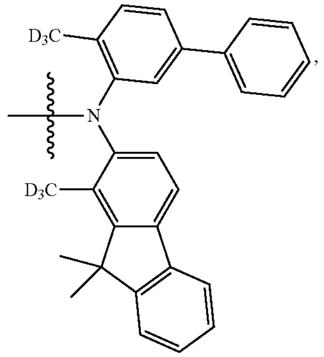
B-1-66
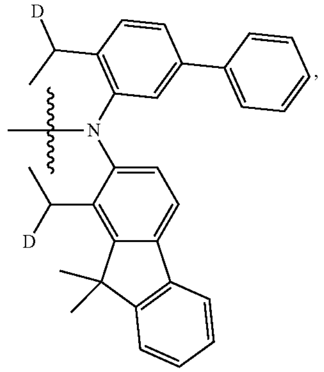
B-1-67
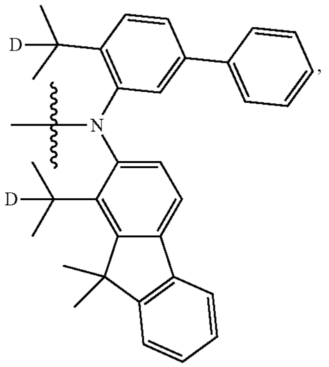
-continued
B-1-68
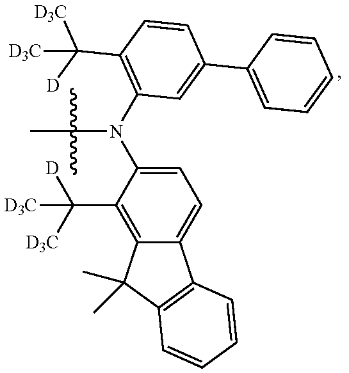
B-1-69
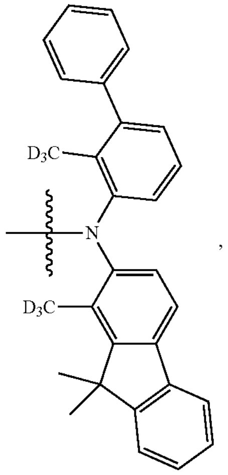
B-1-70
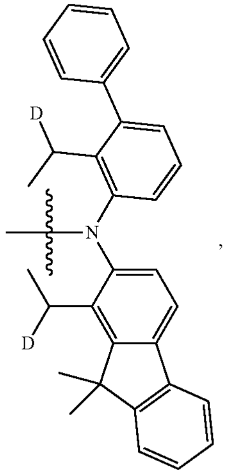

-continued
B-1-71
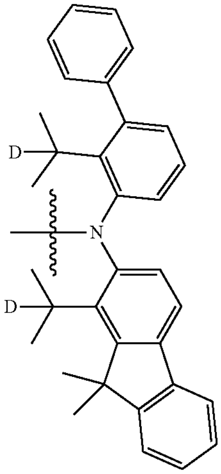
,
B-1-72
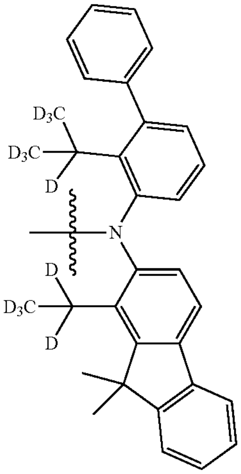
,
B-2-1
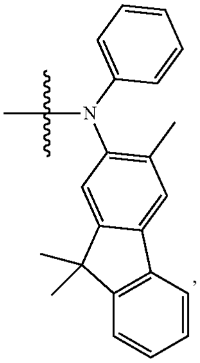
,
-continued
B-2-2
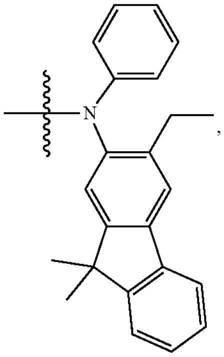
,
B-2-3
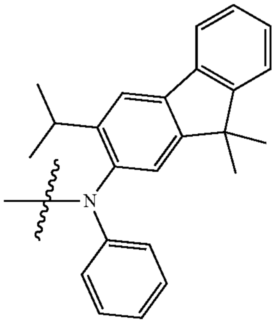
,
B-2-4
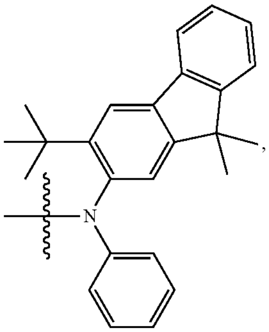
,
B-2-5
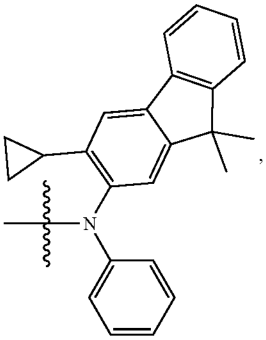
, -continued
B-2-6
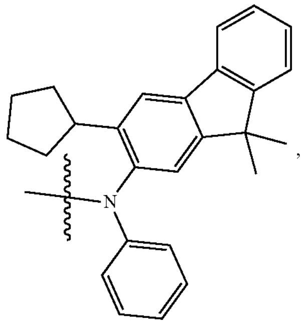
B-2-7
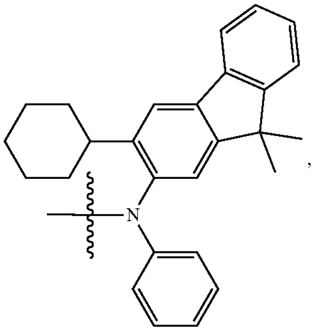
B-2-8
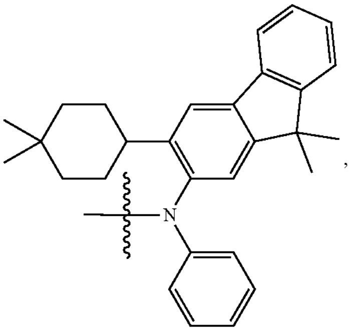
B-2-9
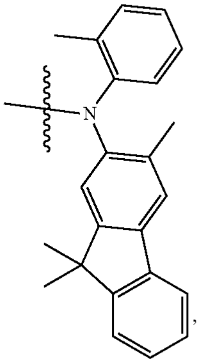
-continued
B-2-10
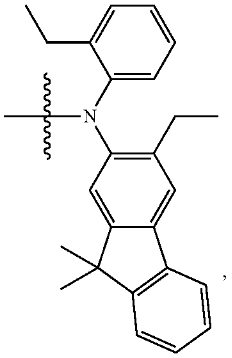
B-2-11
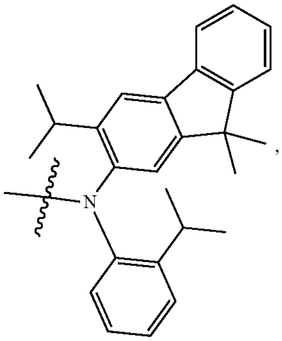
B-2-12
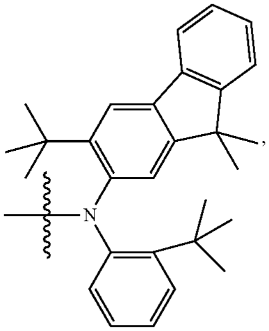
B-2-13
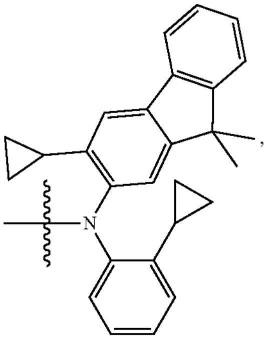

-continued
B-2-14
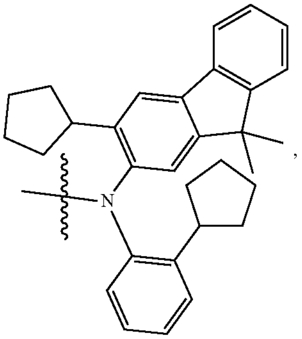
B-2-15
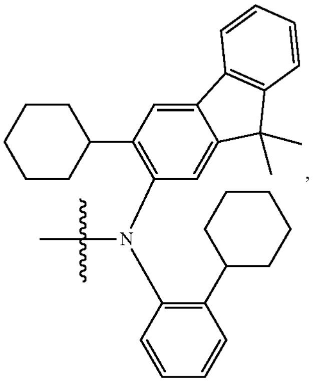
B-2-16
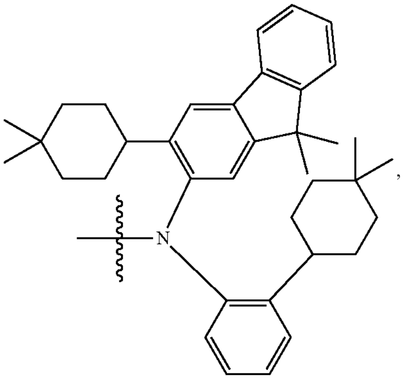
B-2-17
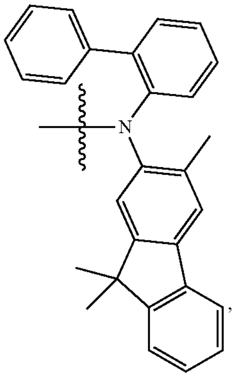
-continued
B-2-18
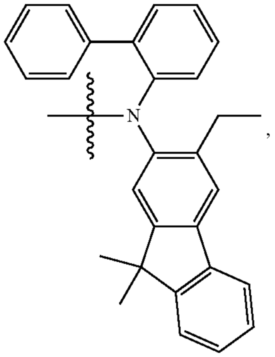
B-2-19
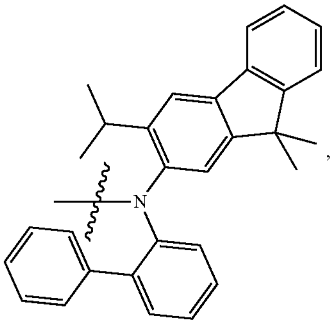
B-2-20
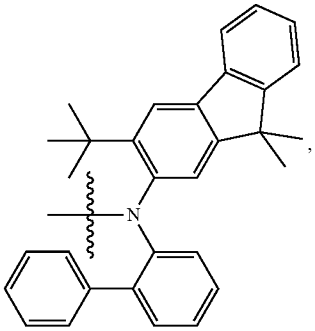
B-2-21
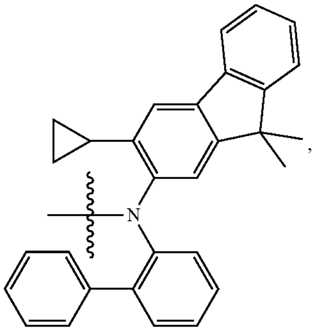

-continued
B-2-22
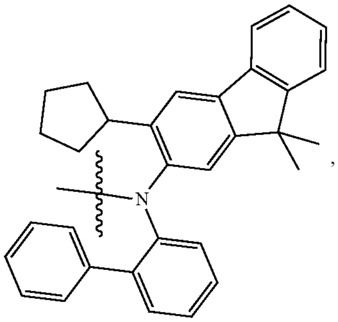
,
B-2-23
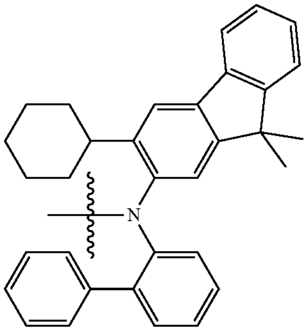
,
B-2-24
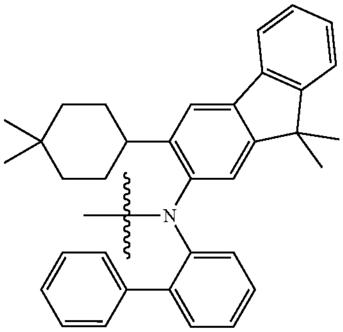
,
B-2-25
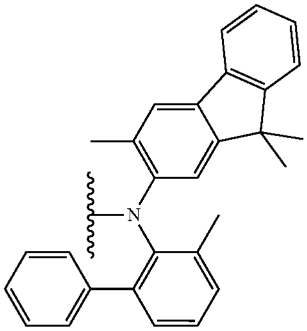
,
-continued
B-2-26
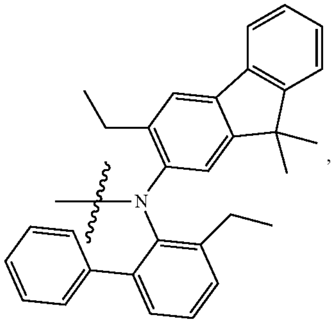
,
B-2-27
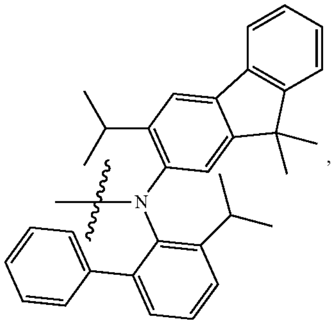
,
B-2-28
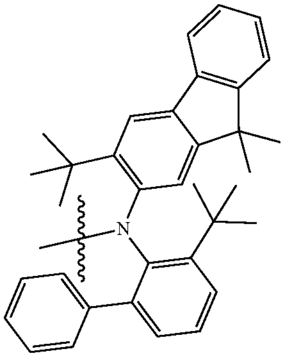
,
B-2-29
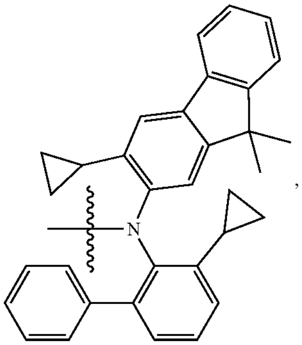
, -continued
B-2-30
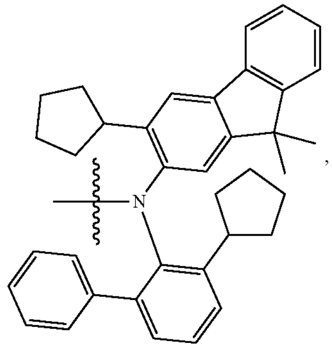
,
B-2-31
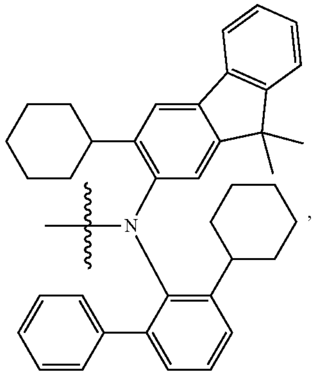
,
B-2-32
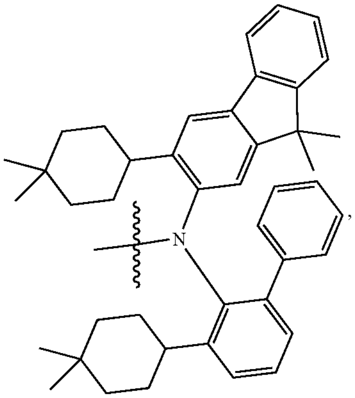
,
B-2-33
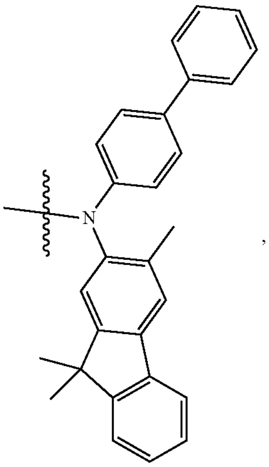
,
-continued
B-2-34
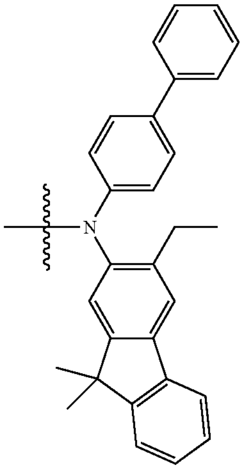
,
B-2-35
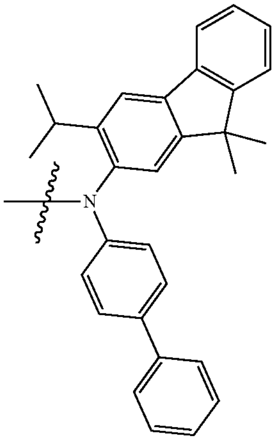
,
B-2-36
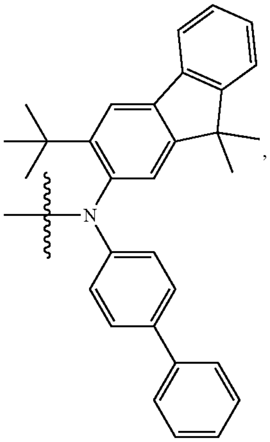
, B-2-37
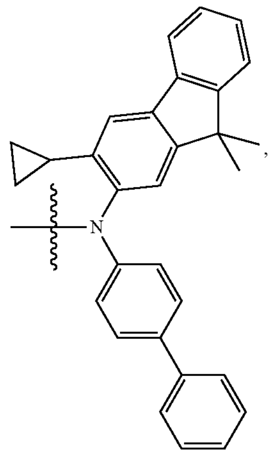
B-2-38
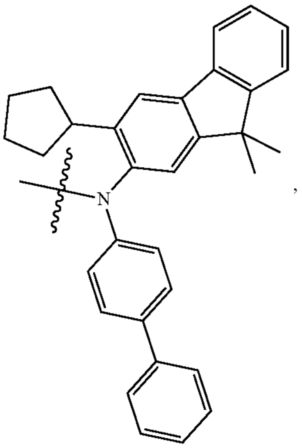
B-2-39
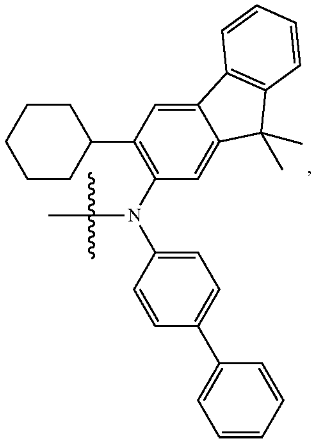
B-2-40
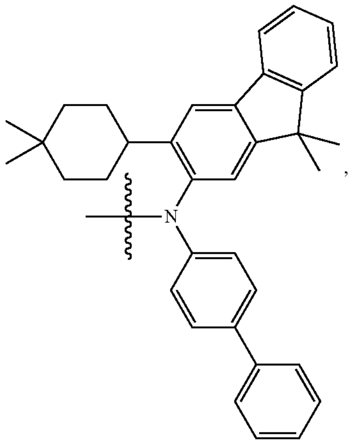
B-2-41
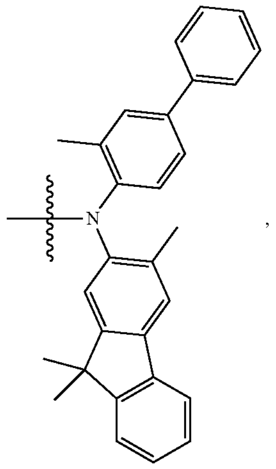
B-2-42
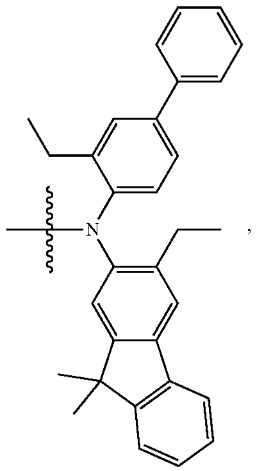

-continued
B-2-43
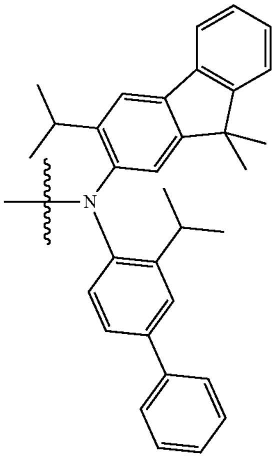
,
B-2-44
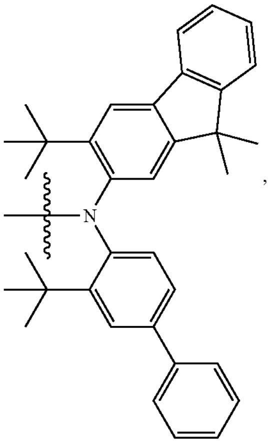
,
B-2-45
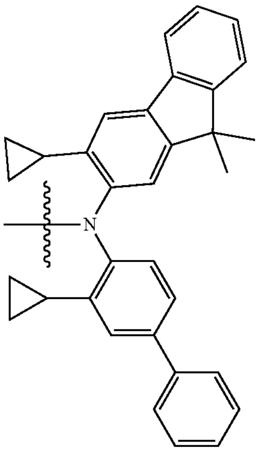
,
-continued
B-2-46
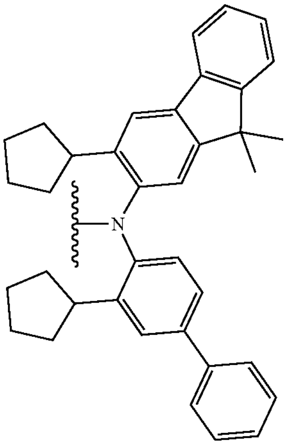
,
B-2-47
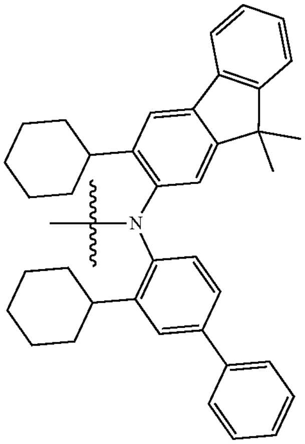
,
B-2-48
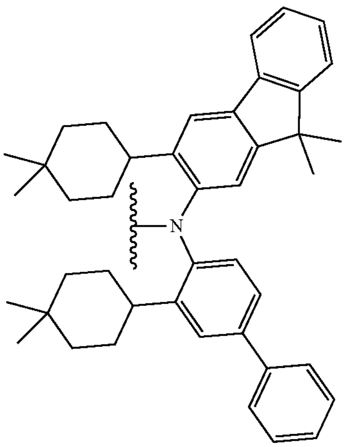
, -continued
B-2-49
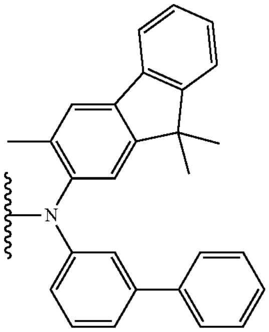
,
B-2-50
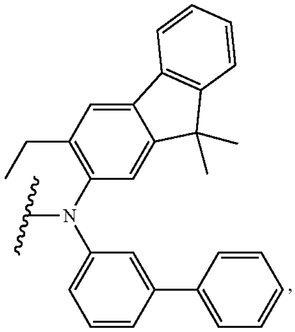
,
B-2-51
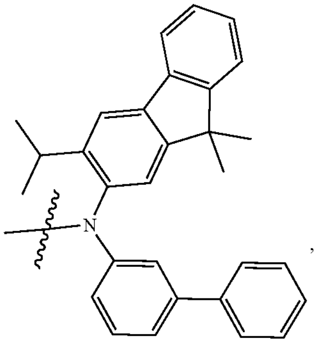
,
B-2-52
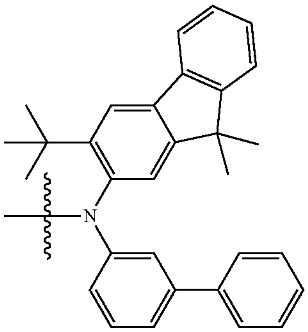
,
-continued
B-2-53
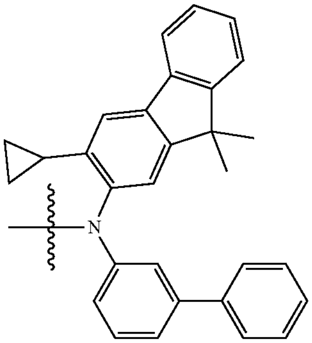
,
B-2-54
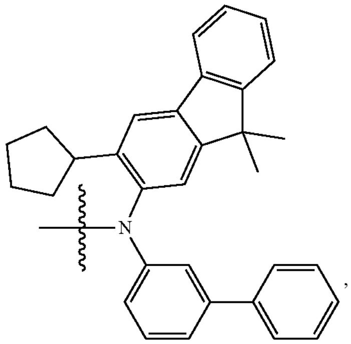
,
B-2-55
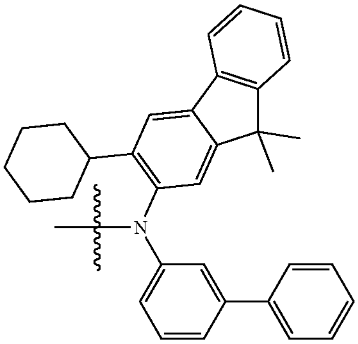
,
B-2-56
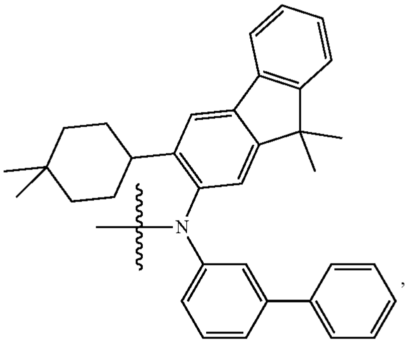
, -continued
B-2-57
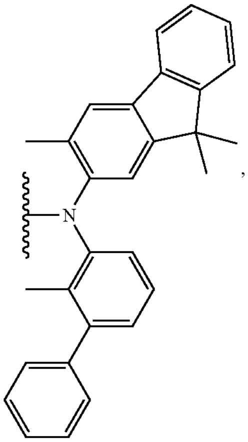
,
B-2-58
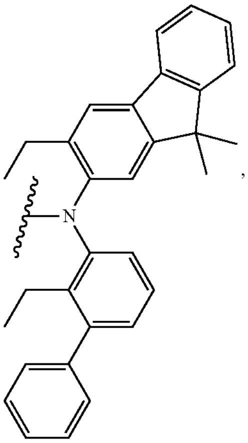
,
B-2-59
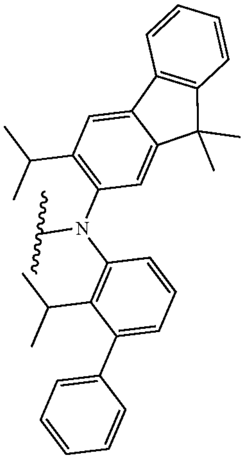
,
-continued
B-2-60
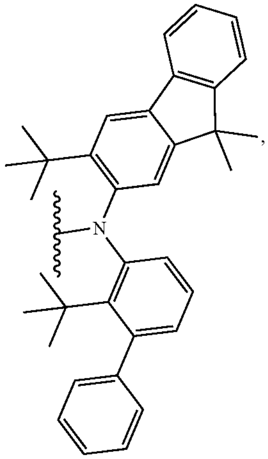
,
B-2-61
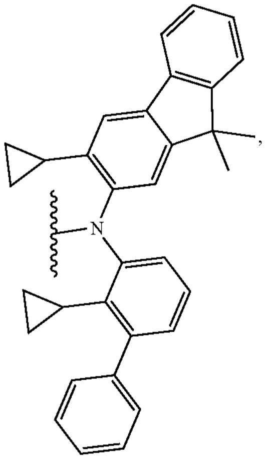
,
B-2-62
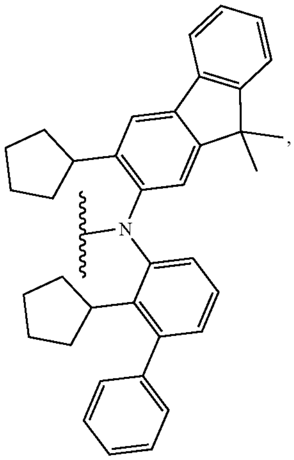
, B-2-63
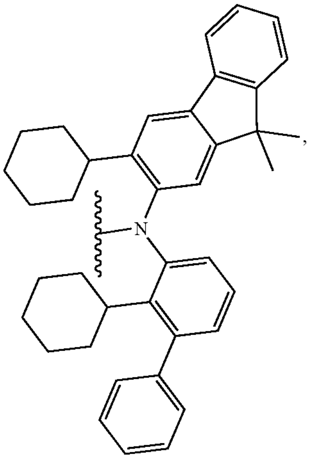
,
B-2-64
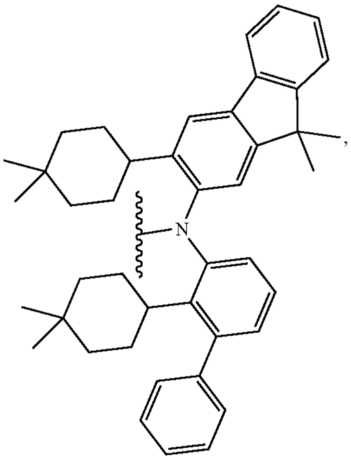
,
B-2-65
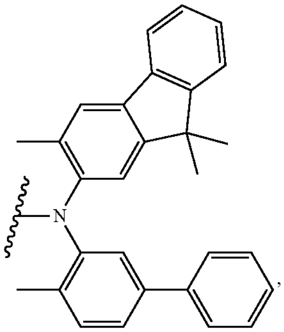
,
B-2-66
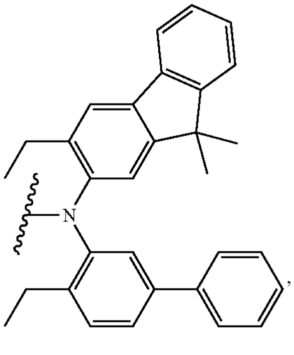
,
B-2-67
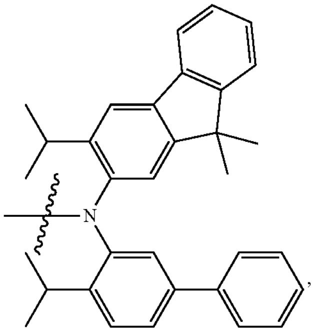
,
B-2-68
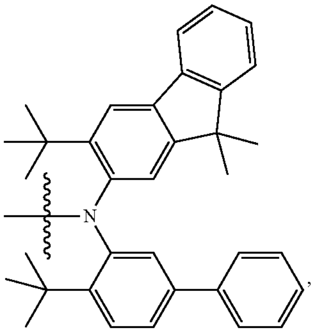
,
B-2-69
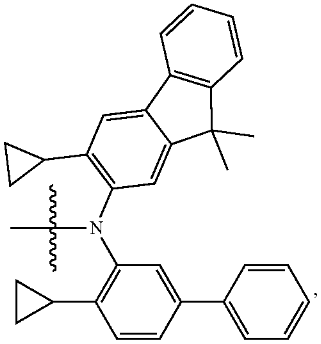
,
B-2-70
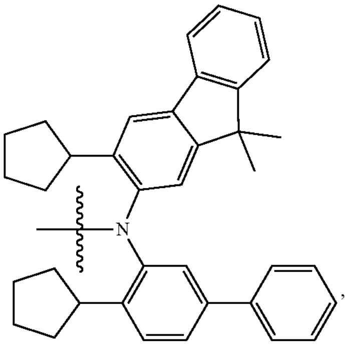
, -continued
B-2-71
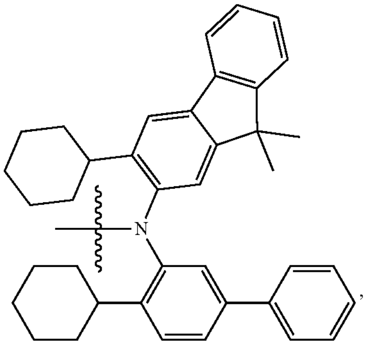
B-2-72
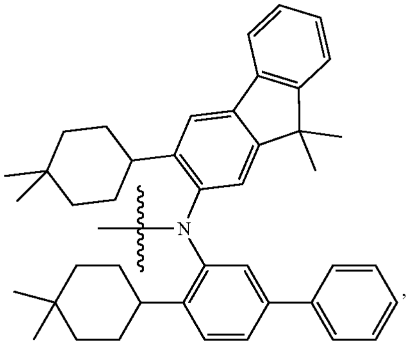
B-2-73
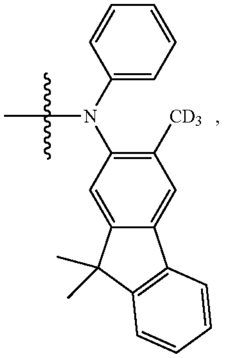
B-2-74
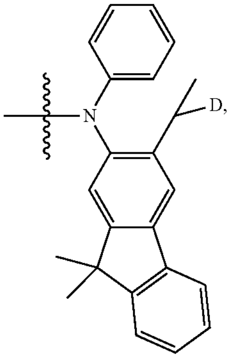
-continued
B-2-75
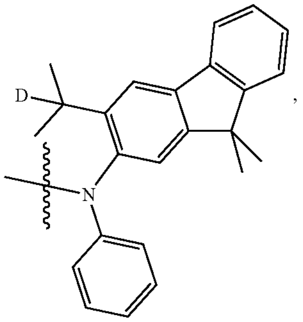
B-2-76
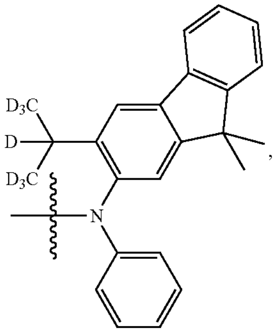
B-2-77
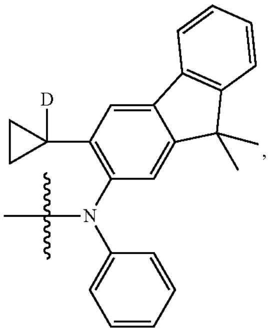
B-2-78
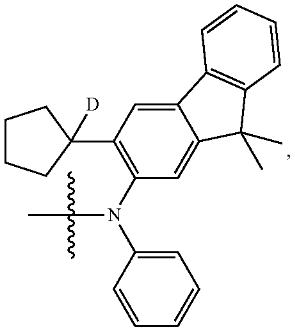

-continued
B-2-79
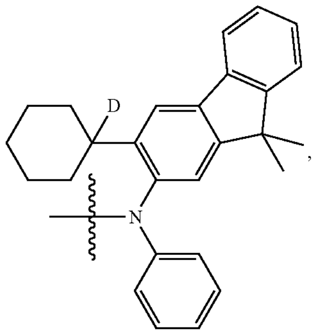
B-2-80
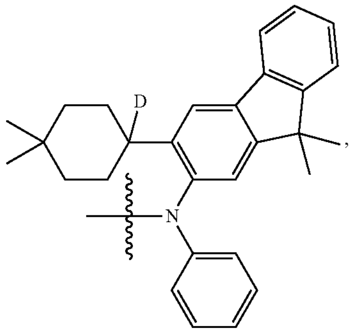
B-2-81
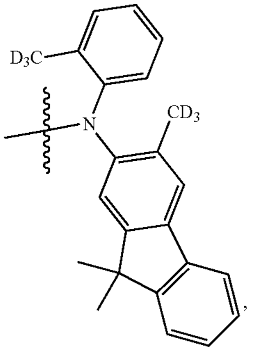
B-2-82
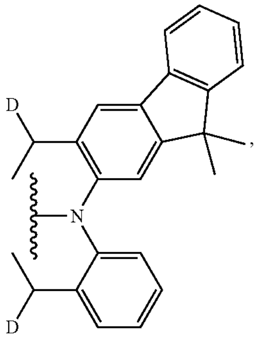
-continued
B-2-83
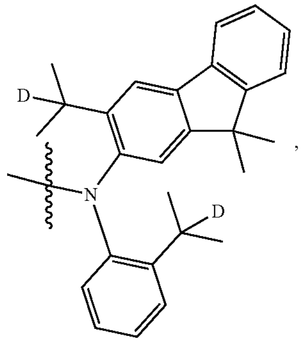
B-2-84
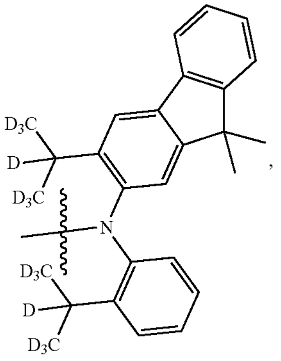
B-2-85
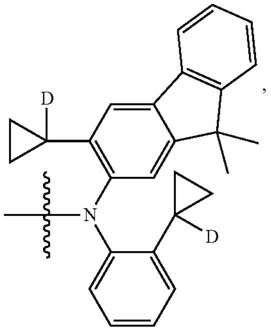
B-2-86
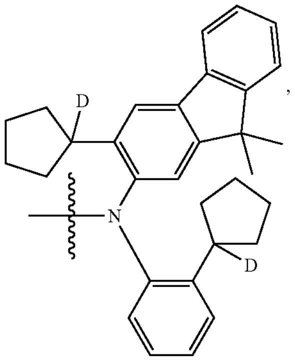

-continued
B-2-87
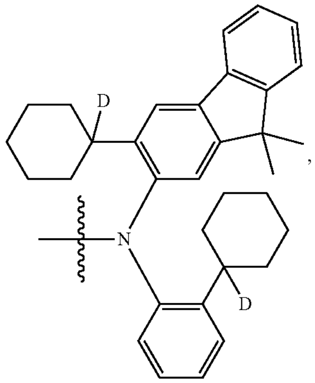
B-2-88
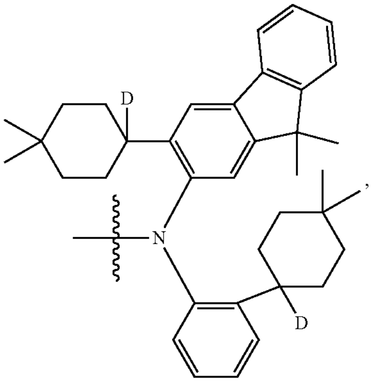
B-2-89
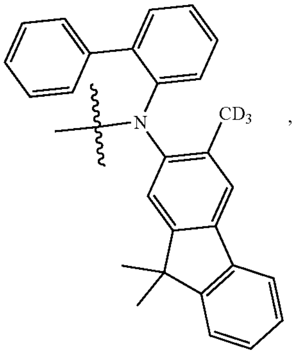
B-2-90
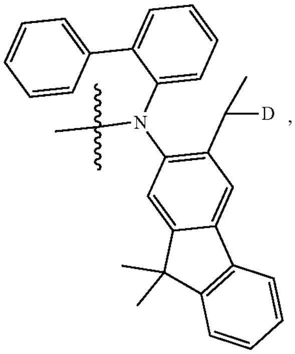
-continued
B-2-91
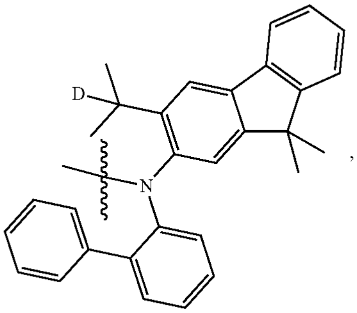
B-2-92
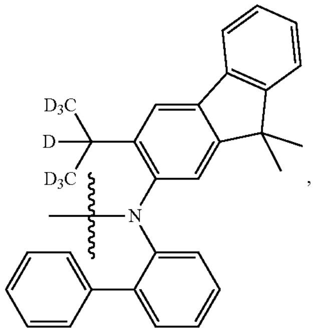
B-2-93
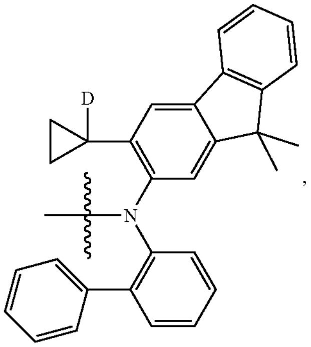
B-2-94
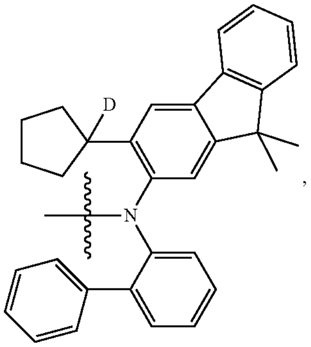

-continued
B-2-95
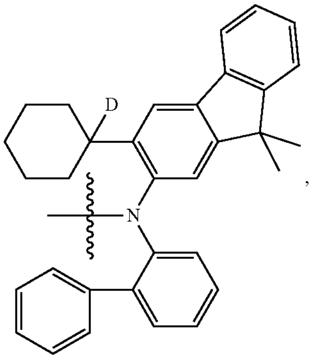
,
B-2-96
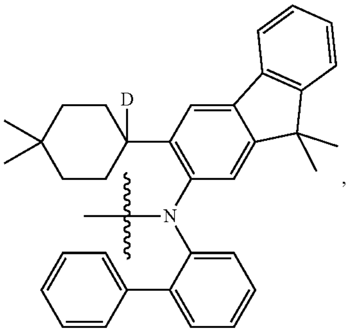
,
B-2-97
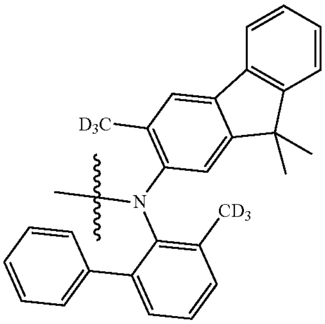
,
B-2-98
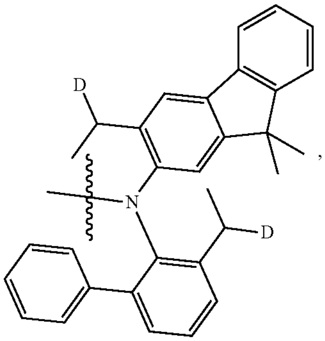
,
-continued
B-2-99
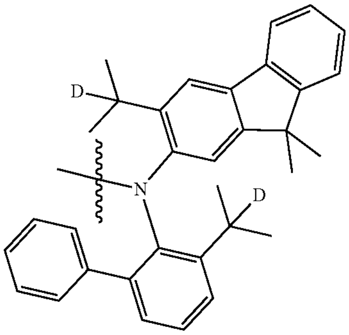
,
B-2-100
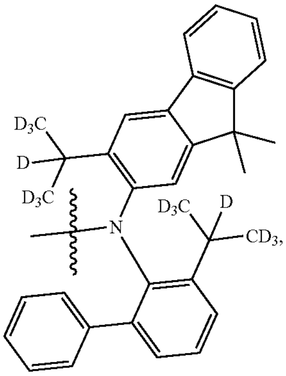
,
B-2-101
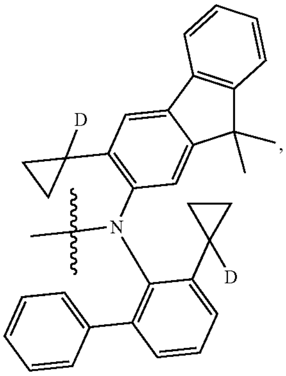
,
B-2-102
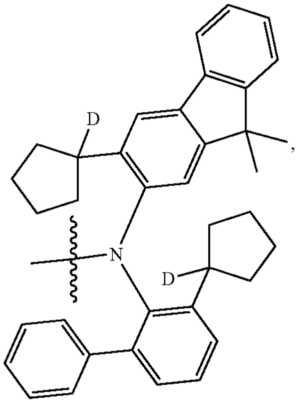
, -continued
B-2-103
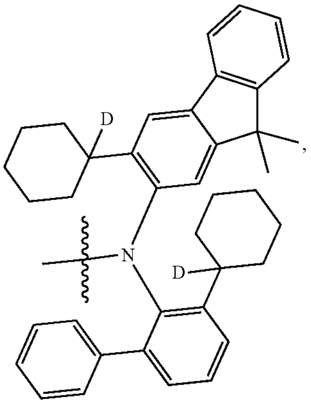
B-2-104
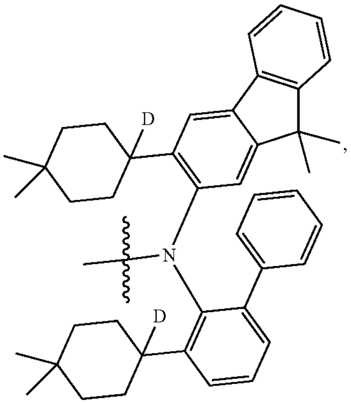
B-2-105
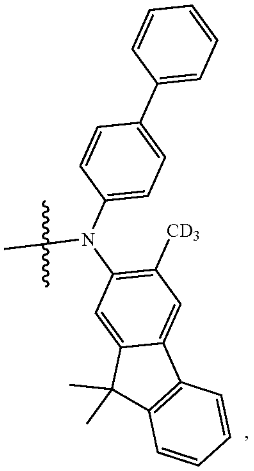
-continued
B-2-106
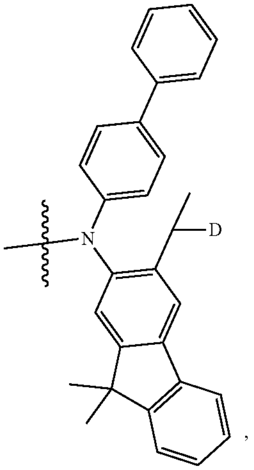
B-2-107
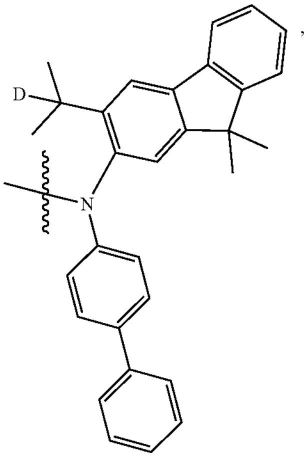
B-2-108
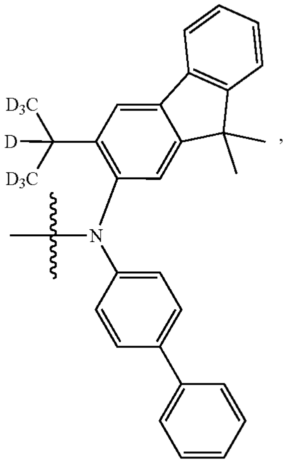

-continued
B-2-109
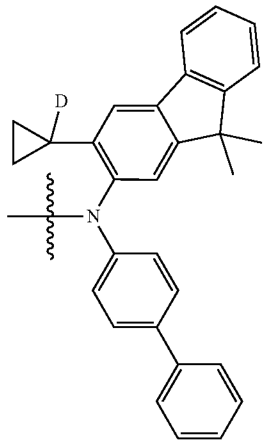
,
B-2-110
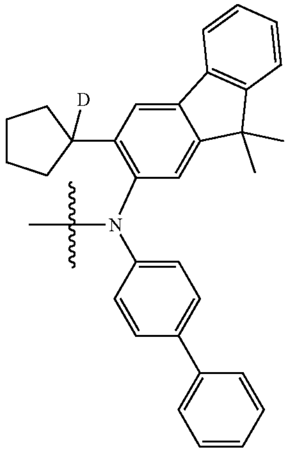
,
B-2-111
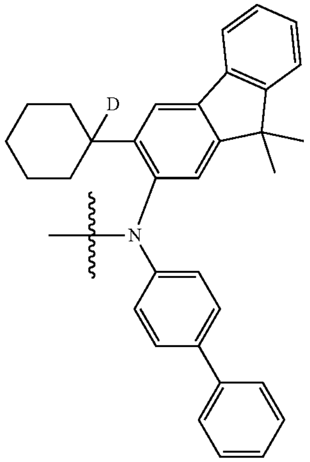
,
-continued
B-2-112
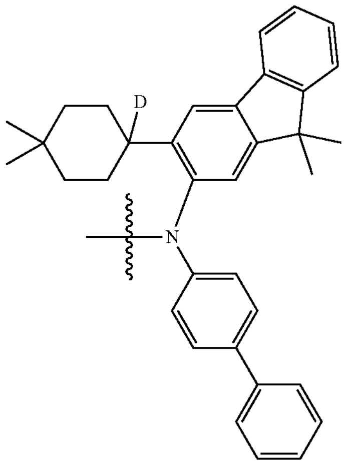
,
B-2-113
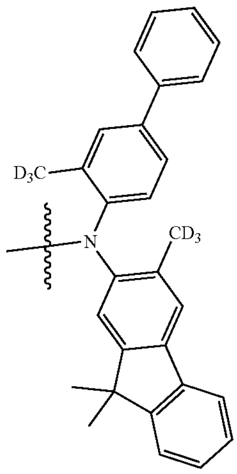
,
B-2-114
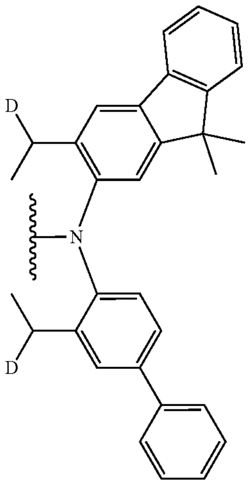
, -continued
B-2-115
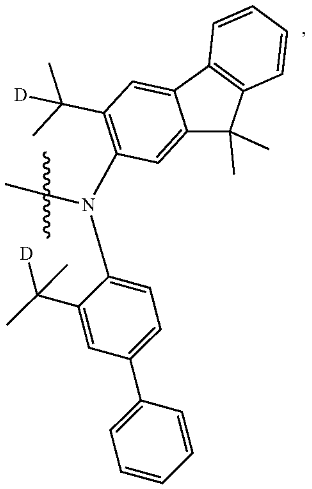
B-2-116
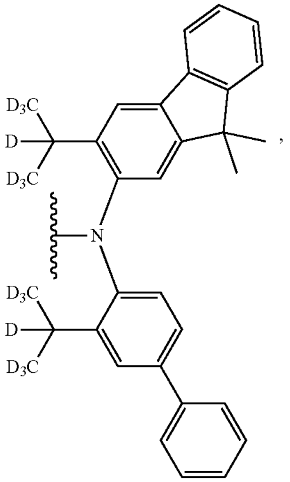
B2-117
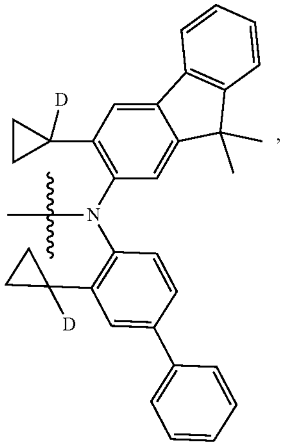
-continued
B-2-118
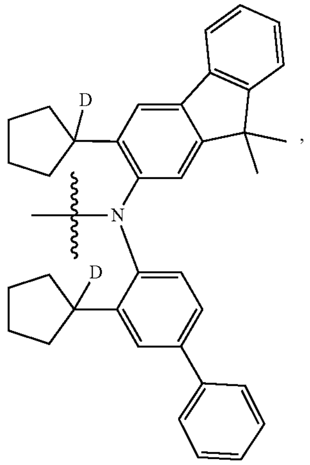
B-2-119
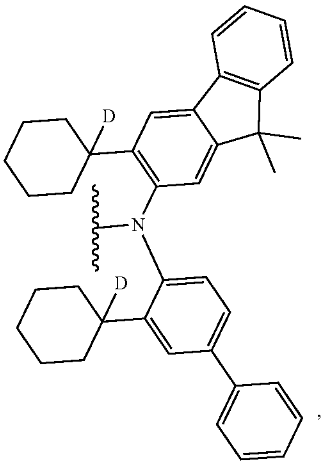
B-2-120
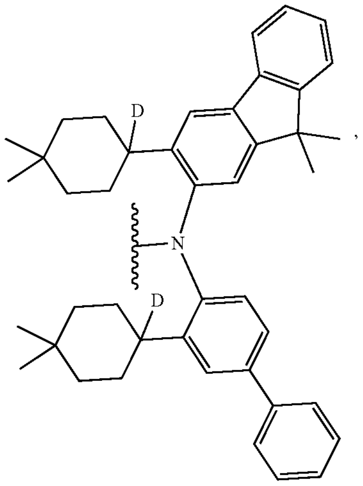

-continued
B-2-121
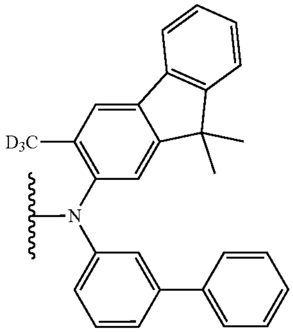
,
B-2-122
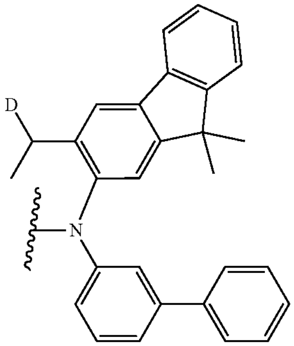
,
B-2-123
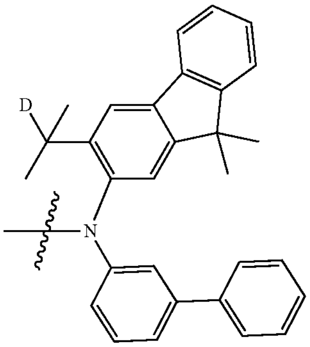
,
B-2-124
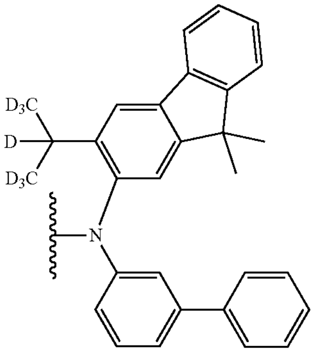
,
-continued
B-2-125
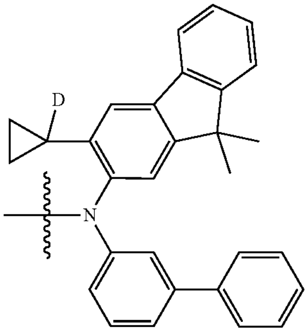
,
B-2-126
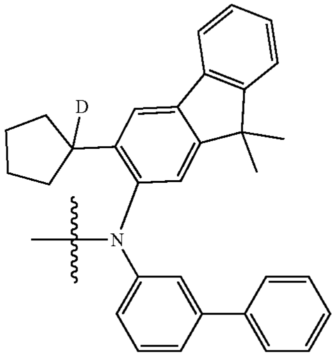
,
B-2-127
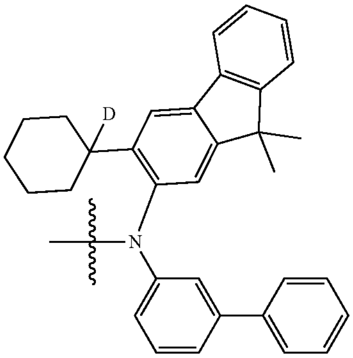
,
B-2-128
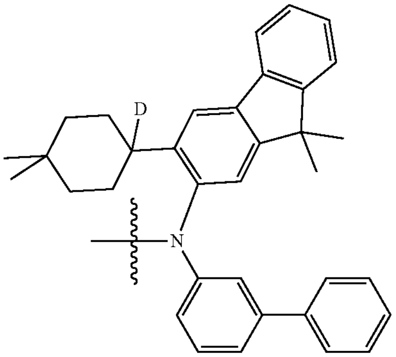
, -continued
B-2-129
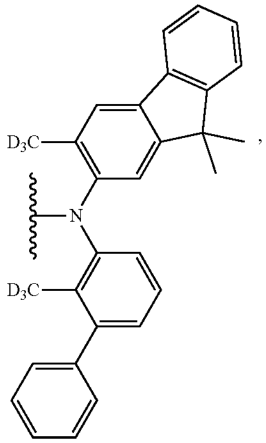
B-2-130
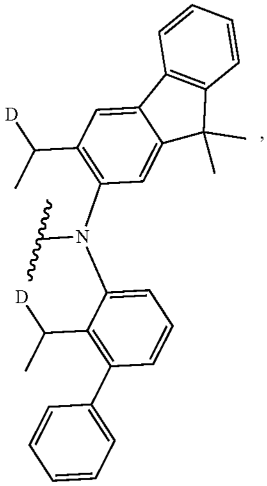
B-2-131
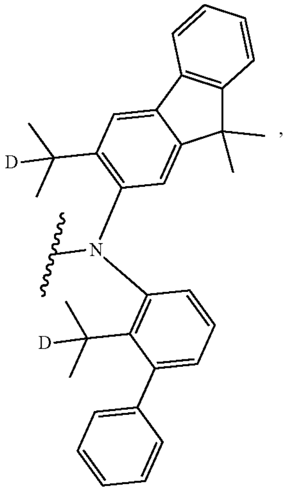
-continued
B-2-132
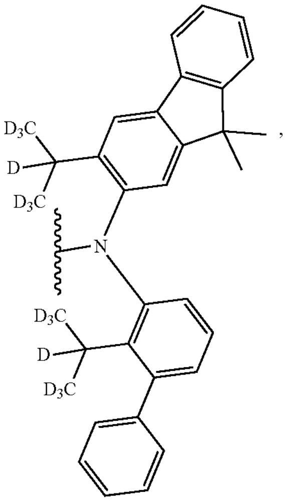
B-2-133
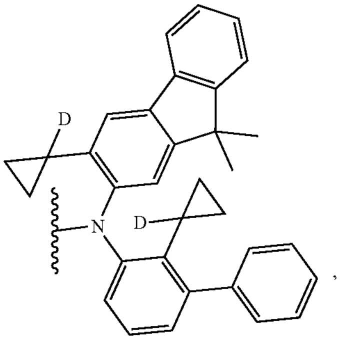
B-2-134
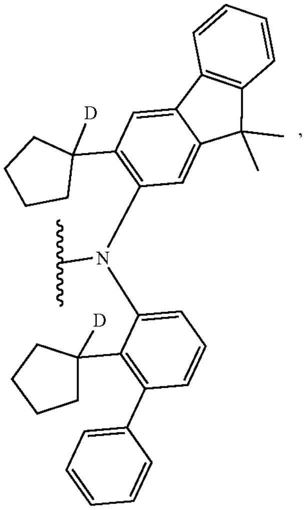

-continued
B-2-135
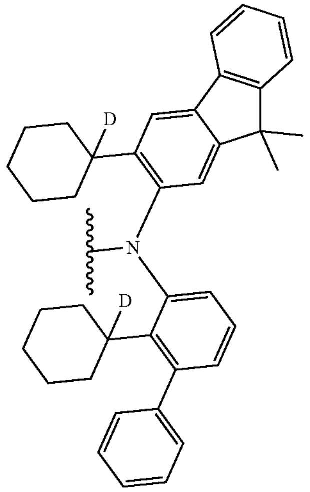
,
B-2-136
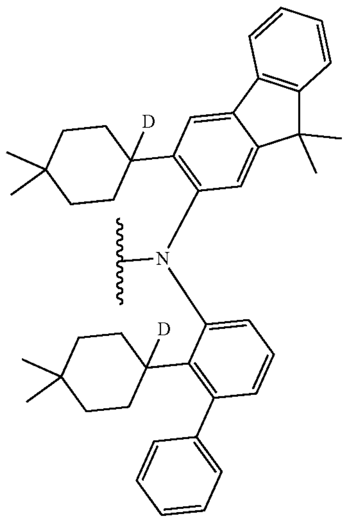
,
B-2-137
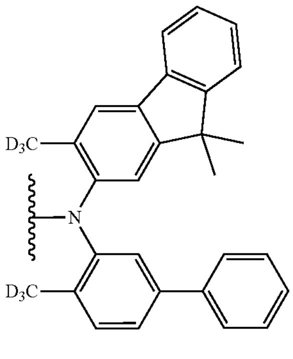
,
-continued
B-2-138
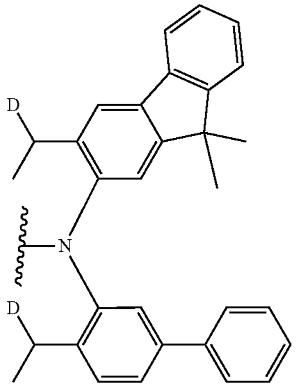
,
B-2-139
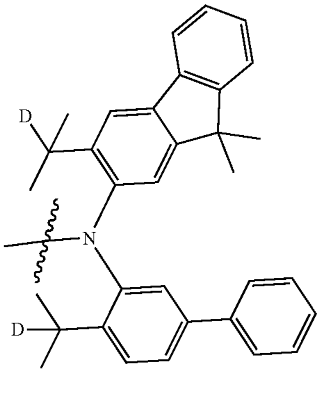
,
B-2-140
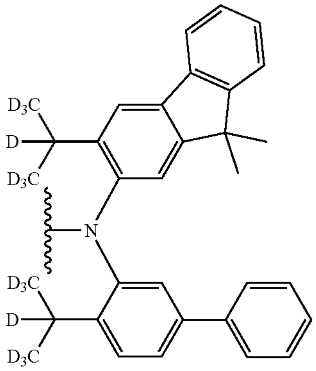
,
B-2-141
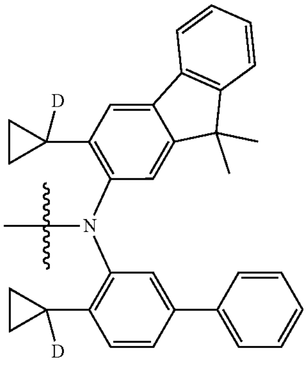
, -continued
B-2-142
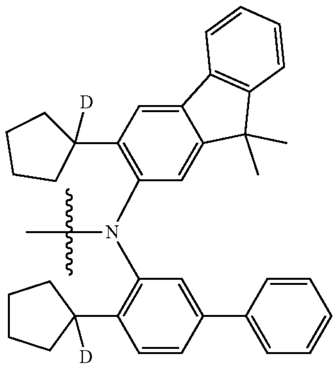
,
B-2-143
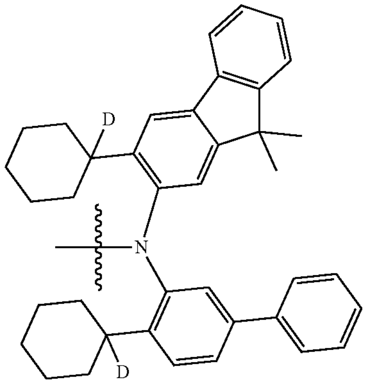
,
B-2-144
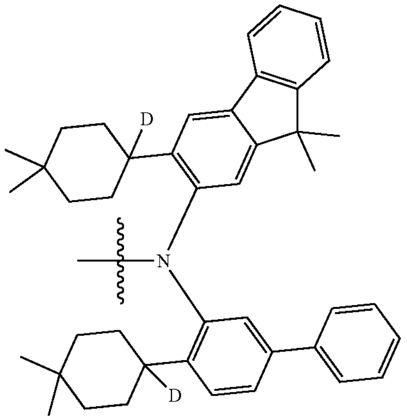
,
B-2-145
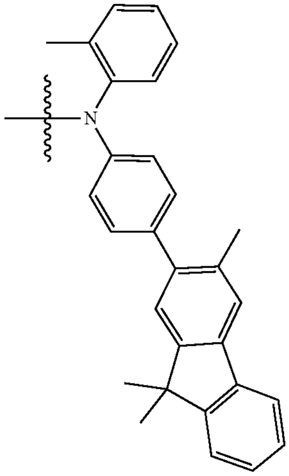
,
-continued
B-2-146
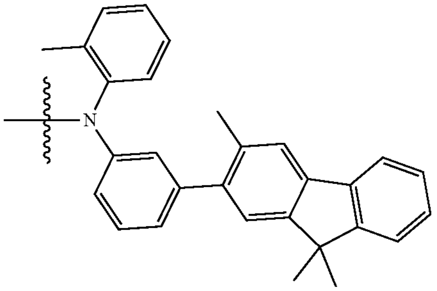
,
B-2-147
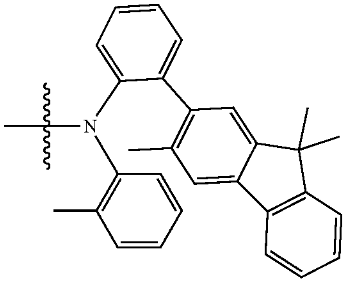
,
B-2-148
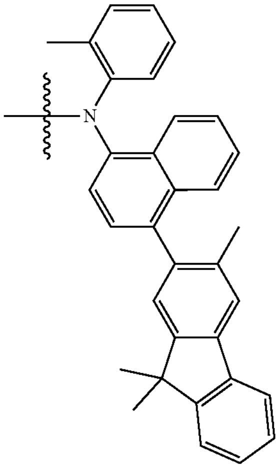
,
B-2-149
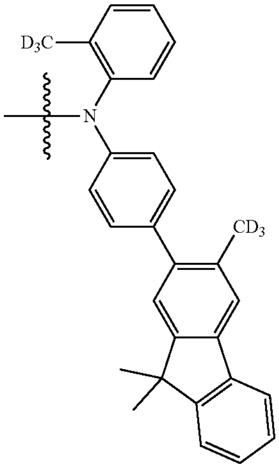
, B-2-150
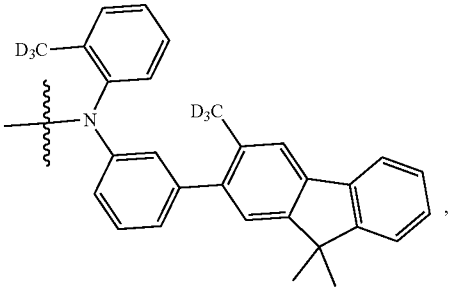
B-2-151
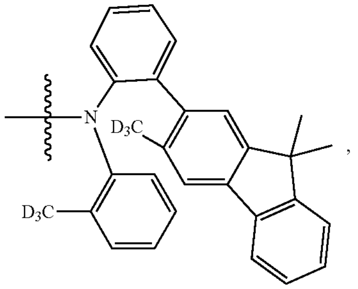
B-2-152
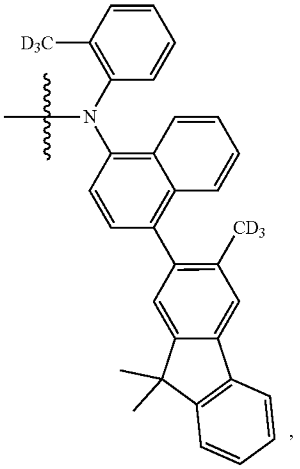
B-2-153
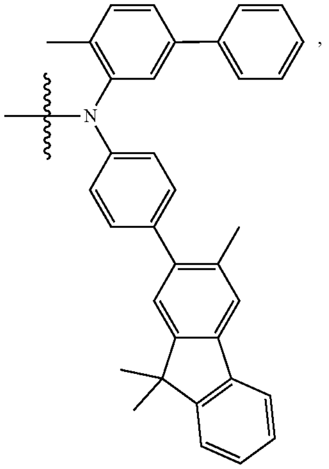
B-2-154
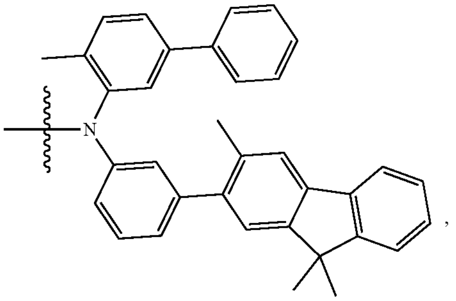
B-2-155
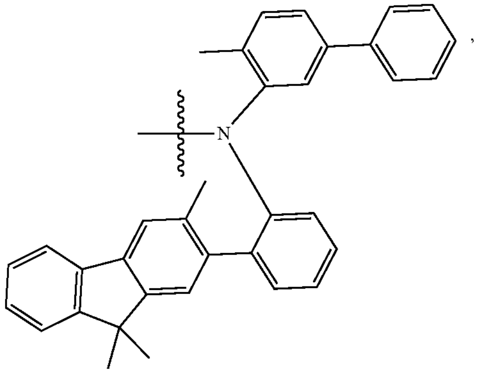
B-2-156
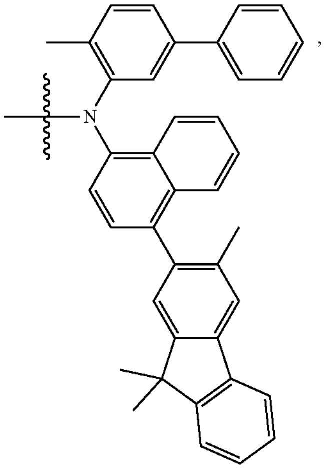
B-2-157
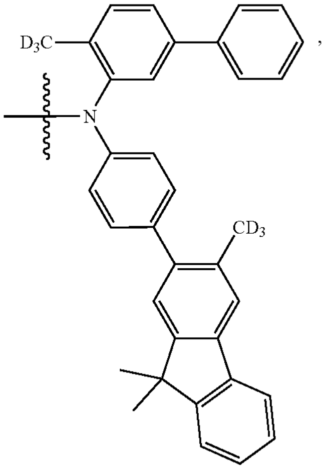

-continued
B-2-158
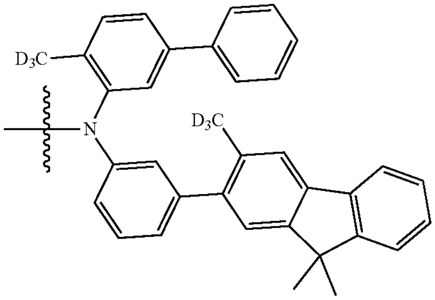
,
B-2-159
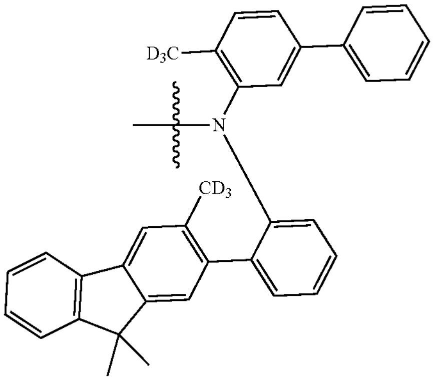
,
B-2-160
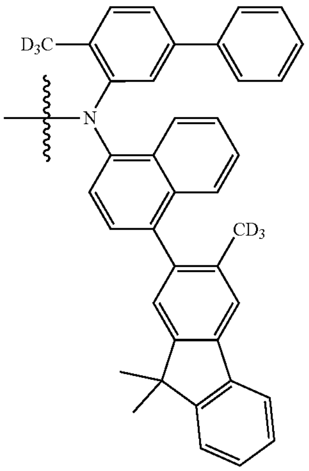
,
-continued
B-2-161
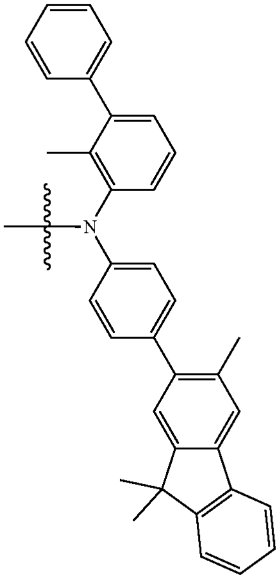
,
B-2-162
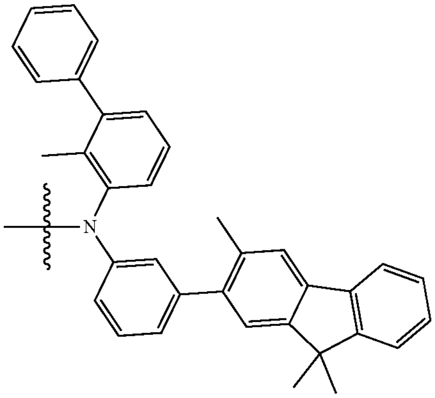
,
B-2-163
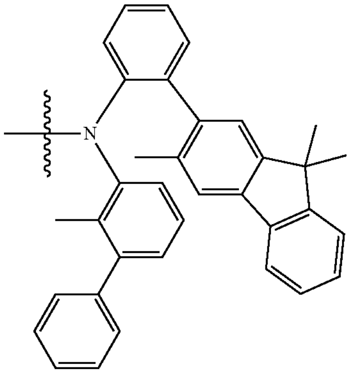
, -continued
B-2-164
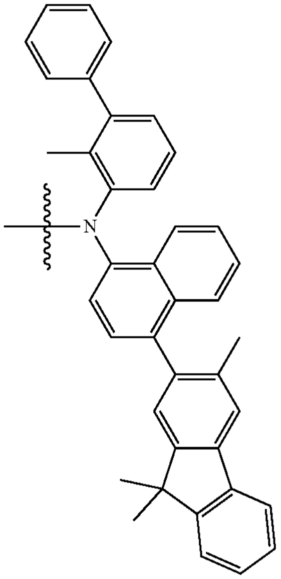
,
B-2-165
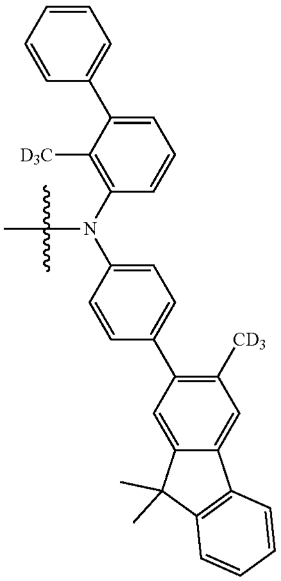
,
B-2-166
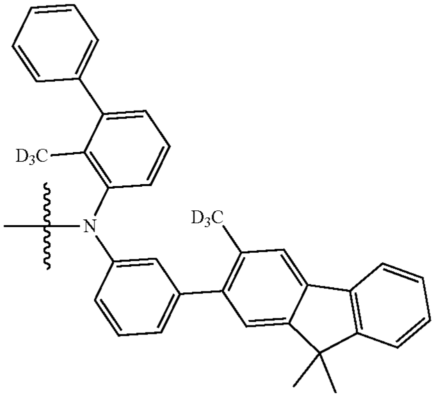
,
-continued
B-2-167
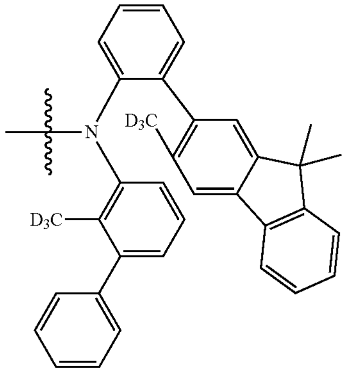
,
B-2-168
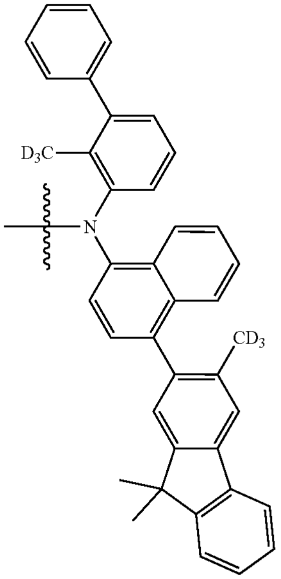
,
B-2-169
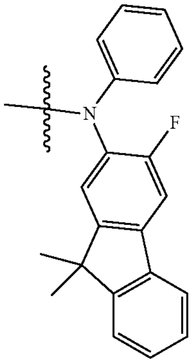
, -continued
B-2-170
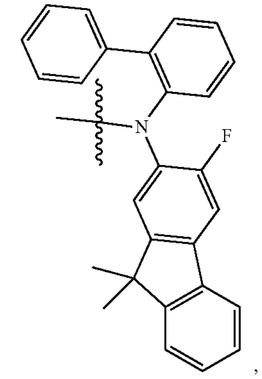
,
B-2-171
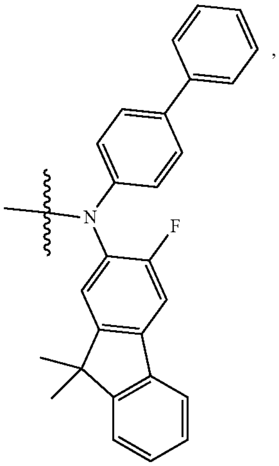
,
B-2-172
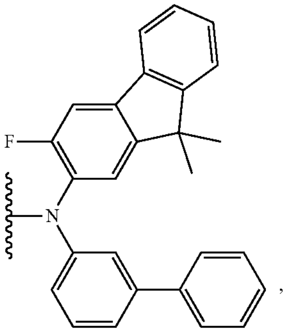
,
B-2-173
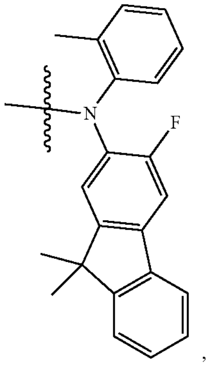
,
-continued
B-2-174
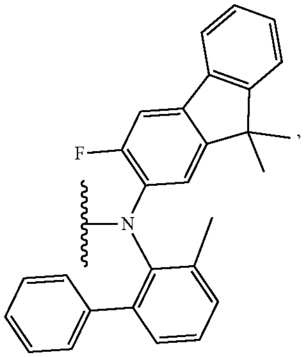
,
B-2-175
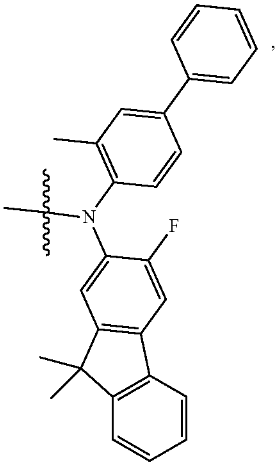
,
B-2-176
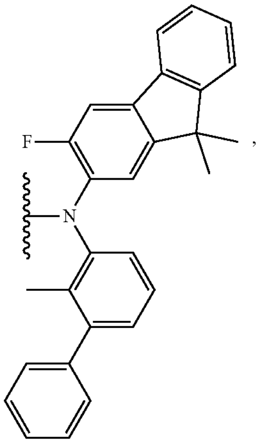
,
B-2-177
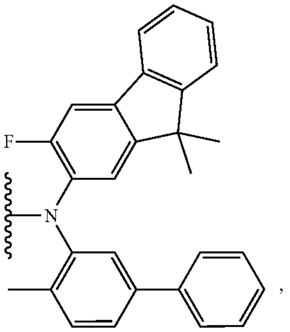
, -continued
B-2-178
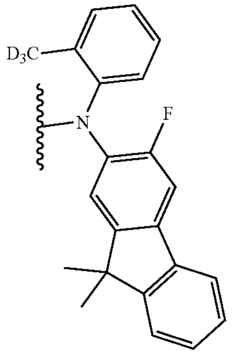
,
B-2-179
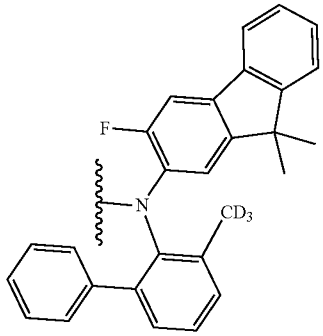
,
B-2-180
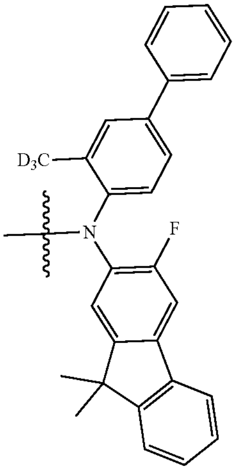
,
B-2-181
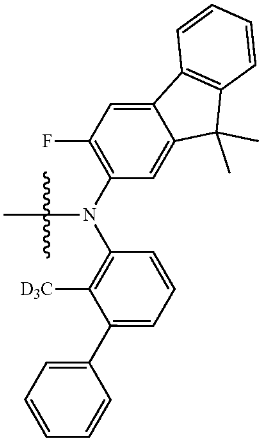
,
-continued
B-2-182
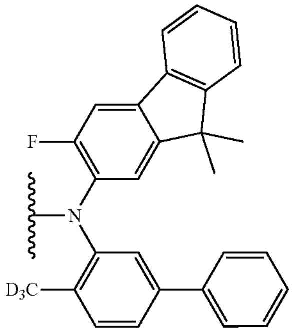
,
B-2-183
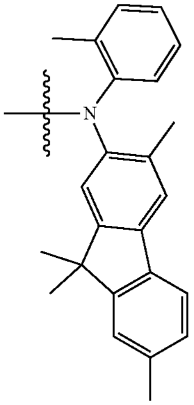
,
B-2-184
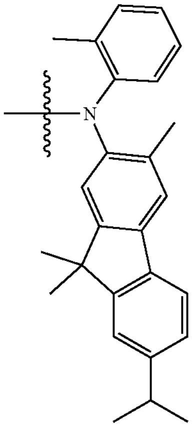
, -continued
B-2-185
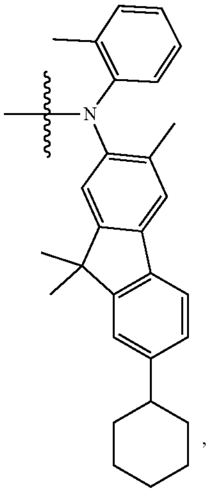
B-2-186
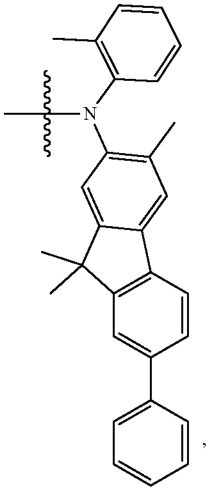
B-2-187
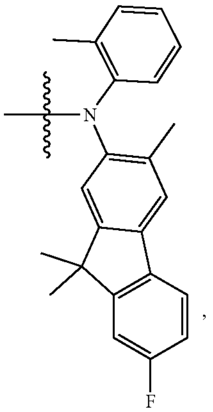
-continued
B-2-188
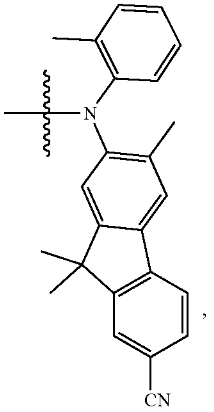
B-2-189
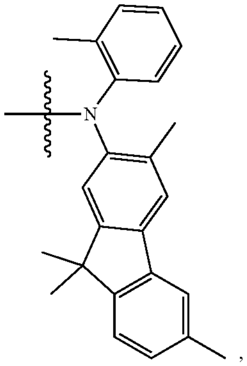
B-2-190
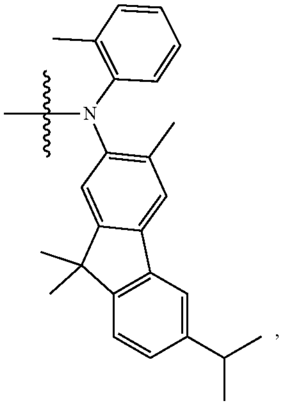
B-2-191
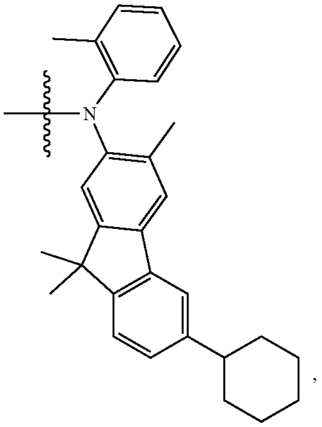

-continued
B-2-192
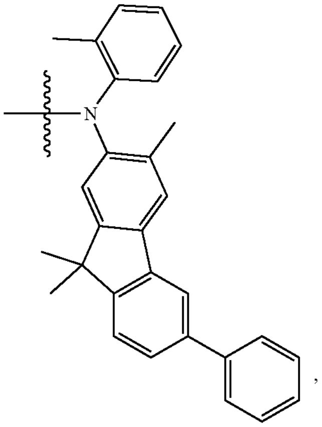
B-2-193
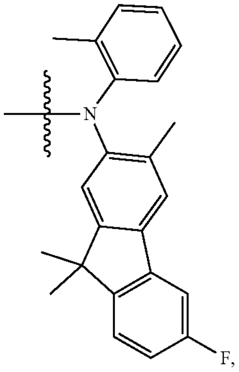
B-2-194
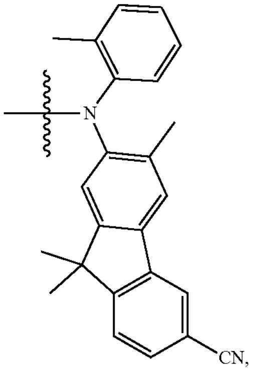
B-2-195
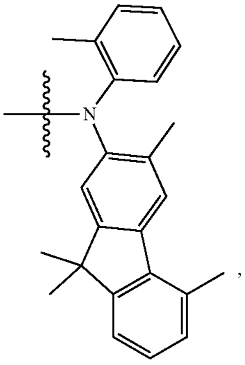
-continued
B-2-196
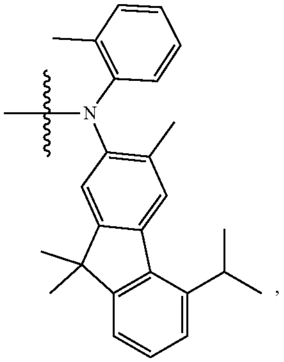
B-2-197
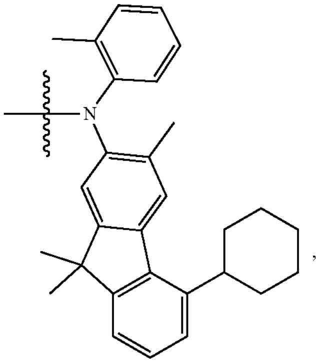
B-2-198
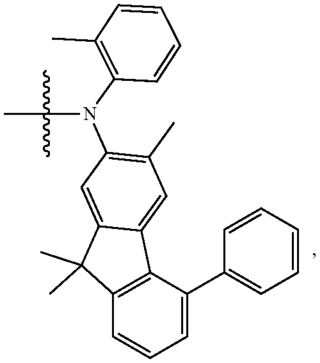
B-2-199
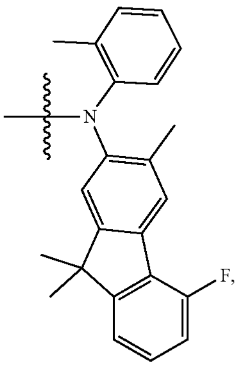

-continued
B-2-200
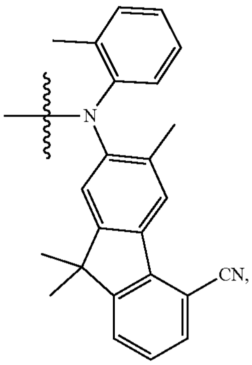
CN,
B-2-201
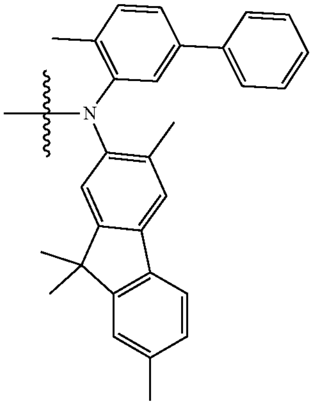
,
B-2-202
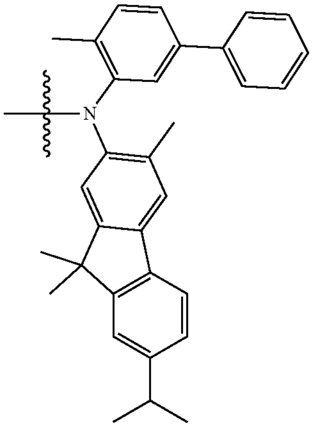
,
-continued
B-2-203
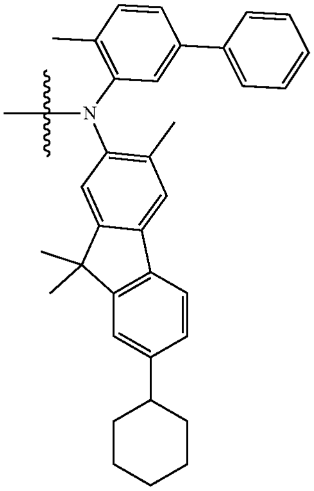
,
B-2-204
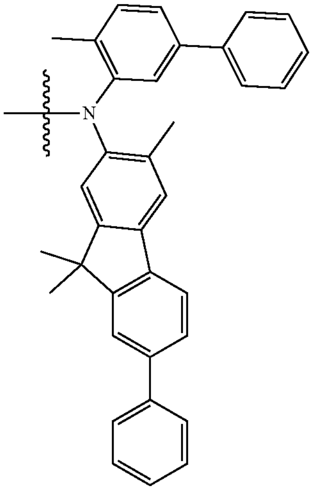
,
B-2-205
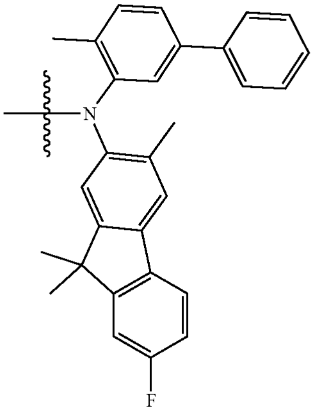
, -continued
B-2-206
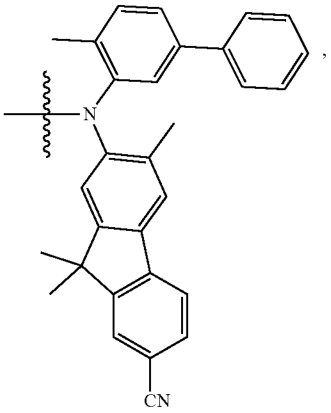
B-2-207
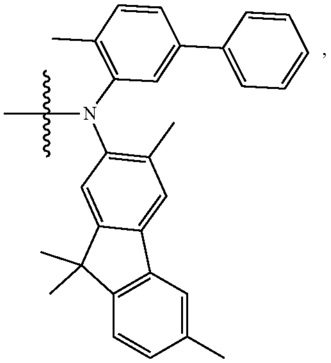
B-2-208
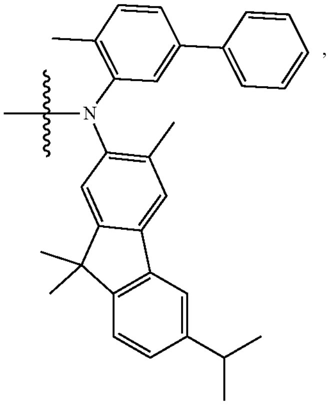
B-2-209
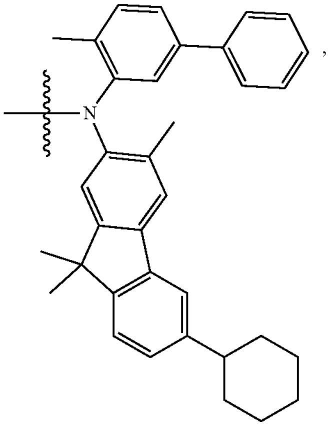
-continued
B-2-210
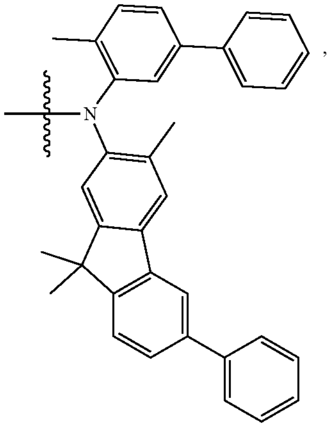
B-2-211
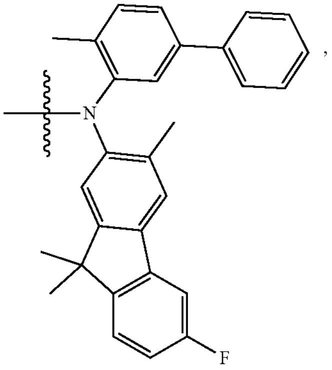
B-2-212
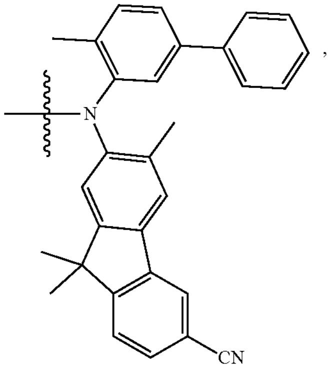
B-2-213
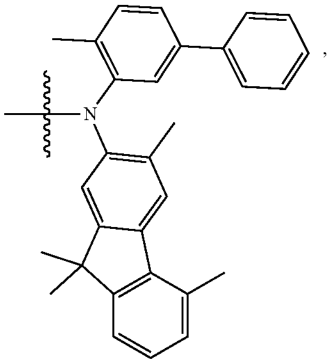

-continued
B-2-214
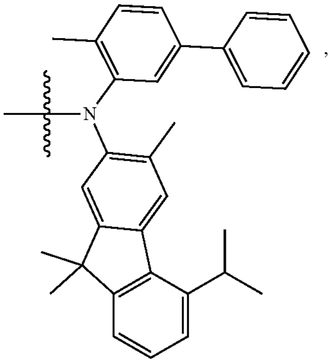
B-2-215
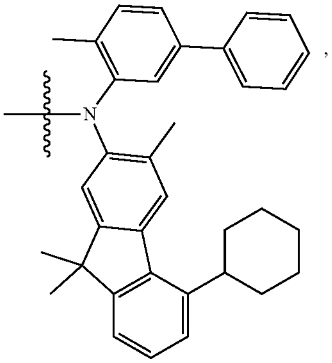
B-2-216
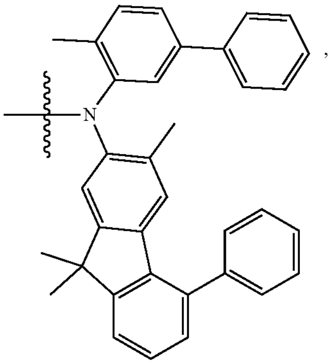
B-2-217
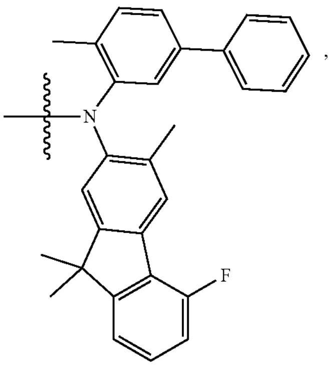
B-2-218
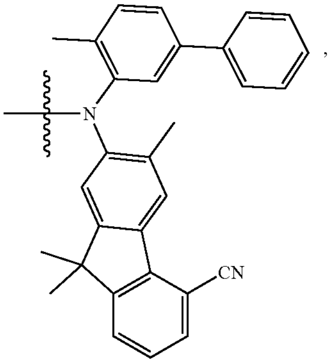
B-3-1
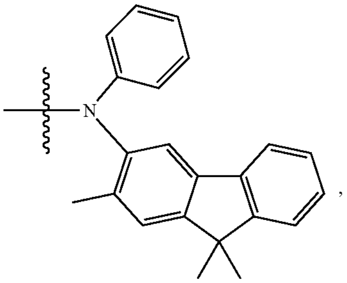
B-3-2
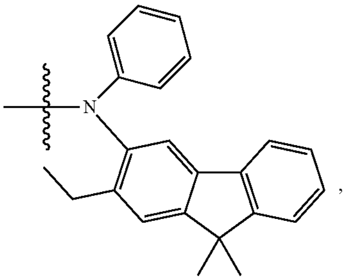
B-3-3
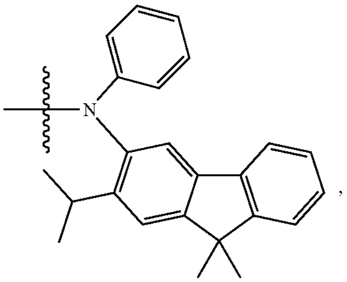
B-3-4
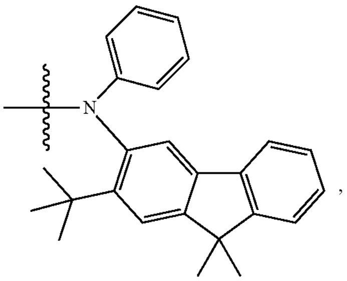

-continued
B-3-5
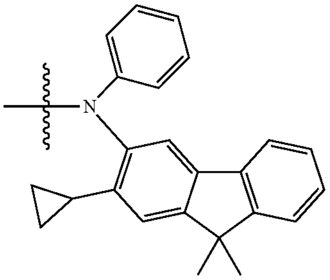
,
B-3-6
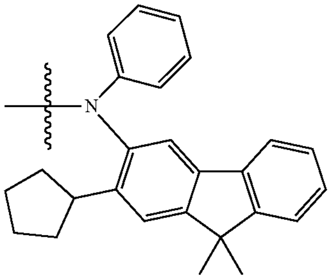
,
B-3-7
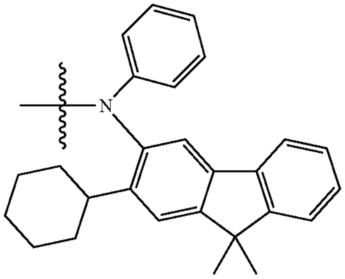
,
B-3-8
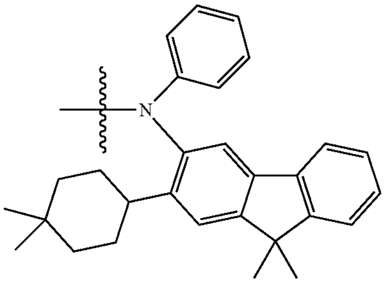
,
B-3-9
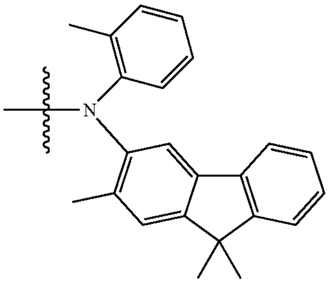
,
-continued
B-3-10
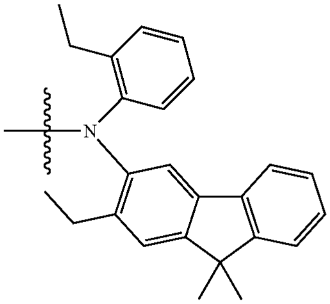
,
B-3-11
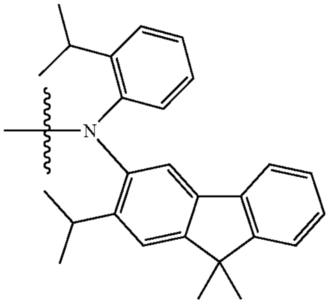
,
B-3-12
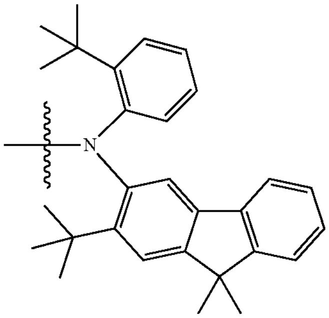
,
B-3-13
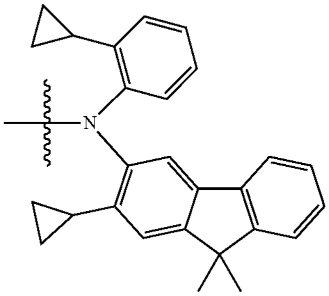
,
B-3-14
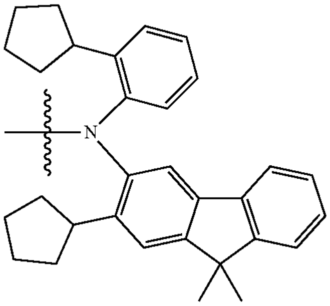
, -continued
B-3-15
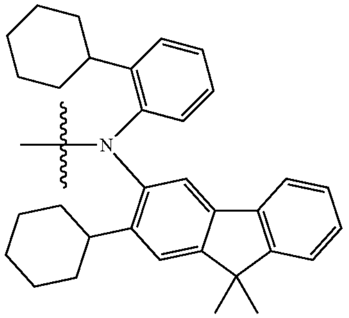
,
B-3-16
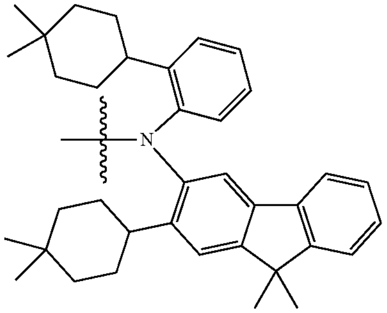
,
B-3-17
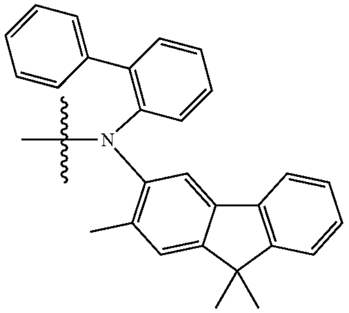
,
B-3-18
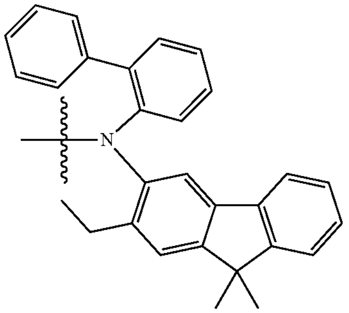
,
B-3-19
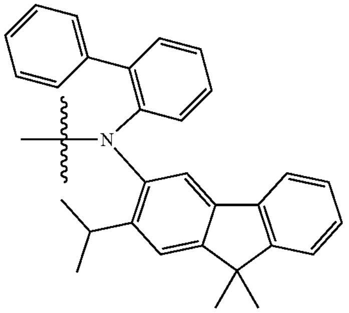
,
-continued
B-3-20
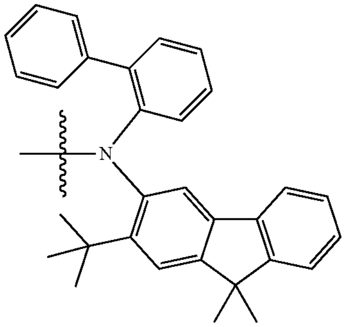
,
B-3-21
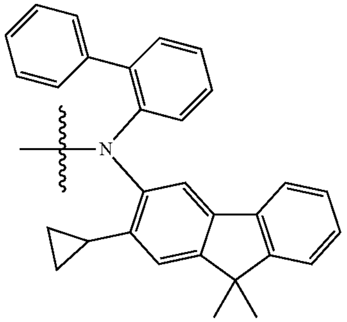
,
B-3-22
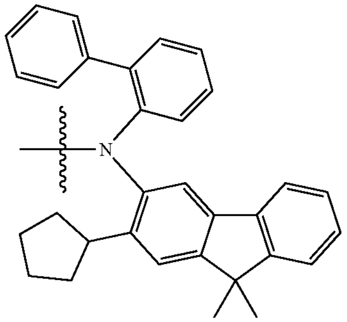
,
B-3-23
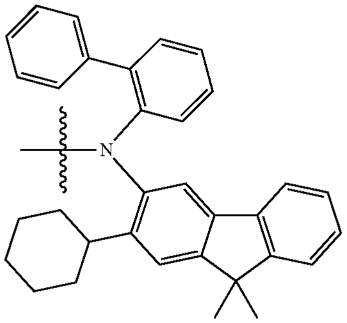
,
B-3-24
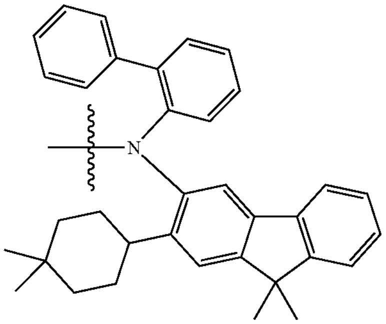
, -continued
B-3-25
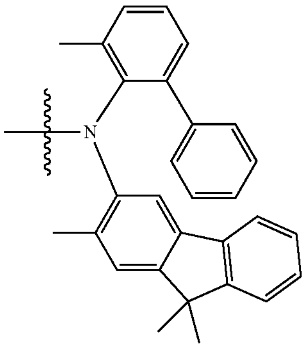
,
B-3-26
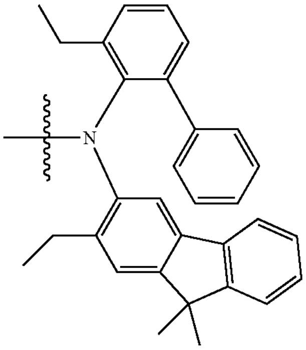
,
B-3-27
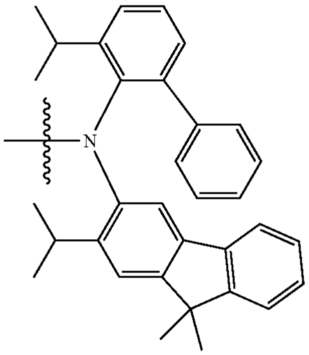
,
B-3-28
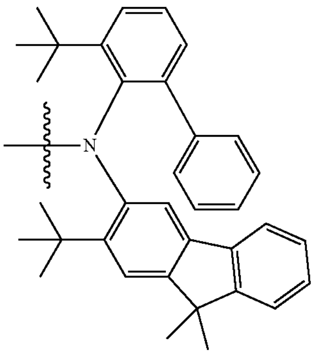
,
-continued
B-3-29
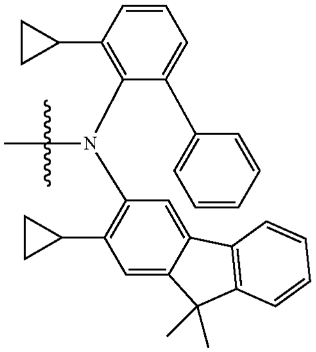
,
B-3-30
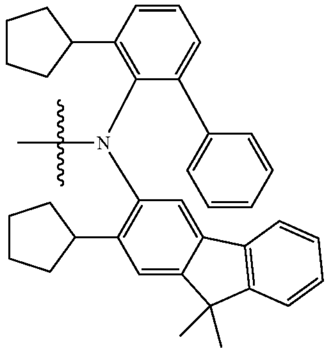
,
B-3-31
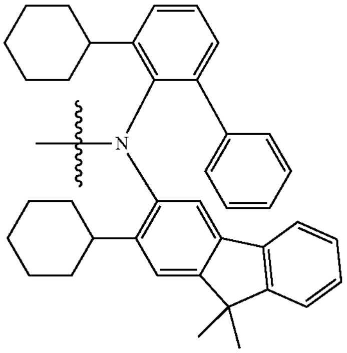
,
B-3-32
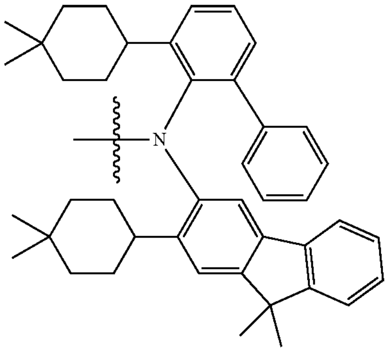
, -continued
B-3-33
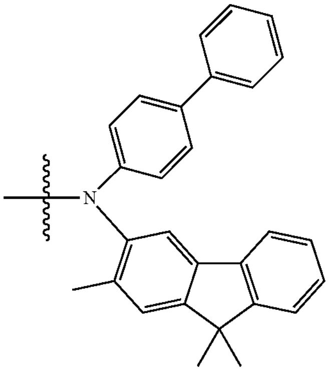
,
B-3-34
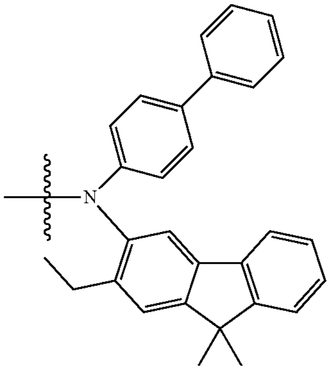
,
B-3-35
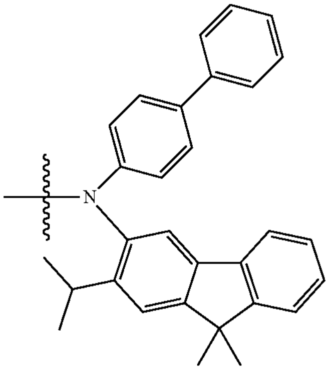
,
B-3-36
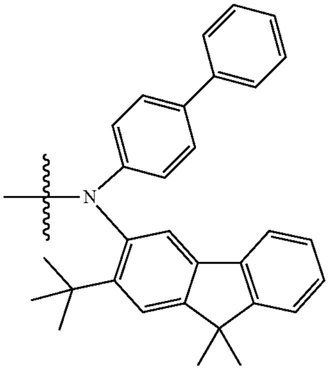
,
-continued
B-3-37
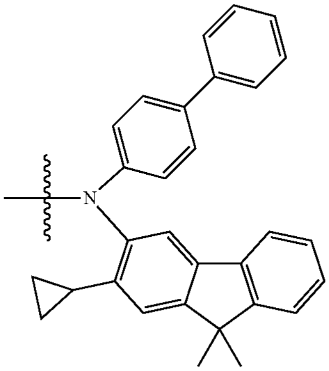
,
B-3-38
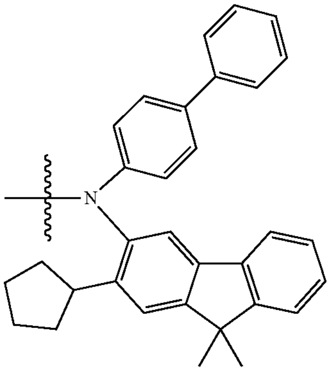
,
B-3-39
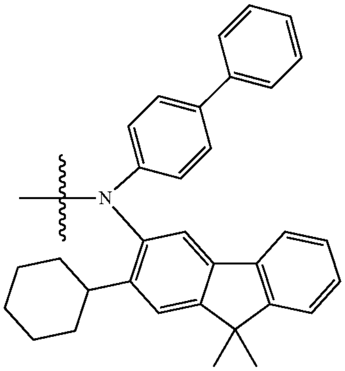
,
B-3-40
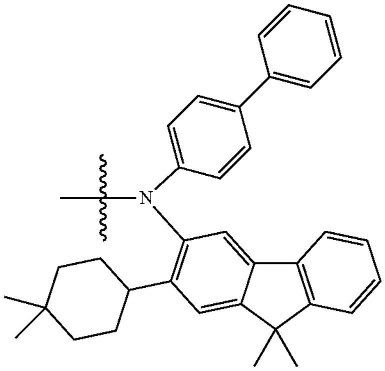
, -continued
B-3-41
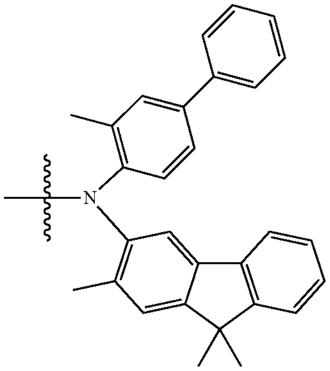
,
B-3-42
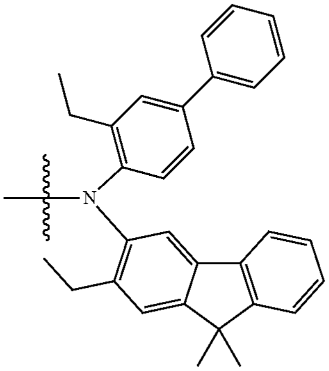
,
B-3-43
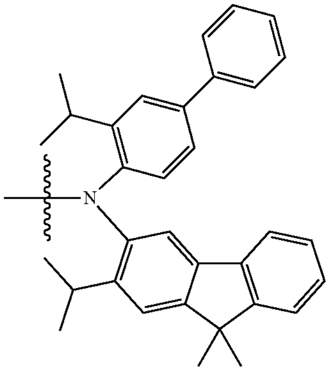
,
B-3-44
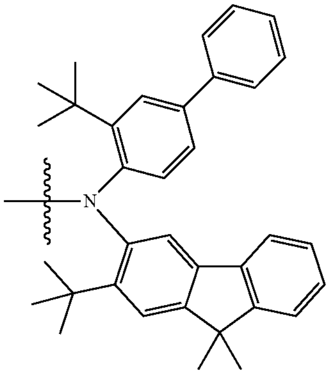
,
-continued
B-3-45
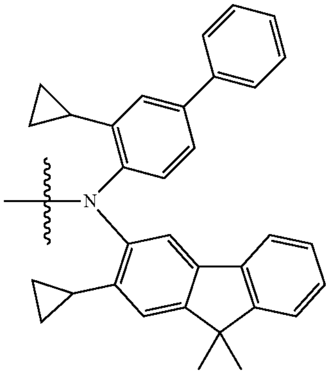
,
B-3-46
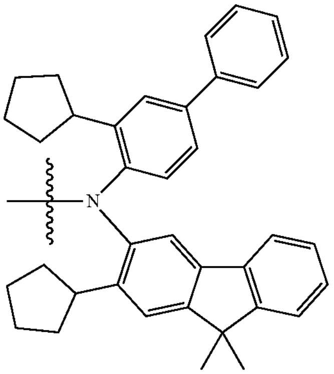
,
B-3-47
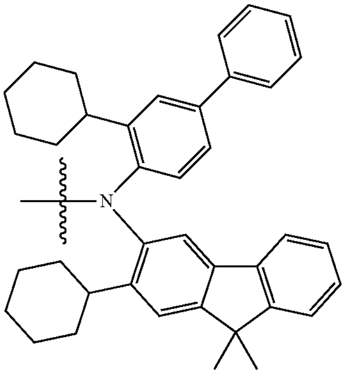
,
B-3-48
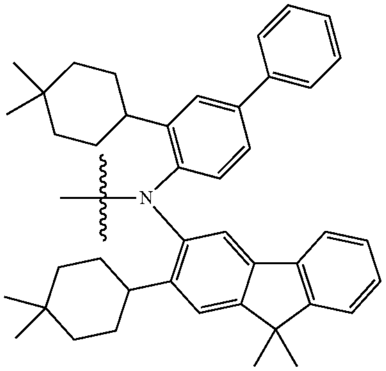
, -continued
B-3-49
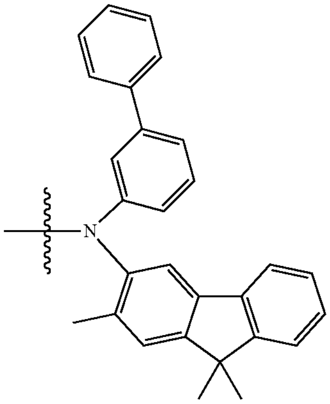
,
B-3-50
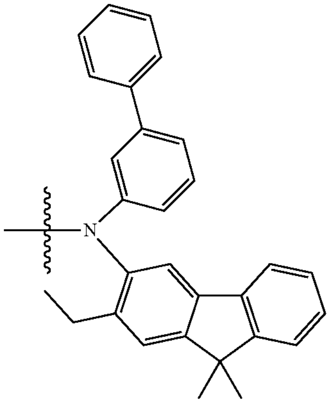
,
B-3-51
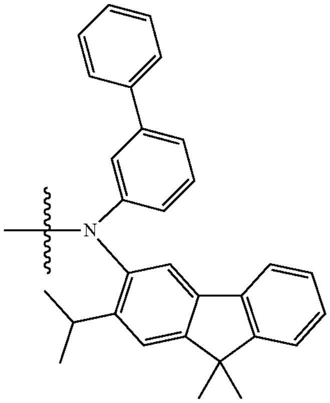
,
B-3-52
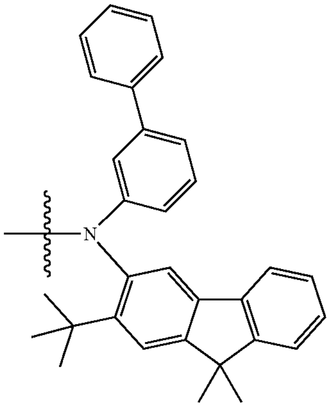
,
-continued
B-3-53
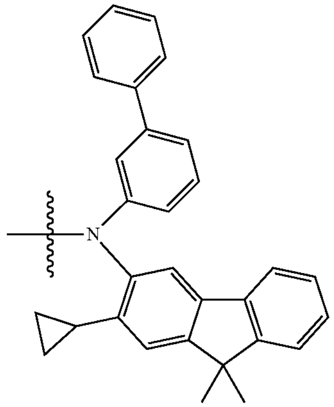
,
B-3-54
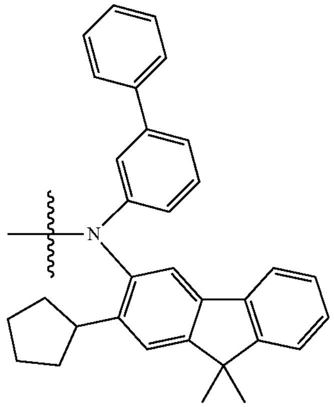
,
B-3-55
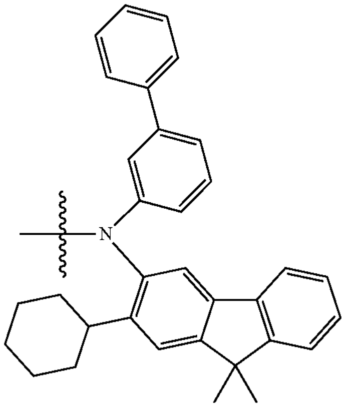
,
B-3-56
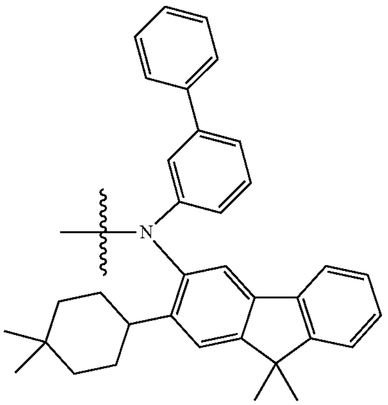
, -continued
B-3-57
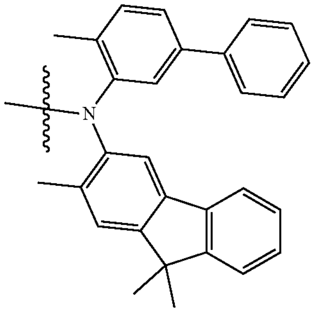
,
B-3-58
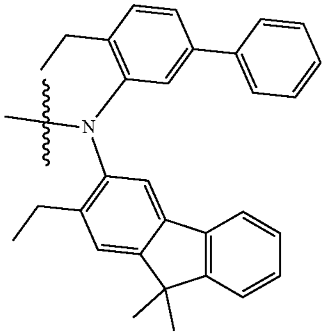
,
B-3-59
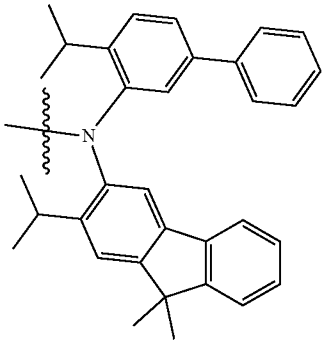
,
B-3-60
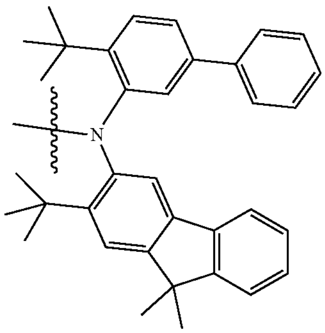
,
-continued
B-3-61
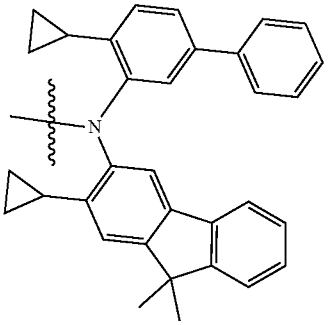
,
B-3-62
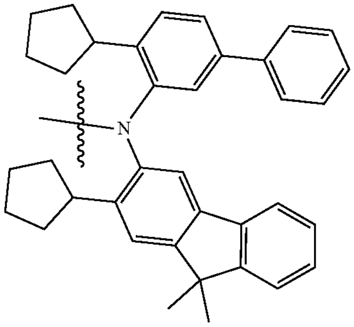
,
B-3-63
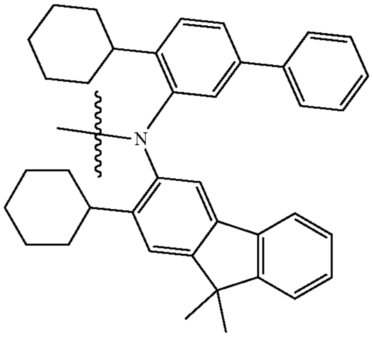
,
B-3-64
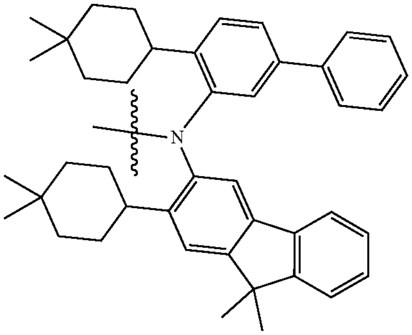
, -continued
B-3-65
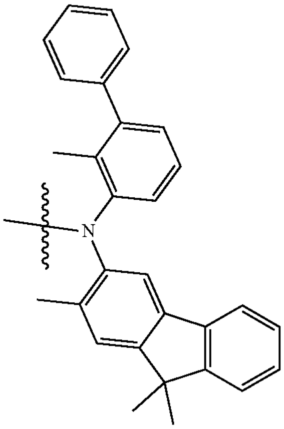
,
B-3-68
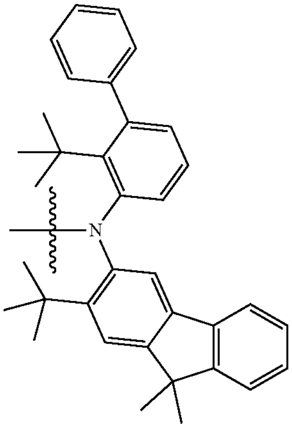
,
B-3-66
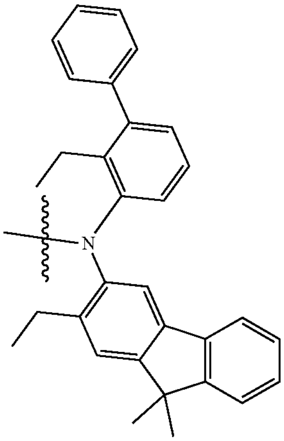
,
B-3-69
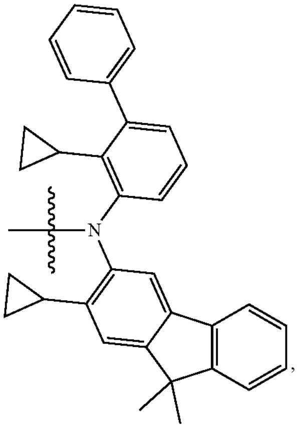
,
B-3-67
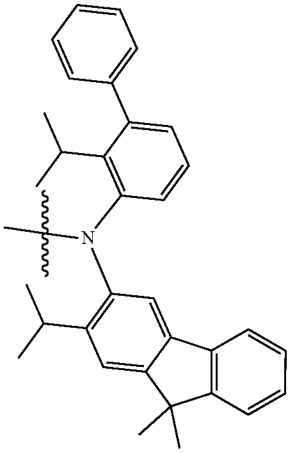
,
B-3-70
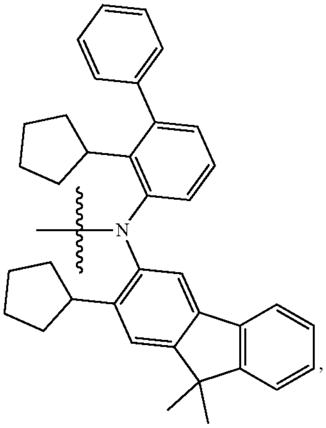
, B-3-71
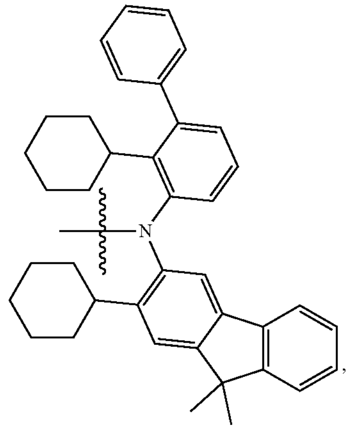
B-3-72
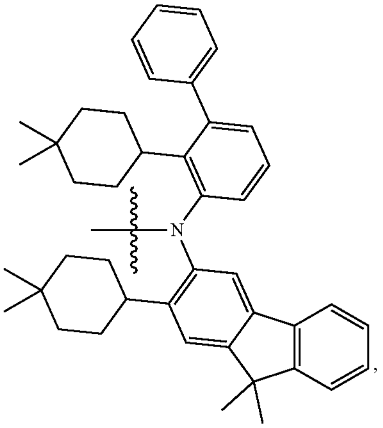
B-3-73
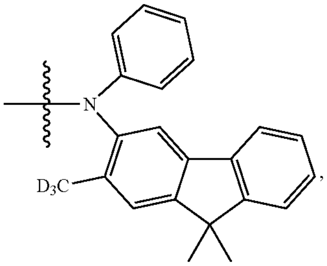
B-3-74
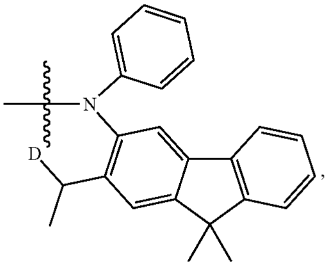
B-3-75
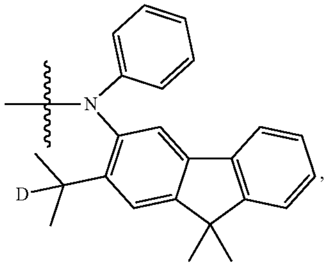
B-3-76
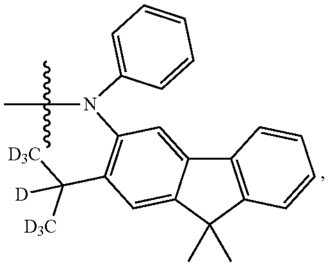
B-3-77
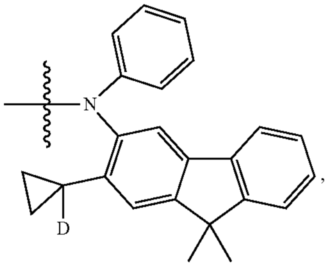
B-3-78
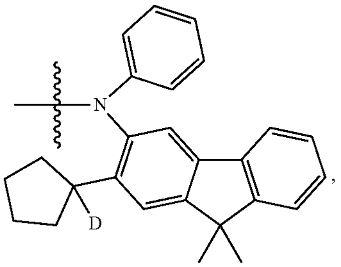
B-3-79
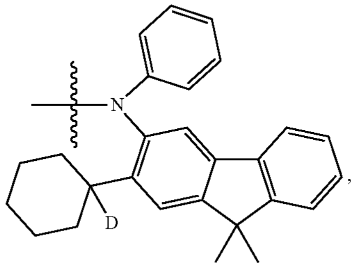
B-3-80
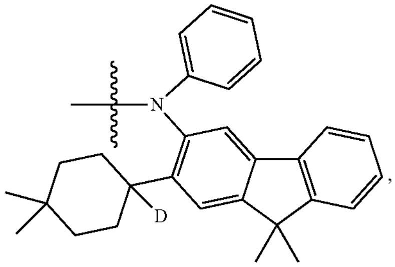

-continued
B-3-81
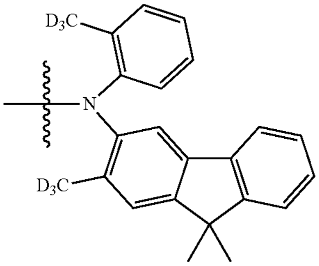,
B-3-82
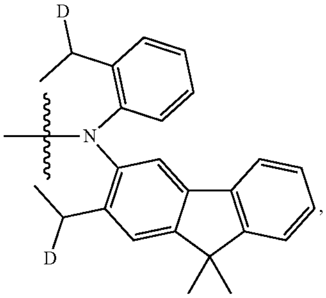,
B-3-83
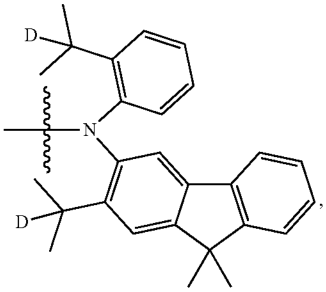,
B-3-84
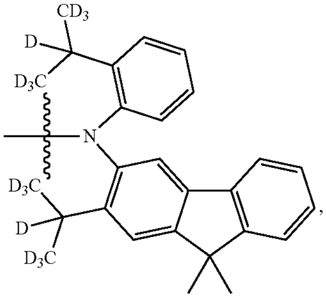,
B-3-85
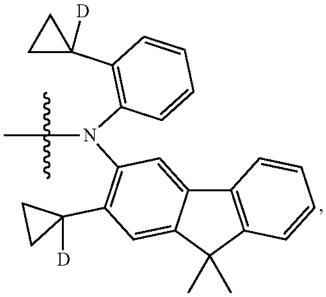,
-continued
B-3-86
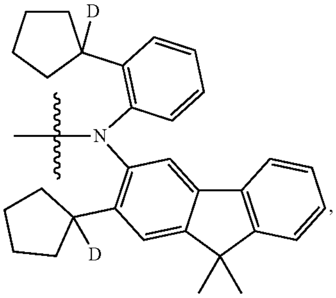,
B-3-87
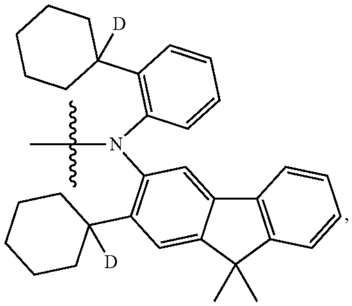,
B-3-88
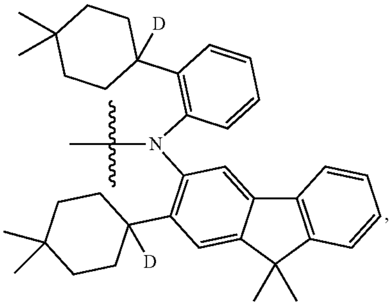,
B-3-89
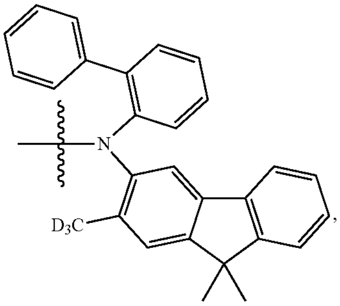,
B-3-90
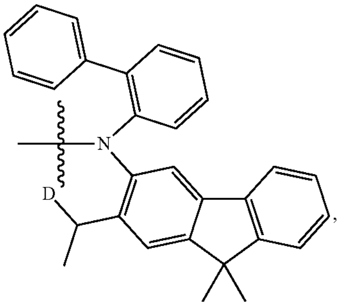, -continued
B-3-91
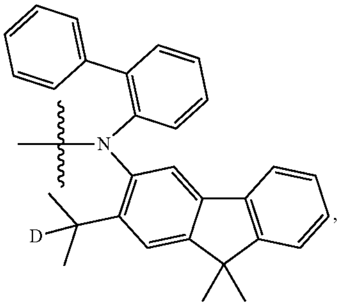
B-3-92
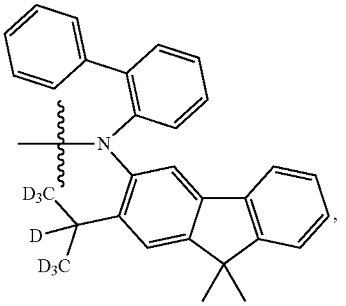
B-3-93
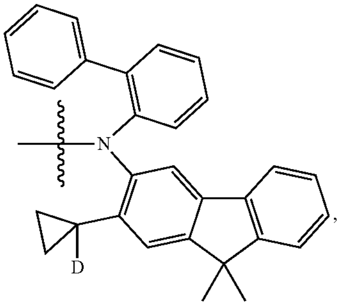
B-3-94
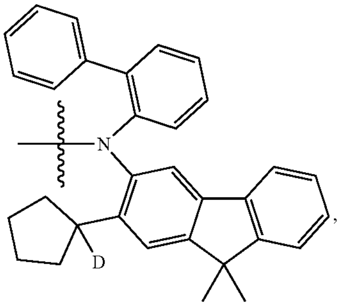
B-3-95
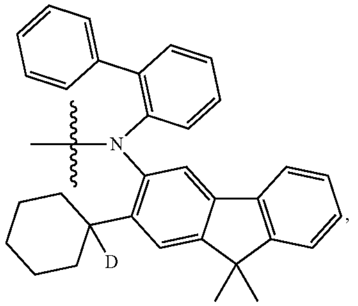
-continued
B-3-96
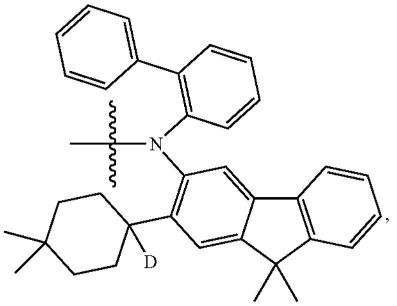
B-3-97
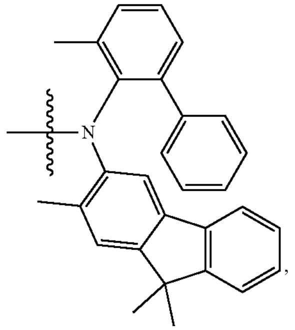
B-3-98
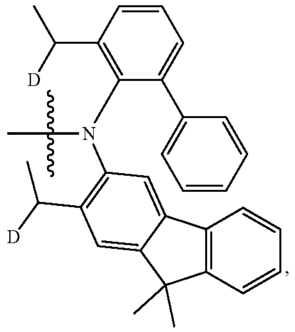
B-3-99
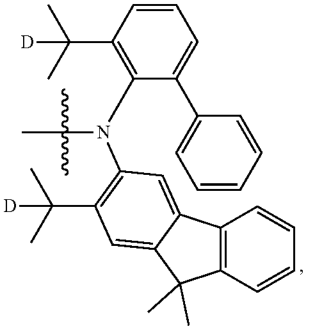

-continued
B-3-100
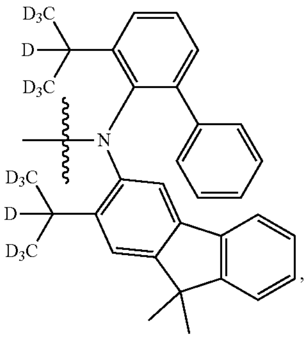
,
B-3-101
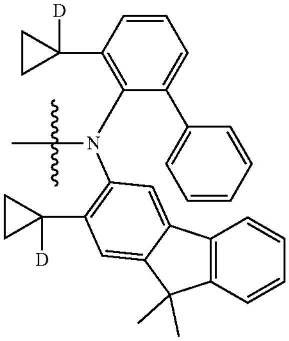
,
B-3-102
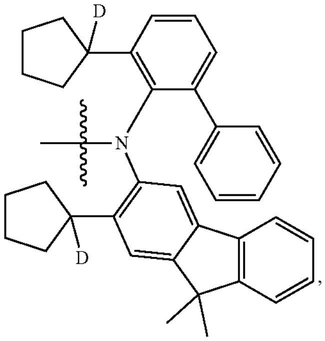
,
B-3-103
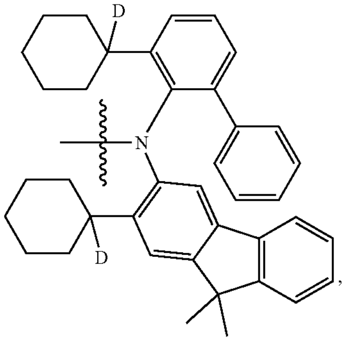
,
-continued
B-3-104
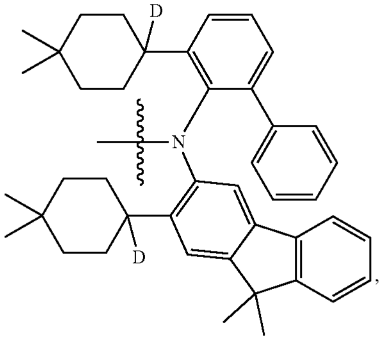
,
B-3-105
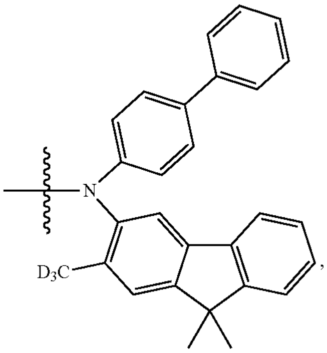
,
B-3-106
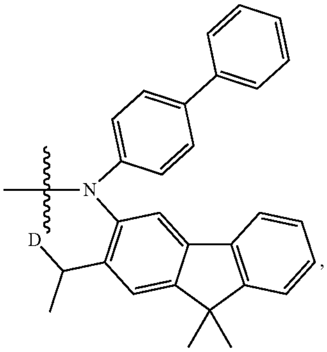
,
B-3-107
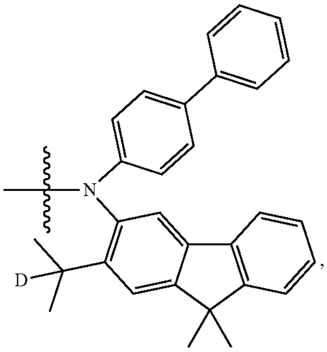
, B-3-108
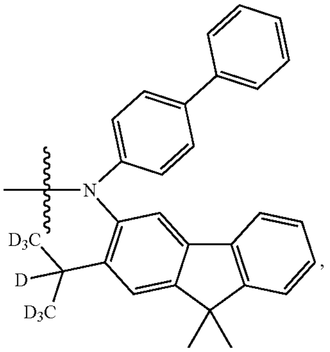
B-3-109
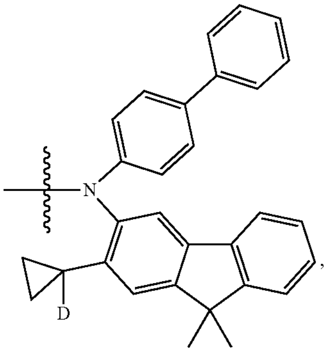
B-3-110
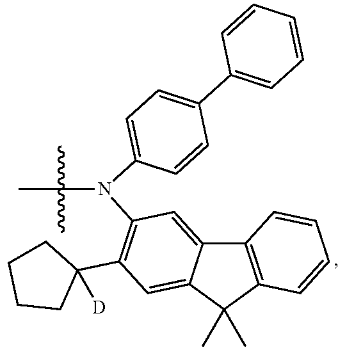
B-3-111
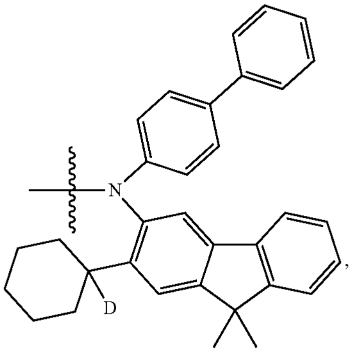
B-3-112
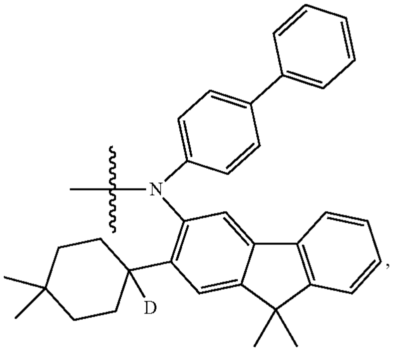
B-3-113
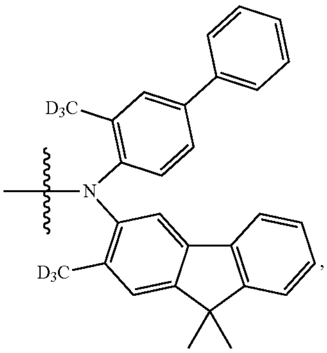
B-3-114
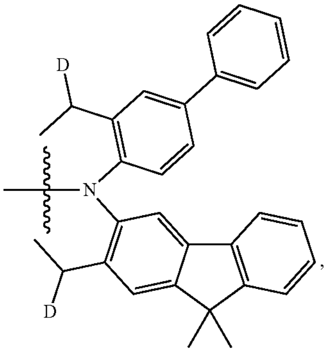
B-3-115
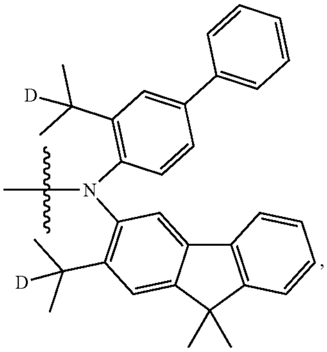

-continued
B-3-116
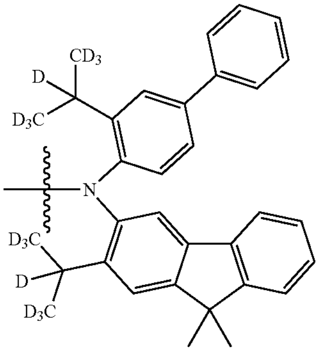
,
B-3-117
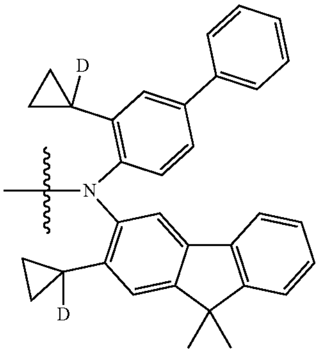
,
B-3-118
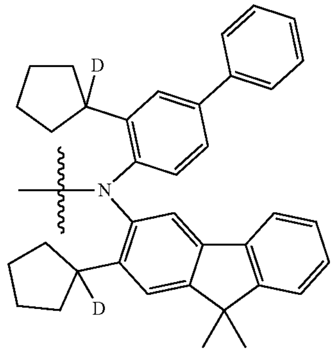
,
B-3-119
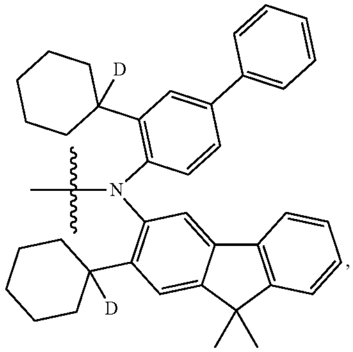
,
-continued
B-3-120
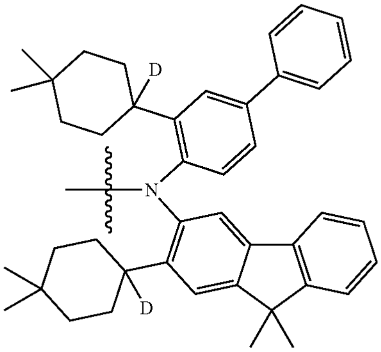
,
B-3-121
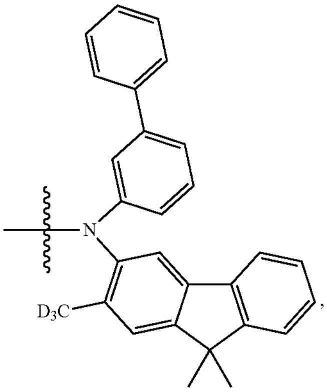
,
B-3-122
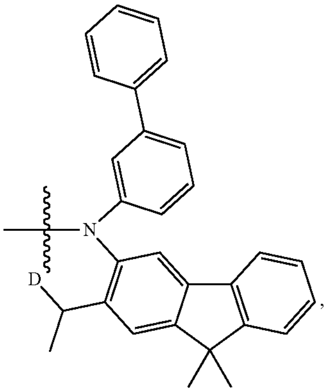
,
B-3-123
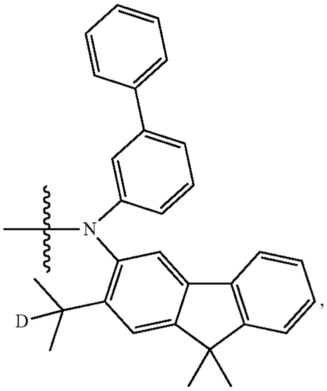
, -continued
B-3-124
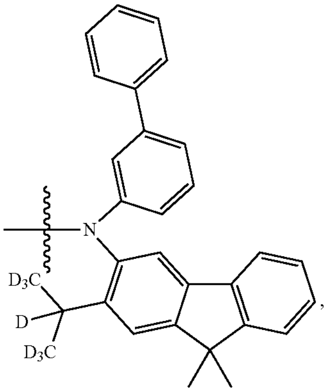
B-3-125
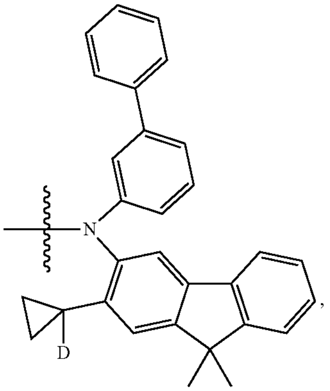
B-3-126
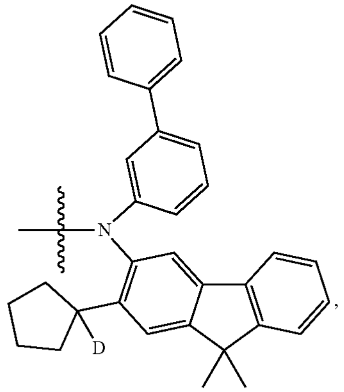
B-3-127
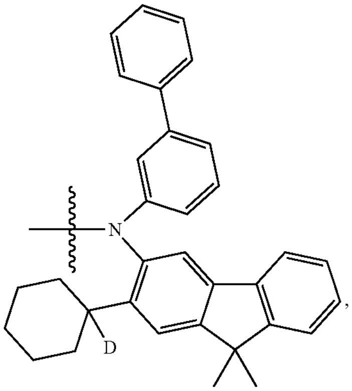
-continued
B-3-128
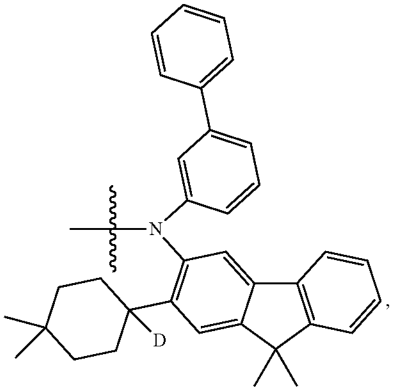
B-3-129
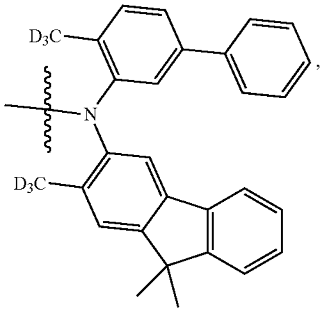
B-3-130
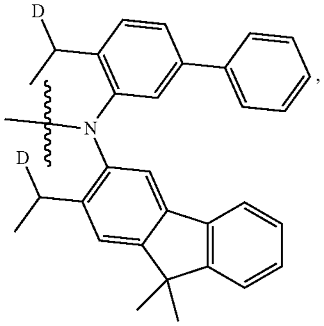
B-3-131
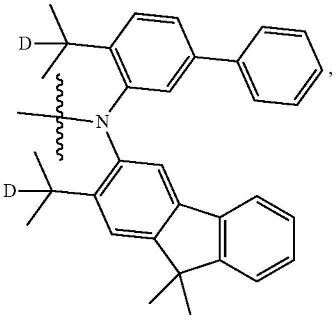

-continued
B-3-132
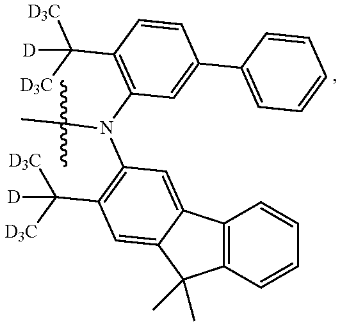
B-3-133
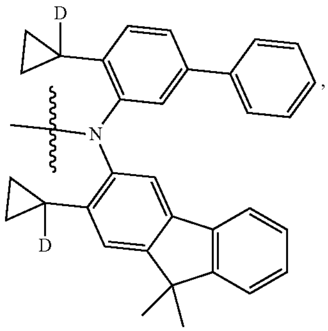
B-3-134
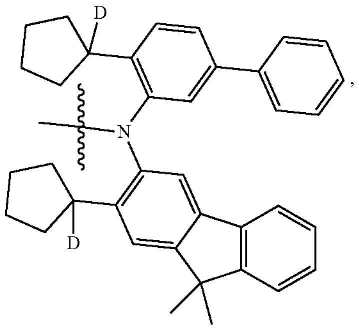
B-3-135
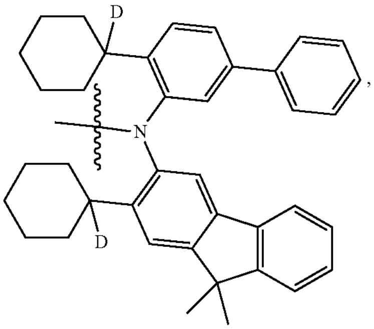
-continued
B-3-136
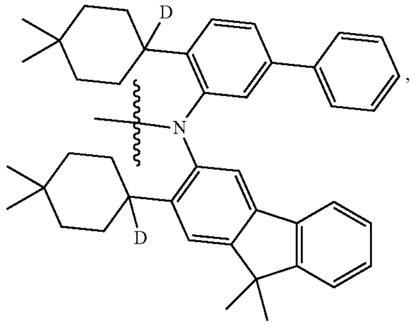
B-3-137
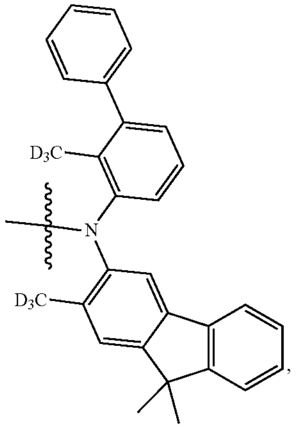
B-3-138
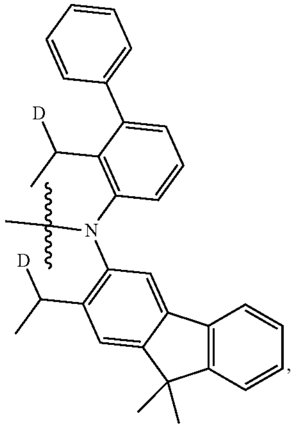
B-3-139
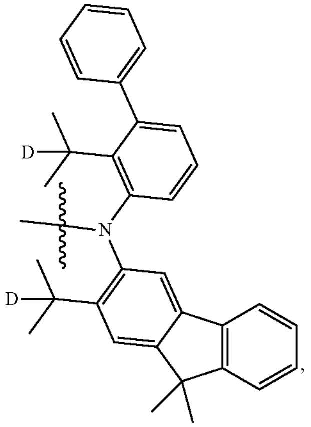

-continued
B-3-140
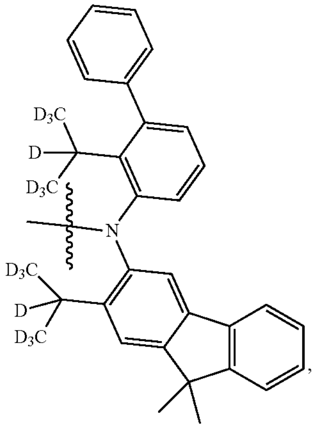
B-3-141
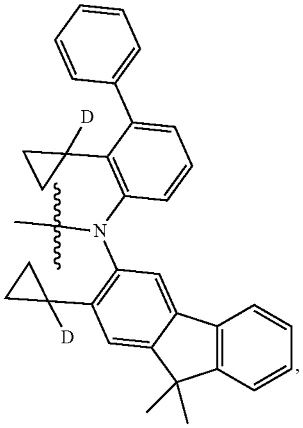
B-3-142
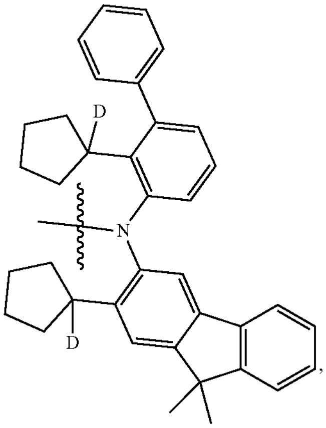
-continued
B-3-143
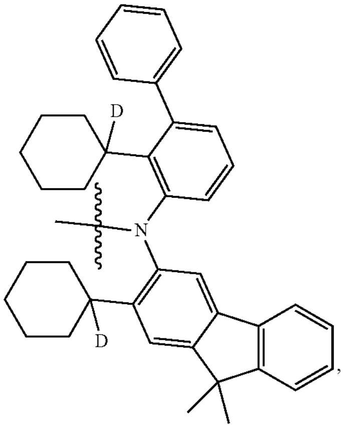
B-3-144
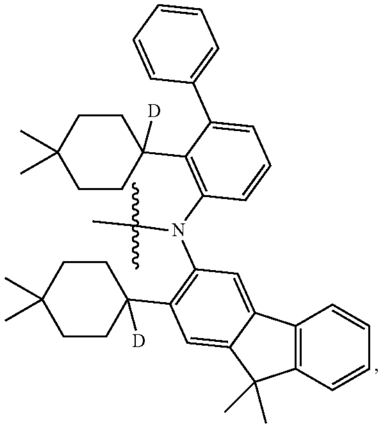
B-3-145
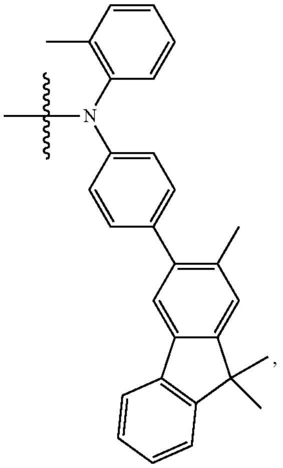
B-3-146
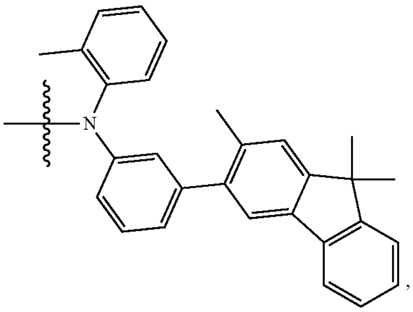

-continued
B-3-147
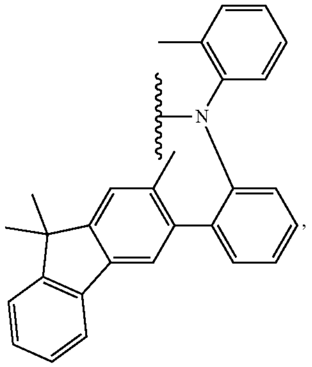
B-3-148
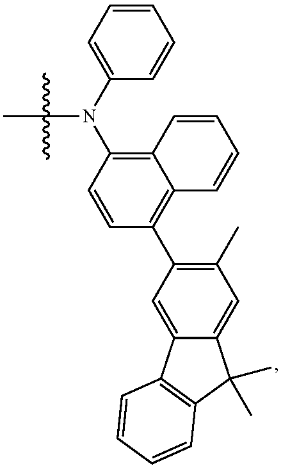
B-3-149
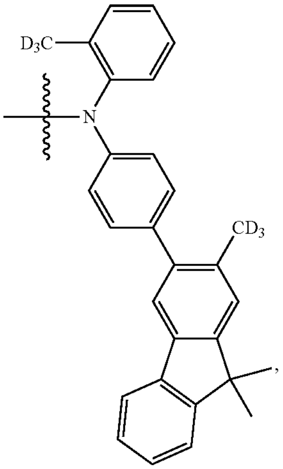
B-3-150
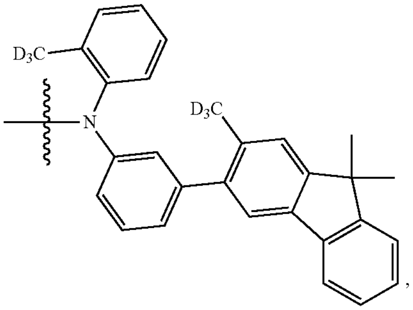
-continued
B-3-151
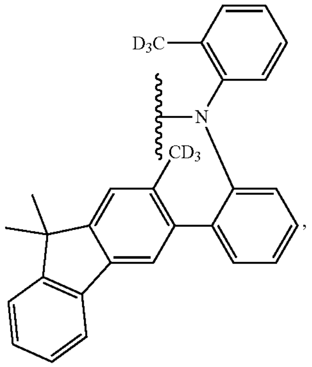
B-3-152
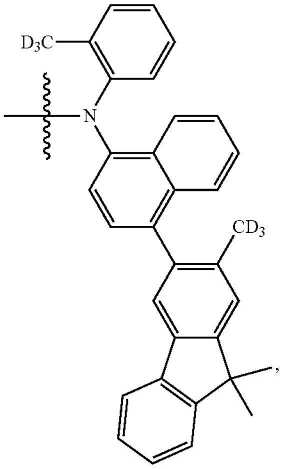
B-3-153
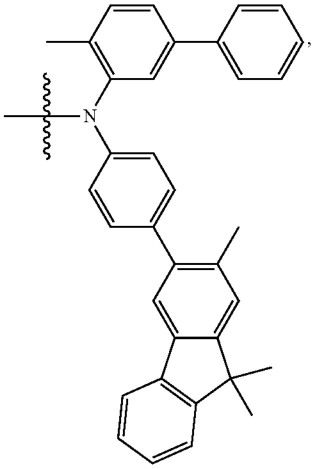
B-3-154
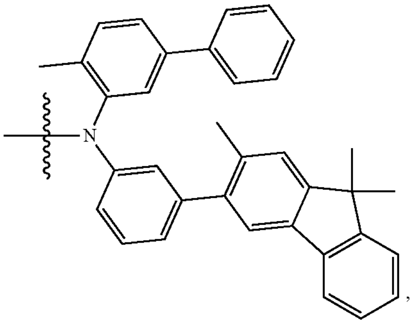

-continued
B-3-155
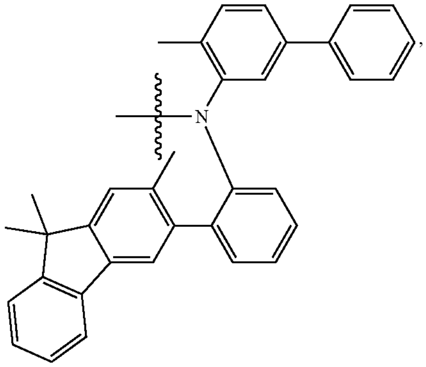
B-3-156
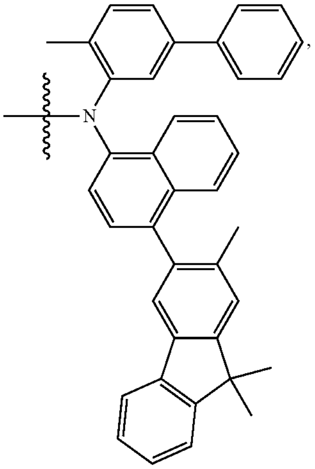
B-3-157
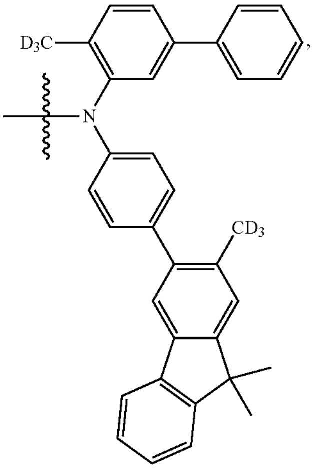
B-3-158
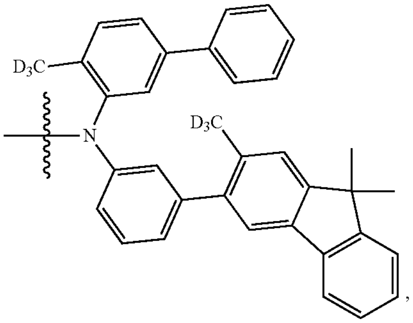
-continued
B-3-159
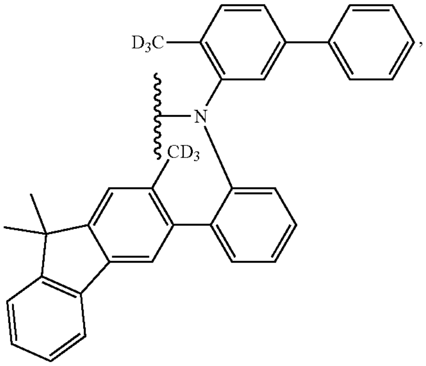
B-3-160
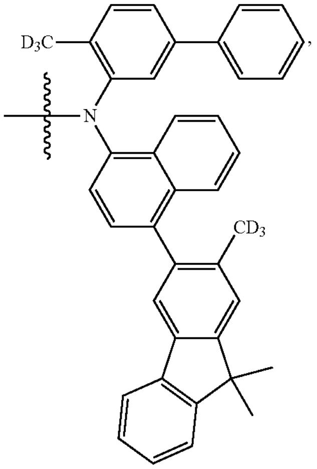
B-3-161
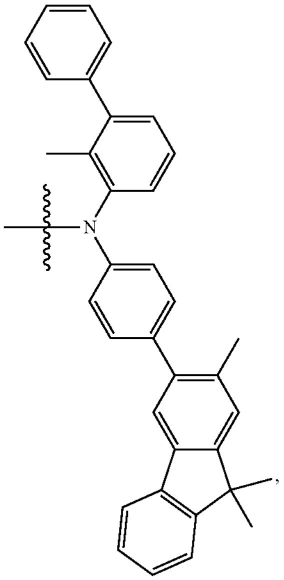

-continued
B-3-162
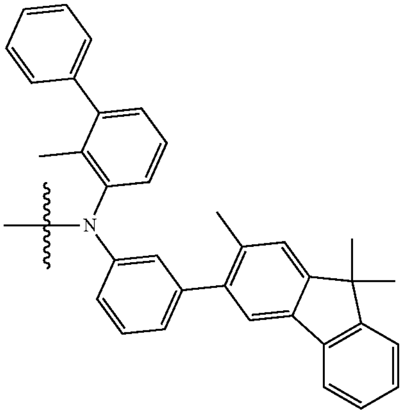
,
B-3-163
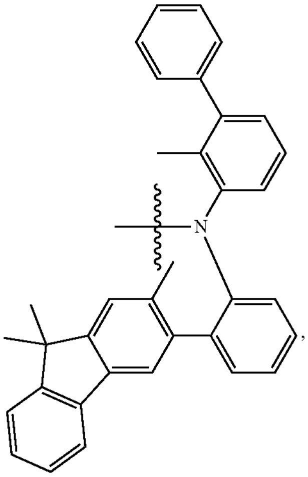
,
B-3-164
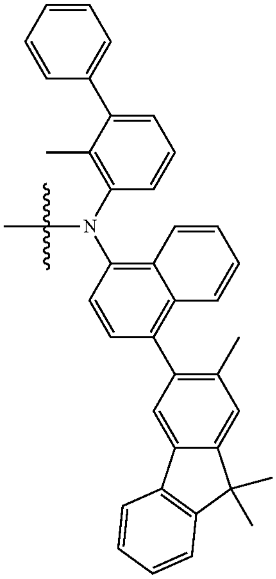
,
-continued
B-3-165
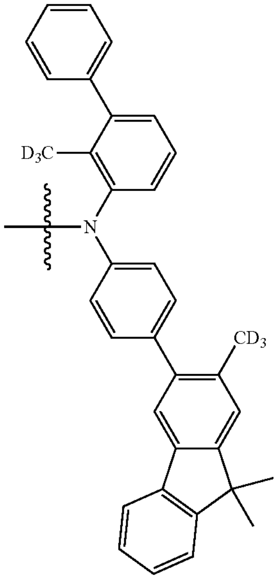
,
B-3-166
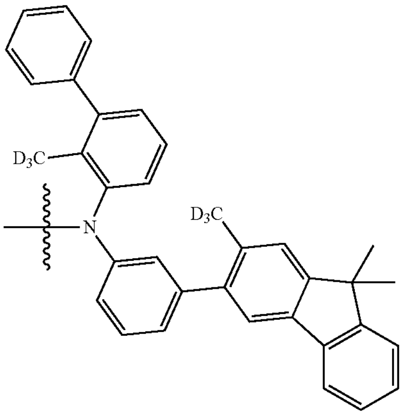
,
B-3-167
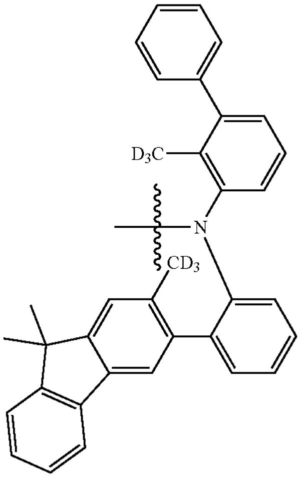
, -continued
B-3-168
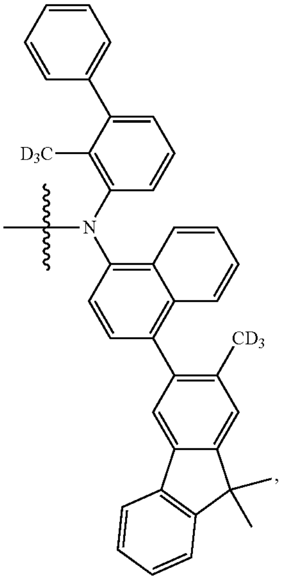
,
B-3-169
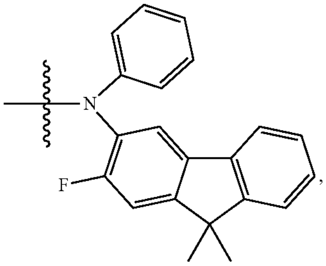
,
B-3-170
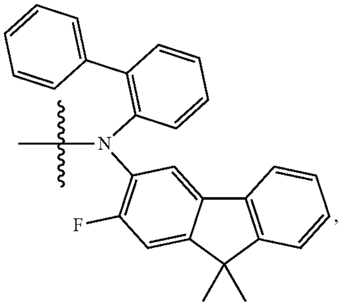
,
B-3-171
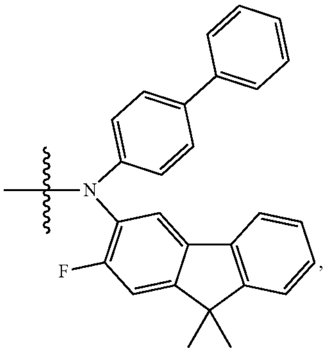
,
-continued
B-3-172
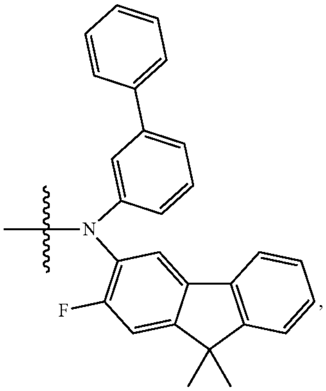
,
B-3-173
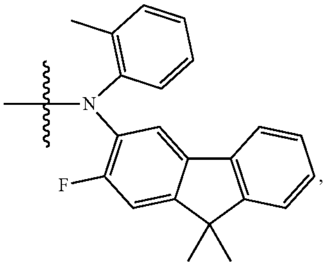
,
B-3-174
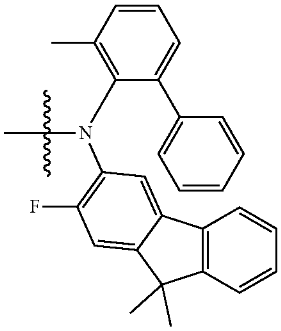
,
B-3-175
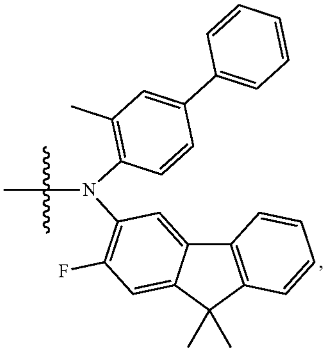
, -continued
B-3-176
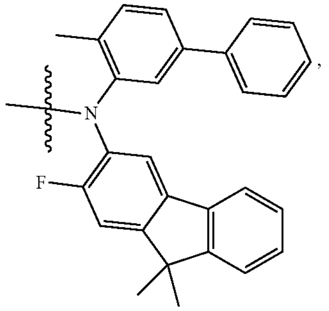
B-3-177
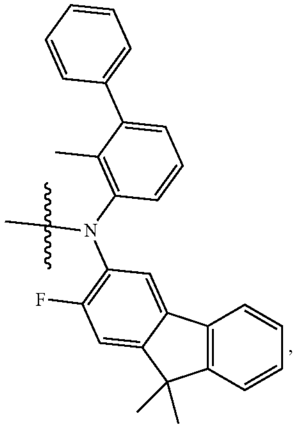
B-3-178
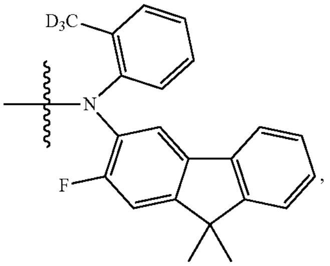
B-3-179
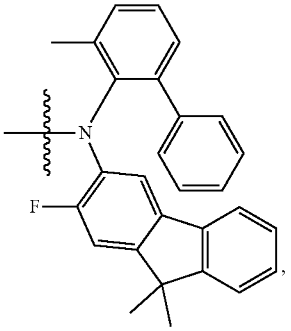
-continued
B-3-180
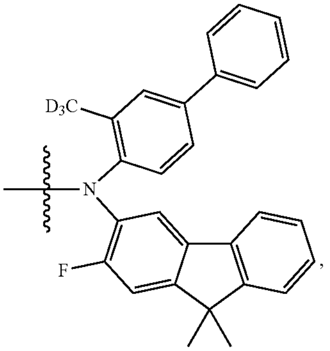
B-3-181
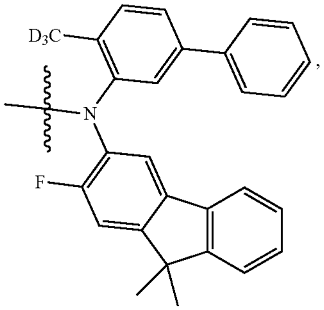
B-3-182
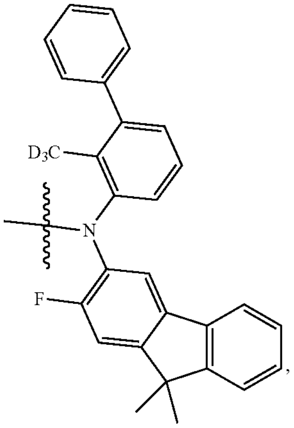
B-3-183
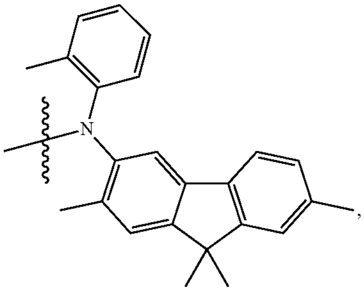

-continued
B-3-184
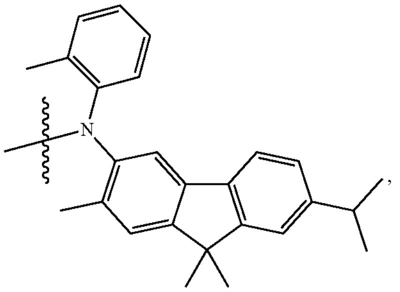
B-3-185
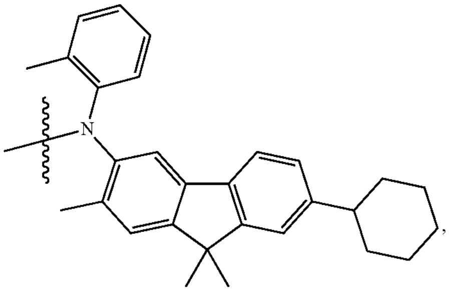
B-3-186
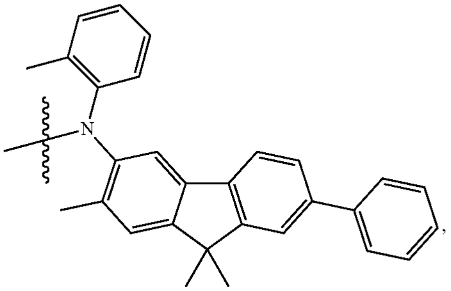
B-3-187
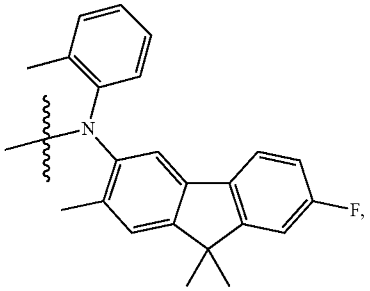
B-3-188
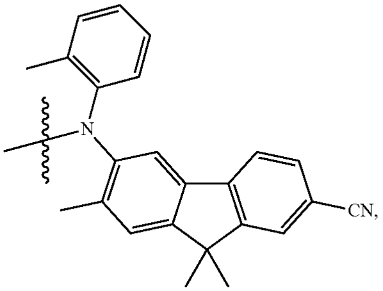
-continued
B-3-189
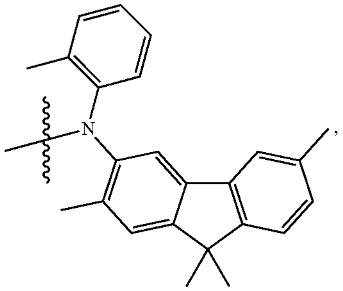
B-3-190
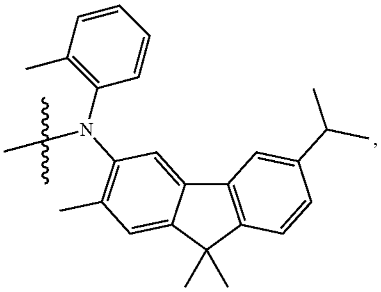
B-3-191
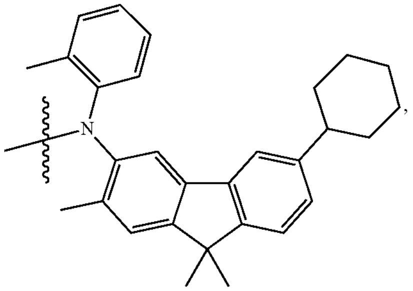
B-3-192
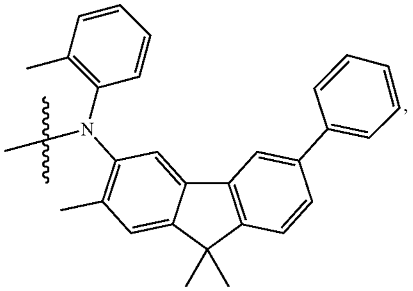
B-3-193
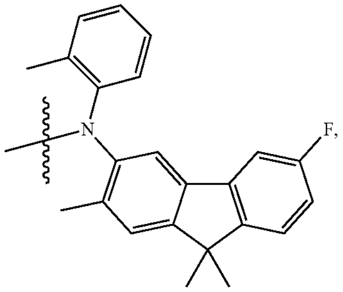

-continued
B-3-194
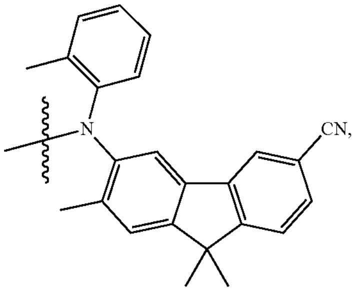
B-3-195
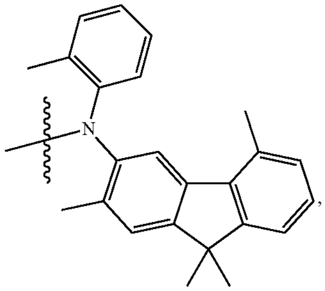
B-3-196
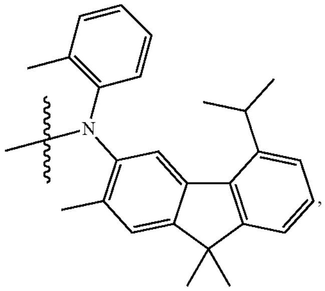
B-3-197
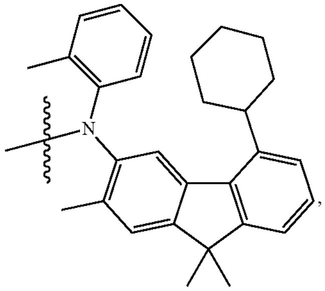
B-3-198
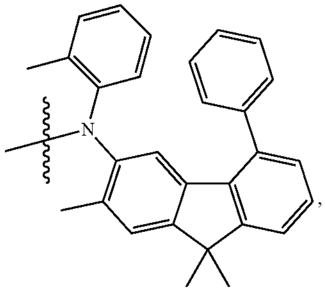
-continued
B-3-199
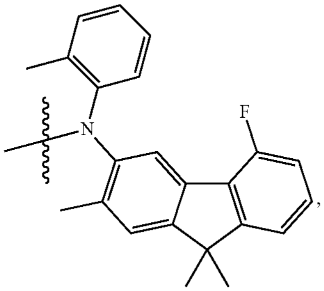
B-200
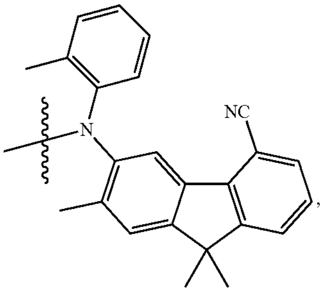
B-3-201
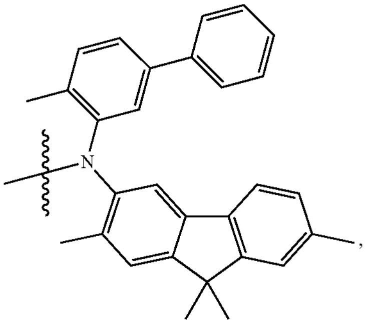
B-3-202
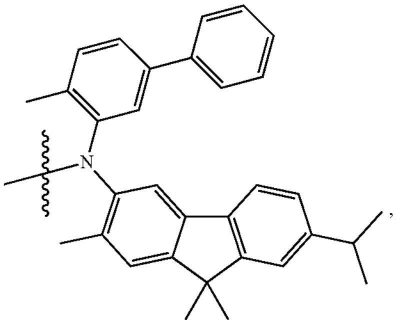
B-3-203
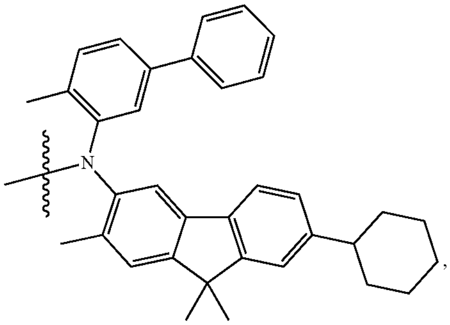

-continued
B-3-204
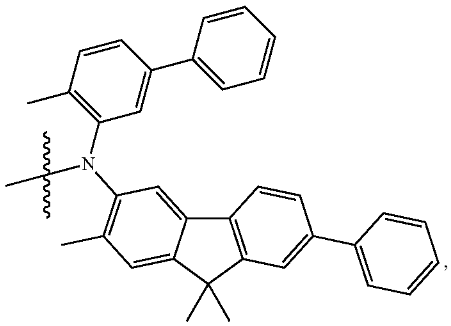
,
B-3-205
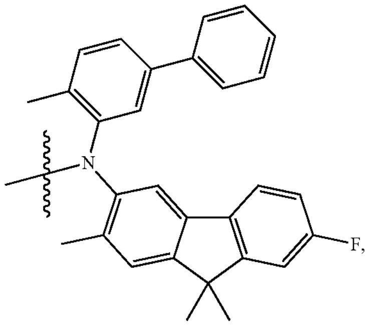
F,
B-3-206
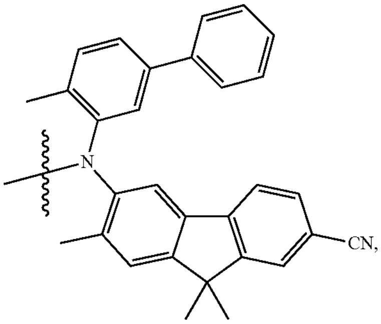
CN,
B-3-207
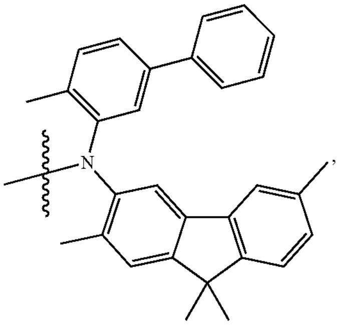
,
B-3-208
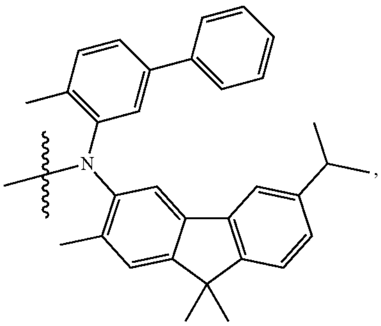
,
-continued
B-3-209
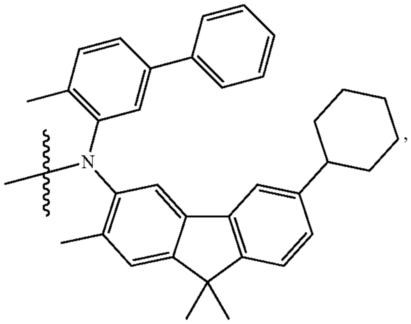
,
B-3-210
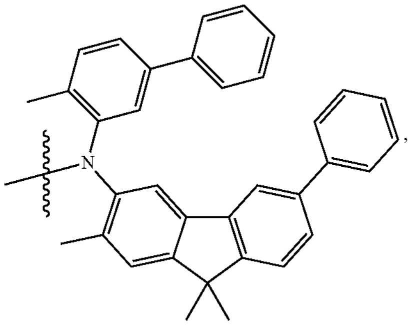
,
B-3-211
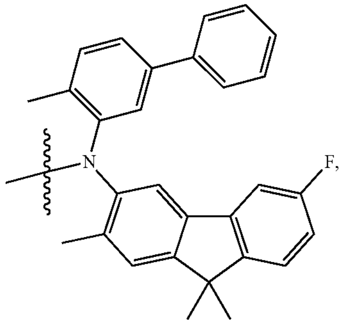
F,
B-3-212
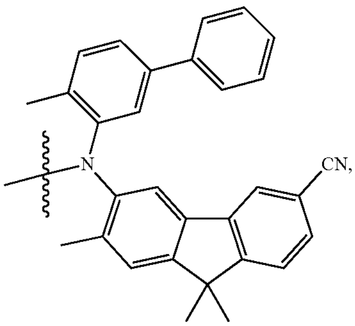
CN,
B-3-213
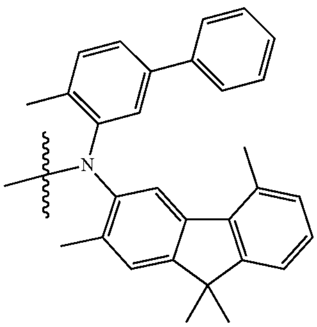
, -continued
B-3-214
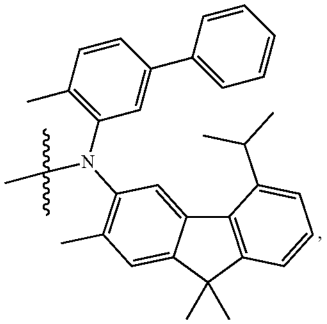
B-3-215
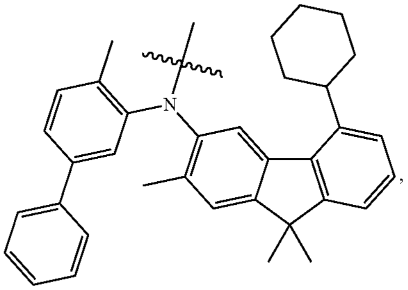
B-3-216
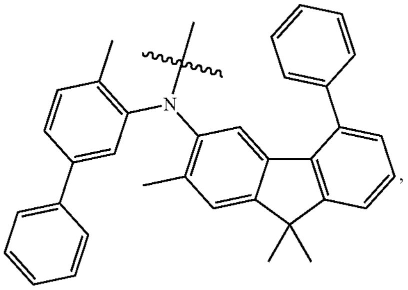
B-3-217
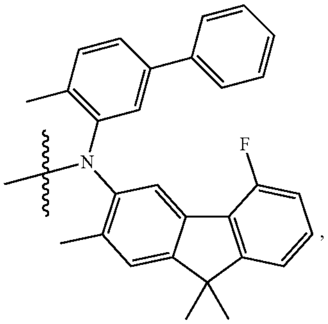
B-3-218
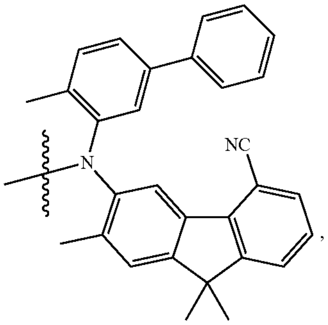
-continued
B-3-219
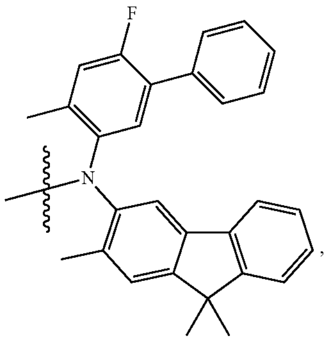
B-3-220
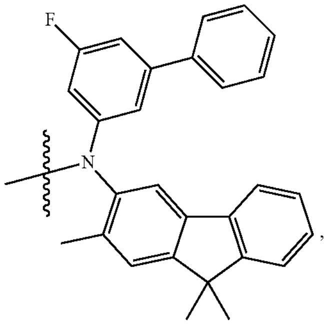
B-3-221
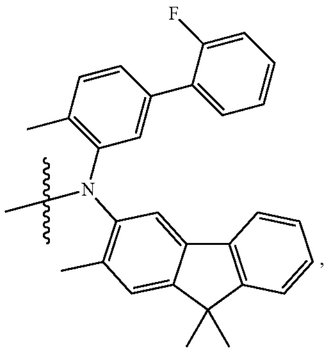
B-3-222
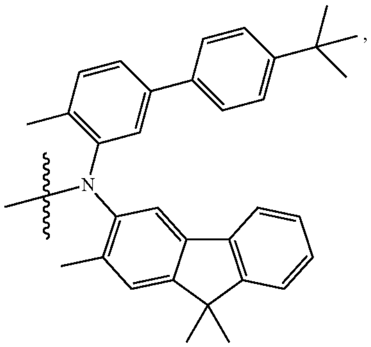

-continued
B-3-223
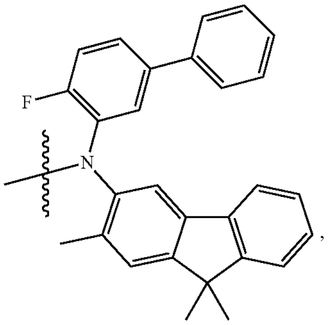
B-3-224
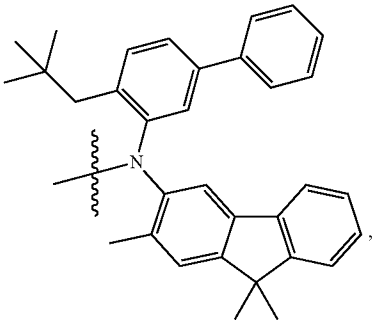
B-3-225
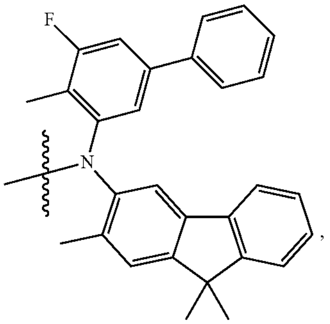
B-3-226
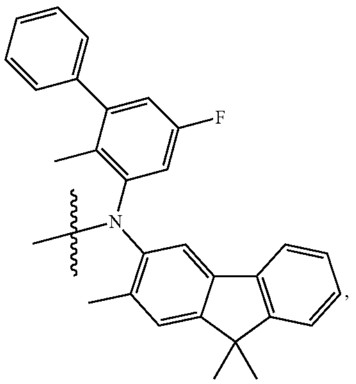
-continued
B-3-227
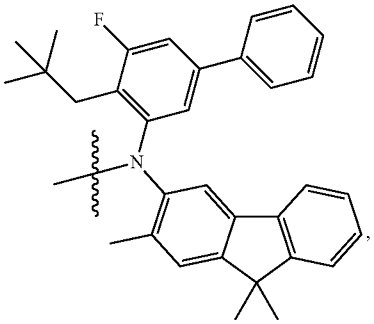
B-3-228
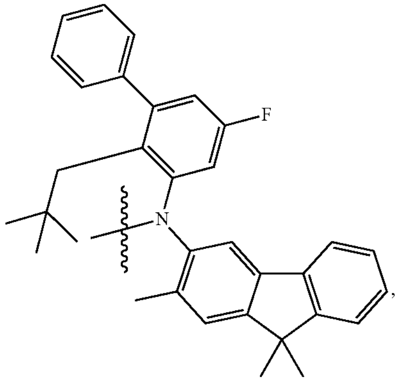
B-3-229
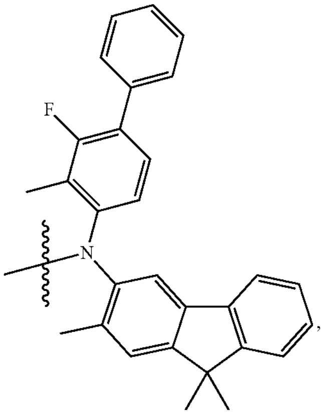
B-3-230
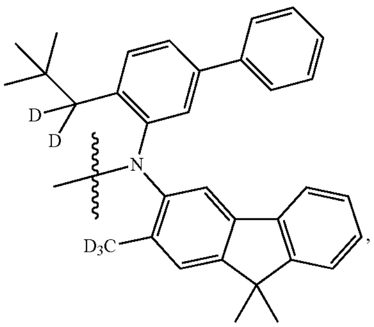

-continued
B-3-231
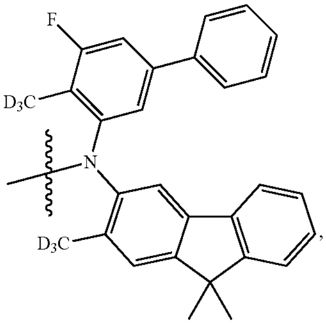
,
B-3-232
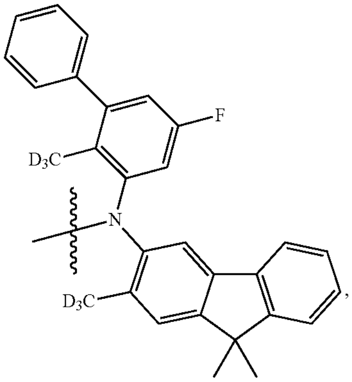
,
B-3-233
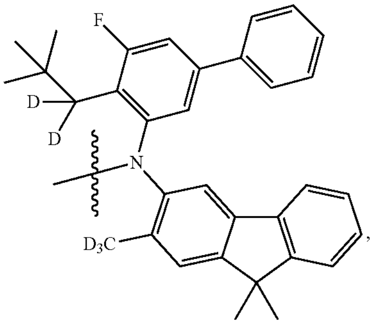
,
B-3-234
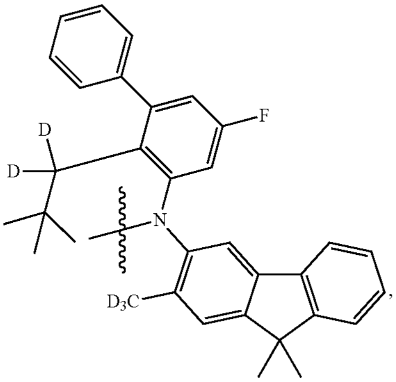
,
-continued
B-3-235
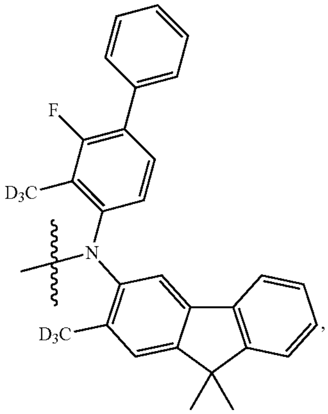
,
B-4-1
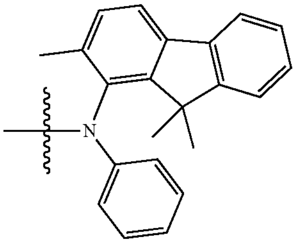
,
B-4-2
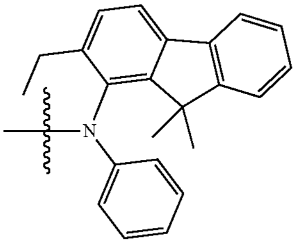
,
B-4-3
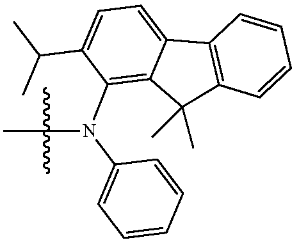
,
B-4-4
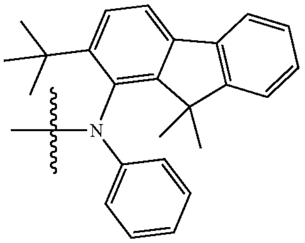
, -continued
B-4-5
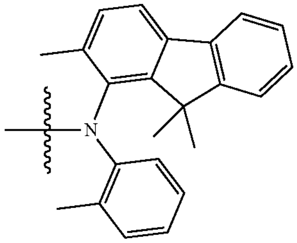
,
B-4-6
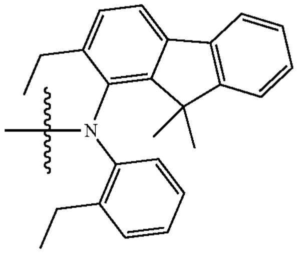
,
B-4-7
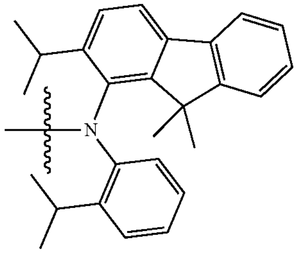
,
B-4-8
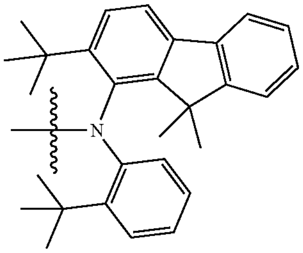
,
B-4-9
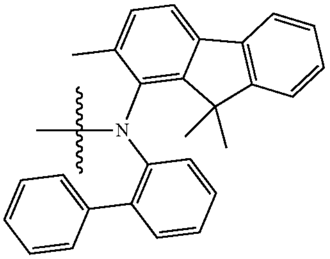
,
B-4-10
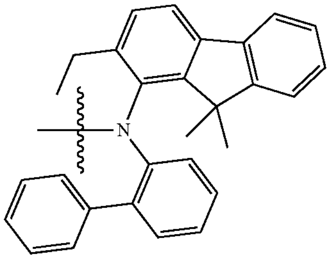
,
B-4-11
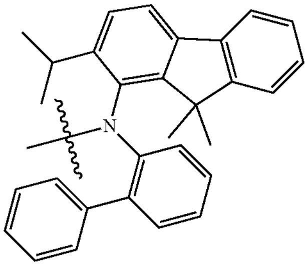
,
B-4-12
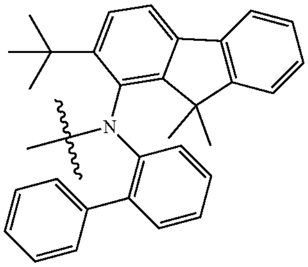
,
B-4-13
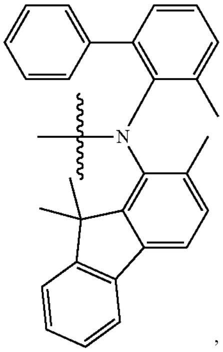
,
B-4-14
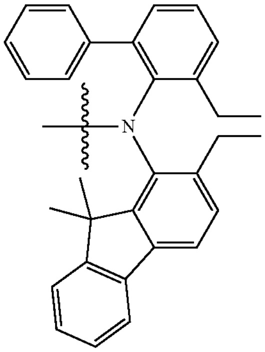
, B-4-15
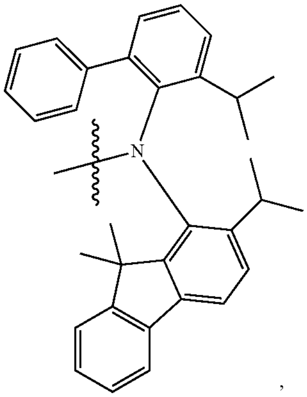
,
B-4-16
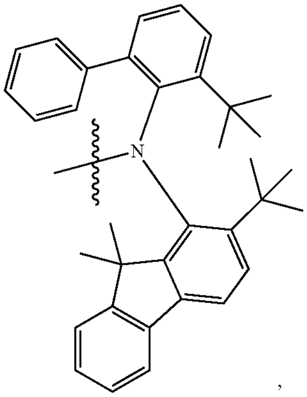
,
B-4-17
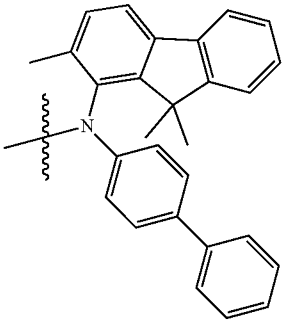
,
B-4-18
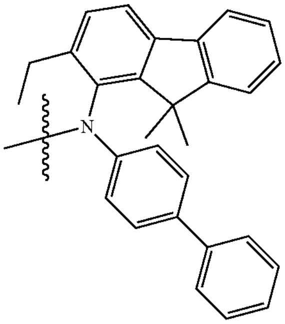
,
B-4-19
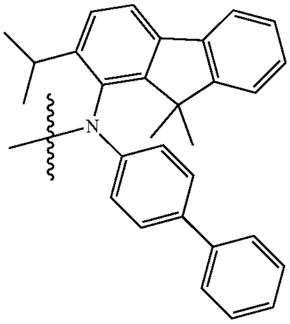
,
B-4-20
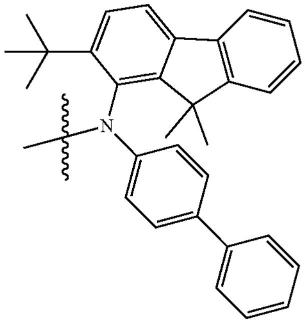
,
B-4-21
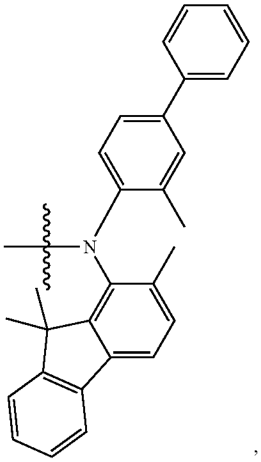
,
B-4-22
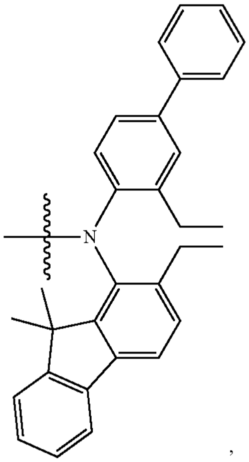
, B-4-23
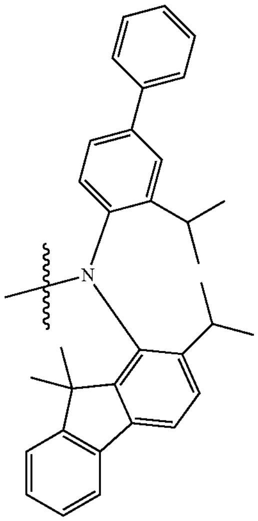
,
B-4-24
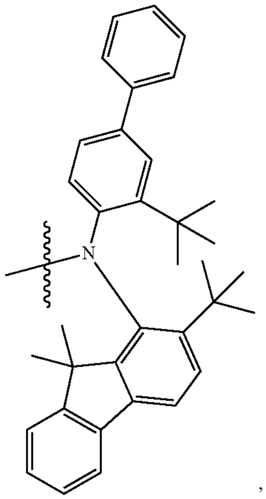
,
B-4-25
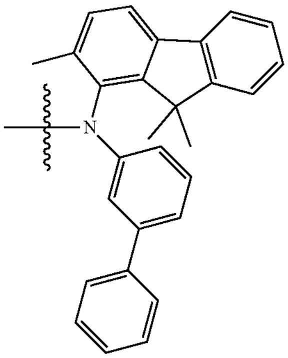
,
B-4-26
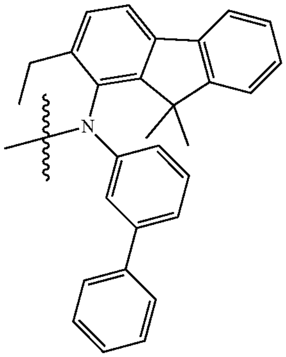
,
B-4-27
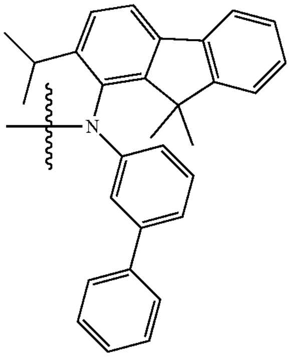
,
B-4-28
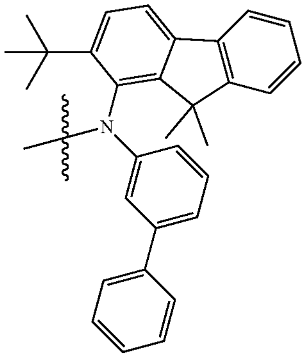
,
B-4-29
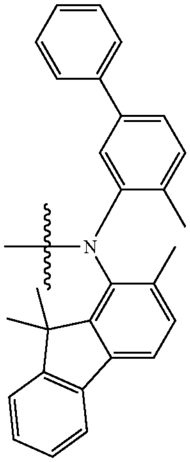
, -continued
B-4-30
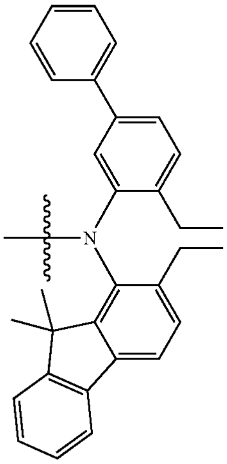
,
B-4-31
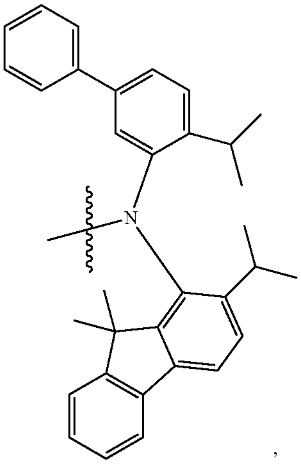
,
B-4-32
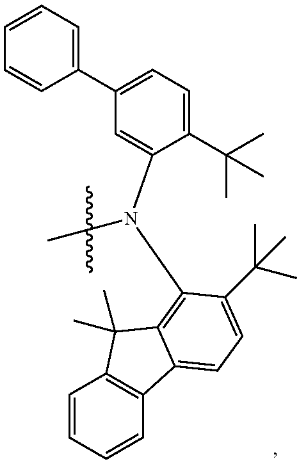
,
B-4-33
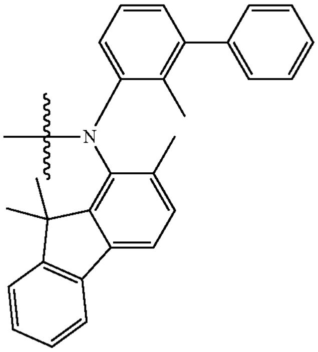
,
B-4-34
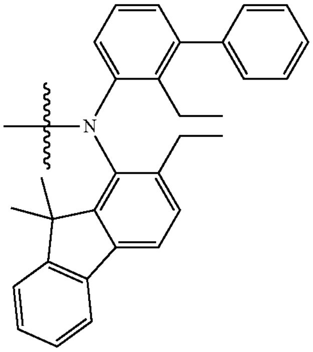
,
B-4-35
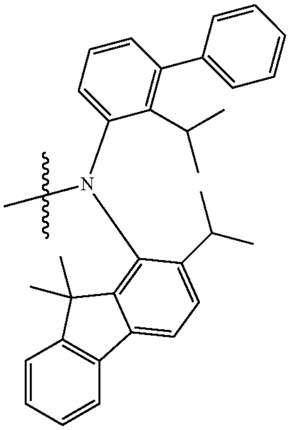
,
B-4-36
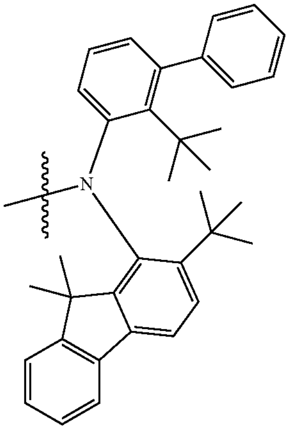
, -continued
B-4-37
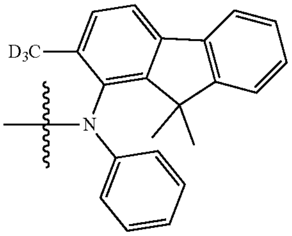
,
B-4-38
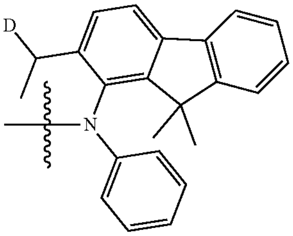
,
B-4-39
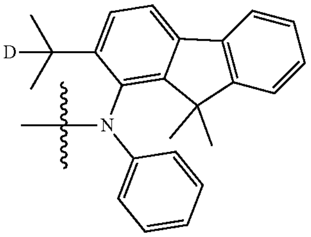
,
B-4-40
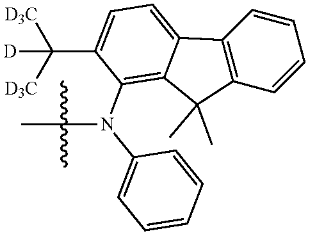
,
B-4-41
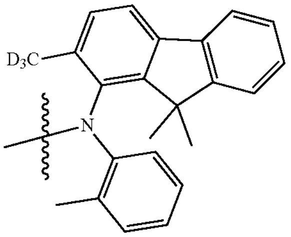
,
B-4-42
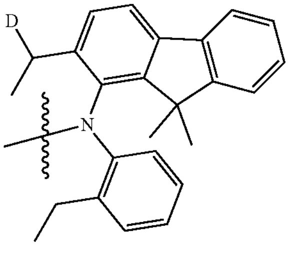
,
-continued
B-4-43
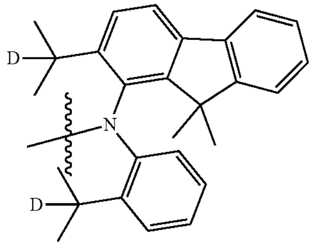
,
B-4-44
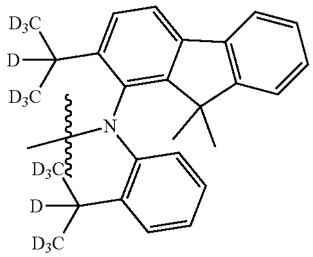
,
B-4-45
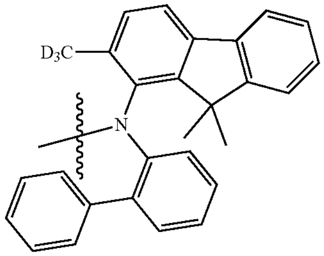
,
B-4-46
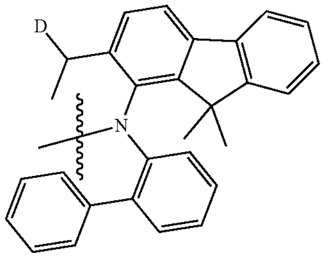
,
B-4-47
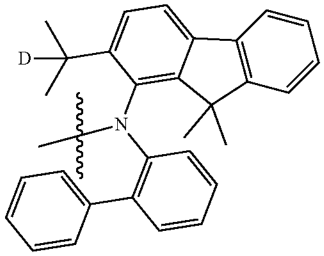
,
B-4-48
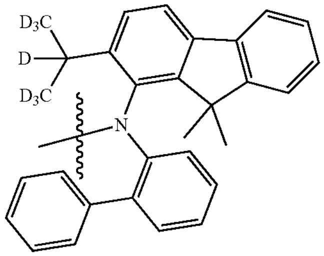
, -continued
B-4-49
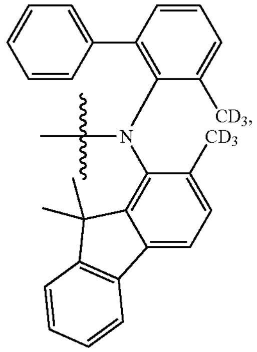
B-4-50
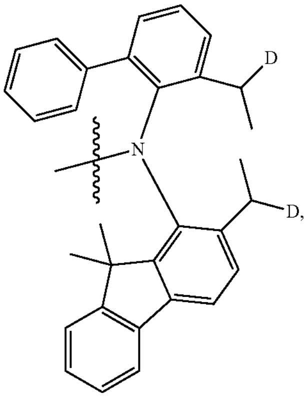
B-4-51
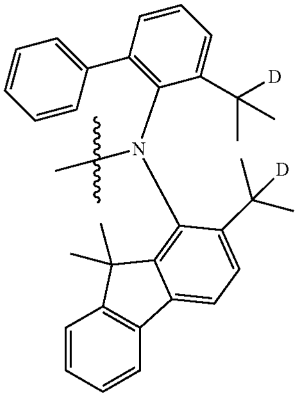
,
B-4-52
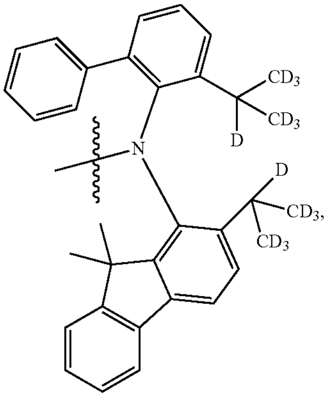
-continued
B-4-53
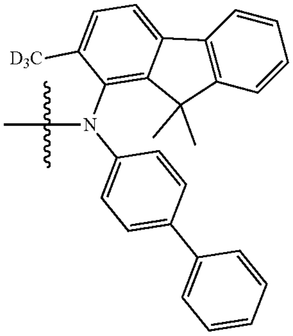
,
B-4-54
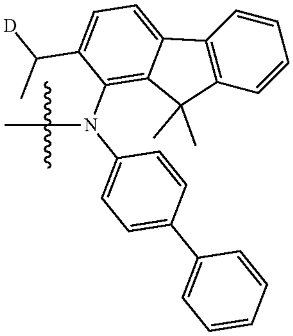
,
B-4-55
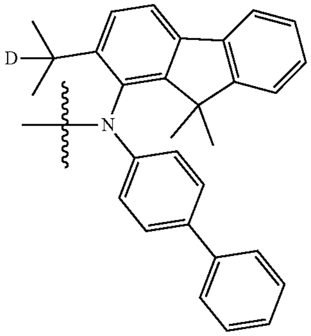
,
B-4-56
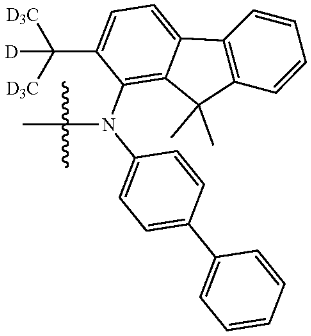
, -continued
B-4-57
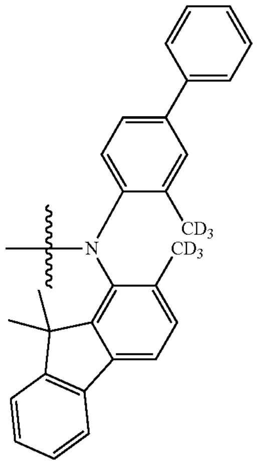
,
B-4-58
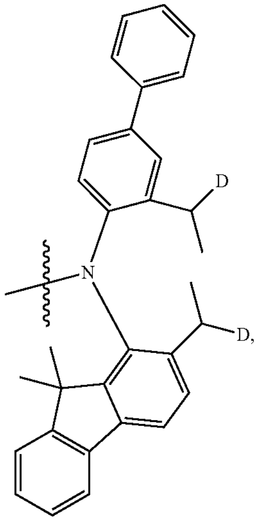
B-4-59
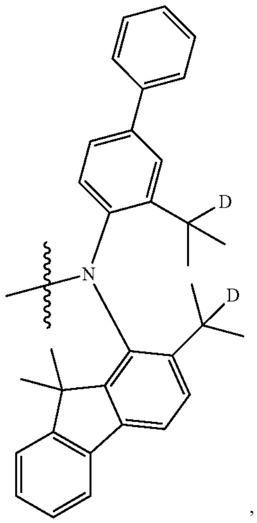
,
-continued
B-4-60
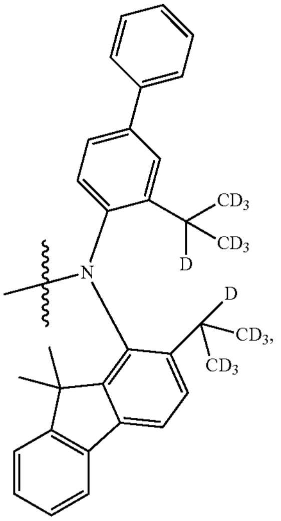
B-4-61
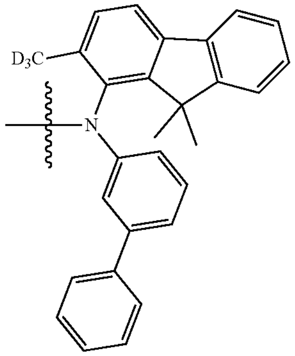
,
B-4-62
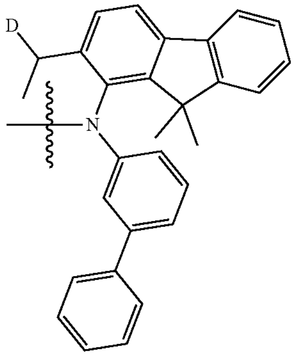
,
B-4-63
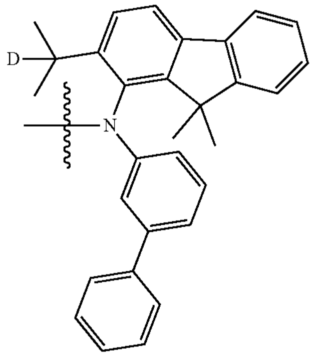
, -continued
B-4-64
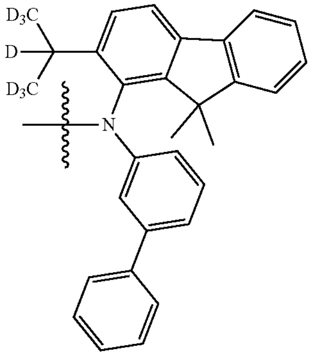
,
B-4-65
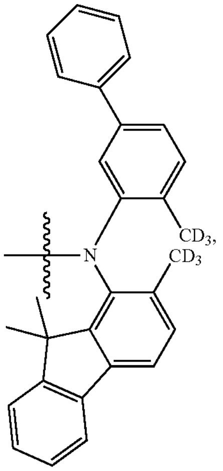
B-4-66
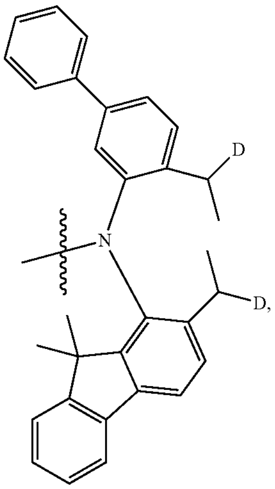
-continued
B-4-67
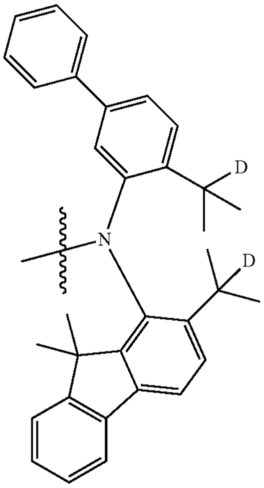
,
B-4-68
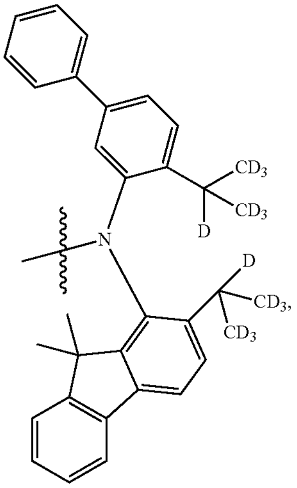
B-4-69
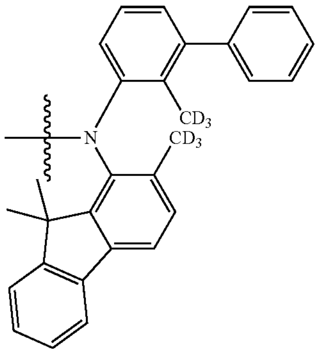
, -continued
B-4-70
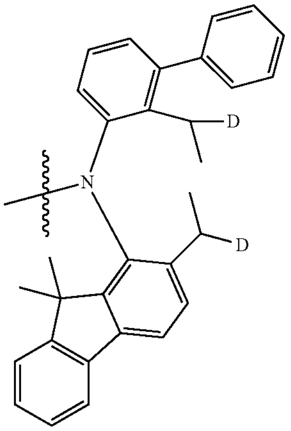
,
B-4-71
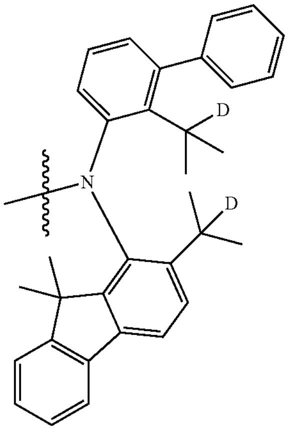
,
B-4-72
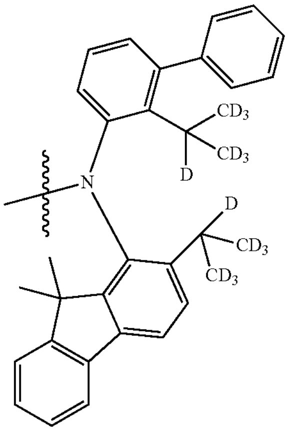
,
B-5-1
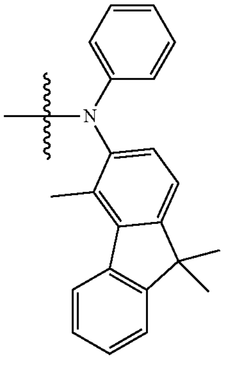
,
-continued
B-5-2
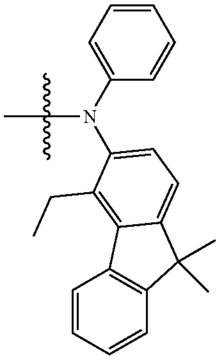
,
B-5-3
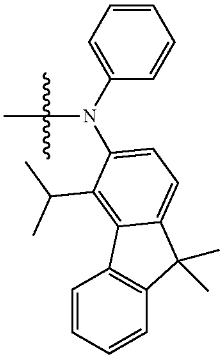
,
B-5-4
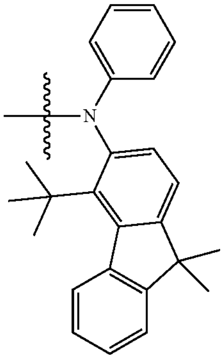
,
B-5-5
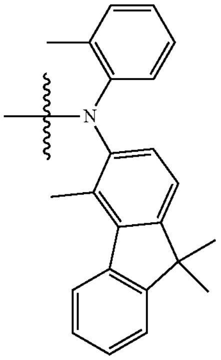
, -continued
B-5-6
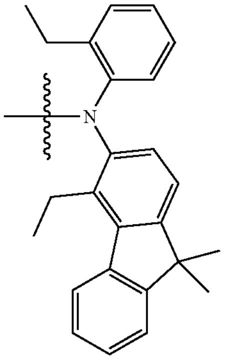
,
B-5-7
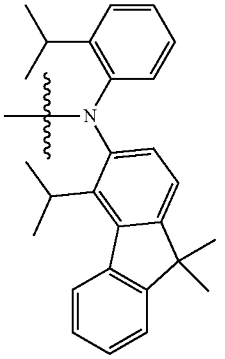
,
B-5-8
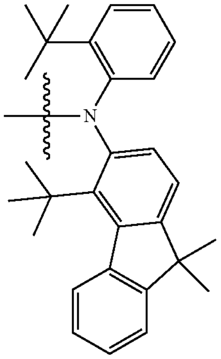
,
B-5-9
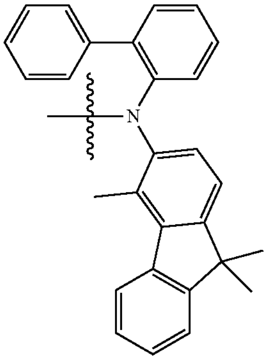
,
-continued
B-5-10
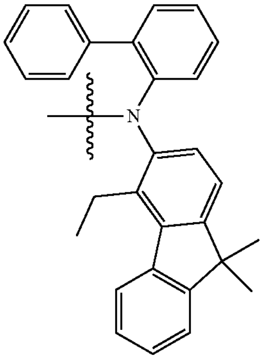
,
B-5-11
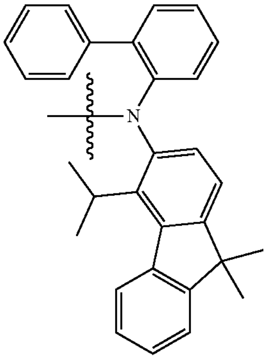
,
B-5-12
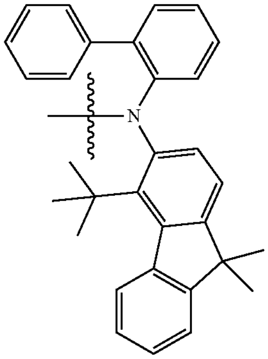
,
B-5-13
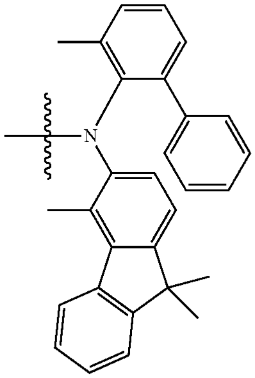
, -continued
B-5-14
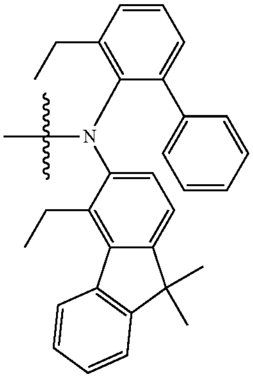
,
B-5-15
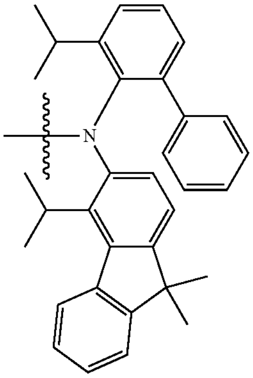
,
B-5-16
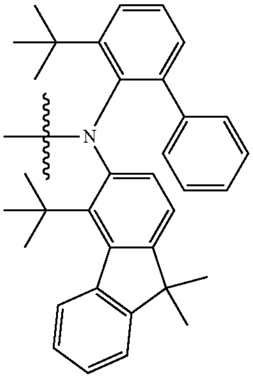
,
B-5-17
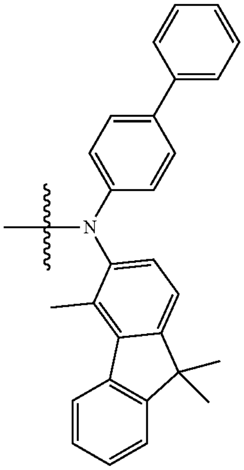
,
-continued
B-5-18
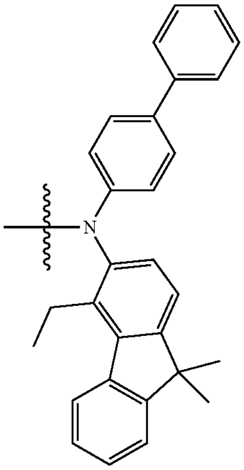
,
B-5-19
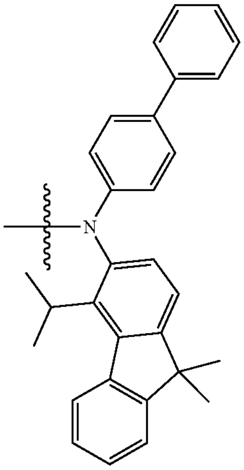
,
B-5-20
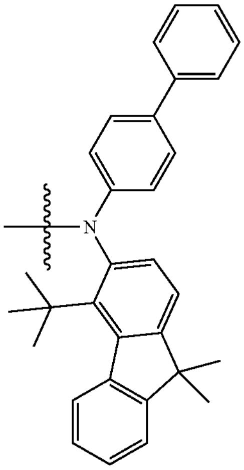
, -continued
B-5-21
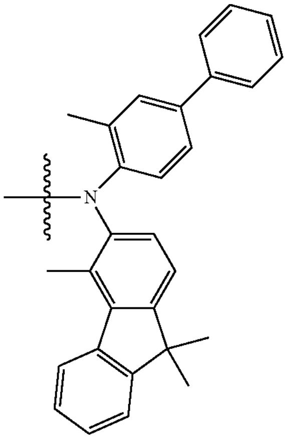
,
B-5-22
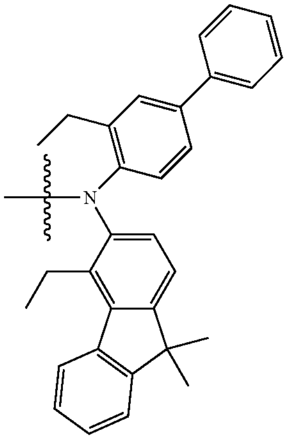
,
B-5-23
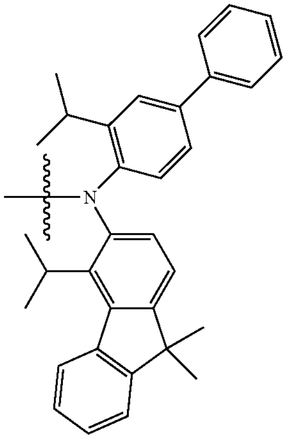
,
-continued
B-5-24
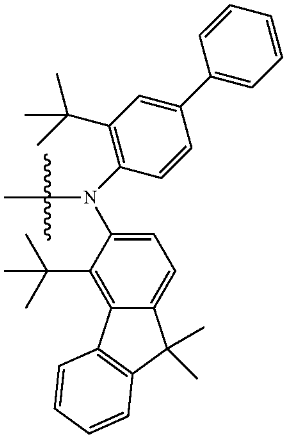
,
B-5-25
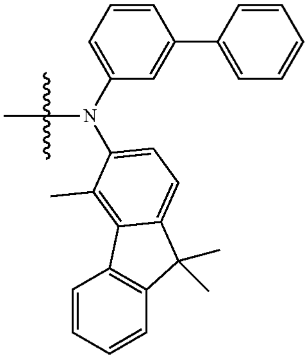
,
B-5-26
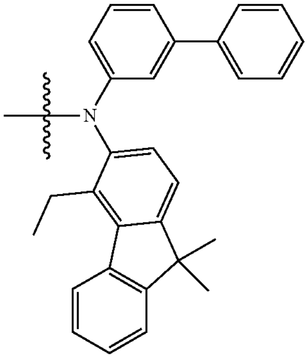
,
B-5-27
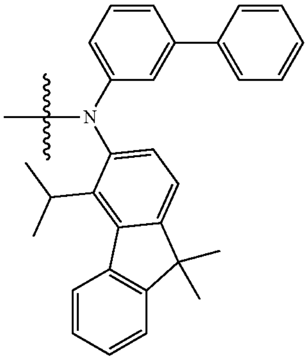
, -continued
B-5-28
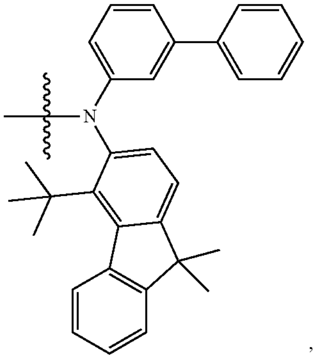
,
B-5-29
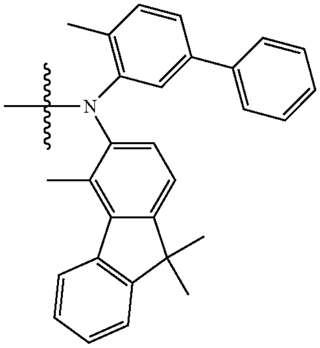
,
B-5-30
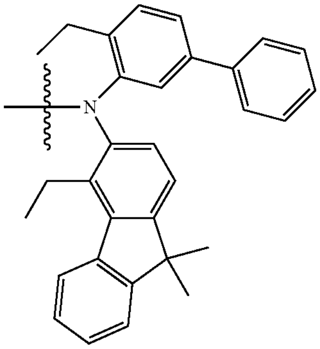
,
B-5-31
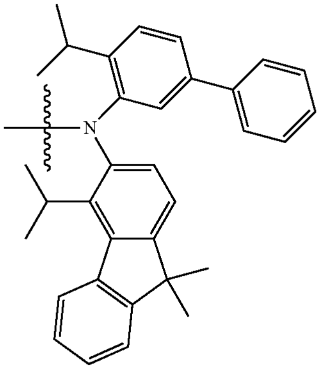
,
-continued
B-5-32
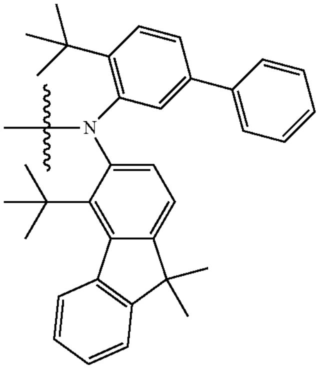
,
B-5-33
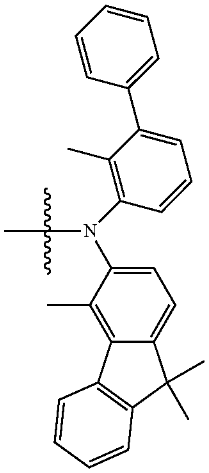
,
B-5-34
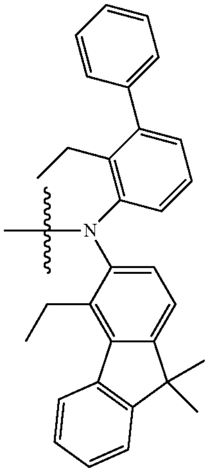
, -continued
B-5-35
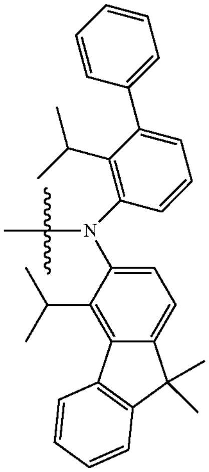
,
B-5-36
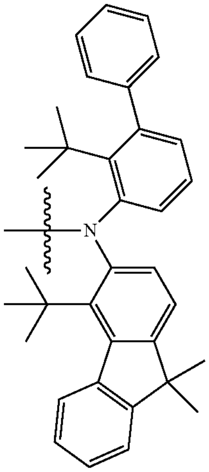
,
B-5-37
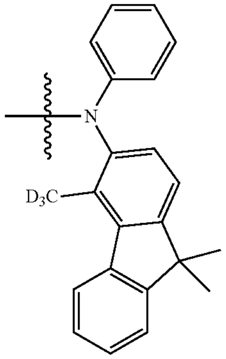
,
-continued
B-5-38
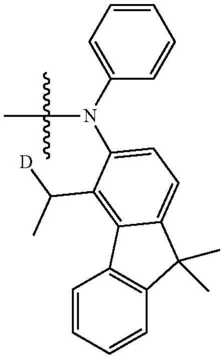
,
B-5-39
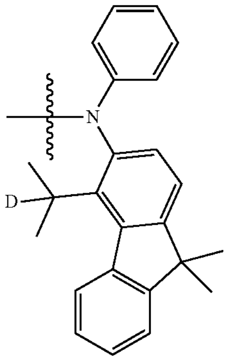
,
B-5-40
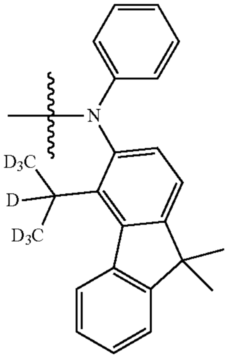
,
B-5-41
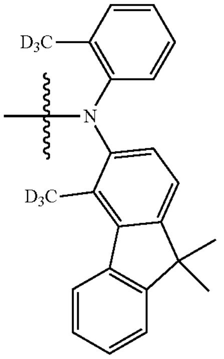
, -continued
B-5-42
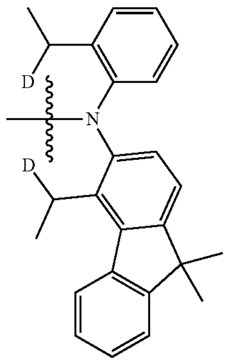
,
B-5-43
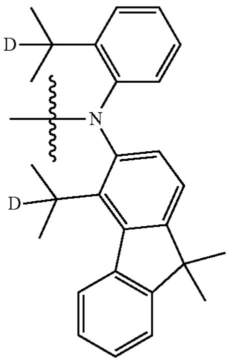
,
B-5-44
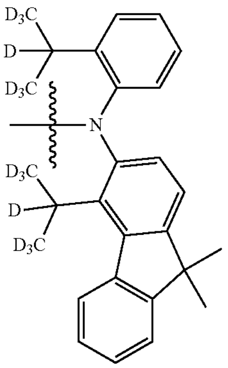
,
B-5-45
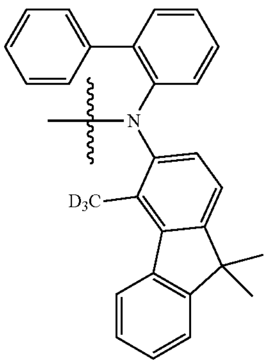
,
-continued
B-5-46
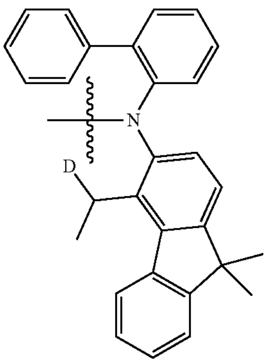
,
B-5-47
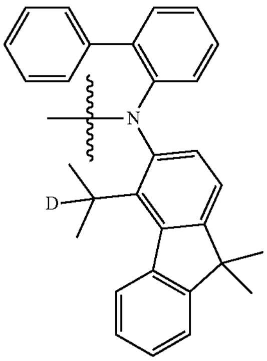
,
B-5-48
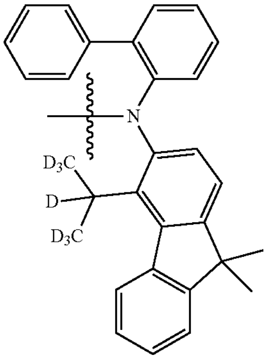
,
B-5-49
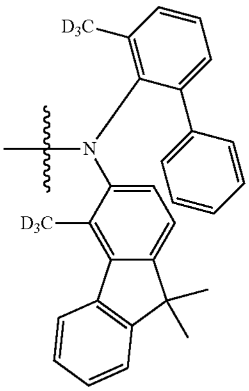
, -continued
B-5-50
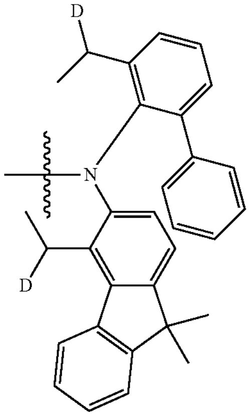
,
B-5-51
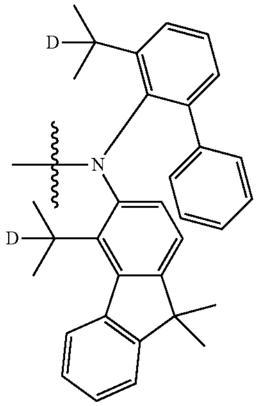
,
B-5-52
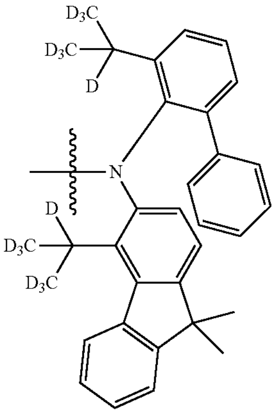
,
-continued
B-5-53
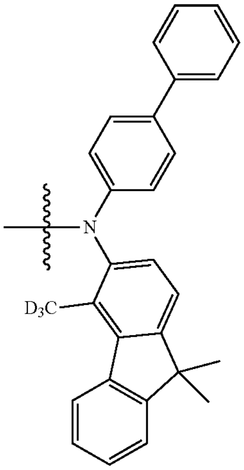
,
B-5-54
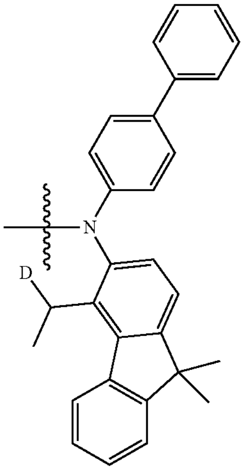
,
B-5-55
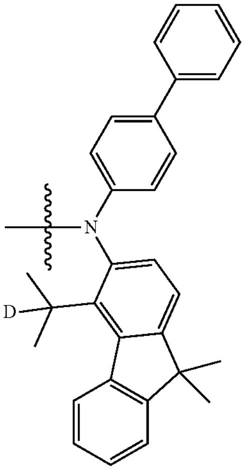
, -continued
B-5-56
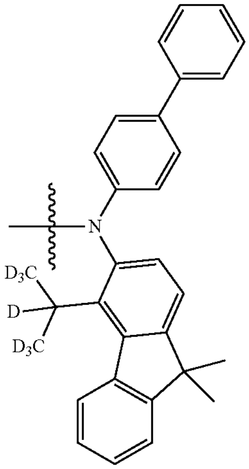
,
B-5-57
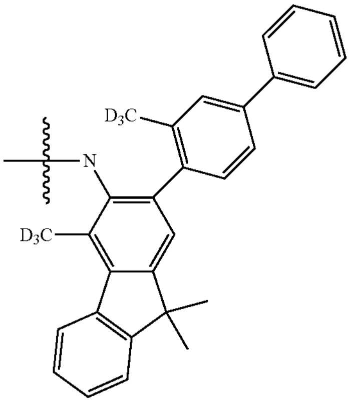
,
B-5-58
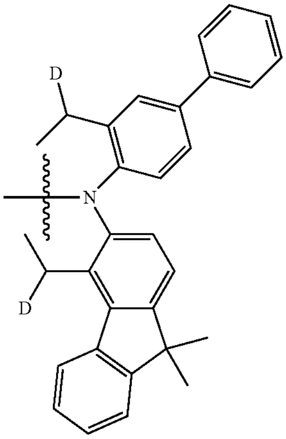
,
-continued
B-5-59
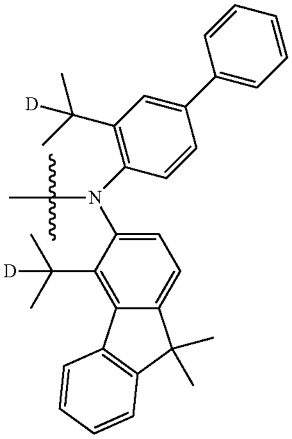
,
B-5-60
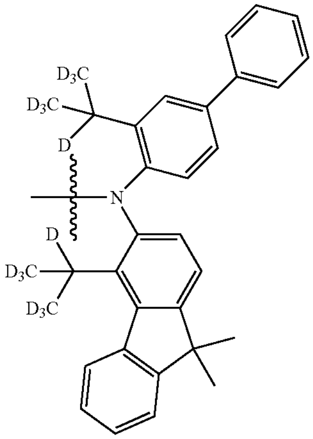
,
B-5-61
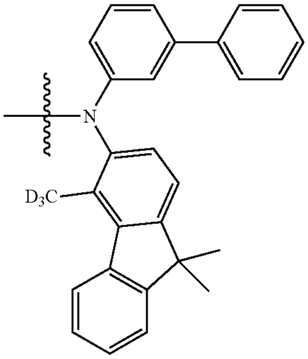
,
B-5-62
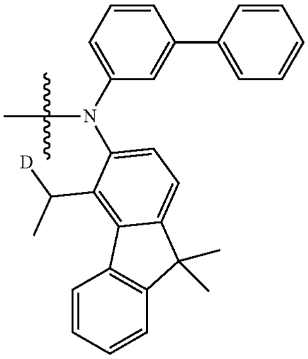
, -continued
B-5-63
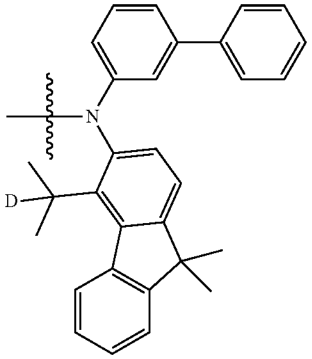
,
B-5-64
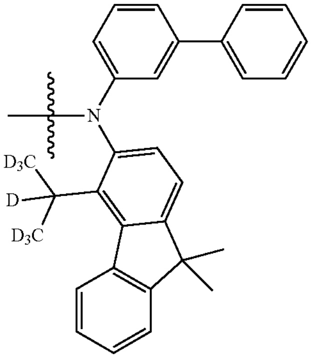
,
B-5-65
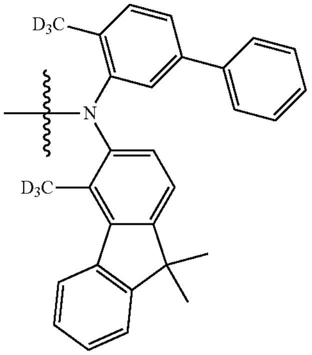
,
B-5-66
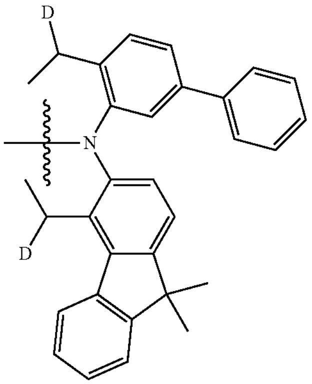
,
-continued
B-5-67
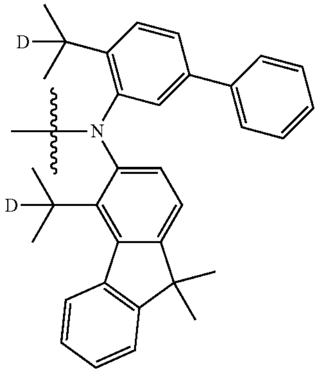
,
B-5-68
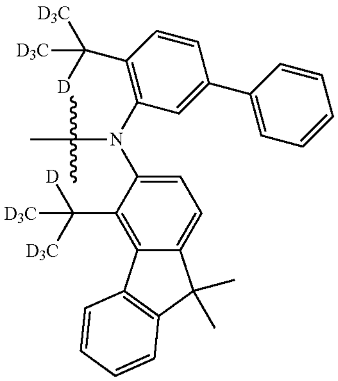
,
B-5-69
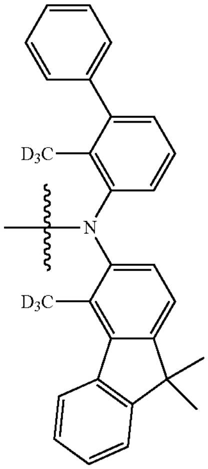
, -continued
B-5-70
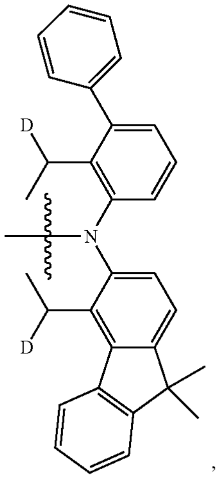
B-5-71
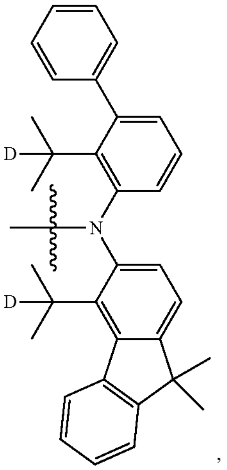
B-5-72
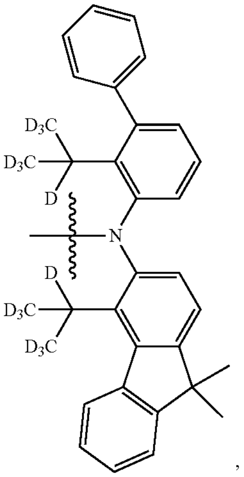
-continued
B-6-1
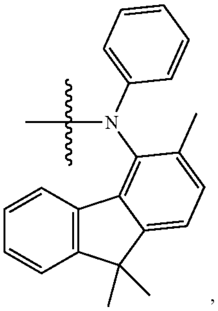
B-6-2
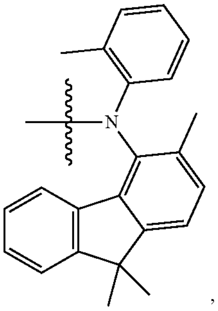
B-6-3
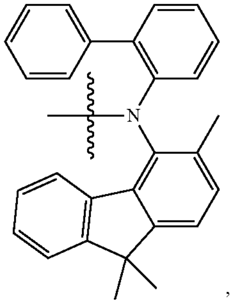
B-6-4
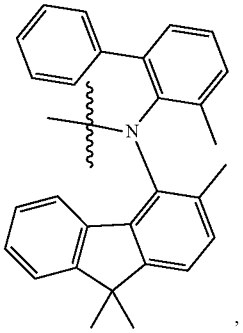

-continued
B-6-5
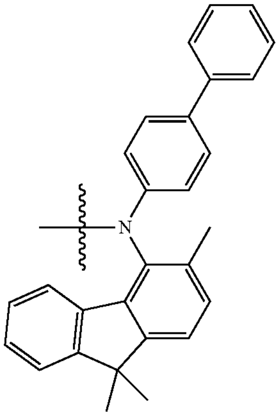
,
B-6-6
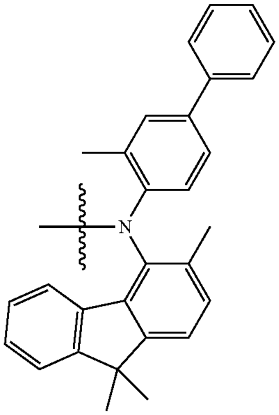
,
B-6-7
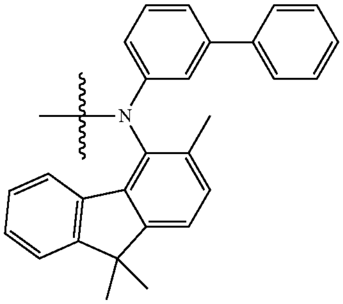
,
B-6-8
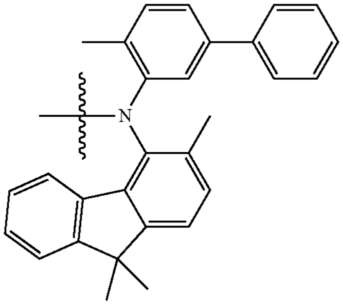
,
-continued
B-6-9
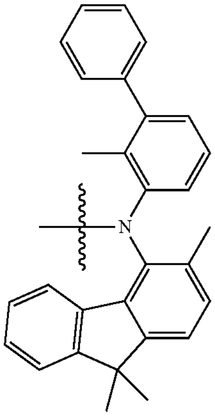
,
B-6-10
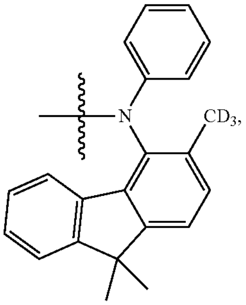
B-6-11
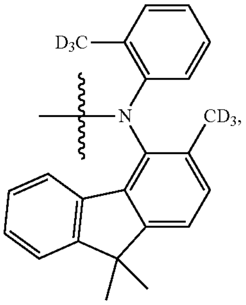
B-6-12
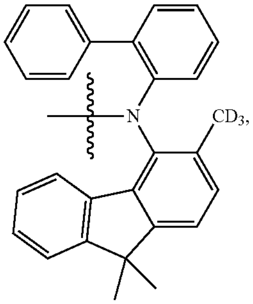

-continued

B-6-13

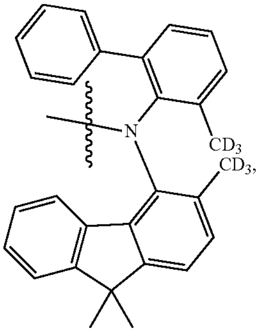

B-6-14

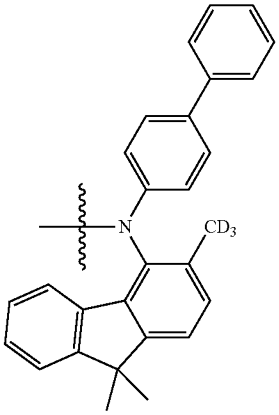

,

B-6-15

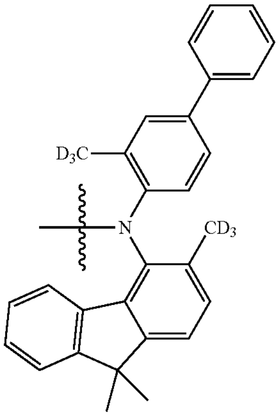

,

B-6-16

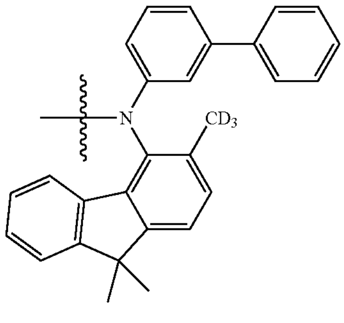

,

-continued

B-6-17

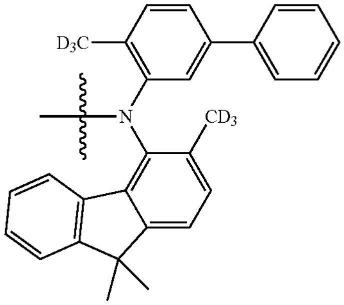

,

B-6-18

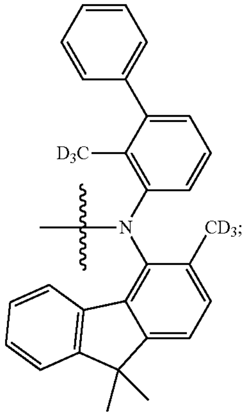

in the above specific structures of B, represents a position where B is joined to A.

12. The compound of claim 11, wherein compounds 1 to 1240 and compounds 2333 to 2349 have a structure represented by Formula 15:

$$A\!\left(\!-B\right)_n \qquad \text{Formula 15,}$$

wherein n in the structure of Formula 15 equals 2, and two B are the same;

A and B in structures of compounds 1 to 1240 and compounds 2333 to 2349 have structures listed in the following table, separately:

| Compound | A Structure | B Structure |
|---|---|---|
| 1 | $A_1$ | B-1-1 |
| 2 | $A_1$ | B-1-2 |
| 3 | $A_1$ | B-1-3 |
| 4 | $A_1$ | B-1-4 |
| 5 | $A_1$ | B-1-5 |
| 6 | $A_1$ | B-1-6 |
| 7 | $A_1$ | B-1-7 |
| 8 | $A_1$ | B-1-8 |
| 9 | $A_1$ | B-1-9 |
| 10 | $A_1$ | B-1-10 |
| 11 | $A_1$ | B-1-11 |
| 12 | $A_1$ | B-1-12 |
| 13 | $A_1$ | B-1-13 |
| 14 | $A_1$ | B-1-14 |
| 15 | $A_1$ | B-1-15 |
| 16 | $A_1$ | B-1-16 |
| 17 | $A_1$ | B-1-17 |
| 18 | $A_1$ | B-1-18 |
| 19 | $A_1$ | B-1-19 |
| 20 | $A_1$ | B-1-20 |
| 21 | $A_1$ | B-1-21 |
| 22 | $A_1$ | B-1-22 |
| 23 | $A_1$ | B-1-23 |

-continued

| Compound | A Structure | B Structure |
|---|---|---|
| 24 | $A_1$ | B-1-24 |
| 25 | $A_1$ | B-1-25 |
| 26 | $A_1$ | B-1-26 |
| 27 | $A_1$ | B-1-27 |
| 28 | $A_1$ | B-1-28 |
| 29 | $A_1$ | B-1-29 |
| 30 | $A_1$ | B-1-30 |
| 31 | $A_1$ | B-1-31 |
| 32 | $A_1$ | B-1-32 |
| 33 | $A_1$ | B-1-33 |
| 34 | $A_1$ | B-1-34 |
| 35 | $A_1$ | B-1-35 |
| 36 | $A_1$ | B-1-36 |
| 37 | $A_1$ | B-1-37 |
| 38 | $A_1$ | B-1-38 |
| 39 | $A_1$ | B-1-39 |
| 40 | $A_1$ | B-1-40 |
| 41 | $A_1$ | B-1-41 |
| 42 | $A_1$ | B-1-42 |
| 43 | $A_1$ | B-1-43 |
| 44 | $A_1$ | B-1-44 |
| 45 | $A_1$ | B-1-45 |
| 46 | $A_1$ | B-1-46 |
| 47 | $A_1$ | B-1-47 |
| 48 | $A_1$ | B-1-48 |
| 49 | $A_1$ | B-1-49 |
| 50 | $A_1$ | B-1-50 |
| 51 | $A_1$ | B-1-51 |
| 52 | $A_1$ | B-1-52 |
| 53 | $A_1$ | B-1-53 |
| 54 | $A_1$ | B-1-54 |
| 55 | $A_1$ | B-1-55 |
| 56 | $A_1$ | B-1-56 |
| 57 | $A_1$ | B-1-57 |
| 58 | $A_1$ | B-1-58 |
| 59 | $A_1$ | B-1-59 |
| 60 | $A_1$ | B-1-60 |
| 61 | $A_1$ | B-1-61 |
| 62 | $A_1$ | B-1-62 |
| 63 | $A_1$ | B-1-63 |
| 64 | $A_1$ | B-1-64 |
| 65 | $A_1$ | B-1-65 |
| 66 | $A_1$ | B-1-66 |
| 67 | $A_1$ | B-1-67 |
| 68 | $A_1$ | B-1-68 |
| 69 | $A_1$ | B-1-69 |
| 70 | $A_1$ | B-1-70 |
| 71 | $A_1$ | B-1-71 |
| 72 | $A_1$ | B-1-72 |
| 73 | $A_1$ | B-2-1 |
| 74 | $A_1$ | B-2-2 |
| 75 | $A_1$ | B-2-3 |
| 76 | $A_1$ | B-2-4 |
| 77 | $A_1$ | B-2-5 |
| 78 | $A_1$ | B-2-6 |
| 79 | $A_1$ | B-2-7 |
| 80 | $A_1$ | B-2-8 |
| 81 | $A_1$ | B-2-9 |
| 82 | $A_1$ | B-2-10 |
| 83 | $A_1$ | B-2-11 |
| 84 | $A_1$ | B-2-12 |
| 85 | $A_1$ | B-2-13 |
| 86 | $A_1$ | B-2-14 |
| 87 | $A_1$ | B-2-15 |
| 88 | $A_1$ | B-2-16 |
| 89 | $A_1$ | B-2-17 |
| 90 | $A_1$ | B-2-18 |
| 91 | $A_1$ | B-2-19 |
| 92 | $A_1$ | B-2-20 |
| 93 | $A_1$ | B-2-21 |
| 94 | $A_1$ | B-2-22 |
| 95 | $A_1$ | B-2-23 |
| 96 | $A_1$ | B-2-24 |
| 97 | $A_1$ | B-2-25 |
| 98 | $A_1$ | B-2-26 |
| 99 | $A_1$ | B-2-27 |

-continued

| Compound | A Structure | B Structure |
|---|---|---|
| 100 | $A_1$ | B-2-28 |
| 101 | $A_1$ | B-2-29 |
| 102 | $A_1$ | B-2-30 |
| 103 | $A_1$ | B-2-31 |
| 104 | $A_1$ | B-2-32 |
| 105 | $A_1$ | B-2-33 |
| 106 | $A_1$ | B-2-34 |
| 107 | $A_1$ | B-2-35 |
| 108 | $A_1$ | B-2-36 |
| 109 | $A_1$ | B-2-37 |
| 110 | $A_1$ | B-2-38 |
| 111 | $A_1$ | B-2-39 |
| 112 | $A_1$ | B-2-40 |
| 113 | $A_1$ | B-2-41 |
| 114 | $A_1$ | B-2-42 |
| 115 | $A_1$ | B-2-43 |
| 116 | $A_1$ | B-2-44 |
| 117 | $A_1$ | B-2-45 |
| 118 | $A_1$ | B-2-46 |
| 119 | $A_1$ | B-2-47 |
| 120 | $A_1$ | B-2-48 |
| 121 | $A_1$ | B-2-49 |
| 122 | $A_1$ | B-2-50 |
| 123 | $A_1$ | B-2-51 |
| 124 | $A_1$ | B-2-52 |
| 125 | $A_1$ | B-2-53 |
| 126 | $A_1$ | B-2-54 |
| 127 | $A_1$ | B-2-55 |
| 128 | $A_1$ | B-2-56 |
| 129 | $A_1$ | B-2-57 |
| 130 | $A_1$ | B-2-58 |
| 131 | $A_1$ | B-2-59 |
| 132 | $A_1$ | B-2-60 |
| 133 | $A_1$ | B-2-61 |
| 134 | $A_1$ | B-2-62 |
| 135 | $A_1$ | B-2-63 |
| 136 | $A_1$ | B-2-64 |
| 137 | $A_1$ | B-2-65 |
| 138 | $A_1$ | B-2-66 |
| 139 | $A_1$ | B-2-67 |
| 140 | $A_1$ | B-2-68 |
| 141 | $A_1$ | B-2-69 |
| 142 | $A_1$ | B-2-70 |
| 143 | $A_1$ | B-2-71 |
| 144 | $A_1$ | B-2-72 |
| 145 | $A_1$ | B-2-73 |
| 146 | $A_1$ | B-2-74 |
| 147 | $A_1$ | B-2-75 |
| 148 | $A_1$ | B-2-76 |
| 149 | $A_1$ | B-2-77 |
| 150 | $A_1$ | B-2-78 |
| 151 | $A_1$ | B-2-79 |
| 152 | $A_1$ | B-2-80 |
| 153 | $A_1$ | B-2-81 |
| 154 | $A_1$ | B-2-82 |
| 155 | $A_1$ | B-2-83 |
| 156 | $A_1$ | B-2-84 |
| 157 | $A_1$ | B-2-85 |
| 158 | $A_1$ | B-2-86 |
| 159 | $A_1$ | B-2-87 |
| 160 | $A_1$ | B-2-88 |
| 161 | $A_1$ | B-2-89 |
| 162 | $A_1$ | B-2-90 |
| 163 | $A_1$ | B-2-91 |
| 164 | $A_1$ | B-2-92 |
| 165 | $A_1$ | B-2-93 |
| 166 | $A_1$ | B-2-94 |
| 167 | $A_1$ | B-2-95 |
| 168 | $A_1$ | B-2-96 |
| 169 | $A_1$ | B-2-97 |
| 170 | $A_1$ | B-2-98 |
| 171 | $A_1$ | B-2-99 |
| 172 | $A_1$ | B-2-100 |
| 173 | $A_1$ | B-2-101 |
| 174 | $A_1$ | B-2-102 |
| 175 | $A_1$ | B-2-103 |

-continued

| Compound | A Structure | B Structure |
|---|---|---|
| 176 | $A_1$ | B-2-104 |
| 177 | $A_1$ | B-2-105 |
| 178 | $A_1$ | B-2-106 |
| 179 | $A_1$ | B-2-107 |
| 180 | $A_1$ | B-2-108 |
| 181 | $A_1$ | B-2-109 |
| 182 | $A_1$ | B-2-110 |
| 183 | $A_1$ | B-2-111 |
| 184 | $A_1$ | B-2-112 |
| 185 | $A_1$ | B-2-113 |
| 186 | $A_1$ | B-2-114 |
| 187 | $A_1$ | B-2-115 |
| 188 | $A_1$ | B-2-116 |
| 189 | $A_1$ | B-2-117 |
| 190 | $A_1$ | B-2-118 |
| 191 | $A_1$ | B-2-119 |
| 192 | $A_1$ | B-2-120 |
| 193 | $A_1$ | B-2-121 |
| 194 | $A_1$ | B-2-122 |
| 195 | $A_1$ | B-2-123 |
| 196 | $A_1$ | B-2-124 |
| 197 | $A_1$ | B-2-125 |
| 198 | $A_1$ | B-2-126 |
| 199 | $A_1$ | B-2-127 |
| 200 | $A_1$ | B-2-128 |
| 201 | $A_1$ | B-2-129 |
| 202 | $A_1$ | B-2-130 |
| 203 | $A_1$ | B-2-131 |
| 204 | $A_1$ | B-2-132 |
| 205 | $A_1$ | B-2-133 |
| 206 | $A_1$ | B-2-134 |
| 207 | $A_1$ | B-2-135 |
| 208 | $A_1$ | B-2-136 |
| 209 | $A_1$ | B-2-137 |
| 210 | $A_1$ | B-2-138 |
| 211 | $A_1$ | B-2-139 |
| 212 | $A_1$ | B-2-140 |
| 213 | $A_1$ | B-2-141 |
| 214 | $A_1$ | B-2-142 |
| 215 | $A_1$ | B-2-143 |
| 216 | $A_1$ | B-2-144 |
| 217 | $A_1$ | B-2-145 |
| 218 | $A_1$ | B-2-146 |
| 219 | $A_1$ | B-2-147 |
| 220 | $A_1$ | B-2-148 |
| 221 | $A_1$ | B-2-149 |
| 222 | $A_1$ | B-2-150 |
| 223 | $A_1$ | B-2-151 |
| 224 | $A_1$ | B-2-152 |
| 225 | $A_1$ | B-2-153 |
| 226 | $A_1$ | B-2-154 |
| 227 | $A_1$ | B-2-155 |
| 228 | $A_1$ | B-2-156 |
| 229 | $A_1$ | B-2-157 |
| 230 | $A_1$ | B-2-158 |
| 231 | $A_1$ | B-2-159 |
| 232 | $A_1$ | B-2-160 |
| 233 | $A_1$ | B-2-161 |
| 234 | $A_1$ | B-2-162 |
| 235 | $A_1$ | B-2-163 |
| 236 | $A_1$ | B-2-164 |
| 237 | $A_1$ | B-2-165 |
| 238 | $A_1$ | B-2-166 |
| 239 | $A_1$ | B-2-167 |
| 240 | $A_1$ | B-2-168 |
| 241 | $A_1$ | B-2-169 |
| 242 | $A_1$ | B-2-170 |
| 243 | $A_1$ | B-2-171 |
| 244 | $A_1$ | B-2-172 |
| 245 | $A_1$ | B-2-173 |
| 246 | $A_1$ | B-2-174 |
| 247 | $A_1$ | B-2-175 |
| 248 | $A_1$ | B-2-176 |
| 249 | $A_1$ | B-2-177 |
| 250 | $A_1$ | B-2-178 |
| 251 | $A_1$ | B-2-179 |

-continued

| Compound | A Structure | B Structure |
|---|---|---|
| 252 | $A_1$ | B-2-180 |
| 253 | $A_1$ | B-2-181 |
| 254 | $A_1$ | B-2-182 |
| 255 | $A_1$ | B-2-183 |
| 256 | $A_1$ | B-2-184 |
| 257 | $A_1$ | B-2-185 |
| 258 | $A_1$ | B-2-186 |
| 259 | $A_1$ | B-2-187 |
| 260 | $A_1$ | B-2-188 |
| 261 | $A_1$ | B-2-189 |
| 262 | $A_1$ | B-2-190 |
| 263 | $A_1$ | B-2-191 |
| 264 | $A_1$ | B-2-192 |
| 265 | $A_1$ | B-2-193 |
| 266 | $A_1$ | B-2-194 |
| 267 | $A_1$ | B-2-195 |
| 268 | $A_1$ | B-2-196 |
| 269 | $A_1$ | B-2-197 |
| 270 | $A_1$ | B-2-198 |
| 271 | $A_1$ | B-2-199 |
| 272 | $A_1$ | B-2-200 |
| 273 | $A_1$ | B-2-201 |
| 274 | $A_1$ | B-2-202 |
| 275 | $A_1$ | B-2-203 |
| 276 | $A_1$ | B-2-204 |
| 277 | $A_1$ | B-2-205 |
| 278 | $A_1$ | B-2-206 |
| 279 | $A_1$ | B-2-207 |
| 280 | $A_1$ | B-2-208 |
| 281 | $A_1$ | B-2-209 |
| 282 | $A_1$ | B-2-210 |
| 283 | $A_1$ | B-2-211 |
| 284 | $A_1$ | B-2-212 |
| 285 | $A_1$ | B-2-213 |
| 286 | $A_1$ | B-2-214 |
| 287 | $A_1$ | B-2-215 |
| 288 | $A_1$ | B-2-216 |
| 289 | $A_1$ | B-2-217 |
| 290 | $A_1$ | B-2-218 |
| 291 | $A_1$ | B-3-1 |
| 292 | $A_1$ | B-3-2 |
| 293 | $A_1$ | B-3-3 |
| 294 | $A_1$ | B-3-4 |
| 295 | $A_1$ | B-3-5 |
| 296 | $A_1$ | B-3-6 |
| 297 | $A_1$ | B-3-7 |
| 298 | $A_1$ | B-3-8 |
| 299 | $A_1$ | B-3-9 |
| 300 | $A_1$ | B-3-10 |
| 301 | $A_1$ | B-3-11 |
| 302 | $A_1$ | B-3-12 |
| 303 | $A_1$ | B-3-13 |
| 304 | $A_1$ | B-3-14 |
| 305 | $A_1$ | B-3-15 |
| 306 | $A_1$ | B-3-16 |
| 307 | $A_1$ | B-3-17 |
| 308 | $A_1$ | B-3-18 |
| 309 | $A_1$ | B-3-19 |
| 310 | $A_1$ | B-3-20 |
| 311 | $A_1$ | B-3-21 |
| 312 | $A_1$ | B-3-22 |
| 313 | $A_1$ | B-3-23 |
| 314 | $A_1$ | B-3-24 |
| 315 | $A_1$ | B-3-25 |
| 316 | $A_1$ | B-3-26 |
| 317 | $A_1$ | B-3-27 |
| 318 | $A_1$ | B-3-28 |
| 319 | $A_1$ | B-3-29 |
| 320 | $A_1$ | B-3-30 |
| 321 | $A_1$ | B-3-31 |
| 322 | $A_1$ | B-3-32 |
| 323 | $A_1$ | B-3-33 |
| 324 | $A_1$ | B-3-34 |
| 325 | $A_1$ | B-3-35 |
| 326 | $A_1$ | B-3-36 |
| 327 | $A_1$ | B-3-37 |

-continued

| Compound | A Structure | B Structure |
|---|---|---|
| 328 | $A_1$ | B-3-38 |
| 329 | $A_1$ | B-3-39 |
| 330 | $A_1$ | B-3-40 |
| 331 | $A_1$ | B-3-41 |
| 332 | $A_1$ | B-3-42 |
| 333 | $A_1$ | B-3-43 |
| 334 | $A_1$ | B-3-44 |
| 335 | $A_1$ | B-3-45 |
| 336 | $A_1$ | B-3-46 |
| 337 | $A_1$ | B-3-47 |
| 338 | $A_1$ | B-3-48 |
| 339 | $A_1$ | B-3-49 |
| 340 | $A_1$ | B-3-50 |
| 341 | $A_1$ | B-3-51 |
| 342 | $A_1$ | B-3-52 |
| 343 | $A_1$ | B-3-53 |
| 344 | $A_1$ | B-3-54 |
| 345 | $A_1$ | B-3-55 |
| 346 | $A_1$ | B-3-56 |
| 347 | $A_1$ | B-3-57 |
| 348 | $A_1$ | B-3-58 |
| 349 | $A_1$ | B-3-59 |
| 350 | $A_1$ | B-3-60 |
| 351 | $A_1$ | B-3-61 |
| 352 | $A_1$ | B-3-62 |
| 353 | $A_1$ | B-3-63 |
| 354 | $A_1$ | B-3-64 |
| 355 | $A_1$ | B-3-65 |
| 356 | $A_1$ | B-3-66 |
| 357 | $A_1$ | B-3-67 |
| 358 | $A_1$ | B-3-68 |
| 359 | $A_1$ | B-3-69 |
| 360 | $A_1$ | B-3-70 |
| 361 | $A_1$ | B-3-71 |
| 362 | $A_1$ | B-3-72 |
| 363 | $A_1$ | B-3-73 |
| 364 | $A_1$ | B-3-74 |
| 365 | $A_1$ | B-3-75 |
| 366 | $A_1$ | B-3-76 |
| 367 | $A_1$ | B-3-77 |
| 368 | $A_1$ | B-3-78 |
| 369 | $A_1$ | B-3-79 |
| 370 | $A_1$ | B-3-80 |
| 371 | $A_1$ | B-3-81 |
| 372 | $A_1$ | B-3-82 |
| 373 | $A_1$ | B-3-83 |
| 374 | $A_1$ | B-3-84 |
| 375 | $A_1$ | B-3-85 |
| 376 | $A_1$ | B-3-86 |
| 377 | $A_1$ | B-3-87 |
| 378 | $A_1$ | B-3-88 |
| 379 | $A_1$ | B-3-89 |
| 380 | $A_1$ | B-3-90 |
| 381 | $A_1$ | B-3-91 |
| 382 | $A_1$ | B-3-92 |
| 383 | $A_1$ | B-3-93 |
| 384 | $A_1$ | B-3-94 |
| 385 | $A_1$ | B-3-95 |
| 386 | $A_1$ | B-3-96 |
| 387 | $A_1$ | B-3-97 |
| 388 | $A_1$ | B-3-98 |
| 389 | $A_1$ | B-3-99 |
| 390 | $A_1$ | B-3-100 |
| 391 | $A_1$ | B-3-101 |
| 392 | $A_1$ | B-3-102 |
| 393 | $A_1$ | B-3-103 |
| 394 | $A_1$ | B-3-104 |
| 395 | $A_1$ | B-3-105 |
| 396 | $A_1$ | B-3-106 |
| 397 | $A_1$ | B-3-107 |
| 398 | $A_1$ | B-3-108 |
| 399 | $A_1$ | B-3-109 |
| 400 | $A_1$ | B-3-110 |
| 401 | $A_1$ | B-3-111 |
| 402 | $A_1$ | B-3-112 |
| 403 | $A_1$ | B-3-113 |

-continued

| Compound | A Structure | B Structure |
|---|---|---|
| 404 | $A_1$ | B-3-114 |
| 405 | $A_1$ | B-3-115 |
| 406 | $A_1$ | B-3-116 |
| 407 | $A_1$ | B-3-117 |
| 408 | $A_1$ | B-3-118 |
| 409 | $A_1$ | B-3-119 |
| 410 | $A_1$ | B-3-120 |
| 411 | $A_1$ | B-3-121 |
| 412 | $A_1$ | B-3-122 |
| 413 | $A_1$ | B-3-123 |
| 414 | $A_1$ | B-3-124 |
| 415 | $A_1$ | B-3-125 |
| 416 | $A_1$ | B-3-126 |
| 417 | $A_1$ | B-3-127 |
| 418 | $A_1$ | B-3-128 |
| 419 | $A_1$ | B-3-129 |
| 420 | $A_1$ | B-3-130 |
| 421 | $A_1$ | B-3-131 |
| 422 | $A_1$ | B-3-132 |
| 423 | $A_1$ | B-3-133 |
| 424 | $A_1$ | B-3-134 |
| 425 | $A_1$ | B-3-135 |
| 426 | $A_1$ | B-3-136 |
| 427 | $A_1$ | B-3-137 |
| 428 | $A_1$ | B-3-138 |
| 429 | $A_1$ | B-3-139 |
| 430 | $A_1$ | B-3-140 |
| 431 | $A_1$ | B-3-141 |
| 432 | $A_1$ | B-3-142 |
| 433 | $A_1$ | B-3-143 |
| 434 | $A_1$ | B-3-144 |
| 435 | $A_1$ | B-3-145 |
| 436 | $A_1$ | B-3-146 |
| 437 | $A_1$ | B-3-147 |
| 438 | $A_1$ | B-3-148 |
| 439 | $A_1$ | B-3-149 |
| 440 | $A_1$ | B-3-150 |
| 441 | $A_1$ | B-3-151 |
| 442 | $A_1$ | B-3-152 |
| 443 | $A_1$ | B-3-153 |
| 444 | $A_1$ | B-3-154 |
| 445 | $A_1$ | B-3-155 |
| 446 | $A_1$ | B-3-156 |
| 447 | $A_1$ | B-3-157 |
| 448 | $A_1$ | B-3-158 |
| 449 | $A_1$ | B-3-159 |
| 450 | $A_1$ | B-3-160 |
| 451 | $A_1$ | B-3-161 |
| 452 | $A_1$ | B-3-162 |
| 453 | $A_1$ | B-3-163 |
| 454 | $A_1$ | B-3-164 |
| 455 | $A_1$ | B-3-165 |
| 456 | $A_1$ | B-3-166 |
| 457 | $A_1$ | B-3-167 |
| 458 | $A_1$ | B-3-168 |
| 459 | $A_1$ | B-3-169 |
| 460 | $A_1$ | B-3-170 |
| 461 | $A_1$ | B-3-171 |
| 462 | $A_1$ | B-3-172 |
| 463 | $A_1$ | B-3-173 |
| 464 | $A_1$ | B-3-174 |
| 465 | $A_1$ | B-3-175 |
| 466 | $A_1$ | B-3-176 |
| 467 | $A_1$ | B-3-177 |
| 468 | $A_1$ | B-3-178 |
| 469 | $A_1$ | B-3-179 |
| 470 | $A_1$ | B-3-180 |
| 471 | $A_1$ | B-3-181 |
| 472 | $A_1$ | B-3-182 |
| 473 | $A_1$ | B-3-183 |
| 474 | $A_1$ | B-3-184 |
| 475 | $A_1$ | B-3-185 |
| 476 | $A_1$ | B-3-186 |
| 477 | $A_1$ | B-3-187 |
| 478 | $A_1$ | B-3-188 |
| 479 | $A_1$ | B-3-189 |

-continued

| Compound | A Structure | B Structure |
|---|---|---|
| 480 | $A_1$ | B-3-190 |
| 481 | $A_1$ | B-3-191 |
| 482 | $A_1$ | B-3-192 |
| 483 | $A_1$ | B-3-193 |
| 484 | $A_1$ | B-3-194 |
| 485 | $A_1$ | B-3-195 |
| 486 | $A_1$ | B-3-196 |
| 487 | $A_1$ | B-3-197 |
| 488 | $A_1$ | B-3-198 |
| 489 | $A_1$ | B-3-199 |
| 490 | $A_1$ | B-3-200 |
| 491 | $A_1$ | B-3-201 |
| 492 | $A_1$ | B-3-202 |
| 493 | $A_1$ | B-3-203 |
| 494 | $A_1$ | B-3-204 |
| 495 | $A_1$ | B-3-205 |
| 496 | $A_1$ | B-3-206 |
| 497 | $A_1$ | B-3-207 |
| 498 | $A_1$ | B-3-208 |
| 499 | $A_1$ | B-3-209 |
| 500 | $A_1$ | B-3-210 |
| 501 | $A_1$ | B-3-211 |
| 502 | $A_1$ | B-3-212 |
| 503 | $A_1$ | B-3-213 |
| 504 | $A_1$ | B-3-214 |
| 505 | $A_1$ | B-3-215 |
| 506 | $A_1$ | B-3-216 |
| 507 | $A_1$ | B-3-217 |
| 508 | $A_1$ | B-3-218 |
| 509 | $A_1$ | B-4-1 |
| 510 | $A_1$ | B-4-2 |
| 511 | $A_1$ | B-4-3 |
| 512 | $A_1$ | B-4-4 |
| 513 | $A_1$ | B-4-5 |
| 514 | $A_1$ | B-4-6 |
| 515 | $A_1$ | B-4-7 |
| 516 | $A_1$ | B-4-8 |
| 517 | $A_1$ | B-4-9 |
| 518 | $A_1$ | B-4-10 |
| 519 | $A_1$ | B-4-11 |
| 520 | $A_1$ | B-4-12 |
| 521 | $A_1$ | B-4-13 |
| 522 | $A_1$ | B-4-14 |
| 523 | $A_1$ | B-4-15 |
| 524 | $A_1$ | B-4-16 |
| 525 | $A_1$ | B-4-17 |
| 526 | $A_1$ | B-4-18 |
| 527 | $A_1$ | B-4-19 |
| 528 | $A_1$ | B-4-20 |
| 529 | $A_1$ | B-4-21 |
| 530 | $A_1$ | B-4-22 |
| 531 | $A_1$ | B-4-23 |
| 532 | $A_1$ | B-4-24 |
| 533 | $A_1$ | B-4-25 |
| 534 | $A_1$ | B-4-26 |
| 535 | $A_1$ | B-4-27 |
| 536 | $A_1$ | B-4-28 |
| 537 | $A_1$ | B-4-29 |
| 538 | $A_1$ | B-4-30 |
| 539 | $A_1$ | B-4-31 |
| 540 | $A_1$ | B-4-32 |
| 541 | $A_1$ | B-4-33 |
| 542 | $A_1$ | B-4-34 |
| 543 | $A_1$ | B-4-35 |
| 544 | $A_1$ | B-4-36 |
| 545 | $A_1$ | B-4-37 |
| 546 | $A_1$ | B-4-38 |
| 547 | $A_1$ | B-4-39 |
| 548 | $A_1$ | B-4-40 |
| 549 | $A_1$ | B-4-41 |
| 550 | $A_1$ | B-4-42 |
| 551 | $A_1$ | B-4-43 |
| 552 | $A_1$ | B-4-44 |
| 553 | $A_1$ | B-4-45 |
| 554 | $A_1$ | B-4-46 |
| 555 | $A_1$ | B-4-47 |

-continued

| Compound | A Structure | B Structure |
|---|---|---|
| 556 | $A_1$ | B-4-48 |
| 557 | $A_1$ | B-4-49 |
| 558 | $A_1$ | B-4-50 |
| 559 | $A_1$ | B-4-51 |
| 560 | $A_1$ | B-4-52 |
| 561 | $A_1$ | B-4-53 |
| 562 | $A_1$ | B-4-54 |
| 563 | $A_1$ | B-4-55 |
| 564 | $A_1$ | B-4-56 |
| 565 | $A_1$ | B-4-57 |
| 566 | $A_1$ | B-4-58 |
| 567 | $A_1$ | B-4-59 |
| 568 | $A_1$ | B-4-60 |
| 569 | $A_1$ | B-4-61 |
| 570 | $A_1$ | B-4-62 |
| 571 | $A_1$ | B-4-63 |
| 572 | $A_1$ | B-4-64 |
| 573 | $A_1$ | B-4-65 |
| 574 | $A_1$ | B-4-66 |
| 575 | $A_1$ | B-4-67 |
| 576 | $A_1$ | B-4-68 |
| 577 | $A_1$ | B-4-69 |
| 578 | $A_1$ | B-4-70 |
| 579 | $A_1$ | B-4-71 |
| 580 | $A_1$ | B-4-72 |
| 581 | $A_1$ | B-5-1 |
| 582 | $A_1$ | B-5-2 |
| 583 | $A_1$ | B-5-3 |
| 584 | $A_1$ | B-5-4 |
| 585 | $A_1$ | B-5-5 |
| 586 | $A_1$ | B-5-6 |
| 587 | $A_1$ | B-5-7 |
| 588 | $A_1$ | B-5-8 |
| 589 | $A_1$ | B-5-9 |
| 590 | $A_1$ | B-5-10 |
| 591 | $A_1$ | B-5-11 |
| 592 | $A_1$ | B-5-12 |
| 593 | $A_1$ | B-5-13 |
| 594 | $A_1$ | B-5-14 |
| 595 | $A_1$ | B-5-15 |
| 596 | $A_1$ | B-5-16 |
| 597 | $A_1$ | B-5-17 |
| 598 | $A_1$ | B-5-18 |
| 599 | $A_1$ | B-5-19 |
| 600 | $A_1$ | B-5-20 |
| 601 | $A_1$ | B-5-21 |
| 602 | $A_1$ | B-5-22 |
| 603 | $A_1$ | B-5-23 |
| 604 | $A_1$ | B-5-24 |
| 605 | $A_1$ | B-5-25 |
| 606 | $A_1$ | B-5-26 |
| 607 | $A_1$ | B-5-27 |
| 608 | $A_1$ | B-5-28 |
| 609 | $A_1$ | B-5-29 |
| 610 | $A_1$ | B-5-30 |
| 611 | $A_1$ | B-5-31 |
| 612 | $A_1$ | B-5-32 |
| 613 | $A_1$ | B-5-33 |
| 614 | $A_1$ | B-5-34 |
| 615 | $A_1$ | B-5-35 |
| 616 | $A_1$ | B-5-36 |
| 617 | $A_1$ | B-5-37 |
| 618 | $A_1$ | B-5-38 |
| 619 | $A_1$ | B-5-39 |
| 620 | $A_1$ | B-5-40 |
| 621 | $A_1$ | B-5-41 |
| 622 | $A_1$ | B-5-42 |
| 623 | $A_1$ | B-5-43 |
| 624 | $A_1$ | B-5-44 |
| 625 | $A_1$ | B-5-45 |
| 626 | $A_1$ | B-5-46 |
| 627 | $A_1$ | B-5-47 |
| 628 | $A_1$ | B-5-48 |
| 629 | $A_1$ | B-5-49 |
| 630 | $A_1$ | B-5-50 |
| 631 | $A_1$ | B-5-51 |

-continued

| Compound | A Structure | B Structure |
|---|---|---|
| 632 | $A_1$ | B-5-52 |
| 633 | $A_1$ | B-5-53 |
| 634 | $A_1$ | B-5-54 |
| 635 | $A_1$ | B-5-55 |
| 636 | $A_1$ | B-5-56 |
| 637 | $A_1$ | B-5-57 |
| 638 | $A_1$ | B-5-58 |
| 639 | $A_1$ | B-5-59 |
| 640 | $A_1$ | B-5-60 |
| 641 | $A_1$ | B-5-61 |
| 642 | $A_1$ | B-5-62 |
| 643 | $A_1$ | B-5-63 |
| 644 | $A_1$ | B-5-64 |
| 645 | $A_1$ | B-5-65 |
| 646 | $A_1$ | B-5-66 |
| 647 | $A_1$ | B-5-67 |
| 648 | $A_1$ | B-5-68 |
| 649 | $A_1$ | B-5-69 |
| 650 | $A_1$ | B-5-70 |
| 651 | $A_1$ | B-5-71 |
| 652 | $A_1$ | B-5-72 |
| 653 | $A_1$ | B-6-1 |
| 654 | $A_1$ | B-6-2 |
| 655 | $A_1$ | B-6-3 |
| 656 | $A_1$ | B-6-4 |
| 657 | $A_1$ | B-6-5 |
| 658 | $A_1$ | B-6-6 |
| 659 | $A_1$ | B-6-7 |
| 660 | $A_1$ | B-6-8 |
| 661 | $A_1$ | B-6-9 |
| 662 | $A_1$ | B-6-10 |
| 663 | $A_1$ | B-6-11 |
| 664 | $A_1$ | B-6-12 |
| 665 | $A_1$ | B-6-13 |
| 666 | $A_1$ | B-6-14 |
| 667 | $A_1$ | B-6-15 |
| 668 | $A_1$ | B-6-16 |
| 669 | $A_1$ | B-6-17 |
| 670 | $A_1$ | B-6-18 |
| 671 | $A_2$ | B-1-1 |
| 672 | $A_2$ | B-1-2 |
| 673 | $A_2$ | B-1-3 |
| 674 | $A_2$ | B-1-4 |
| 675 | $A_2$ | B-1-5 |
| 676 | $A_2$ | B-1-6 |
| 677 | $A_2$ | B-1-7 |
| 678 | $A_2$ | B-1-8 |
| 679 | $A_2$ | B-1-9 |
| 680 | $A_2$ | B-1-10 |
| 681 | $A_2$ | B-1-11 |
| 682 | $A_2$ | B-1-12 |
| 683 | $A_2$ | B-1-13 |
| 684 | $A_2$ | B-1-14 |
| 685 | $A_2$ | B-1-15 |
| 686 | $A_2$ | B-1-16 |
| 687 | $A_2$ | B-1-17 |
| 688 | $A_2$ | B-1-18 |
| 689 | $A_2$ | B-1-19 |
| 690 | $A_2$ | B-1-20 |
| 691 | $A_2$ | B-1-21 |
| 692 | $A_2$ | B-1-22 |
| 693 | $A_2$ | B-1-23 |
| 694 | $A_2$ | B-1-24 |
| 695 | $A_2$ | B-1-25 |
| 696 | $A_2$ | B-1-26 |
| 697 | $A_2$ | B-1-27 |
| 698 | $A_2$ | B-1-28 |
| 699 | $A_2$ | B-1-29 |
| 700 | $A_2$ | B-1-30 |
| 701 | $A_2$ | B-1-31 |
| 702 | $A_2$ | B-1-32 |
| 703 | $A_2$ | B-1-33 |
| 704 | $A_2$ | B-1-34 |
| 705 | $A_2$ | B-1-35 |
| 706 | $A_2$ | B-1-36 |
| 707 | $A_2$ | B-1-37 |

-continued

| Compound | A Structure | B Structure |
|---|---|---|
| 708 | $A_2$ | B-1-38 |
| 709 | $A_2$ | B-1-39 |
| 710 | $A_2$ | B-1-40 |
| 711 | $A_2$ | B-1-41 |
| 712 | $A_2$ | B-1-42 |
| 713 | $A_2$ | B-1-43 |
| 714 | $A_2$ | B-1-44 |
| 715 | $A_2$ | B-1-45 |
| 716 | $A_2$ | B-1-46 |
| 717 | $A_2$ | B-1-47 |
| 718 | $A_2$ | B-1-48 |
| 719 | $A_2$ | B-1-49 |
| 720 | $A_2$ | B-1-50 |
| 721 | $A_2$ | B-1-51 |
| 722 | $A_2$ | B-1-52 |
| 723 | $A_2$ | B-1-53 |
| 724 | $A_2$ | B-1-54 |
| 725 | $A_2$ | B-1-55 |
| 726 | $A_2$ | B-1-56 |
| 727 | $A_2$ | B-1-57 |
| 728 | $A_2$ | B-1-58 |
| 729 | $A_2$ | B-1-59 |
| 730 | $A_2$ | B-1-60 |
| 731 | $A_2$ | B-1-61 |
| 732 | $A_2$ | B-1-62 |
| 733 | $A_2$ | B-1-63 |
| 734 | $A_2$ | B-1-64 |
| 735 | $A_2$ | B-1-65 |
| 736 | $A_2$ | B-1-66 |
| 737 | $A_2$ | B-1-67 |
| 738 | $A_2$ | B-1-68 |
| 739 | $A_2$ | B-1-69 |
| 740 | $A_2$ | B-1-70 |
| 741 | $A_2$ | B-1-71 |
| 742 | $A_2$ | B-1-72 |
| 743 | $A_2$ | B-2-1 |
| 744 | $A_2$ | B-2-2 |
| 745 | $A_2$ | B-2-3 |
| 746 | $A_2$ | B-2-4 |
| 747 | $A_2$ | B-2-5 |
| 748 | $A_2$ | B-2-6 |
| 749 | $A_2$ | B-2-7 |
| 750 | $A_2$ | B-2-8 |
| 751 | $A_2$ | B-2-9 |
| 752 | $A_2$ | B-2-10 |
| 753 | $A_2$ | B-2-11 |
| 754 | $A_2$ | B-2-12 |
| 755 | $A_2$ | B-2-13 |
| 756 | $A_2$ | B-2-14 |
| 757 | $A_2$ | B-2-15 |
| 758 | $A_2$ | B-2-16 |
| 759 | $A_2$ | B-2-17 |
| 760 | $A_2$ | B-2-18 |
| 761 | $A_2$ | B-2-19 |
| 762 | $A_2$ | B-2-20 |
| 763 | $A_2$ | B-2-21 |
| 764 | $A_2$ | B-2-22 |
| 765 | $A_2$ | B-2-23 |
| 766 | $A_2$ | B-2-24 |
| 767 | $A_2$ | B-2-25 |
| 768 | $A_2$ | B-2-26 |
| 769 | $A_2$ | B-2-27 |
| 770 | $A_2$ | B-2-28 |
| 771 | $A_2$ | B-2-29 |
| 772 | $A_2$ | B-2-30 |
| 773 | $A_2$ | B-2-31 |
| 774 | $A_2$ | B-2-32 |
| 775 | $A_2$ | B-2-33 |
| 776 | $A_2$ | B-2-34 |
| 777 | $A_2$ | B-2-35 |
| 778 | $A_2$ | B-2-36 |
| 779 | $A_2$ | B-2-37 |
| 780 | $A_2$ | B-2-38 |
| 781 | $A_2$ | B-2-39 |
| 782 | $A_2$ | B-2-40 |
| 783 | $A_2$ | B-2-41 |

-continued

| Compound | A Structure | B Structure |
|---|---|---|
| 784 | $A_2$ | B-2-42 |
| 785 | $A_2$ | B-2-43 |
| 786 | $A_2$ | B-2-44 |
| 787 | $A_2$ | B-2-45 |
| 788 | $A_2$ | B-2-46 |
| 789 | $A_2$ | B-2-47 |
| 790 | $A_2$ | B-2-48 |
| 791 | $A_2$ | B-2-49 |
| 792 | $A_2$ | B-2-50 |
| 793 | $A_2$ | B-2-51 |
| 794 | $A_2$ | B-2-52 |
| 795 | $A_2$ | B-2-53 |
| 796 | $A_2$ | B-2-54 |
| 797 | $A_2$ | B-2-55 |
| 798 | $A_2$ | B-2-56 |
| 799 | $A_2$ | B-2-57 |
| 800 | $A_2$ | B-2-58 |
| 801 | $A_2$ | B-2-59 |
| 802 | $A_2$ | B-2-60 |
| 803 | $A_2$ | B-2-61 |
| 804 | $A_2$ | B-2-62 |
| 805 | $A_2$ | B-2-63 |
| 806 | $A_2$ | B-2-64 |
| 807 | $A_2$ | B-2-65 |
| 808 | $A_2$ | B-2-66 |
| 809 | $A_2$ | B-2-67 |
| 810 | $A_2$ | B-2-68 |
| 811 | $A_2$ | B-2-69 |
| 812 | $A_2$ | B-2-70 |
| 813 | $A_2$ | B-2-71 |
| 814 | $A_2$ | B-2-72 |
| 815 | $A_2$ | B-2-73 |
| 816 | $A_2$ | B-2-74 |
| 817 | $A_2$ | B-2-75 |
| 818 | $A_2$ | B-2-76 |
| 819 | $A_2$ | B-2-77 |
| 820 | $A_2$ | B-2-78 |
| 821 | $A_2$ | B-2-79 |
| 822 | $A_2$ | B-2-80 |
| 823 | $A_2$ | B-2-81 |
| 824 | $A_2$ | B-2-82 |
| 825 | $A_2$ | B-2-83 |
| 826 | $A_2$ | B-2-84 |
| 827 | $A_2$ | B-2-85 |
| 828 | $A_2$ | B-2-86 |
| 829 | $A_2$ | B-2-87 |
| 830 | $A_2$ | B-2-88 |
| 831 | $A_2$ | B-2-89 |
| 832 | $A_2$ | B-2-90 |
| 833 | $A_2$ | B-2-91 |
| 834 | $A_2$ | B-2-92 |
| 835 | $A_2$ | B-2-93 |
| 836 | $A_2$ | B-2-94 |
| 837 | $A_2$ | B-2-95 |
| 838 | $A_2$ | B-2-96 |
| 839 | $A_2$ | B-2-97 |
| 840 | $A_2$ | B-2-98 |
| 841 | $A_2$ | B-2-99 |
| 842 | $A_2$ | B-2-100 |
| 843 | $A_2$ | B-2-101 |
| 844 | $A_2$ | B-2-102 |
| 845 | $A_2$ | B-2-103 |
| 846 | $A_2$ | B-2-104 |
| 847 | $A_2$ | B-2-105 |
| 848 | $A_2$ | B-2-106 |
| 849 | $A_2$ | B-2-107 |
| 850 | $A_2$ | B-2-108 |
| 851 | $A_2$ | B-2-109 |
| 852 | $A_2$ | B-2-110 |
| 853 | $A_2$ | B-2-111 |
| 854 | $A_2$ | B-2-112 |
| 855 | $A_2$ | B-2-113 |
| 856 | $A_2$ | B-2-114 |
| 857 | $A_2$ | B-2-115 |
| 858 | $A_2$ | B-2-116 |
| 859 | $A_2$ | B-2-117 |

-continued

| Compound | A Structure | B Structure |
|---|---|---|
| 860 | $A_2$ | B-2-118 |
| 861 | $A_2$ | B-2-119 |
| 862 | $A_2$ | B-2-120 |
| 863 | $A_2$ | B-2-121 |
| 864 | $A_2$ | B-2-122 |
| 865 | $A_2$ | B-2-123 |
| 866 | $A_2$ | B-2-124 |
| 867 | $A_2$ | B-2-125 |
| 868 | $A_2$ | B-2-126 |
| 869 | $A_2$ | B-2-127 |
| 870 | $A_2$ | B-2-128 |
| 871 | $A_2$ | B-2-129 |
| 872 | $A_2$ | B-2-130 |
| 873 | $A_2$ | B-2-131 |
| 874 | $A_2$ | B-2-132 |
| 875 | $A_2$ | B-2-133 |
| 876 | $A_2$ | B-2-134 |
| 877 | $A_2$ | B-2-135 |
| 878 | $A_2$ | B-2-136 |
| 879 | $A_2$ | B-2-137 |
| 880 | $A_2$ | B-2-138 |
| 881 | $A_2$ | B-2-139 |
| 882 | $A_2$ | B-2-140 |
| 883 | $A_2$ | B-2-141 |
| 884 | $A_2$ | B-2-142 |
| 885 | $A_2$ | B-2-143 |
| 886 | $A_2$ | B-2-144 |
| 887 | $A_2$ | B-2-145 |
| 888 | $A_2$ | B-2-146 |
| 889 | $A_2$ | B-2-147 |
| 890 | $A_2$ | B-2-148 |
| 891 | $A_2$ | B-2-149 |
| 892 | $A_2$ | B-2-150 |
| 893 | $A_2$ | B-2-151 |
| 894 | $A_2$ | B-2-152 |
| 895 | $A_2$ | B-2-153 |
| 896 | $A_2$ | B-2-154 |
| 897 | $A_2$ | B-2-155 |
| 898 | $A_2$ | B-2-156 |
| 899 | $A_2$ | B-2-157 |
| 900 | $A_2$ | B-2-158 |
| 901 | $A_2$ | B-2-159 |
| 902 | $A_2$ | B-2-160 |
| 903 | $A_2$ | B-2-161 |
| 904 | $A_2$ | B-2-162 |
| 905 | $A_2$ | B-2-163 |
| 906 | $A_2$ | B-2-164 |
| 907 | $A_2$ | B-2-165 |
| 908 | $A_2$ | B-2-166 |
| 909 | $A_2$ | B-2-167 |
| 910 | $A_2$ | B-2-168 |
| 911 | $A_2$ | B-3-1 |
| 912 | $A_2$ | B-3-2 |
| 913 | $A_2$ | B-3-3 |
| 914 | $A_2$ | B-3-4 |
| 915 | $A_2$ | B-3-5 |
| 916 | $A_2$ | B-3-6 |
| 917 | $A_2$ | B-3-7 |
| 918 | $A_2$ | B-3-8 |
| 919 | $A_2$ | B-3-9 |
| 920 | $A_2$ | B-3-10 |
| 921 | $A_2$ | B-3-11 |
| 922 | $A_2$ | B-3-12 |
| 923 | $A_2$ | B-3-13 |
| 924 | $A_2$ | B-3-14 |
| 925 | $A_2$ | B-3-15 |
| 926 | $A_2$ | B-3-16 |
| 927 | $A_2$ | B-3-17 |
| 928 | $A_2$ | B-3-18 |
| 929 | $A_2$ | B-3-19 |
| 930 | $A_2$ | B-3-20 |
| 931 | $A_2$ | B-3-21 |
| 932 | $A_2$ | B-3-22 |
| 933 | $A_2$ | B-3-23 |
| 934 | $A_2$ | B-3-24 |
| 935 | $A_2$ | B-3-25 |

-continued

| Compound | A Structure | B Structure |
|---|---|---|
| 936 | $A_2$ | B-3-26 |
| 937 | $A_2$ | B-3-27 |
| 938 | $A_2$ | B-3-28 |
| 939 | $A_2$ | B-3-29 |
| 940 | $A_2$ | B-3-30 |
| 941 | $A_2$ | B-3-31 |
| 942 | $A_2$ | B-3-32 |
| 943 | $A_2$ | B-3-33 |
| 944 | $A_2$ | B-3-34 |
| 945 | $A_2$ | B-3-35 |
| 946 | $A_2$ | B-3-36 |
| 947 | $A_2$ | B-3-37 |
| 948 | $A_2$ | B-3-38 |
| 949 | $A_2$ | B-3-39 |
| 950 | $A_2$ | B-3-40 |
| 951 | $A_2$ | B-3-41 |
| 952 | $A_2$ | B-3-42 |
| 953 | $A_2$ | B-3-43 |
| 954 | $A_2$ | B-3-44 |
| 955 | $A_2$ | B-3-45 |
| 956 | $A_2$ | B-3-46 |
| 957 | $A_2$ | B-3-47 |
| 958 | $A_2$ | B-3-48 |
| 959 | $A_2$ | B-3-49 |
| 960 | $A_2$ | B-3-50 |
| 961 | $A_2$ | B-3-51 |
| 962 | $A_2$ | B-3-52 |
| 963 | $A_2$ | B-3-53 |
| 964 | $A_2$ | B-3-54 |
| 965 | $A_2$ | B-3-55 |
| 966 | $A_2$ | B-3-56 |
| 967 | $A_2$ | B-3-57 |
| 968 | $A_2$ | B-3-58 |
| 969 | $A_2$ | B-3-59 |
| 970 | $A_2$ | B-3-60 |
| 971 | $A_2$ | B-3-61 |
| 972 | $A_2$ | B-3-62 |
| 973 | $A_2$ | B-3-63 |
| 974 | $A_2$ | B-3-64 |
| 975 | $A_2$ | B-3-65 |
| 976 | $A_2$ | B-3-66 |
| 977 | $A_2$ | B-3-67 |
| 978 | $A_2$ | B-3-68 |
| 979 | $A_2$ | B-3-69 |
| 980 | $A_2$ | B-3-70 |
| 981 | $A_2$ | B-3-71 |
| 982 | $A_2$ | B-3-72 |
| 983 | $A_2$ | B-3-73 |
| 984 | $A_2$ | B-3-74 |
| 985 | $A_2$ | B-3-75 |
| 986 | $A_2$ | B-3-76 |
| 987 | $A_2$ | B-3-77 |
| 988 | $A_2$ | B-3-78 |
| 989 | $A_2$ | B-3-79 |
| 990 | $A_2$ | B-3-80 |
| 991 | $A_2$ | B-3-81 |
| 992 | $A_2$ | B-3-82 |
| 993 | $A_2$ | B-3-83 |
| 994 | $A_2$ | B-3-84 |
| 995 | $A_2$ | B-3-85 |
| 996 | $A_2$ | B-3-86 |
| 997 | $A_2$ | B-3-87 |
| 998 | $A_2$ | B-3-88 |
| 999 | $A_2$ | B-3-89 |
| 1000 | $A_2$ | B-3-90 |
| 1001 | $A_2$ | B-3-91 |
| 1002 | $A_2$ | B-3-92 |
| 1003 | $A_2$ | B-3-93 |
| 1004 | $A_2$ | B-3-94 |
| 1005 | $A_2$ | B-3-95 |
| 1006 | $A_2$ | B-3-96 |
| 1007 | $A_2$ | B-3-97 |
| 1008 | $A_2$ | B-3-98 |
| 1009 | $A_2$ | B-3-99 |
| 1010 | $A_2$ | B-3-100 |
| 1011 | $A_2$ | B-3-101 |

-continued

| Compound | A Structure | B Structure |
|---|---|---|
| 1012 | $A_2$ | B-3-102 |
| 1013 | $A_2$ | B-3-103 |
| 1014 | $A_2$ | B-3-104 |
| 1015 | $A_2$ | B-3-105 |
| 1016 | $A_2$ | B-3-106 |
| 1017 | $A_2$ | B-3-107 |
| 1018 | $A_2$ | B-3-108 |
| 1019 | $A_2$ | B-3-109 |
| 1020 | $A_2$ | B-3-110 |
| 1021 | $A_2$ | B-3-111 |
| 1022 | $A_2$ | B-3-112 |
| 1023 | $A_2$ | B-3-113 |
| 1024 | $A_2$ | B-3-114 |
| 1025 | $A_2$ | B-3-115 |
| 1026 | $A_2$ | B-3-116 |
| 1027 | $A_2$ | B-3-117 |
| 1028 | $A_2$ | B-3-118 |
| 1029 | $A_2$ | B-3-119 |
| 1030 | $A_2$ | B-3-120 |
| 1031 | $A_2$ | B-3-121 |
| 1032 | $A_2$ | B-3-122 |
| 1033 | $A_2$ | B-3-123 |
| 1034 | $A_2$ | B-3-124 |
| 1035 | $A_2$ | B-3-125 |
| 1036 | $A_2$ | B-3-126 |
| 1037 | $A_2$ | B-3-127 |
| 1038 | $A_2$ | B-3-128 |
| 1039 | $A_2$ | B-3-129 |
| 1040 | $A_2$ | B-3-130 |
| 1041 | $A_2$ | B-3-131 |
| 1042 | $A_2$ | B-3-132 |
| 1043 | $A_2$ | B-3-133 |
| 1044 | $A_2$ | B-3-134 |
| 1045 | $A_2$ | B-3-135 |
| 1046 | $A_2$ | B-3-136 |
| 1047 | $A_2$ | B-3-137 |
| 1048 | $A_2$ | B-3-138 |
| 1049 | $A_2$ | B-3-139 |
| 1050 | $A_2$ | B-3-140 |
| 1051 | $A_2$ | B-3-141 |
| 1052 | $A_2$ | B-3-142 |
| 1053 | $A_2$ | B-3-143 |
| 1054 | $A_2$ | B-3-144 |
| 1055 | $A_2$ | B-3-145 |
| 1056 | $A_2$ | B-3-146 |
| 1057 | $A_2$ | B-3-147 |
| 1058 | $A_2$ | B-3-148 |
| 1059 | $A_2$ | B-3-149 |
| 1060 | $A_2$ | B-3-150 |
| 1061 | $A_2$ | B-3-151 |
| 1062 | $A_2$ | B-3-152 |
| 1063 | $A_2$ | B-3-153 |
| 1064 | $A_2$ | B-3-154 |
| 1065 | $A_2$ | B-3-155 |
| 1066 | $A_2$ | B-3-156 |
| 1067 | $A_2$ | B-3-157 |
| 1068 | $A_2$ | B-3-158 |
| 1069 | $A_2$ | B-3-159 |
| 1070 | $A_2$ | B-3-160 |
| 1071 | $A_2$ | B-3-161 |
| 1072 | $A_2$ | B-3-162 |
| 1073 | $A_2$ | B-3-163 |
| 1074 | $A_2$ | B-3-164 |
| 1075 | $A_2$ | B-3-165 |
| 1076 | $A_2$ | B-3-166 |
| 1077 | $A_2$ | B-3-167 |
| 1078 | $A_2$ | B-3-168 |
| 1079 | $A_2$ | B-4-1 |
| 1080 | $A_2$ | B-4-2 |
| 1081 | $A_2$ | B-4-3 |
| 1082 | $A_2$ | B-4-4 |
| 1083 | $A_2$ | B-4-5 |
| 1084 | $A_2$ | B-4-6 |
| 1085 | $A_2$ | B-4-7 |
| 1086 | $A_2$ | B-4-8 |
| 1087 | $A_2$ | B-4-9 |

-continued

| Compound | A Structure | B Structure |
|---|---|---|
| 1088 | $A_2$ | B-4-10 |
| 1089 | $A_2$ | B-4-11 |
| 1090 | $A_2$ | B-4-12 |
| 1091 | $A_2$ | B-4-13 |
| 1092 | $A_2$ | B-4-14 |
| 1093 | $A_2$ | B-4-15 |
| 1094 | $A_2$ | B-4-16 |
| 1095 | $A_2$ | B-4-17 |
| 1096 | $A_2$ | B-4-18 |
| 1097 | $A_2$ | B-4-19 |
| 1098 | $A_2$ | B-4-20 |
| 1099 | $A_2$ | B-4-21 |
| 1100 | $A_2$ | B-4-22 |
| 1101 | $A_2$ | B-4-23 |
| 1102 | $A_2$ | B-4-24 |
| 1103 | $A_2$ | B-4-25 |
| 1104 | $A_2$ | B-4-26 |
| 1105 | $A_2$ | B-4-27 |
| 1106 | $A_2$ | B-4-28 |
| 1107 | $A_2$ | B-4-29 |
| 1108 | $A_2$ | B-4-30 |
| 1109 | $A_2$ | B-4-31 |
| 1110 | $A_2$ | B-4-32 |
| 1111 | $A_2$ | B-4-33 |
| 1112 | $A_2$ | B-4-34 |
| 1113 | $A_2$ | B-4-35 |
| 1114 | $A_2$ | B-4-36 |
| 1115 | $A_2$ | B-4-37 |
| 1116 | $A_2$ | B-4-38 |
| 1117 | $A_2$ | B-4-39 |
| 1118 | $A_2$ | B-4-40 |
| 1119 | $A_2$ | B-4-41 |
| 1120 | $A_2$ | B-4-42 |
| 1121 | $A_2$ | B-4-43 |
| 1122 | $A_2$ | B-4-44 |
| 1123 | $A_2$ | B-4-45 |
| 1124 | $A_2$ | B-4-46 |
| 1125 | $A_2$ | B-4-47 |
| 1126 | $A_2$ | B-4-48 |
| 1127 | $A_2$ | B-4-49 |
| 1128 | $A_2$ | B-4-50 |
| 1129 | $A_2$ | B-4-51 |
| 1130 | $A_2$ | B-4-52 |
| 1131 | $A_2$ | B-4-53 |
| 1132 | $A_2$ | B-4-54 |
| 1133 | $A_2$ | B-4-55 |
| 1134 | $A_2$ | B-4-56 |
| 1135 | $A_2$ | B-4-57 |
| 1136 | $A_2$ | B-4-58 |
| 1137 | $A_2$ | B-4-59 |
| 1138 | $A_2$ | B-4-60 |
| 1139 | $A_2$ | B-4-61 |
| 1140 | $A_2$ | B-4-62 |
| 1141 | $A_2$ | B-4-63 |
| 1142 | $A_2$ | B-4-64 |
| 1143 | $A_2$ | B-4-65 |
| 1144 | $A_2$ | B-4-66 |
| 1145 | $A_2$ | B-4-67 |
| 1146 | $A_2$ | B-4-68 |
| 1147 | $A_2$ | B-4-69 |
| 1148 | $A_2$ | B-4-70 |
| 1149 | $A_2$ | B-4-71 |
| 1150 | $A_2$ | B-4-72 |
| 1151 | $A_2$ | B-5-1 |
| 1152 | $A_2$ | B-5-2 |
| 1153 | $A_2$ | B-5-3 |
| 1154 | $A_2$ | B-5-4 |
| 1155 | $A_2$ | B-5-5 |
| 1156 | $A_2$ | B-5-6 |
| 1157 | $A_2$ | B-5-7 |
| 1158 | $A_2$ | B-5-8 |
| 1159 | $A_2$ | B-5-9 |
| 1160 | $A_2$ | B-5-10 |
| 1161 | $A_2$ | B-5-11 |
| 1162 | $A_2$ | B-5-12 |
| 1163 | $A_2$ | B-5-13 |

-continued

| Compound | A Structure | B Structure |
|---|---|---|
| 1164 | $A_2$ | B-5-14 |
| 1165 | $A_2$ | B-5-15 |
| 1166 | $A_2$ | B-5-16 |
| 1167 | $A_2$ | B-5-17 |
| 1168 | $A_2$ | B-5-18 |
| 1169 | $A_2$ | B-5-19 |
| 1170 | $A_2$ | B-5-20 |
| 1171 | $A_2$ | B-5-21 |
| 1172 | $A_2$ | B-5-22 |
| 1173 | $A_2$ | B-5-23 |
| 1174 | $A_2$ | B-5-24 |
| 1175 | $A_2$ | B-5-25 |
| 1176 | $A_2$ | B-5-26 |
| 1177 | $A_2$ | B-5-27 |
| 1178 | $A_2$ | B-5-28 |
| 1179 | $A_2$ | B-5-29 |
| 1180 | $A_2$ | B-5-30 |
| 1181 | $A_2$ | B-5-31 |
| 1182 | $A_2$ | B-5-32 |
| 1183 | $A_2$ | B-5-33 |
| 1184 | $A_2$ | B-5-34 |
| 1185 | $A_2$ | B-5-35 |
| 1186 | $A_2$ | B-5-36 |
| 1187 | $A_2$ | B-5-37 |
| 1188 | $A_2$ | B-5-38 |
| 1189 | $A_2$ | B-5-39 |
| 1190 | $A_2$ | B-5-40 |
| 1191 | $A_2$ | B-5-41 |
| 1192 | $A_2$ | B-5-42 |
| 1193 | $A_2$ | B-5-43 |
| 1194 | $A_2$ | B-5-44 |
| 1195 | $A_2$ | B-5-45 |
| 1196 | $A_2$ | B-5-46 |
| 1197 | $A_2$ | B-5-47 |
| 1198 | $A_2$ | B-5-48 |
| 1199 | $A_2$ | B-5-49 |
| 1200 | $A_2$ | B-5-50 |
| 1201 | $A_2$ | B-5-51 |
| 1202 | $A_2$ | B-5-52 |
| 1203 | $A_2$ | B-5-53 |
| 1204 | $A_2$ | B-5-54 |
| 1205 | $A_2$ | B-5-55 |
| 1206 | $A_2$ | B-5-56 |
| 1207 | $A_2$ | B-5-57 |
| 1208 | $A_2$ | B-5-58 |
| 1209 | $A_2$ | B-5-59 |
| 1210 | $A_2$ | B-5-60 |
| 1211 | $A_2$ | B-5-61 |
| 1212 | $A_2$ | B-5-62 |
| 1213 | $A_2$ | B-5-63 |
| 1214 | $A_2$ | B-5-64 |
| 1215 | $A_2$ | B-5-65 |
| 1216 | $A_2$ | B-5-66 |
| 1217 | $A_2$ | B-5-67 |
| 1218 | $A_2$ | B-5-68 |
| 1219 | $A_2$ | B-5-69 |
| 1220 | $A_2$ | B-5-70 |
| 1221 | $A_2$ | B-5-71 |
| 1222 | $A_2$ | B-5-72 |
| 1223 | $A_2$ | B-6-1 |
| 1224 | $A_2$ | B-6-2 |
| 1225 | $A_2$ | B-6-3 |
| 1226 | $A_2$ | B-6-4 |
| 1227 | $A_2$ | B-6-5 |
| 1228 | $A_2$ | B-6-6 |
| 1229 | $A_2$ | B-6-7 |
| 1230 | $A_2$ | B-6-8 |
| 1231 | $A_2$ | B-6-9 |
| 1232 | $A_2$ | B-6-10 |
| 1233 | $A_2$ | B-6-11 |
| 1234 | $A_2$ | B-6-12 |
| 1235 | $A_2$ | B-6-13 |
| 1236 | $A_2$ | B-6-14 |
| 1237 | $A_2$ | B-6-15 |
| 1238 | $A_2$ | B-6-16 |
| 1239 | $A_2$ | B-6-17 |

-continued

| Compound | A Structure | B Structure |
|---|---|---|
| 1240 | $A_2$ | B-6-18 |
| 2333 | $A_1$ | B-3-219 |
| 2334 | $A_1$ | B-3-220 |
| 2335 | $A_1$ | B-3-221 |
| 2336 | $A_1$ | B-3-222 |
| 2337 | $A_1$ | B-3-223 |
| 2338 | $A_1$ | B-3-224 |
| 2339 | $A_1$ | B-3-225 |
| 2340 | $A_1$ | B-3-226 |
| 2341 | $A_1$ | B-3-227 |
| 2342 | $A_1$ | B-3-228 |
| 2343 | $A_1$ | B-3-229 |
| 2344 | $A_1$ | B-3-230 |
| 2345 | $A_1$ | B-3-231 |
| 2346 | $A_1$ | B-3-232 |
| 2347 | $A_1$ | B-3-233 |
| 2348 | $A_1$ | B-3-234 |
| 2349 | $A_1$ | B-3-235 |

wherein $A_1$ to $A_2$ in the above table have the following structures:

$A_1$

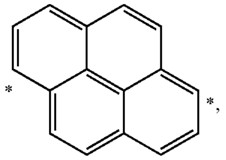

-continued $A_2$

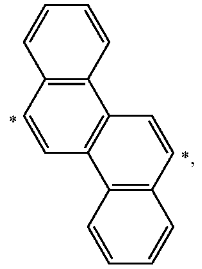

wherein in the structures of $A_1$ to $A_2$, * represents a position where B is joined.

13. The compound of claim 12, wherein hydrogen in the compounds 1 to 1240 and compounds 2333 to 2349 may be partially or fully deuterated.

14. An electroluminescent device, comprising:

an anode, a cathode, and an organic layer disposed between the anode and the cathode, wherein the organic layer comprises the compound of claim 1.

15. The electroluminescent device of claim 14, wherein the organic layer is a light-emitting layer, and the compound is a light-emitting material.

16. A compound formulation, comprising the compound of claim 1.

17. The compound of claim 1, wherein R" is selected from the group consisting of: fluorine, methyl, ethyl, n-propyl, isopropyl, cyclopropyl, n-butyl, isobutyl, t-butyl, cyclopentyl, neopentyl, cyclohexyl, 4,4-dimethylcyclohexyl, deuterated methyl, deuterated ethyl, deuterated n-propyl, deuterated isopropyl, deuterated cyclopropyl, deuterated n-butyl, deuterated isobutyl, deuterated t-butyl, deuterated cyclopentyl, deuterated neopentyl, deuterated cyclohexyl, and deuterated 4,4-dimethylcyclohexyl.

* * * * *